US010349660B2

(12) United States Patent
Thompson et al.

(10) Patent No.: US 10,349,660 B2
(45) Date of Patent: Jul. 16, 2019

(54) FUSION PROTEINS AND METHODS FOR STIMULATING PLANT GROWTH, PROTECTING PLANTS, AND IMMOBILIZING BACILLUS SPORES ON PLANTS

(71) Applicant: Spogen Biotech Inc., St. Louis, MO (US)

(72) Inventors: Brian Thompson, Creve Coeur, MO (US); Katie Thompson, Creve Coeur, MO (US)

(73) Assignee: Spogen Biotech Inc., St. Louis, MO (US)

( * ) Notice: Subject to any disclaimer, the term of this patent is extended or adjusted under 35 U.S.C. 154(b) by 0 days.

(21) Appl. No.: 15/846,487

(22) Filed: Dec. 19, 2017

(65) Prior Publication Data

US 2018/0208630 A1 Jul. 26, 2018

Related U.S. Application Data

(63) Continuation of application No. 14/775,892, filed as application No. PCT/US2014/030824 on Mar. 17, 2014, now Pat. No. 9,850,289.

(60) Provisional application No. 61/799,262, filed on Mar. 15, 2013.

(51) Int. Cl.

| | |
|---|---|
| ***A01N 63/00*** | (2006.01) |
| ***A01N 63/02*** | (2006.01) |
| ***A01N 37/46*** | (2006.01) |
| ***C07K 14/32*** | (2006.01) |
| ***C12N 9/02*** | (2006.01) |
| ***C12N 9/16*** | (2006.01) |
| ***C12N 9/24*** | (2006.01) |
| ***A01N 37/48*** | (2006.01) |
| ***C12N 9/20*** | (2006.01) |
| ***C12N 9/42*** | (2006.01) |
| ***C12N 9/48*** | (2006.01) |

(52) U.S. Cl.

CPC ............. *A01N 63/00* (2013.01); *A01N 37/46* (2013.01); *A01N 37/48* (2013.01); *A01N 63/02* (2013.01); *C07K 14/32* (2013.01); *C12N 9/0095* (2013.01); *C12N 9/16* (2013.01); *C12N 9/20* (2013.01); *C12N 9/2402* (2013.01); *C12N 9/2437* (2013.01); *C12N 9/48* (2013.01); *C12Y 118/06001* (2013.01); *C12Y 301/01003* (2013.01); *C12Y 302/01004* (2013.01); *C12Y 304/00* (2013.01); *C07K 2319/035* (2013.01); *C12Y 301/03008* (2013.01)

(58) Field of Classification Search

CPC ........ A01N 63/00; A01N 63/02; A01N 37/46; A01N 25/00; A01N 37/44; C07K 14/32; C07K 2319/035; C07K 2319/01; C07K 2319/40; A61K 39/07; A61K 2035/11; A61K 2039/522; A61K 2039/523; A61K 39/00; A61K 39/12

See application file for complete search history.

(56) References Cited

U.S. PATENT DOCUMENTS

| | | | |
|---|---|---|---|
| 5,290,914 | A | 3/1994 | Wilcox et al. |
| 5,348,743 | A | 9/1994 | Ryals et al. |
| 5,776,448 | A | 7/1998 | Suslow et al. |
| 6,184,440 | B1 | 2/2001 | Shoseyov et al. |
| 6,232,270 | B1 | 5/2001 | Branly et al. |
| 6,333,302 | B1 | 12/2001 | Beer et al. |
| 6,548,743 | B1 | 4/2003 | Sheen et al. |
| 6,630,340 | B2 | 10/2003 | Wilting et al. |
| 7,417,181 | B2 | 8/2008 | Wang et al. |
| 7,432,097 | B2 | 10/2008 | Short et al. |
| 7,504,120 | B2 | 3/2009 | Steer et al. |
| 7,615,681 | B2 | 11/2009 | Georges et al. |
| 7,919,678 | B2 | 4/2011 | Mironov |
| 7,960,148 | B2 | 6/2011 | Steer et al. |
| 8,030,064 | B2 | 10/2011 | Lee et al. |
| 8,097,769 | B2 | 1/2012 | Sarria-Millan et al. |
| 8,461,419 | B2 | 6/2013 | He et al. |
| 9,068,194 | B2 | 6/2015 | Unkefer et al. |

(Continued)

FOREIGN PATENT DOCUMENTS

| | | | |
|---|---|---|---|
| CA | 2146822 | A1 | 10/1995 |
| EP | 0 792 363 | B1 | 12/2003 |

(Continued)

OTHER PUBLICATIONS

Smirnova, I., et al., "The Effect of Inoculation by Cellulolytic Bacteria Bacillus cytaseus on Wheat Productivity," Institute of Microbiology and Virology Ministry of Education and Science, Kazakhstan, Almaty, pp. 185-191.

(Continued)

*Primary Examiner* — Padmavathi Baskar
(74) *Attorney, Agent, or Firm* — Stinson LLP

(57) ABSTRACT

The present invention is generally directed to fusion proteins containing a targeting sequence that targets the fusion protein to the exosporium of a *Bacillus cereus* family member. The invention also relates to recombinant *Bacillus cereus* family members expressing such fusion proteins and formulations containing the recombinant *Bacillus cereus* family members expressing the fusion proteins. Methods for stimulating plant growth, for protecting plants from pathogens, and for enhancing stress resistance in a plant by applying the recombinant *Bacillus cereus* family members or the formulations to plants or a plant growth medium are also described. The invention also relates to methods for immobilizing spores of a recombinant *Bacillus cereus* family member expressing a fusion protein on plants.

22 Claims, 2 Drawing Sheets

Specification includes a Sequence Listing.

(56) References Cited

U.S. PATENT DOCUMENTS

| | | | |
|---|---|---|---|
| 9,125,419 | B2 | 9/2015 | Asolkar et al. |
| 9,132,175 | B2 | 9/2015 | Stewart et al. |
| 9,133,251 | B2 | 9/2015 | Stewart et al. |
| 9,392,796 | B2 | 7/2016 | Thompson et al. |
| 9,573,980 | B2 | 2/2017 | Thompson et al. |
| 9,826,743 | B2 | 11/2017 | Curtis et al. |
| 9,845,342 | B2 | 12/2017 | Thompson et al. |
| 2003/0228679 | A1 | 12/2003 | Smith et al. |
| 2004/0077090 | A1 | 4/2004 | Short |
| 2007/0184018 | A1 | 8/2007 | Lahm et al. |
| 2008/0233175 | A1 | 9/2008 | Steer et al. |
| 2008/0248953 | A1 | 10/2008 | Smith et al. |
| 2009/0192040 | A1 | 7/2009 | Grobler |
| 2010/0071093 | A1 | 3/2010 | Sarria-Millan |
| 2010/0205690 | A1 | 8/2010 | Blasing et al. |
| 2010/0233124 | A1 | 9/2010 | Stewart et al. |
| 2010/0291100 | A1 | 11/2010 | Macinga |
| 2011/0281316 | A1 | 11/2011 | Stewart et al. |
| 2011/0321197 | A1 | 12/2011 | Schon et al. |
| 2012/0227134 | A1 | 9/2012 | Schon et al. |
| 2012/0259101 | A1 | 10/2012 | Tan et al. |
| 2012/0266327 | A1 | 10/2012 | Sanz Molinero et al. |
| 2013/0216653 | A1 | 8/2013 | Perkins et al. |
| 2013/0345056 | A1 | 12/2013 | Sada |
| 2014/0259225 | A1 | 9/2014 | Frank et al. |
| 2014/0274707 | A1 | 9/2014 | Thompson et al. |
| 2014/0342905 | A1 | 11/2014 | Bullis et al. |
| 2016/0051656 | A1 | 2/2016 | Stewart et al. |
| 2016/0053222 | A1 | 2/2016 | Stewart et al. |
| 2016/0236996 | A1 | 8/2016 | Chaudhry |
| 2016/0340658 | A1 | 11/2016 | Lessl et al. |

FOREIGN PATENT DOCUMENTS

| | | | |
|---|---|---|---|
| EP | 1 590 466 | B1 | 9/2010 |
| EP | 2 069 504 | B1 | 6/2015 |
| IN | 801/CHE/2011 | | 7/2014 |
| JP | 2007-117066 | A | 5/2007 |
| RU | 2 458 132 | C2 | 8/2012 |
| WO | 02/00232 | A2 | 1/2002 |
| WO | 2003/066846 | A1 | 8/2003 |
| WO | 2005/028654 | A1 | 3/2005 |
| WO | 2006/012366 | A2 | 2/2006 |
| WO | 2007/078127 | A1 | 7/2007 |
| WO | 2007/086898 | A2 | 8/2007 |
| WO | 2008/017483 | A2 | 2/2008 |
| WO | 2009/037329 | A2 | 3/2009 |
| WO | 2010/046221 | A1 | 4/2010 |
| WO | 2011/106794 | A1 | 9/2011 |
| WO | 2011/121408 | A1 | 10/2011 |
| WO | 2013/090628 | A1 | 6/2013 |
| WO | 2013/178649 | A1 | 12/2013 |
| WO | 2013/178658 | A1 | 12/2013 |
| WO | 2014/004487 | A1 | 1/2014 |
| WO | 2014/079773 | A1 | 5/2014 |
| WO | 2014/079814 | A1 | 5/2014 |
| WO | 2015/118516 | A1 | 8/2015 |

OTHER PUBLICATIONS

Stearns, J. C., et al., "Effects of Bacterial ACC Deaminase on *Brassica napus* Gene Expression," Molecular Plant-Microbe Interactions, May 2012, pp. 668-676, vol. 25, No. 5.

Steichen, C. T., et al., "Non-Uniform Assembly of the Bacillus anthracis Exosporium and a Bottle Cap Model for Spore Germination and Outgrowth," Molecular Microbiology, Apr. 2007, pp. 359-367, vol. 64, No. 2.

Tan, L., et al., "An Unusual Mechanism of Isopeptide Bond Formation Attaches the Collagenlike Glycoprotein BclA to the Exosporium of Bacillus anthracis," May-Jun. 2011, 20 pages, vol. 2, No. 3.

Tan, L., et al., "An Unusual Mechanism of Isopeptide Bond Formation Attaches the Collagenlike Glycoprotein BclA to be Exosporium of Bacillus anthracis," May-Jun. 2011, 20 pages, vol. 2, No. 3 (Retraction).

Tan, L., et al., "Sequence Motifs and Proteolytic Cleavage of the Collagen-Like Glycoprotein BclA Required for Its Attachment to the Exosporium of Bacillus anthracis," Journal of Bacteriology, Mar. 2010, pp. 1259-1268, vol. 192, No. 5.

Thompson, B. M., et al., "Localization and Assembly of the Novel Exosporium Protein BetA of Bacillus anthracis," Journal of Bacteriology, 2011, pp. 5098-5104, vol. 193, No. 19.

Thompson, B. M. et al., "A System of Efficient, Cost-Effective, and Customizable Vaccines for Use with Multiple Vaccine Candidates," Oct. 2010 post presentation, 1 page.

Thompson, B. M., et al., "Targeting of the BclA and BclB Proteins to the Bacillus anthracis Spore Surface," Molecular Microbiology, 2008, pp. 421-434, vol. 70, No. 2.

Thompson, B. M., et al., "The BclB Glycoprotein of Bacillus anthracis is Involved in Exosporium Integrity," Journal of Bacteriology, 2007, pp. 6704-6713, vol. 189, No. 18.

Thompson, B. M., et al., "The Co-Dependence of BxpB/ExsFA and BclA for Proper Incorporation into the Exosporium of Bacillus anthracis," Molecular Microbiology, 2011, pp. 799-813, vol. 79, No. 3.

Thompson, B. M., "The Role of the Glycoprotein BclB in the Exosporium in the Exosporium of Bacillus anthracis," Doctoral Dissertation presented to the Department of Diagnostic Medicine/Pathobiology, College of Veterinary Medicine, Kansas State University, 2002, 178 pages.

Thompson, B. M., "Amino-Terminal Sequences of the Bacillus Anthracis Exosporium Proteins BclA and BclB Important for Localization and Attachment to the Spore Surface," A Thesis presented to the Faculty of the Graduate School at the University of Missouri, Columbia, Aug. 2008, 165 pages.

Thompson, B. M., et al., "Assembly of the BclB Glycoprotein into the Exosporium and Evidence for its Role in the Formation of the Exosporium 'cap' Structure in Bacillus anthracis," Molecular Microbiology, Dec. 2012, pp. 1073-1084, vol. 86, No. 5.

U.S. Appl. No. 14/213,525, Response to Notice of Missing Parts and Preliminary Amendment A dated Jun. 2, 2014.

U.S. Appl. No. 14/213,525, Restriction Requirement dated May 8, 2015.

U.S. Appl. No. 14/213,525, Response to Restriction Requirement and Amendment B dated Aug. 7, 2015.

U.S. Appl. No. 14/213,525, Non-Final Office Action dated Sep. 3, 2015.

U.S. Appl. No. 14/213,525, Response to Office Action and Amendment C dated Dec. 3, 2015.

U.S. Appl. No. 14/213,525, Final Office Action dated Dec. 22, 2015.

U.S. Appl. No. 14/213,525, Response to Office Action and Amendment D dated Apr. 5, 2016.

U.S. Appl. No. 14/213,525, Non-Final Office Action dated Apr. 18, 2016.

U.S. Appl. No. 14/213,525, Response to Office Action and Amendment E dated Aug. 18, 2016.

U.S. Appl. No. 14/213,525, Final Office Action dated Sep. 6, 2016.

U.S. Appl. No. 14/213,525, Response to Final Office Action and Amendment F dated Oct. 12, 2016.

U.S. Appl. No. 14/213,525, Notice of Allowance dated Oct. 21, 2016.

U.S. Appl. No. 15/414,050, Preliminary Amendment A dated Jan. 25, 2017.

Waller, L. N., et al., "Identification of a Second Collagen-Like Glycoprotein Produced by Bacillus anthracis and Demonstration of Associated Spore-Specific Sugars," Journal of Bacteriology, Jul. 2005, pp. 4592-4597, vol. 187, No. 13.

Wang, X., et al., "PLD: Phospholipase Ds in Plant Signaling," Springer, Phospholipases in Plant Signaling, Signaling and Communication in Plants 20, Springer-Verlag Berlin Heidelberg 2014.

Zhou, Z. et al., "Immunogenicity of Recombinant Bacillus subtilis Spores Expressing Clonorchis sinensis tegumental Protein," Parasitology Research, 2008, pp. 293-297, vol. 102, No. 2.

Zhou, Z., et al., "Oral Administration of a Bacillus subtilis Spore-Based Vaccine Expressing Clonorchis sinensis tegumental Protein

(56) References Cited

OTHER PUBLICATIONS 22.3 kDa Confers Protection Against Clonorchis sinensis," Vaccine, 2008, pp. 1817-1825, vol. 26, No. 15.
Ziegler, D. R., Bacillus Thuringiensis Bacillus Cereus, Bacillus Genetic Stock Center Catalog of Strains, 1999, Seventh Edition, vol. 2.
Fan, L., et al., "Antisense Suppression of Phospholipase D(alpha) Retards Abscisic Acid- and Ethylene-Promoted Senescence of Post-harvest Arabidopsis Leaves," The Plant Cell, Dec. 1997, pp. 2183-2196, vol. 9.
Glass, M., et al., "Endo-(beta)-1,4-Glucanases Impact Plant Cell Wall Development by Influencing Cellulose Crystallization," Journal of Integrative Plant Biology, Apr. 2015, pp. 396-410, vol. 57, Issue 4.
Hong, Y., et al., "Phospholipase D(alpha)3 Is Involved in the Hyperormotic Response in Arabidopsis," The Plant Cell, Mar. 2008, pp. 803-816, vol. 20.
Li, M., et al., Overexpression of Patatin-Related Phospholipase AIII(delta) Altered Plant Growth and Increased Seed Oil Content in Camelina, Plant Biotechnology Journal, 2015, pp. 766-778, vol. 13.
Shani, Z., et al., "Growth Enhancement of Transgenic Poplar Plants by Overexpression of Arabidopsis thaliana Endo-1,4-beta-Glucanase (cel1)," Molecular Breeding, 2004, pp. 321-330, vol. 14.
Zhuang, X., et al., "New Advances in Plant Growth-Promoting Rhizobacteria for Bioremediation," Environmental International, 2007, pp. 406-413, vol. 33.
Preliminary Amendment A and Response to Notice to File Missing Parts dated Jan. 9, 2019, for U.S. Appl. No. 16/145,628, 9 pages.
Ahemad, M., et al., "Mechanisms and Applications of Plant Growth Promoting Rhizobacteria: Current Perspective," Journal of King Saud University—Science, 2014, pp. 1-20, vol. 26.
Bae, C., et al., Multiple Classes of Immune Related Ptoteases Associated with the Cell Death Response in Pepper Plants, PLOS ONE, 2013, vol. 8, No. 5, e63533.
Berlemont, R., et al., "Phylogenetic Distribution of Potential Cellulases in Bacteria," Applied and Environmental Microbiology, Mar. 2013, pp. 1545-1554, vol. 79, No. 5.
Chapman, K. D., "Phospholipase Activity During Plant Growth and Development and in Response to Environmental Stress," Trends in Plant Science, Nov. 1998, pp. 419-426, vol. 3, Issue 11.
Choudhary, D. K., et al., "Interactions of *Bacillus* spp. and Plants—With Special Reference to Induced Systemic Resistance (ISR)," Microbiological Research, 2009, pp. 493-513, vol. 164.
Ciabattini, A., et al., "Oral Priming of Mice by Recombinant Spores of Bacillus subtilis," Vaccine, Oct. 2004, pp. 4139-4143, vol. 22, Nos. 31-32.
Corbineau, F., et al., "Improvement of Germination of Terminalia Ivorensis Seeds," Forest Genetic Resources Information No. 21, http://www.fao.org/docrep/006/v3030e/V3030E10.htm, 7 pages.
Dong, Y.-H., et al., "Identification of Quorum-Quenching N-Acyl Homoserine Lactonases from Bacillus Species," Applied and Environmental Microbiology, 2002, pp. 1754-1759, vol. 68, No. 4.
Dowd, P. E., et al., "The Emerging Roles of Phospholipase C in Plant Growth and Development," Lipid Signaling in Plants, 2010, pp. 23-37, vol. 16.
Duc le H., et al., "Bacterial Spores as Vaccine Vehicles," Infection and Immunity, May 2003, pp. 2810-2818, vol. 71, No. 5.
Duc, le H., et al., "Immunization Against Anthrax Using Bacillus subtilis Spores Expressing the Anthrax Protective Antigen," Vaccine, Jan. 2007, pp. 346-355, vol. 25, No. 2.
Frankel, A. E., et al., "Characterization of Diphtheria Fusion Proteins Targeted to the Human Interleukin-3 Receptor," Protein Engineering, 2000, pp. 575-581, vol. 13, No. 8.
Glick, B. R., "Modulation of Plant Ethylene Levels by the Bacterial Enzyme ACC Deaminase," FEMS Microbiology Letters, Oct. 2005, pp. 1-7, vol. 251, Issue 1.
Goldberg, L. J., et al., "A Bacterial Spore Demonstrating Rapid Larvicidal Activity Against Anopheles sergentii, Uranotaenia unguiculata, Culex univitattus, Aedes aegypti and Culex pipiens," Mosquito News, Sep. 1977, pp. 355-358, vol. 37, No. 3.
Guerchicoff, A., et al., "Identification and Characterization of a Previously Undescribed cyt Gene in *Bacillus thuringiensis* subsp. *israelensis*," Applied and Environmental Microbiology, Jul. 1997, pp. 2716-2721, vol. 63, No. 7.
Gujar, P. D., et al., "Effect of Phytase from Aspergillus niger on Plant Growth and Mineral Assimilation in Wheat (*Triticum aestivum* Linn.) and its Potential for Use as a Soil Amendment," Journal of the Science of Food and Agriculture, 2013, pp. 2242-2247, vol. 93, Issue 9.
Hafeez, F. Y., et al., "PGPR: Versatile Tool to Combat Soil Borne Pathogens and Improve Plant Health," Aspects of Applied Biology, 2011, pp. 241-245, vol. 106.
Han, W. et al., "The Application of Exogenous Cellulase to Improve Soil Fertility and Plant Growth Due to Acceleration of Straw Decomposition," Bioresource Technology, May 2010, pp. 3724-3731, vol. 101, Issue 10.
Hartati, S., et al., "Overexpression of Poplar Cellulase Accelerates Growth and Disturbs the Closing Movements of Leaves in Sengon," Plant Physiology, 2008, pp. 552-561, vol. 147, Issue 2.
Hoelscher, B., et al., "Removal of Toxic Contaminants from Polluted Soil and Water via Enzyme-Linked Bacillus Spores," Poster presented at Missouri Life Sciences Week Research Poster Session, Apr. 14, 2010.
Hong, Y. et al., "Phospholipases in Plant Response to Nitrogen and Phosphorus Availability," Springer, Phospholipases in Plant Signaling and Communication in Plants, 2013, pp. 159-180, vol. 20.
Howard, G., et al., "Effects of Cellulolytic Ruminol Bacteria and of Cell Extracts on Germination of *Euonymus americanus* L. Seeds," Applied and Environmental Microbiology, Jan. 1988, pp. 218-224, vol. 54, No. 1.
Idriss, E. E., et al., "Extracellular Phytase Activity of Bacillus amyloliquefaciens FZB45 Contributes to its Plant-Growth-Promoting Effect," Microbiology, 2002, pp. 2097-2109, vol. 148.
International Search Report and Written Opinion issued for PCT/US2014/030824, dated Aug. 1, 2014, 22 pages.
International Search Report and Written Opinion issued for PCT/US2015/050807, dated Dec. 10, 2015, 12 pages.
Isticato, R., et al., "Surface Display of Recombinant Proteins on Bacillus subtilis Spores," Journal of Bacteriology, Nov. 2001, pp. 6294-6301, vol. 183, No. 21.
Jackson, W. T., "Effect of Pectinase and Cellulase Preparations on the Growth and Development of Root Hairs," Physiologia Plantarum, 2006 (first published in 1959), pp. 502-510, vol. 12.
Johnson M. J., et al., "ExsY and CotY are Required for the Correct Assembly of the Exosporium and Spore Coat of Bacillus cereus," Journal of Bacteriology, 2006, pp. 7905-7913, vol. 188, No. 22.
Kim, J. H., et al., "Bacterial Surface Display of GFP(uv) on Bacillus subtilis Spores," Journal of Microbiology and Biotechnology, Apr. 2007, pp. 677-680, vol. 17, No. 4.
Kim, J. H., et al., "Spore-Displayed Streptavidin: A Live Diagnostic Tool in Biotechnology," Biochemical and Biophysical Research Communications, May 2005, pp. 210-214, vol. 331, No. 1.
Leski, T. A., et al., "Identification and Classification of bcl Genes and Proteins of Bacillus cereus Group Organisms and Their Application in Bacillus anthracis Detection and Fingerprinting," Applied and Environmental Microbiology, Nov. 2009, pp. 7163-7172, vol. 75, No. 22.
Li, W., et al., "Cloning of the Thermostable Cellulase Gene From Newly Isolated Bacillus subtilis and its Expression in *Escherichia coli*," Molecular Biotechnology, 2008, pp. 195-201, vol. 40, No. 2.
Luiz, W. B., et al., "Boosting Systemic and Secreted Antibody Responses in Mice Orally Immunized with Recombinant Bacillus subtilis Strains Following Parenteral Priming with a DNA Vaccine Encoding the Enterotoxigenic *Escherichia coli* (ETEC) CFA/I Fimbriae B Subunit," Vaccine, 2008, pp. 3998-4005, vol. 26, No. 32.
Mauriello, E. M., et al., "Display of Heterologous Antigens on the Bacillus subtilis Spore Coat Using CotC as a Fusion Partner," Vaccine, Mar. 2004, pp. 1177-1187, vol. 22, Nos. 9-10.
Medie, F. M., "Genome Analyses Highlight the Different Biological Roles of Cellulases," Nature Reviews Microbiology, Mar. 2012, pp. 227-234, vol. 10.

(56) References Cited

OTHER PUBLICATIONS

Paccez, J. D., et al., "Evaluation of Different Promoter Sequences and Antigen Sorting Signals on the Immunogenicity of Bacillus subtilis Vaccine Vehicles," Vaccine, 2007, pp. 4671-4680, vol. 25, No. 24.
Paccez, J. D., et al., "Stable Episomal Expression System Under Control of a Stress Inducible Promoter Enhances the Immunogenicity of Bacillus subtilis as a Vector for Antigen Delivery," Vaccine, 2006, pp. 2935-2943, vol. 24, No. 15.
Pakula, A. A., et al., "Genetic Analysis of Protein Stability and Function," Annual Review of Genetics, 1989, pp. 289-310, vol. 23 (Abstract Only).
Park, T. J., et al., "Spore Display Using Bacillus thuringiensis Exosporium Protein InhA," Journal of Microbiology and Biotechnology, May 2009, pp. 495-501, vol. 19, No. 5.
Park, T. J., "Surface-Display of Recombinant Proteins on Bacterial Exosporium and its Biotechnological Applications," Doctoral Thesis presented to the Department of Chemical and Biomolecular Engineering, Korea Advanced Institute of Science and Technology, 2004, 104 pages.
Pereira, C. E., et al., "Compatibility Among Fungicide Treatments on Soybean Seeds Through Film Coating and Inoculation with Bradyrhizobium Strains," Acta Scientiarum. Agronomy, 2010, pp. 585-589, vol. 32, No. 4.
Phitsuwan, P., et al., "Present and Potential Applications of Cellulases in Agriculture, Biotechnology, and Bioenergy," Folia Microbiologica, 2013, pp. 163-176, vol. 58, No. 2.
Pilar-Izquierdo, M. C., et al., "Barley Seed Coating with Free and Immobilized Alkaline Phosphatase to Improve P Uptake and Plant Growth," Journal of Agricultural Science, 2012, pp. 691-701, vol. 150, Issue 6.
Ping, R., et al., Abstract, Journal of Northwest Forestry College, 2005, pp. 78-79, vol. 20, No. 1.
Sales, J., et al. "Coffee (*Coffee arabica* L.) Seeds Germination After Treatment with Different Concentrations and Embebding Times in Cellulase," Ciencia e Agrotecnologia [online], 2003, pp. 557-564, vol. 27, No. 3, ISSN 1413-7054. http://dx.doi.org/10.1590/S1413-70542003000300009, Abstract Only, 1 page.
Sequence Listing filed in WO 2007/078127 A1 published Jul. 12, 2007, downloaded from <http://patentscope.wipo.int/search/en/detail.jsf?docId=WO2007078127&recNum=1&tab=PCTDocuments&maxRec=&office=&prevFilter=&sortOption=&queryString=>, 5 pages.
Shani, Z., et al., "Expression of Endo-1,4-beta-glucanase (cel1) in *Arabidopsis thaliana* is Associated with Plant Growth, Xylem Development and Cell Wall Thickening," Plant Cell Reports, 2006, pp. 1067-1074, vol. 25, Issue 10.
Shen, M., et al., "Effect of Plant Growth-Promoting Rhizobacteria (PGPRs) on Plant Growth, Yield, and Quality of Tomato (*Lycopersicon esculentum* Mill.) under Simulated Seawater Irrigation," The Journal of General and Applied Microbiology, 2012, pp. 253-262, vol. 58, No. 4.
Singh, B., et al., "Microbial Phytases in Phosphorous Acquisition and Plant Growth Promotion," Physiology and Molecular Biology of Plants, 2011, pp. 93-103, vol. 17, Issue 2.
Singh, B., et al., "Plant Growth Promotion by an Extracellular HAP-Phytase of a Thermophilic Mold Sporotrichum thermophile," Applied Biochemistry and Biotechnology, 2010, pp. 1267-1276, vol. 160, Issue 5.

FIG. 1

| | SEQ ID NO. | 20~35 %Identity | 25~35 %Identity |
|---|---|---|---|
| MSNNNYSNGLNPDESLSAS**AFDPNLVGPTLPPIPP**FTLPTG | 1 | 100% | 100% |
| MSEKYIILHGT**ALEPNLIGPTLPPIPP**FTFPNG | 3 | 81.3% | 90.9% |
| MVKVVEGNGGKSKIKSPLNSNF**KILSDLVGPTFPPVPT**GMTGIT | 5 | 50.0% | 72.7% |
| MKQNDKLWLDKG**IIGPENIGPTFPVLPP**IHIPTG | 7 | 43.8% | 54.5% |
| MDEFLSSA**ALNPGSVGPTLPPMQP**FQFRTG | 9 | 62.5% | 72.7% |
| MFDKNEIQKINGILQAN**ALNPNLIGPTLPPIPP**FTLPTG | 11 | 81.3% | 90.9% |
| MFDKNEMKKTNEVLQAN**ALDPNIIGPTLPPIPP**FTLPTG | 13 | 81.3% | 81.8% |
| MSRKDKFNRSRMSRKDRFNSPKIKSEI**SISPDLVGPTFPPIPS**FTLPTG | 15 | 62.5% | 81.8% |
| MNEEYSILHGP**ALEPNLIGPTLPSIPP**FTFPTG | 17 | 75.0% | 81.8% |
| MKNRDNNRKQNSLSSNF**RIPPELIGPTFPPVPT**GFTGIG | 19 | 50.0% | 63.6% |
| MSDKHQMKKISEVLQAH**ALDPNLIGPPLPPITP**FTFPTG | 21 | 75.0% | 72.7% |
| MDEFLSFA**ALNPGSIGPTLPPVPP**FQFPTG | 23 | 62.5% | 72.7% |
| MDEFLSST**ALNPCSIGPTLPPMQP**FQFPTG | 25 | 56.2% | 63.6% |
| MKERDRQNSLNSNF**RISPNLIGPTFPPVPT**GFTGIG | 27 | 56.2% | 63.6% |
| VFDKNEIQKINGILQAN**ALNPNLIGPTLPPIPP**FTLPTG | 29 | 81.3% | 90.9% |
| MDEFLYFA**ALNPGSIGPTLPPVQP**FQFPTG | 31 | 56.2% | 63.6% |
| **MDSKNIGPTFPPLPS**INFPTG | 33 | 43.8% | 54.5% |
| **MIGPENIGPTFPILPP**IYIPTG | 35 | 43.8% | 54.5% |
| MSNNNIPSPFFFN**NFNPELIGPTFPPIPP**LTLPTG | 43 | 68.8% | 81.8% |
| MFSEKKRKDLIPDNFLSAP**ALDPNLIGPTFPPIPS**FTLPTG | 45 | 75.0% | 72.7% |
| MTRKDKFNRSRISRRDRFNSPKIKSEI**LISPDLVGPTFPPIPS**FTLPTG | 47 | 62.5% | 81.8% |
| MSRKDRFNSPKIKSEI**SISPDLVGPTFPPIPS**FTLPTG | 49 | 62.5% | 81.8% |
| MKERDNKGKQHSLNSNF**RIPPELIGPTFPPVPT**GFTGIG | 51 | 50.0% | 63.6% |
| MRERDNKRQQHSLNPNF**RISPELIGPTFPPVPT**GFTGIG | 53 | 50.0% | 63.6% |
| MKNRDNKGKQQSNF**RIPPELIGPTFPPVPT**GFTGIG | 55 | 50.0% | 63.6% |
| MKFSKKSTVDSSIVGKRVVSKVNILRFYDARSCQDKDVDGFVDVGELFTIFRKLNMEGSVQFKAHNSI<br>GKTYYITINEVYVFVTVLLQYSTLIGGSYVFDKNEIQKINGILQAN**ALNPNLIGPTLPPIPP**FTLPTG | 57 | 81.3% | 90.9% |

A B C

SEQUENCE LISTING

```
<160> NUMBER OF SEQ ID NOS: 124

<210> SEQ ID NO 1
<211> LENGTH: 41
<212> TYPE: PRT
<213> ORGANISM: Bacillus anthracis

<400> SEQUENCE: 1

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly
        35                  40


<210> SEQ ID NO 2
<211> LENGTH: 332
<212> TYPE: PRT
<213> ORGANISM: Bacillus anthracis

<400> SEQUENCE: 2

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Phe Thr Thr
        35                  40                  45

Gly Pro Thr Gly Pro Thr Gly Pro Thr Gly Pro Thr Gly Pro Thr Gly
    50                  55                  60

Pro Thr Gly Pro Thr Gly Pro Thr Gly Asp Thr Gly Thr Thr Gly Pro
65                  70                  75                  80

Thr Gly Pro Thr Gly Pro Thr Gly Pro Thr Gly Pro Thr Gly Pro Thr
                85                  90                  95

Gly Pro Thr Gly Pro Thr Gly Pro Thr Gly Phe Thr Pro Thr Gly Pro
            100                 105                 110

Thr Gly Pro Thr Gly Pro Thr Gly Asp Thr Gly Thr Thr Gly Pro Thr
        115                 120                 125

Gly Pro Thr Gly Pro Thr Gly Pro Thr Gly Pro Thr Gly Asp Thr Gly
    130                 135                 140
```

-continued

```
Thr Thr Gly Pro Thr Gly Pro Thr Gly Pro Thr Gly Pro Thr Gly Pro
145                 150                 155                 160

Thr Gly Pro Thr Gly Pro Thr Phe Thr Gly Pro Thr Gly Pro Thr Gly
                165                 170                 175

Pro Thr Gly Ala Thr Gly Leu Thr Gly Pro Thr Gly Pro Thr Gly Pro
            180                 185                 190

Ser Gly Leu Gly Leu Pro Ala Gly Leu Tyr Ala Phe Asn Ser Gly Gly
        195                 200                 205

Ile Ser Leu Asp Leu Gly Ile Asn Asp Pro Val Pro Phe Asn Thr Val
    210                 215                 220

Gly Ser Gln Phe Phe Thr Gly Thr Ala Ile Ser Gln Leu Asp Ala Asp
225                 230                 235                 240

Thr Phe Val Ile Ser Glu Thr Gly Phe Tyr Lys Ile Thr Val Ile Ala
                245                 250                 255

Asn Thr Ala Thr Ala Ser Val Leu Gly Gly Leu Thr Ile Gln Val Asn
            260                 265                 270

Gly Val Pro Val Pro Gly Thr Gly Ser Ser Leu Ile Ser Leu Gly Ala
        275                 280                 285

Pro Phe Thr Ile Val Ile Gln Ala Ile Thr Gln Ile Thr Thr Thr Pro
    290                 295                 300

Ser Leu Val Glu Val Ile Val Thr Gly Leu Gly Leu Ser Leu Ala Leu
305                 310                 315                 320

Gly Thr Ser Ala Ser Ile Ile Ile Glu Lys Val Ala
                325                 330


<210> SEQ ID NO 3
<211> LENGTH: 33
<212> TYPE: PRT
<213> ORGANISM: Bacillus anthracis

<400> SEQUENCE: 3

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro Asn
            20                  25                  30

Gly


<210> SEQ ID NO 4
<211> LENGTH: 209
<212> TYPE: PRT
<213> ORGANISM: Bacillus anthracis

<400> SEQUENCE: 4

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro Asn
            20                  25                  30

Gly Pro Thr Gly Ile Thr Gly Pro Thr Gly Ala Thr Gly Phe Thr Gly
        35                  40                  45

Ile Gly Ile Thr Gly Pro Thr Gly Val Thr Gly Pro Thr Gly Ile Gly
    50                  55                  60

Ile Thr Gly Pro Thr Gly Ala Thr Gly Leu Gly Ile Leu Pro Val Phe
65                  70                  75                  80

Gly Thr Ile Thr Thr Asp Val Gly Ile Gly Phe Ser Val Ile Val Asn
                85                  90                  95

Thr Asn Ile Asn Phe Thr Leu Pro Gly Pro Val Ser Gly Thr Thr Leu
```

-continued

```
            100                 105                 110

Asn Pro Val Asp Asn Ser Ile Ile Ile Asn Thr Thr Gly Val Tyr Ser
        115                 120                 125

Val Ser Phe Ser Ile Val Phe Val Ile Gln Ala Ile Ser Ser Ser Ile
    130                 135                 140

Leu Asn Leu Thr Ile Asn Asp Ser Ile Gln Phe Ala Ile Glu Ser Arg
145                 150                 155                 160

Ile Gly Gly Gly Pro Gly Val Arg Ala Thr Ser Ala Arg Thr Asp Leu
                165                 170                 175

Leu Ser Leu Asn Gln Gly Asp Val Leu Arg Val Arg Ile Arg Glu Ala
            180                 185                 190

Thr Gly Asp Ile Ile Tyr Ser Asn Ala Ser Leu Val Val Ser Lys Val
        195                 200                 205

Asp


<210> SEQ ID NO 5
<211> LENGTH: 44
<212> TYPE: PRT
<213> ORGANISM: Bacillus anthracis

<400> SEQUENCE: 5

Met Val Lys Val Val Glu Gly Asn Gly Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr
        35                  40


<210> SEQ ID NO 6
<211> LENGTH: 647
<212> TYPE: PRT
<213> ORGANISM: Bacillus anthracis

<400> SEQUENCE: 6

Val Val Lys Val Val Glu Gly Asn Gly Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr Gly Ser Thr Gly
        35                  40                  45

Ala Thr Gly Asn Thr Gly Pro Thr Gly Glu Thr Gly Ala Thr Gly Ser
    50                  55                  60

Ala Gly Ile Thr Gly Ser Thr Gly Pro Thr Gly Asn Thr Gly Gly Thr
65                  70                  75                  80

Gly Ser Thr Gly Pro Thr Gly Asn Thr Gly Ala Thr Gly Ser Thr Gly
                85                  90                  95

Val Thr Gly Ser Thr Gly Val Thr Gly Ser Thr Gly Val Thr Gly Ser
            100                 105                 110

Thr Gly Val Thr Gly Ser Thr Gly Pro Thr Gly Glu Thr Gly Gly Thr
        115                 120                 125

Gly Ser Thr Gly Val Thr Gly Ser Thr Gly Ala Thr Gly Ser Thr Gly
    130                 135                 140

Val Thr Gly Asn Thr Gly Pro Thr Gly Ser Thr Gly Ala Thr Gly Asn
145                 150                 155                 160

Thr Gly Ser Ile Gly Glu Thr Gly Gly Thr Gly Ser Met Gly Pro Thr
                165                 170                 175
```

-continued

```
Gly Glu Thr Gly Val Thr Gly Ser Thr Gly Gly Thr Gly Ser Thr Gly
            180                 185                 190

Val Thr Gly Asn Thr Gly Pro Thr Gly Ser Thr Gly Val Thr Gly Ser
        195                 200                 205

Thr Gly Val Thr Gly Ser Thr Gly Pro Thr Gly Ser Thr Gly Val Thr
    210                 215                 220

Gly Ser Thr Gly Pro Thr Gly Ser Thr Gly Val Thr Gly Ser Thr Gly
225                 230                 235                 240

Val Thr Gly Asn Met Gly Pro Thr Gly Ser Thr Gly Val Thr Gly Asn
                245                 250                 255

Thr Gly Ser Thr Gly Thr Thr Gly Ala Thr Gly Glu Thr Gly Pro Met
            260                 265                 270

Gly Ser Thr Gly Ala Thr Gly Thr Thr Gly Pro Thr Gly Glu Thr Gly
        275                 280                 285

Glu Thr Gly Glu Thr Gly Gly Thr Gly Ser Thr Gly Pro Thr Gly Asn
    290                 295                 300

Thr Gly Ala Thr Gly Ser Thr Gly Val Thr Gly Ser Thr Gly Val Thr
305                 310                 315                 320

Gly Ser Thr Gly Val Thr Gly Glu Thr Gly Pro Thr Gly Ser Thr Gly
                325                 330                 335

Ala Thr Gly Asn Thr Gly Pro Thr Gly Glu Thr Gly Gly Thr Gly Ser
            340                 345                 350

Thr Gly Ala Thr Gly Ser Thr Gly Val Thr Gly Asn Thr Gly Pro Thr
        355                 360                 365

Gly Ser Thr Gly Val Thr Gly Asn Thr Gly Ala Thr Gly Glu Thr Gly
    370                 375                 380

Pro Thr Gly Asn Thr Gly Ala Thr Gly Asn Thr Gly Pro Thr Gly Glu
385                 390                 395                 400

Thr Gly Val Thr Gly Ser Thr Gly Pro Thr Gly Glu Thr Gly Val Thr
                405                 410                 415

Gly Ser Thr Gly Pro Thr Gly Asn Thr Gly Ala Thr Gly Glu Thr Gly
            420                 425                 430

Ala Thr Gly Ser Thr Gly Val Thr Gly Asn Thr Gly Ser Thr Gly Glu
        435                 440                 445

Thr Gly Pro Thr Gly Ser Thr Gly Pro Thr Gly Ser Thr Gly Ala Thr
    450                 455                 460

Gly Val Thr Gly Asn Thr Gly Pro Thr Gly Ser Thr Gly Ala Thr Gly
465                 470                 475                 480

Ala Thr Gly Ser Thr Gly Pro Thr Gly Ser Thr Gly Thr Thr Gly Asn
                485                 490                 495

Thr Gly Val Thr Gly Asp Thr Gly Pro Thr Gly Ala Thr Gly Val Ser
            500                 505                 510

Thr Thr Ala Thr Tyr Ala Phe Ala Asn Asn Thr Ser Gly Ser Val Ile
        515                 520                 525

Ser Val Leu Leu Gly Gly Thr Asn Ile Pro Leu Pro Asn Asn Gln Asn
    530                 535                 540

Ile Gly Pro Gly Ile Thr Val Ser Gly Gly Asn Thr Val Phe Thr Val
545                 550                 555                 560

Ala Asn Ala Gly Asn Tyr Tyr Ile Ala Tyr Thr Ile Asn Leu Thr Ala
                565                 570                 575

Gly Leu Leu Val Ser Ser Arg Ile Thr Val Asn Gly Ser Pro Leu Ala
            580                 585                 590
```

-continued

```
Gly Thr Ile Asn Ser Pro Thr Val Ala Thr Gly Ser Phe Ser Ala Thr
        595                 600                 605

Ile Ile Ala Ser Leu Pro Ala Gly Ala Ala Val Ser Leu Gln Leu Phe
    610                 615                 620

Gly Val Val Ala Leu Ala Thr Leu Ser Thr Ala Thr Pro Gly Ala Thr
625                 630                 635                 640

Leu Thr Ile Ile Arg Leu Ser
                645


<210> SEQ ID NO 7
<211> LENGTH: 34
<212> TYPE: PRT
<213> ORGANISM: Bacillus anthracis

<400> SEQUENCE: 7

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly


<210> SEQ ID NO 8
<211> LENGTH: 366
<212> TYPE: PRT
<213> ORGANISM: Bacillus anthracis

<400> SEQUENCE: 8

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly Ile Thr Gly Ala Thr Gly Ala Thr Gly Ile Thr Gly Ala Thr
        35                  40                  45

Gly Pro Thr Gly Thr Thr Gly Ala Thr Gly Ala Thr Gly Ile Thr Gly
    50                  55                  60

Val Thr Gly Ala Thr Gly Ile Thr Gly Val Thr Gly Ala Thr Gly Ile
65                  70                  75                  80

Thr Gly Val Thr Gly Ala Thr Gly Ile Thr Gly Val Thr Gly Pro Thr
                85                  90                  95

Gly Ile Thr Gly Ala Thr Gly Pro Thr Gly Ile Thr Gly Ala Thr Gly
            100                 105                 110

Pro Ala Gly Ile Thr Gly Val Thr Gly Pro Thr Gly Ile Thr Gly Ala
        115                 120                 125

Thr Gly Pro Thr Gly Thr Thr Gly Val Thr Gly Pro Thr Gly Asp Thr
    130                 135                 140

Gly Leu Ala Gly Ala Thr Gly Pro Thr Gly Ala Thr Gly Leu Ala Gly
145                 150                 155                 160

Ala Thr Gly Pro Thr Gly Asp Thr Gly Ala Thr Gly Pro Thr Gly Ala
                165                 170                 175

Thr Gly Leu Ala Gly Ala Thr Gly Pro Thr Gly Ala Thr Gly Leu Thr
            180                 185                 190

Gly Ala Thr Gly Ala Thr Gly Ala Thr Gly Gly Gly Ala Ile Ile Pro
        195                 200                 205

Phe Ala Ser Gly Thr Thr Pro Ala Leu Leu Val Asn Ala Val Leu Ala
    210                 215                 220

Asn Thr Gly Thr Leu Leu Gly Phe Gly Phe Ser Gln Pro Gly Ile Ala
```

```
225                 230                 235                 240

Pro Gly Val Gly Gly Thr Leu Thr Ile Leu Pro Gly Val Val Gly Asp
                245                 250                 255

Tyr Ala Phe Val Ala Pro Arg Asp Gly Ile Ile Thr Ser Leu Ala Gly
            260                 265                 270

Phe Phe Ser Ala Thr Ala Ala Leu Ala Pro Leu Thr Pro Val Gln Ile
        275                 280                 285

Gln Met Gln Ile Phe Ile Ala Pro Ala Ala Ser Asn Thr Phe Thr Pro
    290                 295                 300

Val Ala Pro Pro Leu Leu Leu Thr Pro Ala Leu Pro Ala Ile Ala Ile
305                 310                 315                 320

Gly Thr Thr Ala Thr Gly Ile Gln Ala Tyr Asn Val Pro Val Val Ala
                325                 330                 335

Gly Asp Lys Ile Leu Val Tyr Val Ser Leu Thr Gly Ala Ser Pro Ile
            340                 345                 350

Ala Ala Val Ala Gly Phe Val Ser Ala Gly Leu Asn Ile Val
        355                 360                 365


<210> SEQ ID NO 9
<211> LENGTH: 30
<212> TYPE: PRT
<213> ORGANISM: Bacillus anthracis

<400> SEQUENCE: 9

Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Arg Thr Gly
            20                  25                  30


<210> SEQ ID NO 10
<211> LENGTH: 77
<212> TYPE: PRT
<213> ORGANISM: Bacillus anthracis

<400> SEQUENCE: 10

Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Arg Thr Gly Pro Thr
            20                  25                  30

Gly Ser Thr Gly Ala Lys Gly Ala Ile Gly Asn Thr Glu Pro Tyr Trp
        35                  40                  45

His Thr Gly Pro Pro Gly Ile Val Leu Leu Thr Tyr Asp Phe Lys Ser
    50                  55                  60

Leu Ile Ile Ser Phe Ala Phe Arg Ile Leu Pro Ile Ser
65                  70                  75


<210> SEQ ID NO 11
<211> LENGTH: 39
<212> TYPE: PRT
<213> ORGANISM: Bacillus weihenstephensis

<400> SEQUENCE: 11

Met Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly
        35
```

<210> SEQ ID NO 12
<211> LENGTH: 299
<212> TYPE: PRT
<213> ORGANISM: Bacillus weihenstephensis

<400> SEQUENCE: 12

```
Met Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly Pro Thr Gly Val Thr Gly Pro Thr Gly
        35                  40                  45

Val Thr Gly Pro Thr Gly Val Thr Gly Pro Thr Gly Val Thr Gly Pro
    50                  55                  60

Thr Gly Val Thr Gly Pro Thr Gly Val Thr Gly Pro Thr Gly Val Thr
65                  70                  75                  80

Gly Pro Thr Gly Val Thr Gly Pro Thr Gly Val Thr Gly Pro Thr Gly
                85                  90                  95

Val Thr Gly Pro Thr Gly Val Thr Gly Pro Thr Gly Val Thr Gly Pro
            100                 105                 110

Thr Gly Val Thr Gly Pro Thr Gly Val Thr Gly Pro Thr Gly Glu Thr
        115                 120                 125

Gly Pro Thr Gly Gly Thr Glu Gly Cys Leu Cys Asp Cys Cys Val Leu
    130                 135                 140

Pro Met Gln Ser Val Leu Gln Gln Leu Ile Gly Glu Thr Val Ile Leu
145                 150                 155                 160

Gly Thr Ile Ala Asp Thr Pro Asn Thr Pro Pro Leu Phe Phe Leu Phe
                165                 170                 175

Thr Ile Thr Ser Val Asn Asp Phe Leu Val Thr Val Thr Asp Gly Thr
            180                 185                 190

Thr Thr Phe Val Val Asn Ile Ser Asp Val Thr Gly Val Gly Phe Leu
        195                 200                 205

Pro Pro Gly Pro Pro Ile Thr Leu Leu Pro Pro Thr Asp Val Gly Cys
    210                 215                 220

Glu Cys Glu Cys Arg Glu Arg Pro Ile Arg Gln Leu Leu Asp Ala Phe
225                 230                 235                 240

Ile Gly Ser Thr Val Ser Leu Leu Ala Ser Asn Gly Ser Ile Ala Ala
                245                 250                 255

Asp Phe Ser Val Glu Gln Thr Gly Leu Gly Ile Val Leu Gly Thr Leu
            260                 265                 270

Pro Ile Asn Pro Thr Thr Thr Val Arg Phe Ala Ile Ser Thr Cys Lys
        275                 280                 285

Ile Thr Ala Val Asn Ile Thr Pro Ile Thr Met
    290                 295
```

<210> SEQ ID NO 13
<211> LENGTH: 39
<212> TYPE: PRT
<213> ORGANISM: Bacillus weihenstephensis

<400> SEQUENCE: 13

```
Met Phe Asp Lys Asn Glu Met Lys Lys Thr Asn Glu Val Leu Gln Ala
1               5                   10                  15

Asn Ala Leu Asp Pro Asn Ile Ile Gly Pro Thr Leu Pro Pro Ile Pro
            20                  25                  30
```

```
Pro Phe Thr Leu Pro Thr Gly
        35


<210> SEQ ID NO 14
<211> LENGTH: 289
<212> TYPE: PRT
<213> ORGANISM: Bacillus weihenstephensis

<400> SEQUENCE: 14

Met Phe Asp Lys Asn Glu Met Lys Lys Thr Asn Glu Val Leu Gln Ala
1               5                   10                  15

Asn Ala Leu Asp Pro Asn Ile Ile Gly Pro Thr Leu Pro Pro Ile Pro
            20                  25                  30

Pro Phe Thr Leu Pro Thr Gly Pro Thr Gly Pro Thr Gly Pro Thr Gly
        35                  40                  45

Pro Thr Gly Pro Thr Gly Pro Thr Gly Pro Thr Gly Pro Thr Gly Pro
    50                  55                  60

Thr Gly Pro Thr Gly Pro Thr Gly Pro Thr Gly Pro Thr Gly Leu Thr
65                  70                  75                  80

Gly Pro Thr Gly Pro Thr Gly Leu Thr Gly Pro Thr Gly Leu Thr Gly
                85                  90                  95

Pro Thr Gly Pro Thr Gly Leu Thr Gly Gln Thr Gly Ser Thr Gly Pro
            100                 105                 110

Thr Gly Ala Thr Glu Gly Cys Leu Cys Asp Cys Cys Val Phe Pro Met
        115                 120                 125

Gln Glu Val Leu Arg Gln Leu Val Gly Gln Thr Val Ile Leu Ala Thr
    130                 135                 140

Ile Ala Asp Ala Pro Asn Val Ala Pro Arg Phe Phe Leu Phe Asn Ile
145                 150                 155                 160

Thr Ser Val Asn Asp Phe Leu Val Thr Val Thr Asp Pro Val Ser Asn
                165                 170                 175

Thr Thr Phe Val Val Asn Ile Ser Asp Val Ile Gly Val Gly Phe Ser
            180                 185                 190

Leu Thr Val Pro Pro Leu Thr Leu Leu Pro Pro Ala Asp Leu Gly Cys
        195                 200                 205

Glu Cys Asp Cys Arg Glu Arg Pro Ile Arg Glu Leu Leu Asp Thr Leu
    210                 215                 220

Ile Gly Ser Thr Val Asn Leu Leu Val Ser Asn Gly Ser Ile Ala Thr
225                 230                 235                 240

Gly Phe Asn Val Glu Gln Thr Ala Leu Gly Ile Val Ile Gly Thr Leu
                245                 250                 255

Pro Ile Pro Ile Asn Pro Pro Pro Pro Thr Leu Phe Arg Phe Ala Ile
            260                 265                 270

Ser Thr Cys Lys Ile Thr Ala Val Asp Ile Thr Pro Thr Pro Thr Ala
        275                 280                 285

Thr


<210> SEQ ID NO 15
<211> LENGTH: 49
<212> TYPE: PRT
<213> ORGANISM: Bacillus cereus

<400> SEQUENCE: 15

Met Ser Arg Lys Asp Lys Phe Asn Arg Ser Arg Met Ser Arg Lys Asp
1               5                   10                  15
```

```
Arg Phe Asn Ser Pro Lys Ile Lys Ser Glu Ile Ser Ile Ser Pro Asp
            20                  25                  30

Leu Val Gly Pro Thr Phe Pro Pro Ile Pro Ser Phe Thr Leu Pro Thr
        35                  40                  45

Gly


<210> SEQ ID NO 16
<211> LENGTH: 189
<212> TYPE: PRT
<213> ORGANISM: Bacillus cereus

<400> SEQUENCE: 16

Met Ser Arg Lys Asp Lys Phe Asn Arg Ser Arg Met Ser Arg Lys Asp
1               5                   10                  15

Arg Phe Asn Ser Pro Lys Ile Lys Ser Glu Ile Ser Ile Ser Pro Asp
            20                  25                  30

Leu Val Gly Pro Thr Phe Pro Pro Ile Pro Ser Phe Thr Leu Pro Thr
        35                  40                  45

Gly Ile Thr Gly Pro Thr Phe Asn Ile Asn Phe Arg Ala Glu Lys Asn
    50                  55                  60

Val Ala Gln Ser Phe Thr Pro Pro Ala Asp Ile Gln Val Ser Tyr Gly
65                  70                  75                  80

Asn Ile Ile Phe Asn Asn Gly Gly Gly Tyr Ser Ser Val Thr Asn Thr
                85                  90                  95

Phe Thr Ala Pro Ile Asn Gly Ile Tyr Leu Phe Ser Ala Ser Ile Gly
            100                 105                 110

Phe Asn Pro Thr Leu Gly Thr Thr Ser Thr Leu Arg Ile Thr Ile Arg
        115                 120                 125

Lys Asn Leu Val Ser Val Ala Ser Gln Thr Gly Thr Ile Thr Thr Gly
    130                 135                 140

Gly Thr Pro Gln Leu Glu Ile Thr Thr Ile Ile Asp Leu Leu Ala Ser
145                 150                 155                 160

Gln Thr Ile Asp Ile Gln Phe Ser Ala Ala Glu Ser Gly Thr Leu Thr
                165                 170                 175

Val Gly Ser Ser Asn Phe Phe Ser Gly Ala Leu Leu Pro
            180                 185


<210> SEQ ID NO 17
<211> LENGTH: 33
<212> TYPE: PRT
<213> ORGANISM: Bacillus cereus

<400> SEQUENCE: 17

Met Asn Glu Glu Tyr Ser Ile Leu His Gly Pro Ala Leu Glu Pro Asn
1               5                   10                  15

Leu Ile Gly Pro Thr Leu Pro Ser Ile Pro Pro Phe Thr Phe Pro Thr
            20                  25                  30

Gly


<210> SEQ ID NO 18
<211> LENGTH: 84
<212> TYPE: PRT
<213> ORGANISM: Bacillus cereus

<400> SEQUENCE: 18

Met Asn Glu Glu Tyr Ser Ile Leu His Gly Pro Ala Leu Glu Pro Asn
1               5                   10                  15
```

```
Leu Ile Gly Pro Thr Leu Pro Ser Ile Pro Pro Phe Thr Phe Pro Thr
            20                  25                  30

Gly Pro Thr Gly Ile Thr Gly Pro Thr Gly Ala Thr Gly Phe Thr Gly
        35                  40                  45

Ile Gly Ile Thr Gly Pro Thr Gly Val Thr Gly Pro Thr Gly Ile Gly
    50                  55                  60

Ile Thr Gly Pro Thr Gly Ala Thr Gly Pro Thr Gly Ile Gly Ile Thr
65                  70                  75                  80

Gly Pro Thr Gly


<210> SEQ ID NO 19
<211> LENGTH: 39
<212> TYPE: PRT
<213> ORGANISM: Bacillus cereus

<400> SEQUENCE: 19

Met Lys Asn Arg Asp Asn Asn Arg Lys Gln Asn Ser Leu Ser Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly
        35


<210> SEQ ID NO 20
<211> LENGTH: 1056
<212> TYPE: PRT
<213> ORGANISM: Bacillus cereus

<400> SEQUENCE: 20

Met Lys Asn Arg Asp Asn Asn Arg Lys Gln Asn Ser Leu Ser Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly Ile Thr Gly Pro Thr Gly Pro Gln Gly
        35                  40                  45

Pro Thr Gly Pro Gln Gly Pro Arg Gly Leu Gln Gly Pro Met Gly Glu
    50                  55                  60

Met Gly Pro Thr Gly Pro Gln Gly Val Gln Gly Ile Gln Gly Ser Val
65                  70                  75                  80

Gly Pro Ile Gly Ala Thr Gly Pro Glu Gly Gln Gln Gly Pro Gln Gly
                85                  90                  95

Leu Arg Gly Pro Gln Gly Glu Thr Gly Ala Thr Gly Pro Gly Gly Val
            100                 105                 110

Gln Gly Leu Gln Gly Pro Ile Gly Pro Thr Gly Ala Thr Gly Ala Gln
        115                 120                 125

Gly Ile Gln Gly Ile Gln Gly Leu Gln Gly Pro Ile Gly Ala Thr Gly
    130                 135                 140

Pro Glu Gly Ser Gln Gly Ile Gln Gly Val Gln Gly Leu Pro Gly Ala
145                 150                 155                 160

Thr Gly Pro Gln Gly Ile Gln Gly Ala Gln Gly Ile Gln Gly Thr Pro
                165                 170                 175

Gly Pro Ser Gly Asn Thr Gly Ala Thr Gly Ala Thr Gly Ala Thr Gly
            180                 185                 190

Gln Gly Ile Thr Gly Pro Thr Gly Ile Thr Gly Pro Thr Gly Ile Thr
        195                 200                 205

Gly Pro Ser Gly Gly Pro Pro Gly Pro Thr Gly Pro Thr Gly Ala Thr
```

```
    210                 215                 220

Gly Pro Gly Gly Gly Pro Ser Gly Ser Thr Gly Ala Thr Gly Ala Thr
225                 230                 235                 240

Gly Asn Thr Gly Ala Thr Gly Ser Thr Gly Val Thr Gly Ala Thr Gly
                245                 250                 255

Ser Thr Gly Pro Thr Gly Ser Thr Gly Ala Gln Gly Leu Gln Gly Ile
            260                 265                 270

Gln Gly Ile Gln Gly Pro Ile Gly Pro Thr Gly Pro Glu Gly Ser Gln
        275                 280                 285

Gly Ile Gln Gly Ile Pro Gly Pro Thr Gly Val Thr Gly Glu Gln Gly
    290                 295                 300

Ile Gln Gly Val Gln Gly Ile Gln Gly Ala Thr Gly Ala Thr Gly Asp
305                 310                 315                 320

Gln Gly Pro Gln Gly Ile Gln Gly Val Ile Gly Pro Gln Gly Val Thr
                325                 330                 335

Gly Ala Thr Gly Asp Gln Gly Pro Gln Gly Ile Gln Gly Val Pro Gly
            340                 345                 350

Pro Ser Gly Glu Thr Gly Pro Gln Gly Val Gln Gly Ile Gln Gly Pro
        355                 360                 365

Met Gly Asp Ile Gly Pro Thr Gly Pro Glu Gly Pro Glu Gly Leu Gln
    370                 375                 380

Gly Pro Gln Gly Ile Gln Gly Val Pro Gly Pro Val Gly Ala Thr Gly
385                 390                 395                 400

Pro Glu Gly Pro Gln Gly Ile Gln Gly Ile Gln Gly Pro Val Gly Ala
                405                 410                 415

Thr Gly Pro Gln Gly Pro Gln Gly Ile Gln Gly Ile Gln Gly Val Gln
            420                 425                 430

Gly Ile Thr Gly Ala Thr Gly Val Gln Gly Ala Thr Gly Ile Gln Gly
        435                 440                 445

Ile Gln Gly Glu Ile Gly Ala Thr Gly Pro Glu Gly Pro Gln Gly Val
    450                 455                 460

Gln Gly Ala Gln Gly Ala Ile Gly Pro Thr Gly Pro Met Gly Pro Gln
465                 470                 475                 480

Gly Val Gln Gly Val Gln Gly Ile Gln Gly Ala Thr Gly Ala Gln Gly
                485                 490                 495

Val Gln Gly Pro Gln Gly Ile Gln Gly Ile Gln Gly Pro Thr Gly Ala
            500                 505                 510

Thr Gly Asp Met Gly Ala Thr Gly Ala Thr Gly Glu Gly Thr Thr Gly
        515                 520                 525

Pro Thr Gly Val Thr Gly Pro Thr Gly Val Thr Gly Pro Ser Gly Gly
    530                 535                 540

Pro Ala Gly Pro Thr Gly Pro Thr Gly Pro Ser Gly Pro Ala Gly Val
545                 550                 555                 560

Thr Gly Pro Ser Gly Gly Pro Pro Gly Pro Thr Gly Ala Thr Gly Ala
                565                 570                 575

Thr Gly Val Thr Gly Asp Thr Gly Ala Thr Gly Ser Thr Gly Val Thr
            580                 585                 590

Gly Ala Thr Gly Glu Thr Gly Ala Thr Gly Val Thr Gly Leu Gln Gly
        595                 600                 605

Pro Gln Gly Ile Gln Gly Val Gln Gly Glu Ile Gly Pro Thr Gly Pro
    610                 615                 620

Gln Gly Val Gln Gly Pro Gln Gly Ile Gln Gly Val Thr Gly Ala Thr
625                 630                 635                 640
```

-continued

```
Gly Asp Gln Gly Pro Gln Gly Ile Gln Gly Pro Gln Gly Asp Ile Gly
                645                 650                 655

Pro Thr Gly Pro Gln Gly Ile Gln Gly Pro Gln Gly Ser Gln Gly Ile
            660                 665                 670

Gln Gly Ala Thr Gly Gly Thr Gly Ala Gln Gly Pro Gln Gly Ile Gln
        675                 680                 685

Gly Pro Gln Gly Asp Ile Gly Leu Thr Gly Ser Gln Gly Pro Thr Gly
    690                 695                 700

Ile Gln Gly Ile Gln Gly Glu Ile Gly Pro Thr Gly Pro Glu Gly Pro
705                 710                 715                 720

Glu Gly Leu Gln Gly Pro Gln Gly Ile Gln Gly Ile Gln Gly Pro Val
                725                 730                 735

Gly Ala Thr Gly Pro Glu Gly Pro Gln Gly Ile Gln Gly Ile Gln Gly
            740                 745                 750

Val Gln Gly Ala Thr Gly Pro Gln Gly Pro Gln Gly Ile Gln Gly Ile
        755                 760                 765

Gln Gly Val Gln Gly Ile Thr Gly Ala Thr Gly Ala Gln Gly Ala Thr
    770                 775                 780

Gly Ile Gln Gly Ile Gln Gly Glu Ile Gly Ala Thr Gly Pro Glu Gly
785                 790                 795                 800

Pro Gln Gly Val Gln Gly Ile Gln Gly Ala Ile Gly Pro Thr Gly Pro
                805                 810                 815

Met Gly Ala Gln Gly Val Gln Gly Ile Gln Gly Ile Gln Gly Ala Thr
            820                 825                 830

Gly Ala Gln Gly Val Gln Gly Pro Gln Gly Ile Gln Gly Val Gln Gly
        835                 840                 845

Pro Thr Gly Ala Thr Gly Glu Thr Gly Ala Thr Gly Ala Thr Gly Glu
    850                 855                 860

Gly Thr Thr Gly Pro Thr Gly Val Thr Gly Pro Thr Gly Val Thr Gly
865                 870                 875                 880

Pro Ser Gly Gly Pro Ala Gly Pro Thr Gly Pro Thr Gly Pro Ser Gly
                885                 890                 895

Pro Ala Gly Val Thr Gly Pro Ser Gly Gly Pro Pro Gly Pro Thr Gly
            900                 905                 910

Ala Thr Gly Ala Thr Gly Val Thr Gly Asp Thr Gly Ala Thr Gly Ser
        915                 920                 925

Thr Gly Val Thr Gly Ala Thr Gly Ala Thr Gly Ala Thr Gly Val Thr
    930                 935                 940

Gly Leu Gln Gly Pro Gln Gly Ile Gln Gly Val Gln Gly Glu Ile Gly
945                 950                 955                 960

Pro Thr Gly Pro Gln Gly Ile Gln Gly Pro Gln Gly Ile Gln Gly Val
                965                 970                 975

Thr Gly Ala Thr Gly Ala Gln Gly Pro Gln Gly Ile Gln Gly Pro Gln
            980                 985                 990

Gly Asp Ile Gly Pro Thr Gly Ser  Gln Gly Ile Gln Gly  Pro Gln Gly
        995                 1000                1005

Pro Gln  Gly Ile Gln Gly Ala  Thr Gly Ala Thr Gly  Ala Gln Gly
    1010                1015                1020

Pro Gln  Gly Ile Gln Gly Pro  Gln Gly Glu Ile Gly  Pro Thr Gly
    1025                1030                1035

Pro Gln  Gly Pro Gln Gly Ile  Gln Gly Pro Gln Gly  Ile Gln Gly
    1040                1045                1050
```

Pro Thr Gly
    1055

<210> SEQ ID NO 21
<211> LENGTH: 39
<212> TYPE: PRT
<213> ORGANISM: Bacillus weihenstephensis

<400> SEQUENCE: 21

Met Ser Asp Lys His Gln Met Lys Lys Ile Ser Glu Val Leu Gln Ala
1               5                   10                  15

His Ala Leu Asp Pro Asn Leu Ile Gly Pro Pro Leu Pro Pro Ile Thr
            20                  25                  30

Pro Phe Thr Phe Pro Thr Gly
        35

<210> SEQ ID NO 22
<211> LENGTH: 365
<212> TYPE: PRT
<213> ORGANISM: Bacillus weihenstephensis

<400> SEQUENCE: 22

Met Ser Asp Lys His Gln Met Lys Lys Ile Ser Glu Val Leu Gln Ala
1               5                   10                  15

His Ala Leu Asp Pro Asn Leu Ile Gly Pro Pro Leu Pro Pro Ile Thr
            20                  25                  30

Pro Phe Thr Phe Pro Thr Gly Ser Thr Gly Pro Thr Gly Ser Thr Gly
        35                  40                  45

Ser Thr Gly Pro Thr Gly Ser Thr Gly Asn Thr Gly Pro Thr Gly Pro
    50                  55                  60

Thr Gly Pro Pro Val Gly Thr Asn Leu Asp Thr Ile Tyr Val Thr Asn
65                  70                  75                  80

Asp Ile Ser Asn Asn Val Ser Ala Ile Asp Gly Asn Thr Asn Thr Val
                85                  90                  95

Leu Thr Thr Ile Pro Val Gly Thr Asn Pro Val Gly Val Gly Val Asn
            100                 105                 110

Ser Ser Thr Asn Leu Ile Tyr Val Val Asn Asn Gly Ser Asp Asn Ile
        115                 120                 125

Ser Val Ile Asn Gly Ser Thr Asn Thr Val Val Ala Thr Ile Pro Val
    130                 135                 140

Gly Thr Gln Pro Phe Gly Val Gly Val Asn Pro Ser Thr Asn Leu Ile
145                 150                 155                 160

Tyr Val Ala Asn Arg Thr Ser Asn Asn Val Ser Val Ile Lys Gly Gly
                165                 170                 175

Thr Asn Thr Val Leu Thr Thr Ile Pro Val Gly Thr Asn Pro Val Gly
            180                 185                 190

Val Gly Val Asn Ser Ser Thr Asn Leu Ile Tyr Val Thr Asn Glu Ile
        195                 200                 205

Pro Asn Ser Val Ser Val Ile Lys Gly Gly Thr Asn Thr Val Val Ala
    210                 215                 220

Thr Ile Pro Val Gly Leu Phe Pro Phe Gly Val Gly Val Asn Ser Leu
225                 230                 235                 240

Thr Asn Leu Ile Tyr Val Val Asn Asn Ser Pro His Asn Val Ser Val
                245                 250                 255

Ile Asp Gly Asn Thr Asn Thr Val Leu Thr Thr Ile Ser Val Gly Thr
            260                 265                 270

-continued

```
Ser Pro Val Gly Val Gly Val Asn Leu Ser Thr Asn Leu Ile Tyr Val
        275                 280                 285

Ala Asn Glu Val Pro Asn Asn Ile Ser Val Ile Asn Gly Asn Thr Asn
    290                 295                 300

Thr Val Leu Thr Thr Ile Pro Val Gly Thr Thr Pro Phe Glu Val Gly
305                 310                 315                 320

Val Asn Ser Ser Thr Asn Leu Ile Tyr Val Ser Asn Leu Asn Ser Asn
                325                 330                 335

Asn Val Ser Val Ile Asn Gly Ser Ala Asn Thr Val Ile Ala Thr Val
            340                 345                 350

Pro Val Gly Ser Val Pro Arg Gly Ile Gly Val Lys Pro
        355                 360                 365


<210> SEQ ID NO 23
<211> LENGTH: 30
<212> TYPE: PRT
<213> ORGANISM: Bacillus weihenstephensis

<400> SEQUENCE: 23

Met Asp Glu Phe Leu Ser Phe Ala Ala Leu Asn Pro Gly Ser Ile Gly
1               5                   10                  15

Pro Thr Leu Pro Pro Val Pro Pro Phe Gln Phe Pro Thr Gly
            20                  25                  30


<210> SEQ ID NO 24
<211> LENGTH: 160
<212> TYPE: PRT
<213> ORGANISM: Bacillus weihenstephensis

<400> SEQUENCE: 24

Met Asp Glu Phe Leu Ser Phe Ala Ala Leu Asn Pro Gly Ser Ile Gly
1               5                   10                  15

Pro Thr Leu Pro Pro Val Pro Pro Phe Gln Phe Pro Thr Gly Pro Thr
            20                  25                  30

Gly Ser Thr Gly Ser Thr Gly Pro Thr Gly Ser Thr Gly Ser Thr Gly
        35                  40                  45

Pro Thr Gly Phe Asn Leu Pro Ala Gly Pro Ala Ser Ile Thr Leu Thr
    50                  55                  60

Ser Asn Glu Thr Thr Ala Cys Val Ser Thr Gln Gly Asn Asn Thr Leu
65                  70                  75                  80

Phe Phe Ser Gly Gln Val Leu Val Asn Gly Ser Pro Thr Pro Gly Val
                85                  90                  95

Val Val Ser Phe Ser Phe Ser Asn Pro Ser Leu Ala Phe Met Val Pro
            100                 105                 110

Leu Ala Val Ile Thr Asn Ala Ser Gly Asn Phe Thr Ala Val Phe Leu
        115                 120                 125

Ala Ala Asn Gly Pro Gly Thr Val Thr Val Thr Ala Ser Leu Leu Asp
    130                 135                 140

Ser Pro Gly Thr Met Ala Ser Val Thr Ile Thr Ile Val Asn Cys Pro
145                 150                 155                 160


<210> SEQ ID NO 25
<211> LENGTH: 30
<212> TYPE: PRT
<213> ORGANISM: Bacillus weihenstephensis

<400> SEQUENCE: 25

Met Asp Glu Phe Leu Ser Ser Thr Ala Leu Asn Pro Cys Ser Ile Gly
```

```
1               5                   10                  15

Pro Thr Leu Pro Pro Met Gln Pro Phe Gln Phe Pro Thr Gly
            20                  25                  30


<210> SEQ ID NO 26
<211> LENGTH: 69
<212> TYPE: PRT
<213> ORGANISM: Bacillus weihenstephensis

<400> SEQUENCE: 26

Met Asp Glu Phe Leu Ser Ser Thr Ala Leu Asn Pro Cys Ser Ile Gly
1               5                   10                  15

Pro Thr Leu Pro Pro Met Gln Pro Phe Gln Phe Pro Thr Gly Pro Thr
            20                  25                  30

Gly Ser Thr Gly Thr Thr Gly Pro Thr Gly Ser Ile Gly Pro Thr Gly
        35                  40                  45

Asn Thr Gly Leu Thr Gly Asn Thr Gly Pro Thr Gly Ile Thr Gly Pro
    50                  55                  60

Thr Gly Asp Thr Gly
65


<210> SEQ ID NO 27
<211> LENGTH: 36
<212> TYPE: PRT
<213> ORGANISM: Bacillus weihenstephensis

<400> SEQUENCE: 27

Met Lys Glu Arg Asp Arg Gln Asn Ser Leu Asn Ser Asn Phe Arg Ile
1               5                   10                  15

Ser Pro Asn Leu Ile Gly Pro Thr Phe Pro Pro Val Pro Thr Gly Phe
            20                  25                  30

Thr Gly Ile Gly
        35


<210> SEQ ID NO 28
<211> LENGTH: 934
<212> TYPE: PRT
<213> ORGANISM: Bacillus weihenstephensis

<400> SEQUENCE: 28

Met Lys Glu Arg Asp Arg Gln Asn Ser Leu Asn Ser Asn Phe Arg Ile
1               5                   10                  15

Ser Pro Asn Leu Ile Gly Pro Thr Phe Pro Pro Val Pro Thr Gly Phe
            20                  25                  30

Thr Gly Ile Gly Ile Thr Gly Pro Thr Gly Pro Gln Gly Pro Thr Gly
        35                  40                  45

Pro Gln Gly Pro Arg Gly Phe Gln Gly Pro Met Gly Glu Met Gly Pro
    50                  55                  60

Thr Gly Pro Gln Gly Val Gln Gly Ile Gln Gly Pro Ala Gly Gln Met
65                  70                  75                  80

Gly Ala Thr Gly Pro Glu Gly Gln Gln Gly Pro Gln Gly Leu Arg Gly
                85                  90                  95

Pro Gln Gly Glu Thr Gly Ala Thr Gly Pro Gln Gly Val Gln Gly Leu
            100                 105                 110

Gln Gly Pro Ile Gly Pro Thr Gly Ala Thr Gly Ala Gln Gly Ile Gln
        115                 120                 125

Gly Ile Gln Gly Leu Gln Gly Pro Ile Gly Ala Thr Gly Pro Glu Gly
    130                 135                 140
```

```
Pro Gln Gly Ile Gln Gly Val Gln Gly Val Pro Gly Ala Thr Gly Ser
145                 150                 155                 160

Gln Gly Ile Gln Gly Ala Gln Gly Ile Gln Gly Pro Gln Gly Pro Ser
                165                 170                 175

Gly Asn Thr Gly Ala Thr Gly Val Thr Gly Gln Gly Ile Ser Gly Pro
            180                 185                 190

Thr Gly Ile Thr Gly Pro Thr Gly Ile Thr Gly Pro Ser Gly Gly Pro
        195                 200                 205

Pro Gly Pro Thr Gly Ala Thr Gly Ala Thr Gly Pro Gly Gly Gly Pro
    210                 215                 220

Ser Gly Ser Thr Gly Ala Thr Gly Ala Thr Gly Asn Thr Gly Val Thr
225                 230                 235                 240

Gly Ser Ala Gly Val Thr Gly Asn Thr Gly Ser Thr Gly Ser Thr Gly
                245                 250                 255

Glu Thr Gly Ala Gln Gly Leu Gln Gly Ile Gln Gly Val Gln Gly Pro
            260                 265                 270

Ile Gly Pro Thr Gly Pro Glu Gly Pro Gln Gly Ile Gln Gly Ile Pro
        275                 280                 285

Gly Pro Thr Gly Val Thr Gly Glu Gln Gly Ile Gln Gly Val Gln Gly
    290                 295                 300

Ile Gln Gly Ile Thr Gly Ala Thr Gly Asp Gln Gly Pro Gln Gly Ile
305                 310                 315                 320

Gln Gly Ala Ile Gly Pro Gln Gly Ile Thr Gly Ala Thr Gly Asp Gln
                325                 330                 335

Gly Pro Gln Gly Ile Gln Gly Val Pro Gly Pro Thr Gly Asp Thr Gly
            340                 345                 350

Ser Gln Gly Val Gln Gly Ile Gln Gly Pro Met Gly Asp Ile Gly Pro
        355                 360                 365

Thr Gly Pro Glu Gly Pro Glu Gly Leu Gln Gly Pro Gln Gly Ile Gln
    370                 375                 380

Gly Val Pro Gly Pro Ala Gly Ala Thr Gly Pro Glu Gly Pro Gln Gly
385                 390                 395                 400

Ile Gln Gly Ile Gln Gly Pro Ile Gly Val Thr Gly Pro Glu Gly Pro
                405                 410                 415

Gln Gly Ile Gln Gly Ile Gln Gly Ile Gln Gly Ile Thr Gly Ala Thr
            420                 425                 430

Gly Ala Gln Gly Ala Thr Gly Val Gln Gly Val Gln Gly Asn Ile Gly
        435                 440                 445

Ala Thr Gly Pro Glu Gly Pro Gln Gly Val Gln Gly Thr Gln Gly Asp
    450                 455                 460

Ile Gly Pro Thr Gly Pro Met Gly Pro Gln Gly Val Gln Gly Ile Gln
465                 470                 475                 480

Gly Ile Gln Gly Pro Thr Gly Ala Gln Gly Val Gln Gly Pro Gln Gly
                485                 490                 495

Ile Gln Gly Ile Gln Gly Pro Thr Gly Val Thr Gly Asp Thr Gly Thr
            500                 505                 510

Thr Gly Ala Thr Gly Glu Gly Thr Thr Gly Ala Thr Gly Val Thr Gly
        515                 520                 525

Pro Ser Gly Val Thr Gly Pro Ser Gly Gly Pro Ala Gly Pro Thr Gly
    530                 535                 540

Pro Thr Gly Pro Ser Gly Pro Thr Gly Leu Thr Gly Pro Ser Gly Gly
545                 550                 555                 560
```

```
Pro Pro Gly Pro Thr Gly Ala Thr Gly Val Thr Gly Gly Val Gly Asp
                565                 570                 575

Thr Gly Ala Thr Gly Ser Thr Gly Val Thr Gly Ala Thr Gly Val Thr
            580                 585                 590

Gly Ala Thr Gly Ala Thr Gly Leu Gln Gly Pro Gln Gly Ile Gln Gly
        595                 600                 605

Val Gln Gly Asp Ile Gly Pro Thr Gly Pro Gln Gly Val Gln Gly Pro
    610                 615                 620

Gln Gly Ile Gln Gly Ile Thr Gly Ala Thr Gly Asp Gln Gly Pro Gln
625                 630                 635                 640

Gly Ile Gln Gly Pro Gln Gly Ile Gln Gly Pro Thr Gly Pro Gln Gly
                645                 650                 655

Ile Gln Gly Gly Gln Gly Pro Gln Gly Ile Gln Gly Ala Thr Gly Ala
            660                 665                 670

Thr Gly Ala Gln Gly Pro Gln Gly Ile Gln Gly Ile Gln Gly Val Gln
        675                 680                 685

Gly Pro Thr Gly Pro Gln Gly Pro Thr Gly Ile Gln Gly Val Gln Gly
    690                 695                 700

Glu Ile Gly Pro Thr Gly Pro Gln Gly Val Gln Gly Leu Gln Gly Pro
705                 710                 715                 720

Gln Gly Pro Thr Gly Asp Thr Gly Pro Thr Gly Pro Gln Gly Pro Gln
                725                 730                 735

Gly Ile Gln Gly Pro Thr Gly Ala Thr Gly Ala Thr Gly Ser Gln Gly
            740                 745                 750

Ile Gln Gly Pro Thr Gly Ala Thr Gly Ala Thr Gly Ser Gln Gly Ile
        755                 760                 765

Gln Gly Pro Thr Gly Ala Thr Gly Ala Thr Gly Ala Thr Gly Ala Thr
    770                 775                 780

Gly Ala Thr Gly Ala Thr Gly Ala Thr Gly Val Thr Gly Val Ser Thr
785                 790                 795                 800

Thr Ala Thr Tyr Ser Phe Ala Asn Asn Thr Ser Gly Ser Ala Ile Ser
                805                 810                 815

Val Leu Leu Gly Gly Thr Asn Ile Pro Leu Pro Asn Asn Gln Asn Ile
            820                 825                 830

Gly Pro Gly Ile Thr Val Ser Gly Gly Asn Thr Val Phe Thr Val Thr
        835                 840                 845

Asn Ala Gly Asn Tyr Tyr Ile Ala Tyr Thr Ile Asn Ile Thr Ala Ala
    850                 855                 860

Leu Leu Val Ser Ser Arg Ile Thr Val Asn Gly Ser Pro Leu Ala Gly
865                 870                 875                 880

Thr Ile Asn Ser Pro Ala Val Ala Thr Gly Ser Phe Asn Ala Thr Ile
                885                 890                 895

Ile Ser Asn Leu Ala Ala Gly Ser Ala Ile Ser Leu Gln Leu Phe Gly
            900                 905                 910

Leu Leu Ala Val Ala Thr Leu Ser Thr Thr Thr Pro Gly Ala Thr Leu
        915                 920                 925

Thr Ile Ile Arg Leu Ser
    930
```

<210> SEQ ID NO 29
<211> LENGTH: 39
<212> TYPE: PRT
<213> ORGANISM: Bacillus mycoides

<400> SEQUENCE: 29

Val Phe Asp Lys Asn Glu Ile Gln Lys Ile Asn Gly Ile Leu Gln Ala
1 5 10 15

Asn Ala Leu Asn Pro Asn Leu Ile Gly Pro Thr Leu Pro Pro Ile Pro
20 25 30

Pro Phe Thr Leu Pro Thr Gly
35

<210> SEQ ID NO 30
<211> LENGTH: 287
<212> TYPE: PRT
<213> ORGANISM: Bacillus mycoides

<400> SEQUENCE: 30

Val Phe Asp Lys Asn Glu Ile Gln Lys Ile Asn Gly Ile Leu Gln Ala
1 5 10 15

Asn Ala Leu Asn Pro Asn Leu Ile Gly Pro Thr Leu Pro Pro Ile Pro
20 25 30

Pro Phe Thr Leu Pro Thr Gly Pro Thr Gly Gly Thr Gly Pro Thr Gly
35 40 45

Val Thr Gly Pro Thr Gly Val Thr Gly Pro Thr Gly Val Thr Gly Pro
50 55 60

Thr Gly Val Thr Gly Pro Thr Gly Val Thr Gly Pro Thr Gly Val Thr
65 70 75 80

Gly Pro Thr Gly Val Thr Gly Pro Thr Gly Val Thr Gly Pro Thr Gly
85 90 95

Val Thr Gly Pro Thr Gly Val Thr Gly Pro Thr Gly Val Thr Gly Pro
100 105 110

Thr Gly Val Thr Gly Pro Thr Gly Gly Thr Glu Gly Cys Leu Cys Asp
115 120 125

Cys Cys Val Leu Pro Met Gln Ser Val Leu Gln Gln Leu Ile Gly Glu
130 135 140

Thr Val Ile Leu Gly Thr Ile Ala Asp Thr Pro Asn Thr Pro Pro Leu
145 150 155 160

Phe Phe Leu Phe Thr Ile Thr Ser Val Asn Asp Phe Leu Val Thr Val
165 170 175

Thr Asp Gly Thr Thr Thr Phe Val Val Asn Ile Ser Asp Val Thr Gly
180 185 190

Val Gly Phe Leu Pro Pro Gly Pro Pro Ile Thr Leu Leu Pro Pro Thr
195 200 205

Asp Val Gly Cys Glu Cys Glu Cys Arg Glu Arg Pro Ile Arg Gln Leu
210 215 220

Leu Asp Ala Phe Ile Gly Ser Thr Val Ser Leu Leu Ala Ser Asn Gly
225 230 235 240

Ser Ile Ala Ala Asp Phe Ser Val Glu Gln Thr Gly Leu Gly Ile Val
245 250 255

Leu Gly Thr Leu Pro Ile Asn Pro Thr Thr Thr Val Arg Phe Ala Ile
260 265 270

Ser Thr Cys Lys Ile Thr Ala Val Asn Ile Thr Pro Ile Thr Met
275 280 285

<210> SEQ ID NO 31
<211> LENGTH: 30
<212> TYPE: PRT
<213> ORGANISM: Bacillus mycoides

<400> SEQUENCE: 31

```
Met Asp Glu Phe Leu Tyr Phe Ala Ala Leu Asn Pro Gly Ser Ile Gly
1               5                   10                  15

Pro Thr Leu Pro Pro Val Gln Pro Phe Gln Phe Pro Thr Gly
            20                  25                  30


<210> SEQ ID NO 32
<211> LENGTH: 190
<212> TYPE: PRT
<213> ORGANISM: Bacillus mycoides

<400> SEQUENCE: 32

Met Asp Glu Phe Leu Tyr Phe Ala Ala Leu Asn Pro Gly Ser Ile Gly
1               5                   10                  15

Pro Thr Leu Pro Pro Val Gln Pro Phe Gln Phe Pro Thr Gly Pro Thr
            20                  25                  30

Gly Ser Thr Gly Ala Thr Gly Ser Thr Gly Ser Thr Gly Ser Thr Gly
        35                  40                  45

Pro Thr Gly Ser Thr Gly Ser Thr Gly Ser Thr Gly Ser Thr Gly Pro
    50                  55                  60

Thr Gly Pro Thr Gly Pro Thr Gly Ser Thr Gly Pro Thr Gly Pro Thr
65                  70                  75                  80

Gly Phe Asn Leu Pro Ala Gly Pro Ala Ser Ile Thr Leu Thr Ser Asn
                85                  90                  95

Glu Thr Thr Ala Cys Val Ser Thr Gln Gly Asn Asn Thr Leu Phe Phe
            100                 105                 110

Ser Gly Gln Val Leu Val Asn Gly Ser Pro Thr Pro Gly Val Val Val
        115                 120                 125

Ser Phe Ser Phe Ser Asn Pro Ser Leu Ala Phe Met Val Pro Leu Ala
    130                 135                 140

Val Ile Thr Asn Ala Ser Gly Asn Phe Thr Ala Val Phe Leu Ala Ala
145                 150                 155                 160

Asn Gly Pro Gly Thr Val Thr Val Thr Ala Ser Leu Leu Asp Ser Pro
                165                 170                 175

Gly Thr Met Ala Ser Val Thr Ile Thr Ile Val Asn Cys Pro
            180                 185                 190


<210> SEQ ID NO 33
<211> LENGTH: 21
<212> TYPE: PRT
<213> ORGANISM: Bacillus mycoides

<400> SEQUENCE: 33

Met Asp Ser Lys Asn Ile Gly Pro Thr Phe Pro Pro Leu Pro Ser Ile
1               5                   10                  15

Asn Phe Pro Thr Gly
            20


<210> SEQ ID NO 34
<211> LENGTH: 335
<212> TYPE: PRT
<213> ORGANISM: Bacillus mycoides

<400> SEQUENCE: 34

Met Asp Ser Lys Asn Ile Gly Pro Thr Phe Pro Pro Leu Pro Ser Ile
1               5                   10                  15

Asn Phe Pro Thr Gly Val Thr Gly Glu Thr Gly Ala Thr Gly Glu Thr
            20                  25                  30
```

```
Gly Ala Thr Gly Ala Thr Gly Glu Thr Gly Ala Thr Gly Glu Thr Gly
        35                  40                  45

Glu Thr Gly Ala Thr Gly Ala Thr Gly Ala Thr Gly Ala Thr Gly Glu
    50                  55                  60

Thr Gly Ala Thr Gly Ala Thr Gly Ala Thr Gly Ala Ala Gly Ala Thr
65                  70                  75                  80

Gly Glu Thr Gly Ala Thr Gly Glu Thr Gly Ala Thr Gly Glu Thr Gly
                85                  90                  95

Ala Thr Gly Glu Thr Gly Ala Thr Gly Val Thr Gly Glu Thr Gly Ala
            100                 105                 110

Thr Gly Glu Thr Gly Ala Ala Gly Glu Thr Gly Ile Thr Gly Val Thr
        115                 120                 125

Gly Pro Thr Gly Glu Thr Gly Ala Thr Gly Glu Thr Gly Ala Thr Gly
    130                 135                 140

Ala Thr Gly Ile Thr Gly Ala Thr Gly Ile Thr Gly Val Ala Gly Ala
145                 150                 155                 160

Thr Gly Glu Thr Gly Ala Ala Gly Glu Thr Gly Pro Thr Gly Ala Thr
                165                 170                 175

Gly Ala Ile Gly Ala Ile Gly Ala Thr Gly Ala Thr Gly Ile Thr Gly
            180                 185                 190

Val Thr Gly Ala Thr Gly Glu Thr Gly Ala Ala Gly Ala Thr Gly Ile
        195                 200                 205

Thr Gly Val Thr Gly Ala Thr Gly Glu Thr Gly Ala Ala Gly Ala Thr
    210                 215                 220

Gly Ile Thr Gly Ala Thr Gly Ile Thr Gly Val Ala Gly Ala Thr Gly
225                 230                 235                 240

Ile Thr Gly Pro Thr Gly Ile Pro Gly Thr Ile Pro Thr Thr Asn Leu
                245                 250                 255

Leu Tyr Phe Thr Phe Ser Asp Gly Glu Lys Leu Ile Tyr Thr Asn Ala
            260                 265                 270

Asp Gly Ile Ala Gln Tyr Gly Thr Thr Gln Ile Leu Ser Pro Ser Glu
        275                 280                 285

Val Ser Tyr Ile Asn Leu Phe Ile Asn Gly Ile Leu Gln Pro Gln Pro
    290                 295                 300

Phe Tyr Glu Val Thr Ala Gly Gln Leu Thr Leu Leu Asp Asp Glu Pro
305                 310                 315                 320

Pro Ser Gln Gly Ser Ser Ile Ile Leu Gln Phe Ile Ile Ile Asn
                325                 330                 335
```

<210> SEQ ID NO 35
<211> LENGTH: 22
<212> TYPE: PRT
<213> ORGANISM: Bacillus thuringiensis

<400> SEQUENCE: 35

```
Met Ile Gly Pro Glu Asn Ile Gly Pro Thr Phe Pro Ile Leu Pro Pro
1               5                   10                  15

Ile Tyr Ile Pro Thr Gly
            20
```

<210> SEQ ID NO 36
<211> LENGTH: 234
<212> TYPE: PRT
<213> ORGANISM: Bacillus thuringiensis

<400> SEQUENCE: 36

-continued

```
Met Ile Gly Pro Glu Asn Ile Gly Pro Thr Phe Pro Ile Leu Pro Pro
1               5                   10                  15

Ile Tyr Ile Pro Thr Gly Glu Thr Gly Pro Thr Gly Ile Thr Gly Ala
            20                  25                  30

Thr Gly Glu Thr Gly Pro Thr Gly Ile Thr Gly Pro Thr Gly Ile Thr
        35                  40                  45

Gly Ala Thr Gly Glu Thr Gly Ser Thr Gly Ile Thr Gly Ala Thr Gly
    50                  55                  60

Glu Thr Gly Ser Thr Gly Ile Thr Gly Pro Ile Gly Ile Thr Gly Ala
65                  70                  75                  80

Thr Gly Glu Thr Gly Pro Ile Gly Ile Thr Gly Ala Thr Gly Glu Thr
                85                  90                  95

Gly Pro Thr Gly Ile Thr Gly Ser Thr Gly Ile Thr Gly Leu Thr Gly
            100                 105                 110

Val Thr Gly Leu Thr Gly Glu Thr Gly Pro Ile Gly Ile Thr Gly Pro
        115                 120                 125

Thr Gly Ile Thr Gly Pro Thr Gly Val Thr Gly Ala Thr Gly Pro Thr
    130                 135                 140

Gly Gly Ile Gly Pro Ile Thr Thr Thr Asn Leu Leu Tyr Tyr Thr Phe
145                 150                 155                 160

Ala Asp Gly Glu Lys Leu Ile Tyr Thr Asp Thr Asp Gly Ile Pro Gln
                165                 170                 175

Tyr Gly Thr Thr Asn Ile Leu Ser Pro Ser Glu Val Ser Tyr Ile Asn
            180                 185                 190

Leu Phe Val Asn Gly Ile Leu Gln Pro Gln Pro Leu Tyr Glu Val Ser
        195                 200                 205

Thr Gly Lys Leu Thr Leu Leu Asp Thr Gln Pro Pro Ser Gln Gly Ser
    210                 215                 220

Ser Ile Ile Leu Gln Phe Ile Ile Ile Asn
225                 230
```

<210> SEQ ID NO 37
<211> LENGTH: 23
<212> TYPE: DNA
<213> ORGANISM: Artificial sequence
<220> FEATURE:
<223> OTHER INFORMATION: Primer

<400> SEQUENCE: 37
ggatccatgg ctgaacacaa tcc 23

<210> SEQ ID NO 38
<211> LENGTH: 24
<212> TYPE: DNA
<213> ORGANISM: Artificial sequence
<220> FEATURE:
<223> OTHER INFORMATION: Primer

<400> SEQUENCE: 38
ggatccttaa ttcgtattct ggcc 24

<210> SEQ ID NO 39
<211> LENGTH: 21
<212> TYPE: DNA
<213> ORGANISM: Artificial sequence
<220> FEATURE:
<223> OTHER INFORMATION: Primer

<400> SEQUENCE: 39

```
ggatccatga aacggtcaat c                                              21


<210> SEQ ID NO 40
<211> LENGTH: 24
<212> TYPE: DNA
<213> ORGANISM: Artificial sequence
<220> FEATURE:
<223> OTHER INFORMATION: Primer

<400> SEQUENCE: 40

ggatccttac taatttggtt ctgt                                           24


<210> SEQ ID NO 41
<211> LENGTH: 21
<212> TYPE: DNA
<213> ORGANISM: Artificial sequence
<220> FEATURE:
<223> OTHER INFORMATION: Primer

<400> SEQUENCE: 41

ggatccatgc taccaaaagc c                                              21


<210> SEQ ID NO 42
<211> LENGTH: 24
<212> TYPE: DNA
<213> ORGANISM: Artificial sequence
<220> FEATURE:
<223> OTHER INFORMATION: Primer

<400> SEQUENCE: 42

ggatccttag tccgcaggcg tagc                                           24


<210> SEQ ID NO 43
<211> LENGTH: 35
<212> TYPE: PRT
<213> ORGANISM: Bacillus cereus

<400> SEQUENCE: 43

Met Ser Asn Asn Asn Ile Pro Ser Pro Phe Phe Phe Asn Asn Phe Asn
1               5                   10                  15

Pro Glu Leu Ile Gly Pro Thr Phe Pro Pro Ile Pro Pro Leu Thr Leu
            20                  25                  30

Pro Thr Gly
        35


<210> SEQ ID NO 44
<211> LENGTH: 222
<212> TYPE: PRT
<213> ORGANISM: Bacillus cereus

<400> SEQUENCE: 44

Met Ser Asn Asn Asn Ile Pro Ser Pro Phe Phe Phe Asn Asn Phe Asn
1               5                   10                  15

Pro Glu Leu Ile Gly Pro Thr Phe Pro Pro Ile Pro Pro Leu Thr Leu
            20                  25                  30

Pro Thr Gly Pro Thr Gly Ser Thr Gly Ala Thr Gly Ala Thr Gly Pro
        35                  40                  45

Thr Gly Ala Thr Gly Pro Thr Gly Ala Thr Gly Pro Thr Gly Ala Thr
    50                  55                  60

Gly Ala Thr Gly Ser Thr Gly Ala Thr Gly Pro Thr Gly Ala Thr Gly
65                  70                  75                  80

Thr Phe Ser Ser Ala Asn Ala Ser Ile Val Thr Pro Ala Pro Gln Thr
```

```
                85                  90                  95

Val Asn Asn Leu Ala Pro Ile Gln Phe Thr Ala Pro Val Leu Ile Ser
            100                 105                 110

Lys Asn Val Thr Phe Asn Gly Ile Asp Thr Phe Thr Ile Gln Ile Pro
        115                 120                 125

Gly Asn Tyr Phe Phe Ile Gly Ala Val Met Thr Ser Asn Asn Gln Ala
    130                 135                 140

Gly Pro Val Ala Val Gly Val Gly Phe Asn Gly Ile Pro Val Pro Ser
145                 150                 155                 160

Leu Asp Gly Ala Asn Tyr Gly Thr Pro Thr Gly Gln Glu Val Val Cys
                165                 170                 175

Phe Gly Phe Ser Gly Gln Ile Pro Ala Gly Thr Thr Ile Asn Leu Tyr
            180                 185                 190

Asn Ile Ser Asp Lys Thr Ile Ser Ile Gly Gly Ala Thr Ala Ala Gly
        195                 200                 205

Ser Ser Ile Val Ala Ala Arg Leu Ser Phe Phe Arg Ile Ser
    210                 215                 220


<210> SEQ ID NO 45
<211> LENGTH: 41
<212> TYPE: PRT
<213> ORGANISM: Bacillus cereus

<400> SEQUENCE: 45

Met Phe Ser Glu Lys Lys Arg Lys Asp Leu Ile Pro Asp Asn Phe Leu
1               5                   10                  15

Ser Ala Pro Ala Leu Asp Pro Asn Leu Ile Gly Pro Thr Phe Pro Pro
            20                  25                  30

Ile Pro Ser Phe Thr Leu Pro Thr Gly
        35                  40


<210> SEQ ID NO 46
<211> LENGTH: 293
<212> TYPE: PRT
<213> ORGANISM: Bacillus cereus

<400> SEQUENCE: 46

Met Phe Ser Glu Lys Lys Arg Lys Asp Leu Ile Pro Asp Asn Phe Leu
1               5                   10                  15

Ser Ala Pro Ala Leu Asp Pro Asn Leu Ile Gly Pro Thr Phe Pro Pro
            20                  25                  30

Ile Pro Ser Phe Thr Leu Pro Thr Gly Ser Thr Gly Pro Thr Gly Pro
        35                  40                  45

Thr Gly Asp Thr Gly Pro Thr Gly Pro Thr Ala Thr Ile Cys Ile Arg
    50                  55                  60

Thr Asp Pro Asp Asn Gly Cys Ser Val Ala Glu Gly Ser Gly Thr Val
65                  70                  75                  80

Ala Ser Gly Phe Ala Ser His Ala Glu Ala Cys Asn Thr Gln Ala Ile
                85                  90                  95

Gly Asp Cys Ser His Ala Glu Gly Gln Phe Ala Thr Ala Ser Gly Thr
            100                 105                 110

Ala Ser His Ala Glu Gly Phe Gln Thr Thr Ala Ser Gly Phe Ala Ser
        115                 120                 125

His Thr Glu Gly Ser Gly Thr Thr Ala Asp Ala Asn Phe Ser His Thr
    130                 135                 140

Glu Gly Ile Asn Thr Ile Val Asp Val Leu His Pro Gly Ser His Ile
```

```
145                 150                 155                 160

Met Gly Lys Asn Gly Thr Thr Arg Ser Ser Phe Ser Trp His Leu Ala
                165                 170                 175

Asn Gly Leu Ala Val Gly Pro Ser Leu Asn Ser Ala Val Ile Glu Gly
            180                 185                 190

Val Thr Gly Asn Leu Tyr Leu Asp Gly Val Val Ile Ser Pro Asn Ala
        195                 200                 205

Ala Asp Tyr Ala Glu Met Phe Glu Thr Ile Asp Gly Asn Leu Ile Asp
    210                 215                 220

Val Gly Tyr Phe Val Thr Leu Tyr Gly Glu Lys Ile Arg Lys Ala Asn
225                 230                 235                 240

Ala Asn Asp Asp Tyr Ile Leu Gly Val Val Ser Ala Thr Pro Ala Met
                245                 250                 255

Ile Ala Asp Ala Ser Asp Leu Arg Trp His Asn Leu Phe Val Arg Asp
            260                 265                 270

Glu Trp Gly Arg Thr Gln Tyr His Glu Val Val Val Pro Glu Lys Lys
        275                 280                 285

Met Ala Met Glu Glu
    290


<210> SEQ ID NO 47
<211> LENGTH: 49
<212> TYPE: PRT
<213> ORGANISM: Bacillus cereus

<400> SEQUENCE: 47

Met Thr Arg Lys Asp Lys Phe Asn Arg Ser Arg Ile Ser Arg Arg Asp
1               5                   10                  15

Arg Phe Asn Ser Pro Lys Ile Lys Ser Glu Ile Leu Ile Ser Pro Asp
            20                  25                  30

Leu Val Gly Pro Thr Phe Pro Pro Ile Pro Ser Phe Thr Leu Pro Thr
        35                  40                  45

Gly


<210> SEQ ID NO 48
<211> LENGTH: 83
<212> TYPE: PRT
<213> ORGANISM: Bacillus cereus

<400> SEQUENCE: 48

Met Thr Arg Lys Asp Lys Phe Asn Arg Ser Arg Ile Ser Arg Arg Asp
1               5                   10                  15

Arg Phe Asn Ser Pro Lys Ile Lys Ser Glu Ile Leu Ile Ser Pro Asp
            20                  25                  30

Leu Val Gly Pro Thr Phe Pro Pro Ile Pro Ser Phe Thr Leu Pro Thr
        35                  40                  45

Gly Val Thr Gly Pro Thr Gly Asn Thr Gly Pro Thr Gly Ile Thr Gly
    50                  55                  60

Pro Thr Gly Asp Thr Gly Pro Thr Gly Asp Thr Gly Pro Thr Gly Ile
65                  70                  75                  80

Thr Gly Pro


<210> SEQ ID NO 49
<211> LENGTH: 38
<212> TYPE: PRT
<213> ORGANISM: Bacillus cereus
```

<400> SEQUENCE: 49

Met Ser Arg Lys Asp Arg Phe Asn Ser Pro Lys Ile Lys Ser Glu Ile
1 5 10 15

Ser Ile Ser Pro Asp Leu Val Gly Pro Thr Phe Pro Pro Ile Pro Ser
20 25 30

Phe Thr Leu Pro Thr Gly
35

<210> SEQ ID NO 50
<211> LENGTH: 163
<212> TYPE: PRT
<213> ORGANISM: Bacillus cereus

<400> SEQUENCE: 50

Met Ser Arg Lys Asp Arg Phe Asn Ser Pro Lys Ile Lys Ser Glu Ile
1 5 10 15

Ser Ile Ser Pro Asp Leu Val Gly Pro Thr Phe Pro Pro Ile Pro Ser
20 25 30

Phe Thr Leu Pro Thr Gly Ile Thr Gly Pro Thr Gly Asn Thr Gly Pro
35 40 45

Thr Gly Asp Thr Gly Pro Thr Gly Pro Thr Phe Asn Ile Asn Phe Arg
50 55 60

Ala Glu Lys Asn Gly Ala Gln Ser Phe Thr Pro Pro Ala Asp Ile Gln
65 70 75 80

Val Ser Tyr Gly Asn Ile Ile Phe Asn Asn Gly Gly Gly Tyr Ser Ser
85 90 95

Val Thr Asn Thr Phe Thr Ala Pro Ile Asn Gly Ile Tyr Leu Phe Ser
100 105 110

Ala Asn Ile Gly Phe Asn Pro Thr Leu Gly Thr Thr Ser Thr Leu Arg
115 120 125

Ile Thr Ile Arg Lys Asn Leu Val Ser Val Ala Ser Gln Thr Ile Asp
130 135 140

Ile Gln Phe Ser Ala Ala Glu Ser Gly Thr Leu Thr Val Gly Ser Ser
145 150 155 160

Asn Phe Phe

<210> SEQ ID NO 51
<211> LENGTH: 39
<212> TYPE: PRT
<213> ORGANISM: Bacillus cereus

<400> SEQUENCE: 51

Met Lys Glu Arg Asp Asn Lys Gly Lys Gln His Ser Leu Asn Ser Asn
1 5 10 15

Phe Arg Ile Pro Pro Glu Leu Ile Gly Pro Thr Phe Pro Pro Val Pro
20 25 30

Thr Gly Phe Thr Gly Ile Gly
35

<210> SEQ ID NO 52
<211> LENGTH: 323
<212> TYPE: PRT
<213> ORGANISM: Bacillus cereus

<400> SEQUENCE: 52

Met Lys Glu Arg Asp Asn Lys Gly Lys Gln His Ser Leu Asn Ser Asn
1 5 10 15

```
Phe Arg Ile Pro Pro Glu Leu Ile Gly Pro Thr Phe Pro Pro Val Pro
            20                  25                  30

Thr Gly Phe Thr Gly Ile Gly Ile Thr Gly Pro Thr Gly Pro Gln Gly
        35                  40                  45

Pro Thr Gly Pro Gln Gly Pro Arg Gly Phe Gln Gly Pro Met Gly Glu
    50                  55                  60

Met Gly Pro Thr Gly Pro Gln Gly Val Gln Gly Ile Gln Gly Pro Ala
65                  70                  75                  80

Gly Gln Met Gly Ala Thr Gly Pro Glu Gly Gln Gln Gly Pro Glu Gly
                85                  90                  95

Leu Arg Gly Pro Val Gly Ala Thr Gly Ala Thr Gly Leu Gln Gly Val
            100                 105                 110

Gln Gly Ile Gln Gly Pro Ile Gly Ser Thr Gly Ala Thr Gly Ala Gln
        115                 120                 125

Gly Ile Gln Gly Ile Gln Gly Leu Gln Gly Pro Ile Gly Ala Thr Gly
    130                 135                 140

Pro Glu Gly Pro Gln Gly Ile Gln Gly Val Gln Gly Leu Pro Gly Ala
145                 150                 155                 160

Thr Gly Pro Gln Gly Val Gln Gly Val Gln Gly Val Ile Gly Pro Gln
                165                 170                 175

Gly Pro Ser Gly Ser Thr Gly Gly Thr Gly Ala Thr Gly Gln Gly Val
            180                 185                 190

Thr Gly Pro Thr Gly Ile Thr Gly Ser Thr Gly Val Thr Gly Pro Ser
        195                 200                 205

Gly Gly Pro Pro Gly Pro Thr Gly Pro Thr Gly Ala Thr Gly Pro Gly
    210                 215                 220

Gly Gly Pro Ser Gly Ser Thr Gly Val Thr Gly Ser Thr Gly Asn Thr
225                 230                 235                 240

Gly Ala Thr Gly Ser Pro Gly Val Thr Gly Ala Thr Gly Pro Thr Gly
                245                 250                 255

Ser Thr Gly Ala Thr Gly Ile Gln Gly Ser Gln Gly Ile Gln Gly Ile
            260                 265                 270

Gln Gly Ile Gln Gly Pro Leu Gly Pro Thr Gly Pro Glu Gly Pro Gln
        275                 280                 285

Gly Ile Gln Gly Ile Pro Gly Pro Thr Gly Ile Thr Gly Glu Gln Gly
    290                 295                 300

Ile Gln Gly Val Gln Gly Ile Gln Gly Ile Thr Gly Ala Thr Gly Asp
305                 310                 315                 320

Gln Gly Thr
```

<210> SEQ ID NO 53
<211> LENGTH: 39
<212> TYPE: PRT
<213> ORGANISM: Bacillus cereus

<400> SEQUENCE: 53

```
Met Arg Glu Arg Asp Asn Lys Arg Gln Gln His Ser Leu Asn Pro Asn
1               5                   10                  15

Phe Arg Ile Ser Pro Glu Leu Ile Gly Pro Thr Phe Pro Pro Val Pro
            20                  25                  30

Thr Gly Phe Thr Gly Ile Gly
        35
```

<210> SEQ ID NO 54
<211> LENGTH: 436

<212> TYPE: PRT
<213> ORGANISM: Bacillus cereus

<400> SEQUENCE: 54

Met Arg Glu Arg Asp Asn Lys Arg Gln Gln His Ser Leu Asn Pro Asn
1 5 10 15

Phe Arg Ile Ser Pro Glu Leu Ile Gly Pro Thr Phe Pro Pro Val Pro
20 25 30

Thr Gly Phe Thr Gly Ile Gly Ile Thr Gly Pro Thr Gly Pro Gln Gly
35 40 45

Pro Thr Gly Pro Gln Gly Pro Arg Gly Phe Gln Gly Pro Met Gly Glu
50 55 60

Met Gly Pro Thr Gly Pro Gln Gly Val Gln Gly Ile Gln Gly Pro Val
65 70 75 80

Gly Pro Ile Gly Ala Thr Gly Pro Glu Gly Gln Gln Gly Pro Gln Gly
85 90 95

Leu Arg Gly Pro Gln Gly Glu Thr Gly Ala Thr Gly Pro Gly Gly Val
100 105 110

Gln Gly Leu Gln Gly Pro Ile Gly Pro Thr Gly Ala Thr Gly Ala Gln
115 120 125

Gly Val Gln Gly Ile Gln Gly Leu Gln Gly Pro Ile Gly Ala Thr Gly
130 135 140

Pro Glu Gly Pro Gln Gly Ile Gln Gly Val Gln Gly Leu Pro Gly Ala
145 150 155 160

Thr Gly Ser Gln Gly Ile Gln Gly Val Gln Gly Ile Gln Gly Pro Gln
165 170 175

Gly Pro Ser Gly Asn Thr Gly Ala Thr Gly Ala Thr Gly Gln Gly Ile
180 185 190

Thr Gly Pro Thr Gly Ile Thr Gly Pro Thr Gly Ile Thr Gly Pro Ser
195 200 205

Gly Gly Pro Pro Gly Pro Thr Gly Pro Thr Gly Ala Thr Gly Pro Gly
210 215 220

Gly Gly Pro Ser Gly Ser Thr Gly Ala Thr Gly Ala Thr Gly Asn Thr
225 230 235 240

Gly Ala Thr Gly Asn Thr Gly Ile Thr Gly Ala Thr Gly Ser Thr Gly
245 250 255

Pro Thr Gly Ser Thr Gly Ala Gln Gly Leu Gln Gly Ile Gln Gly Ile
260 265 270

Gln Gly Pro Ile Gly Pro Thr Gly Pro Glu Gly Pro Gln Gly Ile Gln
275 280 285

Gly Ile Pro Gly Pro Thr Gly Val Thr Gly Glu Gln Gly Ile Gln Gly
290 295 300

Val Gln Gly Ile Gln Gly Ile Thr Gly Ala Thr Gly Asp Gln Gly Pro
305 310 315 320

Gln Gly Ile Gln Gly Val Ile Gly Ala Gln Gly Val Thr Gly Ala Thr
325 330 335

Gly Asp Gln Gly Pro Gln Gly Ile Gln Gly Val Pro Gly Pro Ser Gly
340 345 350

Ala Thr Gly Pro Gln Gly Val Gln Gly Ile Gln Gly Pro Met Gly Asp
355 360 365

Ile Gly Pro Thr Gly Pro Glu Gly Pro Glu Gly Leu Gln Gly Pro Gln
370 375 380

Gly Ile Gln Gly Val Pro Gly Pro Val Gly Ala Thr Gly Pro Glu Gly
385 390 395 400

```
Pro Gln Gly Ile Gln Gly Ile Gln Gly Val Gln Gly Ala Thr Gly Pro
                405                 410                 415

Gln Gly Pro Gln Gly Ile Gln Gly Ile Gln Gly Val Gln Gly Ile Thr
            420                 425                 430

Gly Ala Thr Gly
        435
```

<210> SEQ ID NO 55
<211> LENGTH: 36
<212> TYPE: PRT
<213> ORGANISM: Bacillus thuringiensis

<400> SEQUENCE: 55

```
Met Lys Asn Arg Asp Asn Lys Gly Lys Gln Gln Ser Asn Phe Arg Ile
1               5                   10                  15

Pro Pro Glu Leu Ile Gly Pro Thr Phe Pro Pro Val Pro Thr Gly Phe
            20                  25                  30

Thr Gly Ile Gly
        35
```

<210> SEQ ID NO 56
<211> LENGTH: 470
<212> TYPE: PRT
<213> ORGANISM: Bacillus thuringiensis

<400> SEQUENCE: 56

```
Met Lys Asn Arg Asp Asn Lys Gly Lys Gln Gln Ser Asn Phe Arg Ile
1               5                   10                  15

Pro Pro Glu Leu Ile Gly Pro Thr Phe Pro Pro Val Pro Thr Gly Phe
            20                  25                  30

Thr Gly Ile Gly Ile Thr Gly Pro Thr Gly Pro Gln Gly Pro Thr Gly
        35                  40                  45

Pro Gln Gly Pro Arg Gly Phe Gln Gly Pro Met Gly Glu Met Gly Pro
    50                  55                  60

Thr Gly Pro Gln Gly Val Gln Gly Ile Gln Gly Pro Val Gly Pro Ile
65                  70                  75                  80

Gly Ala Thr Gly Pro Glu Gly Gln Gln Gly Ala Gln Gly Leu Arg Gly
                85                  90                  95

Pro Gln Gly Glu Thr Gly Ala Thr Gly Pro Gln Gly Val Gln Gly Leu
            100                 105                 110

Gln Gly Pro Ile Gly Pro Thr Gly Ala Thr Gly Ala Gln Gly Ile Gln
        115                 120                 125

Gly Ile Gln Gly Leu Gln Gly Pro Ile Gly Ala Thr Gly Pro Glu Gly
    130                 135                 140

Pro Gln Gly Ile Gln Gly Val Gln Gly Leu Pro Gly Ala Thr Gly Pro
145                 150                 155                 160

Gln Gly Ile Gln Gly Ala Gln Gly Ile Gln Gly Thr Gln Gly Pro Ser
                165                 170                 175

Gly Asn Thr Gly Ala Thr Gly Ala Thr Gly Gln Gly Leu Thr Gly Pro
            180                 185                 190

Thr Gly Ile Thr Gly Pro Thr Gly Ile Thr Gly Pro Ser Gly Gly Pro
        195                 200                 205

Pro Gly Pro Thr Gly Pro Thr Gly Ala Thr Gly Pro Gly Gly Gly Pro
    210                 215                 220

Ser Gly Ser Thr Gly Ala Thr Gly Ala Thr Gly Asp Thr Gly Ala Thr
225                 230                 235                 240
```

Gly Ser Thr Gly Val Thr Gly Ala Thr Gly Ala Gln Gly Pro Gln Gly
245 250 255

Val Gln Gly Ile Gln Gly Pro Thr Gly Ala Thr Gly Ala Thr Gly Ala
260 265 270

Thr Gly Pro Gln Gly Ile Gln Gly Pro Gln Gly Ile Gln Gly Pro Thr
275 280 285

Gly Ala Thr Gly Ala Thr Gly Ser Gln Gly Pro Thr Gly Asn Thr Gly
290 295 300

Pro Thr Gly Ser Gln Gly Ile Gln Gly Pro Thr Gly Pro Thr Gly Ala
305 310 315 320

Gly Ala Thr Gly Ala Thr Gly Ala Thr Gly Ala Thr Gly Val Ser Thr
325 330 335

Thr Ala Thr Tyr Ala Phe Ala Asn Asn Thr Ser Gly Ser Ile Ile Ser
340 345 350

Val Leu Leu Gly Gly Thr Asn Ile Pro Leu Pro Asn Asn Gln Asn Ile
355 360 365

Gly Pro Gly Ile Thr Val Ser Gly Gly Asn Thr Val Phe Thr Val Ala
370 375 380

Asn Ala Gly Asn Tyr Tyr Ile Ala Tyr Thr Ile Asn Leu Thr Ala Gly
385 390 395 400

Leu Leu Val Ser Ser Arg Ile Thr Val Asn Gly Ser Pro Leu Ala Gly
405 410 415

Thr Ile Asn Ser Pro Ala Val Ala Ala Gly Ser Phe Ser Ala Thr Ile
420 425 430

Ile Ala Asn Leu Pro Ala Gly Ala Ala Val Ser Leu Gln Leu Phe Gly
435 440 445

Val Ile Ala Leu Ala Thr Leu Ser Thr Ala Thr Pro Gly Ala Thr Leu
450 455 460

Thr Ile Ile Arg Leu Ser
465 470

<210> SEQ ID NO 57
<211> LENGTH: 136
<212> TYPE: PRT
<213> ORGANISM: Bacillus mycoides

<400> SEQUENCE: 57

Met Lys Phe Ser Lys Lys Ser Thr Val Asp Ser Ser Ile Val Gly Lys
1 5 10 15

Arg Val Val Ser Lys Val Asn Ile Leu Arg Phe Tyr Asp Ala Arg Ser
20 25 30

Cys Gln Asp Lys Asp Val Asp Gly Phe Val Asp Val Gly Glu Leu Phe
35 40 45

Thr Ile Phe Arg Lys Leu Asn Met Glu Gly Ser Val Gln Phe Lys Ala
50 55 60

His Asn Ser Ile Gly Lys Thr Tyr Tyr Ile Thr Ile Asn Glu Val Tyr
65 70 75 80

Val Phe Val Thr Val Leu Leu Gln Tyr Ser Thr Leu Ile Gly Gly Ser
85 90 95

Tyr Val Phe Asp Lys Asn Glu Ile Gln Lys Ile Asn Gly Ile Leu Gln
100 105 110

Ala Asn Ala Leu Asn Pro Asn Leu Ile Gly Pro Thr Leu Pro Pro Ile
115 120 125

Pro Pro Phe Thr Leu Pro Thr Gly 130 135

<210> SEQ ID NO 58
<211> LENGTH: 384
<212> TYPE: PRT
<213> ORGANISM: Bacillus mycoides

<400> SEQUENCE: 58

Met Lys Phe Ser Lys Lys Ser Thr Val Asp Ser Ser Ile Val Gly Lys
1 5 10 15

Arg Val Val Ser Lys Val Asn Ile Leu Arg Phe Tyr Asp Ala Arg Ser
20 25 30

Cys Gln Asp Lys Asp Val Asp Gly Phe Val Asp Val Gly Glu Leu Phe
35 40 45

Thr Ile Phe Arg Lys Leu Asn Met Glu Gly Ser Val Gln Phe Lys Ala
50 55 60

His Asn Ser Ile Gly Lys Thr Tyr Tyr Ile Thr Ile Asn Glu Val Tyr
65 70 75 80

Val Phe Val Thr Val Leu Leu Gln Tyr Ser Thr Leu Ile Gly Gly Ser
85 90 95

Tyr Val Phe Asp Lys Asn Glu Ile Gln Lys Ile Asn Gly Ile Leu Gln
100 105 110

Ala Asn Ala Leu Asn Pro Asn Leu Ile Gly Pro Thr Leu Pro Pro Ile
115 120 125

Pro Pro Phe Thr Leu Pro Thr Gly Pro Thr Gly Gly Thr Gly Pro Thr
130 135 140

Gly Val Thr Gly Pro Thr Gly Val Thr Gly Pro Thr Gly Val Thr Gly
145 150 155 160

Pro Thr Gly Val Thr Gly Pro Thr Gly Val Thr Gly Pro Thr Gly Val
165 170 175

Thr Gly Pro Thr Gly Val Thr Gly Pro Thr Gly Val Thr Gly Pro Thr
180 185 190

Gly Val Thr Gly Pro Thr Gly Val Thr Gly Pro Thr Gly Val Thr Gly
195 200 205

Pro Thr Gly Val Thr Gly Pro Thr Gly Gly Thr Glu Gly Cys Leu Cys
210 215 220

Asp Cys Cys Val Leu Pro Met Gln Ser Val Leu Gln Gln Leu Ile Gly
225 230 235 240

Glu Thr Val Ile Leu Gly Thr Ile Ala Asp Thr Pro Asn Thr Pro Pro
245 250 255

Leu Phe Phe Leu Phe Thr Ile Thr Ser Val Asn Asp Phe Leu Val Thr
260 265 270

Val Thr Asp Gly Thr Thr Thr Phe Val Val Asn Ile Ser Asp Val Thr
275 280 285

Gly Val Gly Phe Leu Pro Pro Gly Pro Pro Ile Thr Leu Leu Pro Pro
290 295 300

Thr Asp Val Gly Cys Glu Cys Glu Cys Arg Glu Arg Pro Ile Arg Gln
305 310 315 320

Leu Leu Asp Ala Phe Ile Gly Ser Thr Val Ser Leu Leu Ala Ser Asn
325 330 335

Gly Ser Ile Ala Ala Asp Phe Ser Val Glu Gln Thr Gly Leu Gly Ile
340 345 350

Val Leu Gly Thr Leu Pro Ile Asn Pro Thr Thr Thr Val Arg Phe Ala
355 360 365

```
Ile Ser Thr Cys Lys Ile Thr Ala Val Asn Ile Thr Pro Ile Thr Met
    370                 375                 380


<210> SEQ ID NO 59
<211> LENGTH: 196
<212> TYPE: PRT
<213> ORGANISM: Bacillus anthracis

<400> SEQUENCE: 59

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Phe Thr Thr
        35                  40                  45

Gly Pro Thr Gly Pro Thr Gly Pro Thr Gly Pro Thr Gly Pro Thr Gly
    50                  55                  60

Pro Thr Gly Pro Thr Gly Pro Thr Gly Asp Thr Gly Thr Thr Gly Pro
65                  70                  75                  80

Thr Gly Pro Thr Gly Pro Thr Gly Pro Thr Gly Pro Thr Gly Pro Thr
                85                  90                  95

Gly Pro Thr Gly Pro Thr Gly Pro Thr Gly Phe Thr Pro Thr Gly Pro
            100                 105                 110

Thr Gly Pro Thr Gly Pro Thr Gly Asp Thr Gly Thr Thr Gly Pro Thr
        115                 120                 125

Gly Pro Thr Gly Pro Thr Gly Pro Thr Gly Pro Thr Gly Asp Thr Gly
    130                 135                 140

Thr Thr Gly Pro Thr Gly Pro Thr Gly Pro Thr Gly Pro Thr Gly Pro
145                 150                 155                 160

Thr Gly Pro Thr Gly Pro Thr Phe Thr Gly Pro Thr Gly Pro Thr Gly
                165                 170                 175

Pro Thr Gly Ala Thr Gly Leu Thr Gly Pro Thr Gly Pro Thr Gly Pro
            180                 185                 190

Ser Gly Leu Gly
        195


<210> SEQ ID NO 60
<211> LENGTH: 17
<212> TYPE: PRT
<213> ORGANISM: Bacillus anthracis

<400> SEQUENCE: 60

Met Ala Phe Asp Pro Asn Leu Val Gly Pro Thr Leu Pro Pro Ile Pro
1               5                   10                  15

Pro


<210> SEQ ID NO 61
<211> LENGTH: 17
<212> TYPE: PRT
<213> ORGANISM: Bacillus anthracis

<400> SEQUENCE: 61

Met Ala Leu Glu Pro Asn Leu Ile Gly Pro Thr Leu Pro Pro Ile Pro
1               5                   10                  15

Pro


<210> SEQ ID NO 62
<211> LENGTH: 17
```

<212> TYPE: PRT
<213> ORGANISM: Bacillus weihenstephensis

<400> SEQUENCE: 62

Met Ala Leu Asn Pro Asn Leu Ile Gly Pro Thr Leu Pro Pro Ile Pro
1 5 10 15

Pro

<210> SEQ ID NO 63
<211> LENGTH: 17
<212> TYPE: PRT
<213> ORGANISM: Bacillus weihenstephensis

<400> SEQUENCE: 63

Met Ala Leu Asp Pro Asn Ile Ile Gly Pro Thr Leu Pro Pro Ile Pro
1 5 10 15

Pro

<210> SEQ ID NO 64
<211> LENGTH: 17
<212> TYPE: PRT
<213> ORGANISM: Bacillus cereus

<400> SEQUENCE: 64

Met Ala Leu Glu Pro Asn Leu Ile Gly Pro Thr Leu Pro Ser Ile Pro
1 5 10 15

Pro

<210> SEQ ID NO 65
<211> LENGTH: 17
<212> TYPE: PRT
<213> ORGANISM: Bacillus weihenstephensis

<400> SEQUENCE: 65

Met Ala Leu Asp Pro Asn Leu Ile Gly Pro Pro Leu Pro Pro Ile Thr
1 5 10 15

Pro

<210> SEQ ID NO 66
<211> LENGTH: 17
<212> TYPE: PRT
<213> ORGANISM: Bacillus weihenstephensis

<400> SEQUENCE: 66

Met Ala Leu Asn Pro Gly Ser Ile Gly Pro Thr Leu Pro Pro Val Pro
1 5 10 15

Pro

<210> SEQ ID NO 67
<211> LENGTH: 17
<212> TYPE: PRT
<213> ORGANISM: Bacillus weihenstephensis

<400> SEQUENCE: 67

Met Ala Leu Asn Pro Cys Ser Ile Gly Pro Thr Leu Pro Pro Met Gln
1 5 10 15

Pro

<210> SEQ ID NO 68
<211> LENGTH: 17
<212> TYPE: PRT

```
<213> ORGANISM: Bacillus mycoides

<400> SEQUENCE: 68

Met Ala Leu Asn Pro Gly Ser Ile Gly Pro Thr Leu Pro Pro Val Gln
1               5                   10                  15

Pro


<210> SEQ ID NO 69
<211> LENGTH: 17
<212> TYPE: PRT
<213> ORGANISM: Bacillus anthracis

<400> SEQUENCE: 69

Met Ala Leu Asn Pro Gly Ser Val Gly Pro Thr Leu Pro Pro Met Gln
1               5                   10                  15

Pro


<210> SEQ ID NO 70
<211> LENGTH: 17
<212> TYPE: PRT
<213> ORGANISM: Bacillus cereus

<400> SEQUENCE: 70

Met Ala Leu Asp Pro Asn Leu Ile Gly Pro Thr Phe Pro Pro Ile Pro
1               5                   10                  15

Ser


<210> SEQ ID NO 71
<211> LENGTH: 799
<212> TYPE: PRT
<213> ORGANISM: Bacillus mycoides

<400> SEQUENCE: 71

Met Lys Arg Lys Thr Pro Phe Lys Val Phe Ser Ser Leu Ala Ile Thr
1               5                   10                  15

Thr Met Leu Gly Cys Thr Phe Ala Leu Gly Thr Ser Val Ala Tyr Ala
            20                  25                  30

Glu Thr Thr Ser Gln Ser Lys Gly Ser Ile Ser Thr Thr Pro Ile Asp
        35                  40                  45

Asn Asn Leu Ile Gln Glu Glu Arg Leu Ala Glu Ala Leu Lys Glu Arg
    50                  55                  60

Gly Thr Ile Asp Gln Ser Ala Ser Lys Glu Glu Thr Gln Lys Ala Val
65                  70                  75                  80

Glu Gln Tyr Ile Glu Lys Lys Lys Gly Asp Gln Pro Asn Lys Glu Ile
                85                  90                  95

Leu Pro Asp Asp Pro Ala Lys Glu Ala Ser Asp Phe Val Lys Lys Val
            100                 105                 110

Lys Glu Lys Lys Met Glu Glu Lys Glu Lys Val Lys Lys Ser Val Glu
        115                 120                 125

Asn Ala Ser Ser Glu Gln Thr Pro Ser Gln Asn Lys Lys Gln Leu Asn
    130                 135                 140

Gly Lys Val Pro Thr Ser Pro Ala Lys Gln Ala Pro Tyr Asn Gly Ala
145                 150                 155                 160

Val Arg Thr Asp Lys Val Leu Val Leu Leu Val Glu Phe Ser Asp Tyr
                165                 170                 175

Lys His Asn Asn Ile Glu Gln Ser Pro Gly Tyr Met Tyr Ala Asn Asp
            180                 185                 190
```

-continued

```
Phe Ser Arg Glu His Tyr Gln Lys Met Leu Phe Gly Asn Glu Pro Phe
        195                 200                 205

Thr Leu Phe Asp Gly Ser Lys Val Lys Thr Phe Lys Gln Tyr Tyr Glu
    210                 215                 220

Glu Gln Ser Gly Gly Ser Tyr Thr Thr Asp Gly Tyr Val Thr Glu Trp
225                 230                 235                 240

Leu Thr Val Pro Gly Lys Ala Ala Asp Tyr Gly Ala Asp Gly Lys Thr
                245                 250                 255

Gly His Asp Asn Lys Gly Pro Lys Gly Ala Arg Asp Leu Val Lys Glu
            260                 265                 270

Ala Leu Lys Ala Ala Ala Glu Lys Gly Leu Asp Leu Ser Gln Phe Asp
        275                 280                 285

Gln Phe Asp Arg Tyr Asp Thr Asn Gly Asp Gly Asn Gln Asn Glu Pro
    290                 295                 300

Asp Gly Val Ile Asp His Leu Met Val Ile His Ala Gly Val Gly Gln
305                 310                 315                 320

Glu Ala Gly Gly Gly Lys Leu Gly Asp Asp Ala Ile Trp Ser His Arg
                325                 330                 335

Ser Lys Leu Ala Gln Asp Pro Val Ala Ile Glu Gly Thr Lys Ser Lys
            340                 345                 350

Val Ser Tyr Trp Asp Gly Lys Val Ala Ala His Asp Tyr Thr Ile Glu
        355                 360                 365

Pro Glu Asp Gly Ala Val Gly Val Phe Ala His Glu Phe Gly His Asp
    370                 375                 380

Leu Gly Leu Pro Asp Glu Tyr Asp Thr Asn Tyr Thr Gly Ala Gly Ser
385                 390                 395                 400

Pro Val Glu Ala Trp Ser Leu Met Ser Gly Gly Ser Trp Thr Gly Arg
                405                 410                 415

Ile Ala Gly Thr Glu Pro Thr Ser Phe Ser Pro Gln Asn Lys Asp Phe
            420                 425                 430

Leu Gln Lys Asn Met Asp Gly Asn Trp Ala Lys Ile Val Glu Val Asp
        435                 440                 445

Tyr Asp Lys Ile Lys Arg Gly Val Gly Phe Pro Thr Tyr Ile Asp Gln
    450                 455                 460

Ser Val Thr Lys Ser Asn Arg Pro Gly Leu Val Arg Val Asn Leu Pro
465                 470                 475                 480

Glu Lys Ser Val Glu Thr Ile Lys Thr Gly Phe Gly Lys His Ala Tyr
                485                 490                 495

Tyr Ser Thr Arg Gly Asp Asp Met His Thr Thr Leu Glu Thr Pro Leu
            500                 505                 510

Phe Asp Leu Thr Lys Ala Ala Asn Ala Lys Phe Asp Tyr Lys Ala Asn
        515                 520                 525

Tyr Glu Leu Glu Ala Glu Cys Asp Phe Ile Glu Val His Ala Val Thr
    530                 535                 540

Glu Asp Gly Thr Lys Thr Leu Ile Asp Lys Leu Gly Asp Lys Val Val
545                 550                 555                 560

Lys Gly Asp Gln Asp Thr Thr Glu Gly Lys Trp Ile Asp Lys Ser Tyr
                565                 570                 575

Asp Leu Ser Gln Phe Lys Gly Lys Lys Val Lys Leu Gln Phe Asp Tyr
            580                 585                 590

Ile Thr Asp Pro Ala Leu Thr Tyr Lys Gly Phe Ala Met Asp Asn Val
        595                 600                 605

Asn Val Thr Val Asp Gly Lys Val Val Phe Ser Asp Asp Ala Glu Gly
```

```
    610                 615                 620

Gln Ala Lys Met Lys Leu Asn Gly Phe Val Val Ser Asp Gly Thr Glu
625                 630                 635                 640

Lys Lys Pro His Tyr Tyr Tyr Leu Glu Trp Arg Asn Tyr Ala Gly Ser
                645                 650                 655

Asp Glu Gly Leu Lys Val Gly Arg Gly Pro Val Tyr Asn Thr Gly Leu
            660                 665                 670

Val Val Trp Tyr Ala Asp Asp Ser Phe Lys Asp Asn Trp Val Gly Arg
        675                 680                 685

His Pro Gly Glu Gly Phe Leu Gly Val Val Asp Ser His Pro Glu Ala
    690                 695                 700

Val Val Gly Asn Leu Asn Gly Lys Pro Val Tyr Gly Asn Thr Gly Leu
705                 710                 715                 720

Gln Ile Ala Asp Ala Ala Phe Ser Leu Asp Gln Thr Pro Ala Trp Asn
                725                 730                 735

Val Asn Ser Phe Thr Arg Gly Gln Phe Asn Tyr Pro Gly Leu Pro Gly
            740                 745                 750

Val Ala Thr Phe Asp Asp Ser Lys Val Tyr Ser Asn Thr Gln Ile Pro
        755                 760                 765

Asp Ala Gly Arg Lys Val Pro Gln Leu Gly Leu Lys Phe Gln Val Val
    770                 775                 780

Gly Gln Ala Asp Asp Lys Ser Ala Gly Ala Ile Trp Ile Arg Arg
785                 790                 795


<210> SEQ ID NO 72
<211> LENGTH: 152
<212> TYPE: PRT
<213> ORGANISM: Bacillus anthracis

<400> SEQUENCE: 72

Met Ser Cys Asn Glu Asn Lys His His Gly Ser Ser His Cys Val Val
1               5                   10                  15

Asp Val Val Lys Phe Ile Asn Glu Leu Gln Asp Cys Ser Thr Thr Thr
            20                  25                  30

Cys Gly Ser Gly Cys Glu Ile Pro Phe Leu Gly Ala His Asn Thr Ala
        35                  40                  45

Ser Val Ala Asn Thr Arg Pro Phe Ile Leu Tyr Thr Lys Ala Gly Ala
    50                  55                  60

Pro Phe Glu Ala Phe Ala Pro Ser Ala Asn Leu Thr Ser Cys Arg Ser
65                  70                  75                  80

Pro Ile Phe Arg Val Glu Ser Val Asp Asp Asp Ser Cys Ala Val Leu
                85                  90                  95

Arg Val Leu Ser Val Val Leu Gly Asp Ser Ser Pro Val Pro Pro Thr
            100                 105                 110

Asp Asp Pro Ile Cys Thr Phe Leu Ala Val Pro Asn Ala Arg Leu Val
        115                 120                 125

Ser Thr Ser Thr Cys Ile Thr Val Asp Leu Ser Cys Phe Cys Ala Ile
    130                 135                 140

Gln Cys Leu Arg Asp Val Thr Ile
145                 150


<210> SEQ ID NO 73
<211> LENGTH: 167
<212> TYPE: PRT
<213> ORGANISM: Bacillus anthracis
```

<400> SEQUENCE: 73

```
Met Phe Ser Ser Asp Cys Glu Phe Thr Lys Ile Asp Cys Glu Ala Lys
1               5                   10                  15

Pro Ala Ser Thr Leu Pro Ala Phe Gly Phe Ala Phe Asn Ala Ser Ala
            20                  25                  30

Pro Gln Phe Ala Ser Leu Phe Thr Pro Leu Leu Leu Pro Ser Val Ser
        35                  40                  45

Pro Asn Pro Asn Ile Thr Val Pro Val Ile Asn Asp Thr Val Ser Val
    50                  55                  60

Gly Asp Gly Ile Arg Ile Leu Arg Ala Gly Ile Tyr Gln Ile Ser Tyr
65                  70                  75                  80

Thr Leu Thr Ile Ser Leu Asp Asn Ser Pro Val Ala Pro Glu Ala Gly
                85                  90                  95

Arg Phe Phe Leu Ser Leu Gly Thr Pro Ala Asn Ile Ile Pro Gly Ser
            100                 105                 110

Gly Thr Ala Val Arg Ser Asn Val Ile Gly Thr Gly Glu Val Asp Val
        115                 120                 125

Ser Ser Gly Val Ile Leu Ile Asn Leu Asn Pro Gly Asp Leu Ile Arg
    130                 135                 140

Ile Val Pro Val Glu Leu Ile Gly Thr Val Asp Ile Arg Ala Ala Ala
145                 150                 155                 160

Leu Thr Val Ala Gln Ile Ser
                165
```

<210> SEQ ID NO 74
<211> LENGTH: 156
<212> TYPE: PRT
<213> ORGANISM: Bacillus anthracis

<400> SEQUENCE: 74

```
Met Ser Cys Asn Cys Asn Glu Asp His His His His Asp Cys Asp Phe
1               5                   10                  15

Asn Cys Val Ser Asn Val Val Arg Phe Ile His Glu Leu Gln Glu Cys
            20                  25                  30

Ala Thr Thr Thr Cys Gly Ser Gly Cys Glu Val Pro Phe Leu Gly Ala
        35                  40                  45

His Asn Ser Ala Ser Val Ala Asn Thr Arg Pro Phe Ile Leu Tyr Thr
    50                  55                  60

Lys Ala Gly Ala Pro Phe Glu Ala Phe Ala Pro Ser Ala Asn Leu Thr
65                  70                  75                  80

Ser Cys Arg Ser Pro Ile Phe Arg Val Glu Ser Ile Asp Asp Asp Asp
                85                  90                  95

Cys Ala Val Leu Arg Val Leu Ser Val Val Leu Gly Asp Thr Ser Pro
            100                 105                 110

Val Pro Pro Thr Asp Asp Pro Ile Cys Thr Phe Leu Ala Val Pro Asn
        115                 120                 125

Ala Arg Leu Ile Ser Thr Asn Thr Cys Leu Thr Val Asp Leu Ser Cys
    130                 135                 140

Phe Cys Ala Ile Gln Cys Leu Arg Asp Val Thr Ile
145                 150                 155
```

<210> SEQ ID NO 75
<211> LENGTH: 182
<212> TYPE: PRT
<213> ORGANISM: Bacillus anthracis

<400> SEQUENCE: 75

Met Glu Val Gly Gly Thr Ser Val Lys Asn Lys Asn Lys Ser Ser Thr
1               5                   10                  15

Val Gly Lys Pro Leu Leu Tyr Ile Ala Gln Val Ser Leu Glu Leu Ala
            20                  25                  30

Ala Pro Lys Thr Lys Arg Ile Ile Leu Thr Asn Phe Glu Asn Glu Asp
        35                  40                  45

Arg Lys Glu Glu Ser Asn Arg Asn Glu Asn Val Val Ser Ser Ala Val
    50                  55                  60

Glu Glu Val Ile Glu Gln Glu Glu Gln Gln Gln Glu Gln Glu Gln Glu
65                  70                  75                  80

Gln Glu Glu Gln Val Glu Glu Lys Thr Glu Glu Glu Glu Gln Val Gln
                85                  90                  95

Glu Gln Gln Glu Pro Val Arg Thr Val Pro Tyr Asn Lys Ser Phe Lys
            100                 105                 110

Asp Met Asn Asn Glu Glu Lys Ile His Phe Leu Leu Asn Arg Pro His
        115                 120                 125

Tyr Ile Pro Lys Val Arg Cys Arg Ile Lys Thr Ala Thr Ile Ser Tyr
    130                 135                 140

Val Gly Ser Ile Ile Ser Tyr Arg Asn Gly Ile Val Ala Ile Met Pro
145                 150                 155                 160

Pro Asn Ser Met Arg Asp Ile Arg Leu Ser Ile Glu Glu Ile Lys Ser
                165                 170                 175

Ile Asp Met Ala Gly Phe
            180

<210> SEQ ID NO 76
<211> LENGTH: 174
<212> TYPE: PRT
<213> ORGANISM: Bacillus anthracis

<400> SEQUENCE: 76

Met Lys Glu Arg Ser Glu Asn Met Arg Ser Ser Ser Arg Lys Leu Thr
1               5                   10                  15

Asn Phe Asn Cys Arg Ala Gln Ala Pro Ser Thr Leu Pro Ala Leu Gly
            20                  25                  30

Phe Ala Phe Asn Ala Thr Ser Pro Gln Phe Ala Thr Leu Phe Thr Pro
        35                  40                  45

Leu Leu Leu Pro Ser Thr Gly Pro Asn Pro Asn Ile Thr Val Pro Val
    50                  55                  60

Ile Asn Asp Thr Ile Ser Thr Gly Thr Gly Ile Arg Ile Gln Val Ala
65                  70                  75                  80

Gly Ile Tyr Gln Ile Ser Tyr Thr Leu Thr Ile Ser Leu Asp Asn Val
                85                  90                  95

Pro Val Thr Pro Glu Ala Ala Arg Phe Phe Leu Thr Leu Asn Ser Ser
            100                 105                 110

Thr Asn Ile Ile Ala Gly Ser Gly Thr Ala Val Arg Ser Asn Ile Ile
        115                 120                 125

Gly Thr Gly Glu Val Asp Val Ser Ser Gly Val Ile Leu Ile Asn Leu
    130                 135                 140

Asn Pro Gly Asp Leu Ile Gln Ile Val Pro Val Glu Val Ile Gly Thr
145                 150                 155                 160

Val Asp Ile Arg Ser Ala Ala Leu Thr Val Ala Gln Ile Arg
                165                 170

<210> SEQ ID NO 77
<211> LENGTH: 796
<212> TYPE: PRT
<213> ORGANISM: Bacillus thuringiensis

<400> SEQUENCE: 77

```
Met Ser Lys Lys Pro Phe Lys Val Leu Ser Ser Ile Ala Leu Thr Ala
1               5                   10                  15

Val Leu Gly Leu Ser Phe Gly Ala Gly Thr Gln Ser Ala Tyr Ala Glu
            20                  25                  30

Thr Pro Val Asn Lys Thr Ala Thr Ser Pro Val Asp Asp His Leu Ile
        35                  40                  45

Pro Glu Glu Arg Leu Ala Asp Ala Leu Lys Lys Arg Gly Val Ile Asp
    50                  55                  60

Ser Lys Ala Ser Glu Thr Glu Thr Lys Lys Ala Val Glu Lys Tyr Val
65                  70                  75                  80

Glu Asn Lys Lys Gly Glu Asn Pro Gly Lys Glu Ala Ala Asn Gly Asp
                85                  90                  95

Gln Leu Thr Lys Asp Ala Ser Asp Phe Leu Lys Lys Val Lys Asp Ala
            100                 105                 110

Lys Ala Asp Thr Lys Glu Lys Leu Asn Gln Pro Ala Thr Gly Thr Pro
        115                 120                 125

Ala Ala Thr Gly Pro Val Lys Gly Gly Leu Asn Gly Lys Val Pro Thr
    130                 135                 140

Ser Pro Ala Lys Gln Lys Asp Tyr Asn Gly Glu Val Arg Lys Asp Lys
145                 150                 155                 160

Val Leu Val Leu Leu Val Glu Tyr Ala Asp Phe Lys His Asn Asn Ile
                165                 170                 175

Asp Lys Glu Pro Gly Tyr Met Tyr Ser Asn Asp Phe Asn Lys Glu His
            180                 185                 190

Tyr Glu Lys Met Leu Phe Gly Asn Glu Pro Phe Thr Leu Asp Asp Gly
        195                 200                 205

Ser Lys Ile Glu Thr Phe Lys Gln Tyr Tyr Glu Glu Gln Ser Gly Gly
    210                 215                 220

Ser Tyr Thr Val Asp Gly Thr Val Thr Lys Trp Leu Thr Val Pro Gly
225                 230                 235                 240

Lys Ala Ala Asp Tyr Gly Ala Asp Ala Pro Gly Gly Gly His Asp Asn
                245                 250                 255

Lys Gly Pro Lys Gly Pro Arg Asp Leu Val Lys Asp Ala Leu Lys Ala
            260                 265                 270

Ala Val Asp Ser Gly Ile Asp Leu Ser Glu Phe Asp Gln Phe Asp Gln
        275                 280                 285

Tyr Asp Val Asn Gly Asp Gly Asn Lys Asn Gln Pro Asp Gly Leu Ile
    290                 295                 300

Asp His Leu Met Ile Ile His Ala Gly Val Gly Gln Glu Ala Gly Gly
305                 310                 315                 320

Gly Lys Leu Gly Asp Asp Ala Ile Trp Ser His Arg Trp Thr Val Gly
                325                 330                 335

Pro Lys Pro Phe Pro Ile Glu Gly Thr Gln Ala Lys Val Pro Tyr Trp
            340                 345                 350

Gly Gly Lys Met Ala Ala Phe Asp Tyr Thr Ile Glu Pro Glu Asp Gly
        355                 360                 365

Ala Val Gly Val Phe Ala His Glu Tyr Gly His Asp Leu Gly Leu Pro
    370                 375                 380
```

```
Asp Glu Tyr Asp Thr Gln Tyr Ser Gly Gln Gly Glu Pro Ile Glu Ala
385                 390                 395                 400

Trp Ser Ile Met Ser Gly Gly Ser Trp Ala Gly Lys Ile Ala Gly Thr
                405                 410                 415

Thr Pro Thr Ser Phe Ser Pro Gln Asn Lys Glu Phe Phe Gln Lys Thr
            420                 425                 430

Ile Gly Gly Asn Trp Ala Asn Ile Val Glu Val Asp Tyr Glu Lys Leu
        435                 440                 445

Asn Lys Gly Ile Gly Leu Ala Thr Tyr Leu Asp Gln Ser Val Thr Lys
    450                 455                 460

Ser Ala Arg Pro Gly Met Ile Arg Val Asn Leu Pro Asp Lys Asp Val
465                 470                 475                 480

Lys Thr Ile Glu Pro Ala Phe Gly Lys Gln Tyr Tyr Tyr Ser Thr Lys
                485                 490                 495

Gly Asp Asp Leu His Thr Lys Met Glu Thr Pro Leu Phe Asp Leu Thr
            500                 505                 510

Asn Ala Thr Ser Ala Lys Phe Asp Phe Lys Ser Leu Tyr Glu Ile Glu
        515                 520                 525

Ala Gly Tyr Asp Phe Leu Glu Val His Ala Val Thr Glu Asp Gly Lys
    530                 535                 540

Gln Thr Leu Ile Glu Arg Leu Gly Glu Lys Ala Asn Ser Gly Asn Ala
545                 550                 555                 560

Asp Ser Thr Asn Gly Lys Trp Ile Asp Lys Ser Tyr Asp Leu Ser Gln
                565                 570                 575

Phe Lys Gly Lys Lys Val Lys Leu Thr Phe Asp Tyr Ile Thr Asp Gly
            580                 585                 590

Gly Leu Ala Leu Asn Gly Phe Ala Leu Asp Asn Ala Ser Leu Thr Val
        595                 600                 605

Asp Gly Lys Val Val Phe Ser Asp Asp Ala Glu Gly Thr Pro Gln Leu
    610                 615                 620

Lys Leu Asp Gly Phe Val Val Ser Asn Gly Thr Glu Lys Lys Lys His
625                 630                 635                 640

Asn Tyr Tyr Val Glu Trp Arg Asn Tyr Ala Gly Ala Asp Asn Ala Leu
                645                 650                 655

Lys Phe Ala Arg Gly Pro Val Phe Asn Thr Gly Met Val Val Trp Tyr
            660                 665                 670

Ala Asp Ser Ala Tyr Thr Asp Asn Trp Val Gly Val His Pro Gly His
        675                 680                 685

Gly Phe Leu Gly Val Val Asp Ser His Pro Glu Ala Ile Val Gly Thr
    690                 695                 700

Leu Asn Gly Lys Pro Thr Val Lys Ser Ser Thr Arg Phe Gln Ile Ala
705                 710                 715                 720

Asp Ala Ala Phe Ser Phe Asp Lys Thr Pro Ala Trp Lys Val Val Ser
                725                 730                 735

Pro Thr Arg Gly Thr Phe Thr Tyr Asp Gly Leu Ala Gly Val Pro Lys
            740                 745                 750

Phe Asp Asp Ser Lys Thr Tyr Ile Asn Gln Gln Ile Pro Asp Ala Gly
        755                 760                 765

Arg Ile Leu Pro Lys Leu Gly Leu Lys Phe Glu Val Val Gly Gln Ala
    770                 775                 780

Asp Asp Asn Ser Ala Gly Ala Val Arg Leu Tyr Arg
785                 790                 795
```

<210> SEQ ID NO 78
<211> LENGTH: 430
<212> TYPE: PRT
<213> ORGANISM: Bacillus cereus

<400> SEQUENCE: 78

Met Lys His Asn Asp Cys Phe Asp His Asn Asn Cys Asn Pro Ile Val
1               5                   10                  15

Phe Ser Ala Asp Cys Cys Lys Asn Pro Gln Ser Val Pro Ile Thr Arg
            20                  25                  30

Glu Gln Leu Ser Gln Leu Ile Thr Leu Leu Asn Ser Leu Val Ser Ala
        35                  40                  45

Ile Ser Ala Phe Phe Ala Asn Pro Ser Asn Ala Asn Arg Leu Val Leu
    50                  55                  60

Leu Asp Leu Phe Asn Gln Phe Leu Ile Phe Leu Asn Ser Leu Leu Pro
65                  70                  75                  80

Ser Pro Glu Val Asn Phe Leu Lys Gln Leu Thr Gln Ser Ile Ile Val
                85                  90                  95

Leu Leu Gln Ser Pro Ala Pro Asn Leu Gly Gln Leu Ser Thr Leu Leu
            100                 105                 110

Gln Gln Phe Tyr Ser Ala Leu Ala Gln Phe Phe Phe Ala Leu Asp Leu
        115                 120                 125

Ile Pro Ile Ser Cys Asn Ser Asn Val Asp Ser Ala Thr Leu Gln Leu
    130                 135                 140

Leu Phe Asn Leu Leu Ile Gln Leu Ile Asn Ala Thr Pro Gly Ala Thr
145                 150                 155                 160

Gly Pro Thr Gly Pro Thr Gly Pro Thr Gly Pro Thr Gly Pro Ala Gly
                165                 170                 175

Thr Gly Ala Gly Pro Thr Gly Ala Thr Gly Ala Thr Gly Ala Thr Gly
            180                 185                 190

Pro Thr Gly Ala Thr Gly Pro Ala Gly Thr Gly Gly Ala Thr Gly Ala
        195                 200                 205

Thr Gly Ala Thr Gly Val Thr Gly Ala Thr Gly Ala Thr Gly Ala Thr
    210                 215                 220

Gly Pro Thr Gly Pro Thr Gly Ala Thr Gly Pro Thr Gly Ala Thr Gly
225                 230                 235                 240

Ala Thr Gly Ala Thr Gly Pro Thr Gly Ala Thr Gly Pro Thr Gly Ala
                245                 250                 255

Thr Gly Leu Thr Gly Ala Thr Gly Ala Ala Gly Gly Gly Ala Ile Ile
            260                 265                 270

Pro Phe Ala Ser Gly Thr Thr Pro Ser Ala Leu Val Asn Ala Leu Val
        275                 280                 285

Ala Asn Thr Gly Thr Leu Leu Gly Phe Gly Phe Ser Gln Pro Gly Val
    290                 295                 300

Ala Leu Thr Gly Gly Thr Ser Ile Thr Leu Ala Leu Gly Val Gly Asp
305                 310                 315                 320

Tyr Ala Phe Val Ala Pro Arg Ala Gly Thr Ile Thr Ser Leu Ala Gly
                325                 330                 335

Phe Phe Ser Ala Thr Ala Ala Leu Ala Pro Ile Ser Pro Val Gln Val
            340                 345                 350

Gln Ile Gln Ile Leu Thr Ala Pro Ala Ala Ser Asn Thr Phe Thr Val
        355                 360                 365

Gln Gly Ala Pro Leu Leu Leu Thr Pro Ala Phe Ala Ala Ile Ala Ile
    370                 375                 380

-continued

```
Gly Ser Thr Ala Ser Gly Ile Ile Ala Glu Ala Ile Pro Val Ala Ala
385                 390                 395                 400

Gly Asp Lys Ile Leu Leu Tyr Val Ser Leu Thr Ala Ala Ser Pro Ile
                405                 410                 415

Ala Ala Val Ala Gly Phe Val Ser Ala Gly Ile Asn Ile Val
            420                 425                 430


<210> SEQ ID NO 79
<211> LENGTH: 437
<212> TYPE: PRT
<213> ORGANISM: Bacillus cereus

<400> SEQUENCE: 79

Met Lys His Asn Asp Cys Phe Gly His Asn Asn Cys Asn Asn Pro Ile
1               5                   10                  15

Val Phe Thr Pro Asp Cys Cys Asn Asn Pro Gln Thr Val Pro Ile Thr
            20                  25                  30

Ser Glu Gln Leu Gly Arg Leu Ile Thr Leu Leu Asn Ser Leu Ile Ala
        35                  40                  45

Ala Ile Ala Ala Phe Phe Ala Asn Pro Ser Asp Ala Asn Arg Leu Ala
    50                  55                  60

Leu Leu Asn Leu Phe Thr Gln Leu Leu Asn Leu Leu Asn Glu Leu Ala
65                  70                  75                  80

Pro Ser Pro Glu Gly Asn Phe Leu Lys Gln Leu Ile Gln Ser Ile Ile
                85                  90                  95

Asn Leu Leu Gln Ser Pro Asn Pro Asn Leu Gly Gln Leu Leu Ser Leu
            100                 105                 110

Leu Gln Gln Phe Tyr Ser Ala Leu Ala Pro Phe Phe Phe Ser Leu Ile
        115                 120                 125

Leu Asp Pro Ala Ser Leu Gln Leu Leu Leu Asn Leu Leu Ala Gln Leu
    130                 135                 140

Ile Gly Val Thr Pro Gly Gly Gly Ala Thr Gly Pro Thr Gly Pro Thr
145                 150                 155                 160

Gly Pro Gly Gly Gly Ala Thr Gly Pro Thr Gly Pro Thr Gly Pro Gly
                165                 170                 175

Gly Gly Ala Thr Gly Pro Thr Gly Ala Thr Gly Pro Thr Gly Asp Thr
            180                 185                 190

Gly Leu Ala Gly Ala Thr Gly Ala Thr Gly Pro Thr Gly Asp Thr Gly
        195                 200                 205

Val Ala Gly Pro Ala Gly Pro Thr Gly Pro Thr Gly Asp Thr Gly Leu
    210                 215                 220

Ala Gly Ala Thr Gly Pro Thr Gly Pro Thr Gly Asp Thr Gly Leu Ala
225                 230                 235                 240

Gly Ala Thr Gly Pro Thr Gly Ala Thr Gly Leu Ala Gly Ala Thr Gly
                245                 250                 255

Pro Thr Gly Ala Thr Gly Leu Thr Gly Ala Thr Gly Ala Thr Gly Ala
            260                 265                 270

Ala Gly Gly Gly Ala Ile Ile Pro Phe Ala Ser Gly Thr Thr Pro Ala
        275                 280                 285

Ala Leu Val Asn Ala Leu Ile Ala Asn Thr Gly Thr Leu Leu Gly Phe
    290                 295                 300

Gly Phe Ser Gln Pro Gly Ile Gly Leu Ala Gly Gly Thr Ser Ile Thr
305                 310                 315                 320

Leu Ala Leu Gly Val Gly Asp Tyr Ala Phe Val Ala Pro Arg Asp Gly
```

```
                325                 330                 335

Val Ile Thr Ser Leu Ala Gly Phe Phe Ser Ala Thr Ala Ala Leu Ser
            340                 345                 350

Pro Leu Ser Pro Val Gln Val Gln Ile Gln Ile Leu Thr Ala Pro Ala
        355                 360                 365

Ala Ser Asn Thr Phe Thr Val Gln Gly Ala Pro Leu Leu Leu Thr Pro
    370                 375                 380

Ala Phe Ala Ala Ile Ala Ile Gly Ser Thr Ala Ser Gly Ile Ile Pro
385                 390                 395                 400

Glu Ala Ile Pro Val Val Ala Gly Asp Lys Ile Leu Leu Tyr Val Ser
                405                 410                 415

Leu Thr Ala Ala Ser Pro Ile Ala Ala Val Ala Gly Phe Val Ser Ala
            420                 425                 430

Gly Ile Asn Ile Val
        435


<210> SEQ ID NO 80
<211> LENGTH: 119
<212> TYPE: PRT
<213> ORGANISM: Bacillus anthracis

<400> SEQUENCE: 80

Met Leu Phe Thr Ser Trp Leu Leu Phe Phe Ile Phe Ala Leu Ala Ala
1               5                   10                  15

Phe Arg Leu Thr Arg Leu Ile Val Tyr Asp Lys Ile Thr Gly Phe Leu
            20                  25                  30

Arg Arg Pro Phe Ile Asp Glu Leu Glu Ile Thr Glu Pro Asp Gly Ser
        35                  40                  45

Val Ser Thr Phe Thr Lys Val Lys Gly Lys Gly Leu Arg Lys Trp Ile
    50                  55                  60

Gly Glu Leu Leu Ser Cys Tyr Trp Cys Thr Gly Val Trp Val Ser Ala
65                  70                  75                  80

Phe Leu Leu Val Leu Tyr Asn Trp Ile Pro Ile Val Ala Glu Pro Leu
                85                  90                  95

Leu Ala Leu Leu Ala Ile Ala Gly Ala Ala Ala Ile Ile Glu Thr Ile
            100                 105                 110

Thr Gly Tyr Phe Met Gly Glu
        115


<210> SEQ ID NO 81
<211> LENGTH: 61
<212> TYPE: PRT
<213> ORGANISM: Bacillus anthracis

<400> SEQUENCE: 81

Met Phe Ala Val Ser Asn Asn Pro Arg Gln Asn Ser Tyr Asp Leu Gln
1               5                   10                  15

Gln Trp Tyr His Met Gln Gln Gln His Gln Ala Gln Gln Gln Ala Tyr
            20                  25                  30

Gln Glu Gln Leu Gln Gln Gln Gly Phe Val Lys Lys Lys Gly Cys Asn
        35                  40                  45

Cys Gly Lys Lys Lys Ser Thr Ile Lys His Tyr Glu Glu
    50                  55                  60


<210> SEQ ID NO 82
<211> LENGTH: 481
<212> TYPE: PRT
```

<213> ORGANISM: Bacillus anthracis

<400> SEQUENCE: 82

```
Met Ser Arg Tyr Asp Asp Ser Gln Asn Lys Phe Ser Lys Pro Cys Phe
1               5                   10                  15

Pro Ser Ser Ala Gly Arg Ile Pro Asn Thr Pro Ser Ile Pro Val Thr
            20                  25                  30

Lys Ala Gln Leu Arg Thr Phe Arg Ala Ile Ile Ile Asp Leu Thr Lys
        35                  40                  45

Ile Ile Pro Lys Leu Phe Ala Asn Pro Ser Pro Gln Asn Ile Glu Asp
    50                  55                  60

Leu Ile Asp Thr Leu Asn Leu Leu Ser Lys Phe Ile Cys Ser Leu Asp
65                  70                  75                  80

Ala Ala Ser Ser Leu Lys Ala Gln Gly Leu Ala Ile Ile Lys Asn Leu
                85                  90                  95

Ile Thr Ile Leu Lys Asn Pro Thr Phe Val Ala Ser Ala Val Phe Ile
            100                 105                 110

Glu Leu Gln Asn Leu Ile Asn Tyr Leu Leu Ser Ile Thr Lys Leu Phe
        115                 120                 125

Arg Ile Asp Pro Cys Thr Leu Gln Glu Leu Leu Lys Leu Ile Ala Ala
    130                 135                 140

Leu Gln Thr Ala Leu Val Asn Ser Ala Ser Phe Ile Gln Gly Pro Thr
145                 150                 155                 160

Gly Pro Thr Gly Pro Thr Gly Pro Thr Gly Pro Ala Gly Ala Thr Gly
                165                 170                 175

Ala Thr Gly Pro Gln Gly Val Gln Gly Pro Ala Gly Ala Thr Gly Ala
            180                 185                 190

Thr Gly Pro Gln Gly Val Gln Gly Pro Ala Gly Ala Thr Gly Ala Thr
        195                 200                 205

Gly Pro Gln Gly Ala Gln Gly Pro Ala Gly Ala Thr Gly Ala Thr Gly
    210                 215                 220

Pro Gln Gly Ala Gln Gly Pro Ala Gly Ala Thr Gly Ala Thr Gly Pro
225                 230                 235                 240

Gln Gly Ile Gln Gly Pro Ala Gly Ala Thr Gly Ala Thr Gly Pro Gln
                245                 250                 255

Gly Val Gln Gly Pro Thr Gly Ala Thr Gly Ile Gly Val Thr Gly Pro
            260                 265                 270

Thr Gly Pro Ser Gly Gly Pro Ala Gly Ala Thr Gly Pro Gln Gly Pro
        275                 280                 285

Gln Gly Asn Thr Gly Ala Thr Gly Pro Gln Gly Ile Gln Gly Pro Ala
    290                 295                 300

Gly Ala Thr Gly Ala Thr Gly Pro Gln Gly Ala Gln Gly Pro Ala Gly
305                 310                 315                 320

Ala Thr Gly Ala Thr Gly Pro Gln Gly Val Gln Gly Pro Thr Gly Ala
                325                 330                 335

Thr Gly Ile Gly Val Thr Gly Pro Thr Gly Pro Ser Gly Pro Ser Phe
            340                 345                 350

Pro Val Ala Thr Ile Val Val Thr Asn Asn Ile Gln Gln Thr Val Leu
        355                 360                 365

Gln Phe Asn Asn Phe Ile Phe Asn Thr Ala Ile Asn Val Asn Asn Ile
    370                 375                 380

Ile Phe Asn Gly Thr Asp Thr Val Thr Val Ile Asn Ala Gly Ile Tyr
385                 390                 395                 400
```

-continued

```
Val Ile Ser Val Ser Ile Ser Thr Thr Ala Pro Gly Cys Ala Pro Leu
                405                 410                 415

Gly Val Gly Ile Ser Ile Asn Gly Ala Val Ala Thr Asp Asn Phe Ser
            420                 425                 430

Ser Asn Leu Ile Gly Asp Ser Leu Ser Phe Thr Thr Ile Glu Thr Leu
        435                 440                 445

Thr Ala Gly Ala Asn Ile Ser Val Gln Ser Thr Leu Asn Glu Ile Thr
    450                 455                 460

Ile Pro Ala Thr Gly Asn Thr Asn Ile Arg Leu Thr Val Phe Arg Ile
465                 470                 475                 480

Ala


<210> SEQ ID NO 83
<211> LENGTH: 275
<212> TYPE: PRT
<213> ORGANISM: Bacillus thuringiensis

<400> SEQUENCE: 83

Met Lys Met Lys Arg Gly Ile Thr Thr Leu Leu Ser Val Ala Val Leu
1               5                   10                  15

Ser Thr Ser Leu Val Ala Cys Ser Gly Ile Thr Glu Lys Thr Val Ala
            20                  25                  30

Lys Glu Glu Lys Val Lys Leu Thr Asp Gln Gln Leu Met Ala Asp Leu
        35                  40                  45

Trp Tyr Gln Thr Ala Gly Glu Met Lys Ala Leu Tyr Tyr Gln Gly Tyr
    50                  55                  60

Asn Ile Gly Gln Leu Lys Leu Asp Ala Val Leu Ala Lys Gly Thr Glu
65                  70                  75                  80

Lys Lys Pro Ala Ile Val Leu Asp Leu Asp Glu Thr Val Leu Asp Asn
                85                  90                  95

Ser Pro His Gln Ala Met Ser Val Lys Thr Gly Lys Gly Tyr Pro Tyr
            100                 105                 110

Lys Trp Asp Asp Trp Ile Asn Lys Ala Glu Ala Glu Ala Leu Pro Gly
        115                 120                 125

Ala Ile Asp Phe Leu Lys Tyr Thr Glu Ser Lys Gly Val Asp Ile Tyr
    130                 135                 140

Tyr Ile Ser Asn Arg Lys Thr Asn Gln Leu Asp Ala Thr Ile Lys Asn
145                 150                 155                 160

Leu Glu Arg Val Gly Ala Pro Gln Ala Thr Lys Glu His Ile Leu Leu
                165                 170                 175

Gln Asp Pro Lys Glu Lys Gly Lys Glu Lys Arg Arg Glu Leu Val Ser
            180                 185                 190

Gln Thr His Asp Ile Val Leu Phe Phe Gly Asp Asn Leu Ser Asp Phe
        195                 200                 205

Thr Gly Phe Asp Gly Lys Ser Val Lys Asp Arg Asn Gln Ala Val Ala
    210                 215                 220

Asp Ser Lys Ala Gln Phe Gly Glu Lys Phe Ile Ile Phe Pro Asn Pro
225                 230                 235                 240

Met Tyr Gly Asp Trp Glu Gly Ala Leu Tyr Asp Tyr Asp Phe Lys Lys
                245                 250                 255

Ser Asp Ala Glu Lys Asp Lys Ile Arg Arg Asp Asn Leu Lys Ser Phe
            260                 265                 270

Asp Thr Lys
        275
```

<210> SEQ ID NO 84
<211> LENGTH: 795
<212> TYPE: PRT
<213> ORGANISM: Bacillus thuringiensis

<400> SEQUENCE: 84

Met Lys Lys Lys Lys Lys Leu Lys Pro Leu Ala Val Leu Thr Thr Ala
1               5                   10                  15

Ala Val Leu Ser Ser Thr Phe Ala Phe Gly Gly His Ala Ala Tyr Ala
            20                  25                  30

Glu Thr Pro Thr Ser Ser Leu Pro Ile Asp Glu His Leu Ile Pro Glu
        35                  40                  45

Glu Arg Leu Ala Glu Ala Leu Lys Gln Arg Gly Val Ile Asp Gln Ser
    50                  55                  60

Ala Ser Gln Ala Glu Thr Ser Lys Ala Val Glu Lys Tyr Val Glu Lys
65                  70                  75                  80

Lys Lys Gly Glu Asn Pro Gly Lys Glu Ile Leu Thr Gly Asp Ser Leu
                85                  90                  95

Thr Gln Glu Ala Ser Asp Phe Met Lys Lys Val Lys Asp Ala Lys Met
            100                 105                 110

Arg Glu Asn Glu Gln Ala Gln Gln Pro Glu Val Gly Pro Val Ala Gly
        115                 120                 125

Gln Gly Ala Ala Leu Asn Pro Gly Lys Leu Asn Gly Lys Val Pro Thr
    130                 135                 140

Thr Ser Ala Lys Gln Glu Glu Tyr Asn Gly Ala Val Arg Lys Asp Lys
145                 150                 155                 160

Val Leu Val Leu Leu Val Glu Phe Ser Asp Phe Lys His Asn Asn Ile
                165                 170                 175

Asp Gln Glu Pro Gly Tyr Met Tyr Ser Lys Asp Phe Asn Arg Glu His
            180                 185                 190

Tyr Gln Lys Met Leu Phe Gly Asp Glu Pro Phe Thr Leu Phe Asp Gly
        195                 200                 205

Ser Lys Ile Asn Thr Phe Lys Gln Tyr Tyr Glu Glu Gln Ser Gly Gly
    210                 215                 220

Ser Tyr Thr Val Asp Gly Thr Val Thr Glu Trp Leu Thr Val Pro Gly
225                 230                 235                 240

Lys Ala Ser Asp Tyr Gly Ala Asp Ala Gly Thr Gly His Asp Asn Lys
                245                 250                 255

Gly Pro Leu Gly Pro Lys Asp Leu Val Lys Glu Ala Leu Lys Ala Ala
            260                 265                 270

Val Ala Lys Gly Ile Asn Leu Ala Asp Phe Asp Gln Tyr Asp Gln Tyr
        275                 280                 285

Asp Gln Asn Gly Asn Gly Asn Lys Asn Glu Pro Asp Gly Ile Ile Asp
    290                 295                 300

His Leu Met Val Val His Ala Gly Val Gly Gln Glu Ala Gly Gly Gly
305                 310                 315                 320

Lys Leu Lys Asp Asp Ala Ile Trp Ser His Arg Ser Lys Leu Gly Ser
                325                 330                 335

Lys Pro Tyr Ala Ile Asp Gly Thr Lys Ser Ser Val Ser Asn Trp Gly
            340                 345                 350

Gly Lys Met Ala Ala Tyr Asp Tyr Thr Ile Glu Pro Glu Asp Gly Ala
        355                 360                 365

Val Gly Val Phe Ala His Glu Tyr Gly His Asp Leu Gly Leu Pro Asp
    370                 375                 380

-continued

```
Glu Tyr Asp Thr Lys Tyr Ser Gly Gln Gly Glu Pro Val Glu Ser Trp
385                 390                 395                 400

Ser Ile Met Ser Gly Gly Ser Trp Ala Gly Lys Ile Ala Gly Thr Glu
                405                 410                 415

Pro Thr Ser Phe Ser Pro Gln Asn Lys Glu Phe Phe Gln Lys Asn Met
            420                 425                 430

Lys Gly Asn Trp Ala Asn Ile Leu Glu Val Asp Tyr Asp Lys Leu Ser
        435                 440                 445

Lys Gly Ile Gly Val Ala Thr Tyr Val Asp Gln Ser Thr Thr Lys Ser
    450                 455                 460

Lys Arg Pro Gly Ile Val Arg Val Asn Leu Pro Asp Lys Asp Ile Lys
465                 470                 475                 480

Asn Ile Glu Ser Ala Phe Gly Lys Lys Phe Tyr Tyr Ser Thr Lys Gly
                485                 490                 495

Asn Asp Ile His Thr Thr Leu Glu Thr Pro Val Phe Asp Leu Thr Asn
            500                 505                 510

Ala Lys Asp Ala Lys Phe Asp Tyr Lys Ala Phe Tyr Glu Leu Glu Ala
        515                 520                 525

Lys Tyr Asp Phe Leu Asp Val Tyr Ala Ile Ala Glu Asp Gly Thr Lys
    530                 535                 540

Thr Arg Ile Asp Arg Met Gly Glu Lys Asp Ile Lys Gly Gly Ala Asp
545                 550                 555                 560

Thr Thr Asp Gly Lys Trp Val Asp Lys Ser Tyr Asp Leu Ser Gln Phe
                565                 570                 575

Lys Gly Lys Lys Val Lys Leu Gln Phe Glu Tyr Leu Thr Asp Ile Ala
            580                 585                 590

Val Ala Tyr Lys Gly Phe Ala Leu Asp Asn Ala Ala Leu Thr Val Asp
        595                 600                 605

Gly Lys Val Val Phe Ser Asp Asp Ala Glu Gly Gln Pro Ala Met Thr
    610                 615                 620

Leu Lys Gly Phe Thr Val Ser Asn Gly Phe Glu Gln Lys Lys His Asn
625                 630                 635                 640

Tyr Tyr Val Glu Trp Arg Asn Tyr Ala Gly Ser Asp Thr Ala Leu Gln
                645                 650                 655

Tyr Ala Arg Gly Pro Val Phe Asn Thr Gly Met Val Val Trp Tyr Ala
            660                 665                 670

Asp Gln Ser Phe Thr Asp Asn Trp Val Gly Val His Pro Gly Glu Gly
        675                 680                 685

Phe Leu Gly Val Val Asp Ser His Pro Glu Ala Ile Val Gly Thr Leu
    690                 695                 700

Asn Gly Gln Pro Thr Val Lys Ser Ser Thr Arg Tyr Gln Ile Ala Asp
705                 710                 715                 720

Ala Ala Phe Ser Phe Asp Gln Thr Pro Ala Trp Lys Val Asn Ser Pro
                725                 730                 735

Thr Arg Gly Ile Phe Asp Tyr Lys Gly Leu Pro Gly Val Ala Lys Phe
            740                 745                 750

Asp Asp Ser Lys Gln Tyr Ile Asn Ser Val Ile Pro Asp Ala Gly Arg
        755                 760                 765

Lys Leu Pro Lys Leu Gly Leu Lys Phe Glu Val Val Gly Gln Ala Glu
    770                 775                 780

Asp Lys Ser Ala Gly Ala Val Trp Leu His Arg
785                 790                 795
```

<210> SEQ ID NO 85
<211> LENGTH: 169
<212> TYPE: DNA
<213> ORGANISM: Bacillus anthracis

<400> SEQUENCE: 85

```
taatcaccct cttccaaatc aatcatatgt tatacatata ctaaactttc cattttttta    60

aattgttcaa gtagtttaag atttcttttc aataattcaa atgtccgtgt cattttcttt   120

cggttttgca tctactatat aatgaacgct ttatggaggt gaatttatg              169
```

<210> SEQ ID NO 86
<211> LENGTH: 303
<212> TYPE: DNA
<213> ORGANISM: Bacillus anthracis

<400> SEQUENCE: 86

```
atttatttca ttcaattttt cctatttagt acctaccgca ctcacaaaaa gcacctctca    60

ttaatttata ttatagtcat tgaaatctaa tttaatgaaa tcatcatact atatgtttta   120

taagaagtaa aggtaccata cttaattaat acatatctat acacttcaat atcacagcat   180

gcagttgaat tatatccaac tttcatttca aattaaataa gtgcctccgc tattgtgaat   240

gtcatttact ctccctacta catttaataa ttatgacaag caatcatagg aggttactac   300

atg                                                                303
```

<210> SEQ ID NO 87
<211> LENGTH: 173
<212> TYPE: DNA
<213> ORGANISM: Bacillus anthracis

<400> SEQUENCE: 87

```
aattacataa caagaactac attagggagc aagcagtcta gcgaaagcta actgcttttt    60

tattaaataa ctattttatt aaatttcata tatacaatcg cttgtccatt tcatttggct   120

ctacccacgc atttactatt agtaatatga attttttcaga ggtggatttt att         173
```

<210> SEQ ID NO 88
<211> LENGTH: 124
<212> TYPE: DNA
<213> ORGANISM: Bacillus weihenstephensis

<400> SEQUENCE: 88

```
ctatgattta agatacacaa tagcaaaaga gaaacatatt atataacgat aaatgaaact    60

tatgtatatg tatggtaact gtatatatta ctacaataca gtatactcat aggaggtagg   120

tatg                                                               124
```

<210> SEQ ID NO 89
<211> LENGTH: 376
<212> TYPE: DNA
<213> ORGANISM: Bacillus weihenstephensis

<400> SEQUENCE: 89

```
ggtaggtaga tttgaaatat gatgaagaaa aggaataact aaaaggagtc gatatccgac    60

tccttttagt tataaataat gtggaattag agtataattt tatataggta tattgtatta   120

gatgaacgct ttatccttta attgtgatta atgatggatt gtaagagaag gggcttacag   180

tcctttttt atggtgttct ataagccttt ttaaaagggg taccacccca cacccaaaaa    240

cagggggggt tataactaca tattggatgt tttgtaacgt acaagaatcg gtattaatta   300
```

ccctgtaaat aagttatgtg tatataaggt aactttatat attctcctac aataaaataa 360
aggaggtaat aaagtg 376

<210> SEQ ID NO 90
<211> LENGTH: 225
<212> TYPE: DNA
<213> ORGANISM: Bacillus thuringiensis

<400> SEQUENCE: 90
aacccttaat gcattggtta aacattgtaa agtctaaagc atggataatg ggcgagaagt 60
aagtagattg ttaacaccct gggtcaaaaa ttgatattta gtaaaattag ttgcactttg 120
tgcatttttt cataagatga gtcatatgtt ttaaattgta gtaatgaaaa acagtattat 180
atcataatga attggtatct taataaaaga gatggaggta actta 225

<210> SEQ ID NO 91
<211> LENGTH: 125
<212> TYPE: DNA
<213> ORGANISM: Bacillus thuringiensis

<400> SEQUENCE: 91
taattccacc ttcccttatc ctctttcgcc tatttaaaaa aaggtcttga gattgtgacc 60
aaatctcctc aactccaata tcttattaat gtaaatacaa acaagaagat aaggagtgac 120
attaa 125

<210> SEQ ID NO 92
<211> LENGTH: 144
<212> TYPE: DNA
<213> ORGANISM: Bacillus thuringiensis

<400> SEQUENCE: 92
aggatgtctt tttttatatt gtattatgta catccctact atataaattc cctgctttta 60
tcgtaagaat taacgtaata tcaaccatat cccgttcata ttgtagtagt gtatgtcaga 120
actcacgaga aggagtgaac ataa 144

<210> SEQ ID NO 93
<211> LENGTH: 126
<212> TYPE: DNA
<213> ORGANISM: Bacillus thuringiensis

<400> SEQUENCE: 93
ttaatgtcac tccttatctt cttgtttgta tttacattaa taagatattg gagttgagga 60
gatttggtca caatctcaag accttttttt taaataggcg aaagaggata agggaaggtg 120
gaatta 126

<210> SEQ ID NO 94
<211> LENGTH: 103
<212> TYPE: DNA
<213> ORGANISM: Bacillus thuringiensis

<400> SEQUENCE: 94
atatattttc ataatacgag aaaaagcgga gtttaaaaga atgagggaac ggaaataaag 60
agttgttcat atagtaaata gacagaattg acagtagagg aga 103

<210> SEQ ID NO 95
<211> LENGTH: 169
<212> TYPE: DNA

<213> ORGANISM: Bacillus thuringiensis

<400> SEQUENCE: 95

```
aaactaaata atgagctaag catggattgg gtggcagaat tatctgccac ccaatccatg    60
cttaacgagt attattatgt aaatttctta aaattgggaa cttgtctaga acatagaacc   120
tgtccttttc attaactgaa agtagaaaca gataaaggag tgaaaaaca               169
```

<210> SEQ ID NO 96
<211> LENGTH: 111
<212> TYPE: DNA
<213> ORGANISM: Bacillus thuringiensis

<400> SEQUENCE: 96

```
attcactaca acggggatga gtttgatgcg gatacatatg agaagtaccg gaaagtgttt    60
gtagaacatt acaaagatat attatctcca tcataaagga gagatgcaaa g           111
```

<210> SEQ ID NO 97
<211> LENGTH: 273
<212> TYPE: DNA
<213> ORGANISM: Bacillus anthracis

<400> SEQUENCE: 97

```
cgcgcaccac ttcgtcgtac aacaacgcaa gaagaagttg gggatacagc agtattctta    60
ttcagtgatt tagcacgcgg cgtaacagga gaaaacattc acgttgattc agggtatcat   120
atcttaggat aaatataata ttaattttaa aggacaatct ctacatgttg agattgtcct   180
ttttatttgt tcttagaaag aacgattttt aacgaaagtt cttaccacgt tatgaatata   240
agtataatag tacacgattt attcagctac gta                                273
```

<210> SEQ ID NO 98
<211> LENGTH: 303
<212> TYPE: DNA
<213> ORGANISM: Bacillus anthracis

<400> SEQUENCE: 98

```
tgaagtatct agagctaatt tacgcaaagg aatctcagga caacactttc gcaacaccta    60
tattttaaat ttaataaaaa aagagactcc ggagtcagaa attataaagc tagctgggtt   120
caaatcaaaa atttcactaa aacgatatta tcaatacgca gaaaatggaa aaaacgcctt   180
atcataaggc gttttttcca ttttttcttc aaacaaacga ttttactatg accatttaac   240
taatttttgc atctactatg atgagtttca ttcacattct cattagaaag gagagattta   300
atg                                                                 303
```

<210> SEQ ID NO 99
<211> LENGTH: 240
<212> TYPE: DNA
<213> ORGANISM: Bacillus anthracis

<400> SEQUENCE: 99

```
tatatcatat gtaaaattag ttcttattcc cacatatcat atagaatcgc catattatac    60
atgcagaaaa ctaagtatgg tattattctt aaattgttta gcaccttcta atattacaga   120
tagaatccgt cattttcaac agtgaacatg gatttcttct gaacacaact ctttttcttt   180
ccttatttcc aaaaagaaaa gcagcccatt ttaaaatacg gctgcttgta atgtacatta   240
```

<210> SEQ ID NO 100
<211> LENGTH: 267

<212> TYPE: DNA
<213> ORGANISM: Bacillus thuringiensis

<400> SEQUENCE: 100

```
tatcacataa ctctttattt ttaatatttc gacataaagt gaaactttaa tcagtggggg      60
ctttgttcat ccccccactg attattaatt gaaccaaggg ataaaaagat agagggtctg     120
accagaaaac tggagggcat gattctataa caaaaagctt aatgtttata gaattatgtc     180
tttttatata gggagggtag taaacagaga tttggacaaa aatgcaccga tttatctgaa     240
ttttaagttt tataaagggg agaaatg                                         267
```

<210> SEQ ID NO 101
<211> LENGTH: 124
<212> TYPE: DNA
<213> ORGANISM: Bacillus thuringiensis

<400> SEQUENCE: 101

```
attttttact tagcagtaaa actgatatca gttttactgc tttttcattt ttaaattcaa      60
tcattaaatc ttccttttct acatagtcat aatgttgtat gacattccgt aggaggcact     120
tata                                                                  124
```

<210> SEQ ID NO 102
<211> LENGTH: 170
<212> TYPE: DNA
<213> ORGANISM: Bacillus thuringiensis

<400> SEQUENCE: 102

```
acataaattc acctccataa agcgttcatt atatagtaga tgcaaaaccg aaagaaaatg      60
acacggacat ttgaattatt gaaaagaaat cttaaactac ttgaacaatt taaaaaaatg     120
gaaagtttag tatatgtata acatatgatt gatttggaag agggtgatta                170
```

<210> SEQ ID NO 103
<211> LENGTH: 212
<212> TYPE: DNA
<213> ORGANISM: Bacillus thuringiensis

<400> SEQUENCE: 103

```
ttctattttc caacataaca tgctacgatt aaatggtttt ttgcaaatgc cttcttggga      60
agaaggatta gagcgttttt ttatagaaac caaaagtcat taacaatttt aagttaatga     120
cttttttgtt tgcctttaag aggttttatg ttactataat tatagtatca ggtactaata     180
acaagtataa gtatttctgg gaggatatat ca                                   212
```

<210> SEQ ID NO 104
<211> LENGTH: 717
<212> TYPE: DNA
<213> ORGANISM: Bacillus mycoides
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 104

```
gtctgangga ncacgccgcg tgagtgatga aggctttcgg gtcgtaaaac tctgttgtta      60
gggaagaaca agtgctagtt gaataagctg gcaccttgac ggtacctaac cagaaagcca     120
```

```
cggctaacta cgtgccagca gccgcggtaa tacgtaggtg gcaagcgtta tccggaatta    180

ttgggcgtaa agcgcgcgca ggtggtttct taagtctgat gtgaaagccc acggctcaac    240

cgtggagggt cattggaaac tgggagactt gagtgcagaa gaggaaagtg gaattccatg    300

tgtagcggtg aaatgcgtag agatatggag gaacaccagt ggcgaaggcg actttctggt    360

ctgtaactga cactgaggcg cgaaagcgtg gggagcaaac aggattagat accctggtag    420

tccacgccgt aaacgatgag tgctaagtgt tagagggttt ccgcccttta gtgctgaagt    480

taacgcatta agcactccgc ctggggagta cggccgcaag gctgaaactc aaaggaattg    540

acgggggccc gcacaagcgg tggagcatgt ggtttaattc gaagcaacgc gaagaacctt    600

accaggtctt gacatcctct gacaacccta gagatagggc ttccccttcg gggcagagt     660

gacaggtggt gcatggttgt cgtcagctcg tgtcgtgaga tgttgggtta agtcccg       717


<210> SEQ ID NO 105
<211> LENGTH: 711
<212> TYPE: DNA
<213> ORGANISM: Bacillus mycoides
<220> FEATURE:
<221> NAME/KEY: misc_feature
<222> LOCATION: (20)..(21)
<223> OTHER INFORMATION: n is a, c, g, or t

<400> SEQUENCE: 105

ggagcacgcc gcgtgagtgn ngaaggcttt cgggtcgtaa aactctgttg ttagggaaga     60

acaagtgcta gttgaataag ctggcacctt gacggtacct aaccagaaag ccacggctaa    120

ctacgtgcca gcagccgcgg taatacgtag gtggcaagcg ttatccggaa ttattgggcg    180

taaagcgcgc gcaggtggtt tcttaagtct gatgtgaaag cccacggctc aaccgtggag    240

ggtcattgga aactgggaga cttgagtgca gaagaggaaa gtggaattcc atgtgtagcg    300

gtgaaatgcg tagagatatg gaggaacacc agtggcgaag gcgactttct ggtctgtaac    360

tgacactgag gcgcgaaagc gtggggagca aacaggatta gataccctgg tagtccacgc    420

cgtaaacgat gagtgctaag tgttagaggg tttccgccct ttagtgctga agttaacgca    480

ttaagcactc cgcctgggga gtacggccgc aaggctgaaa ctcaaaggaa ttgacggggg    540

cccgcacaag cggtggagca tgtggtttaa ttcgaagcaa cgcgaagaac cttaccaggt    600

cttgacatcc tctgaaaact ctagagatag agcttctcct tcgggagcag agtgacaggt    660

ggtgcatggt tgtcgtcagc tcgtgtcgtg agatgttggg ttaagtcccg c             711


<210> SEQ ID NO 106
<211> LENGTH: 719
<212> TYPE: DNA
<213> ORGANISM: Bacillus mycoides
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (640)..(642)
<223> OTHER INFORMATION: n is a, c, g, or t

<400> SEQUENCE: 106

aaagtctgac ggagcacgcc gcgtgagtga tgaaggcttt cgggtcgtaa aactctgttg     60

ttagggaaga acaagtgcta gttgaataag ctggcacctt gacggtacct aaccagaaag    120

ccacggctaa ctacgtgcca gcagccgcgg taatacgtag gtggcaagcg ttatccggaa    180

ttattgggcg taaagcgcgc gcaggtggtt tcttaagtct gatgtgaaag cccacggctc    240
```

```
aaccgtggag ggtcattgga aactgggaga cttgagtgca gaagaggaaa gtggaattcc    300

atgtgtagcg gtgaaatgcg tagagatatg gaggaacacc agtggcgaag gcgactttct    360

ggtctgtaac tgacactgag gcgcgaaagc gtggggagca aacaggatta gataccctgg    420

tagtccacgc cgtaaacgat gagtgctaag tgttagaggg tttccgccct ttagtgctga    480

agttaacgca ttaagcactc cgcctgggga gtacggccgc aaggctgaaa ctcaaaggaa    540

ttgacggggg cccgcacaag cggtggagca tgtggtttaa ttcgaagcaa cgcgaagaac    600

cttaccaggt cttgacatcc tctgaaaacn ctagagatan nncttctcct tcgggagcag    660

agtgacaggt ggtgcatggt tgtcgtcagc tcgtgtcgtg agatgttggg ttaagtccc     719
```

<210> SEQ ID NO 107
<211> LENGTH: 709
<212> TYPE: DNA
<213> ORGANISM: Bacillus mycoides

<400> SEQUENCE: 107

```
ggagcacgcc gcgtgagtga tgaaggcttt cgggtcgtaa aactctgttg ttagggaaga     60

acaagtgcta gttgaataag ctggcacctt gacggtacct aaccagaaag ccacggctaa    120

ctacgtgcca gcagccgcgg taatacgtag gtggcaagcg ttatccggaa ttattgggcg    180

taaagcgcgc gcaggtggtt tcttaagtct gatgtgaaag cccacggctc aaccgtggag    240

ggtcattgga aactgggaga cttgagtgca gaagaggaaa gtggaattcc atgtgtagcg    300

gtgaaatgcg tagagatatg gaggaacacc agtggcgaag gcgactttct ggtctgtaac    360

tgacactgag gcgcgaaagc gtggggagca aacaggatta gataccctgg tagtccacgc    420

cgtaaacgat gagtgctaag tgttagaggg tttccgccct ttagtgctga agttaacgca    480

ttaagcactc cgcctgggga gtacggccgc aaggctgaaa ctcaaaggaa ttgacggggg    540

cccgcacaag cggtggagca tgtggtttaa ttcgaagcaa cgcgaagaac cttaccaggt    600

cttgacatcc tctgacaacc ctagagatag ggcttcccct tcgggggcag agtgacaggt    660

ggtgcatggt tgtcgtcagc tcgtgtcgtg agatgttggg ttaagtccc                709
```

<210> SEQ ID NO 108
<211> LENGTH: 713
<212> TYPE: DNA
<213> ORGANISM: Unknown
<220> FEATURE:
<223> OTHER INFORMATION: Bacillus cereus family member
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t

<400> SEQUENCE: 108

```
ggancaacgc cgcgtgagtg angaaggctt tcgggtcgta aaactctgtt gttagggaag     60

aacaagtgct agttgaataa gctggcacct tgacggtacc taaccagaaa gccacggcta    120

actacgtgcc agcagccgcg gtaatacgta ggtggcaagc gttatccgga attattgggc    180

gtaaagcgcg cgcaggtggt ttcttaagtc tgatgtgaaa gcccacggct caaccgtgga    240
```

```
gggtcattgg aaactgggag acttgagtgc agaagaggaa agtggaattc catgtgtagc    300

ggtgaaatgc gtagagatat ggaggaacac cagtggcgaa ggcgactttc tggtctgtaa    360

ctgacactga ggcgcgaaag cgtggggagc aaacaggatt agataccctg gtagtccacg    420

ccgtaaacga tgagtgctaa gtgttagagg gtttccgccc tttagtgctg aagttaacgc    480

attaagcact ccgcctgggg agtacggccg caaggctgaa actcaaagga attgacgggg    540

gcccgcacaa gcggtggagc atgtggttta attcgaagca acgcgaagaa ccttaccagg    600

tcttgacatc ctctgaaaac tctagagata gagcttctcc ttcgggagca gagtgacagg    660

tggtgcatgg ttgtcgtcag ctcgtgtcgt gagatgntgg gttaagtccc gca           713
```

<210> SEQ ID NO 109
<211> LENGTH: 876
<212> TYPE: DNA
<213> ORGANISM: Bacillus thuringiensis

<400> SEQUENCE: 109

```
tctgacggag caacgccgcg tgagtgatga aggctttcgg gtcgtaaaac tctgttgtta     60

gggaagaaca agtgctagtt gaataagctg gcaccttgac ggtacctaac cagaaagcca    120

cggctaacta cgtgccagca gccgcggtaa tacgtaggtg gcaagcgtta tccggaatta    180

ttgggcgtaa agcgcgcgca ggtggtttct taagtctgat gtgaaagccc acggctcaac    240

cgtggagggt cattggaaac tgggagactt gagtgcagaa gaggaaagtg gaattccatg    300

tgtagcggtg aaatgcgtag agatatggag gaacaccagt ggcgaaggcg actttctggt    360

ctgtaactga cactgaggcg cgaaagcgtg gggagcaaac aggattagat accctggtag    420

tccacgccgt aaacgatgag tgctaagtgt tagagggttt ccgcccttta gtgctgaagt    480

taacgcatta agcactccgc ctggggagta cggccgcaag gctgaaactc aaaggaattg    540

acgggggccc gcacaagcgg tggagcatgt ggtttaattc gaagcaacgc gaagaacctt    600

accaggtctt gacatcctct gaaaacccta gagatagggc ttctccttcg ggagcagagt    660

gacaggtggt gcatggttgt cgtcagctcg tgtcgtgaga tgttgggtta agtcccgcaa    720

cgagcgcaac ccttgatctt agttgccatc attaagttgg gcactctaag gtgactgccg    780

gtgacaaacc ggaggaaggt ggggatgacg tcaaatcatc atgcccctta tgacctgggc    840

tacacacgtg ctacaatgga cggtacaaag agctgc                              876
```

<210> SEQ ID NO 110
<211> LENGTH: 686
<212> TYPE: DNA
<213> ORGANISM: Unknown
<220> FEATURE:
<223> OTHER INFORMATION: Bacillus cereus family member

<400> SEQUENCE: 110

```
aaggctttcg ggtcgtaaaa ctctgttgtt agggaagaac aagtgctagt tgaataagct     60

ggcaccttga cggtacctaa ccagaaagcc acggctaact acgtgccagc agccgcggta    120

atacgtaggt ggcaagcgtt atccggaatt attgggcgta aagcgcgcgc aggtggtttc    180

ttaagtctga tgtgaaagcc cacggctcaa ccgtggaggg tcattggaaa ctgggagact    240

tgagtgcaga agaggaaagt ggaattccat gtgtagcggt gaaatgcgta gagatatgga    300

ggaacaccag tggcgaaggc gactttctgg tctgtaactg acactgaggc gcgaaagcgt    360

ggggagcaaa caggattaga taccctggta gtccacgccg taaacgatga gtgctaagtg    420

ttagagggtt tccgcccttt agtgctgaag ttaacgcatt aagcactccg cctggggagt    480
```

acggccgcaa ggctgaaact caaaggaatt gacgggggcc cgcacaagcg gtggagcatg 540
tggtttaatt cgaagcaacg cgaagaacct taccaggtct tgacatcctc tgaaaaccct 600
agagataggg cttctccttc gggagcagag tgacaggtgg tgcatggttg tcgtcagctc 660
gtgtcgtgag atgttgggtt aagtcc 686

<210> SEQ ID NO 111
<211> LENGTH: 717
<212> TYPE: DNA
<213> ORGANISM: Bacillus aryabhattai
<220> FEATURE:
<221> NAME/KEY: misc_feature
<222> LOCATION: (3)..(4)
<223> OTHER INFORMATION: n is a, c, g, or t

<400> SEQUENCE: 111
ggnncaacgc cgcgtgagtg atgaaggctt tcgggtcgta aaactctgtt gttagggaag 60
aacaagtacg agagtaactg ctcgtacctt gacggtacct aaccagaaag ccacggctaa 120
ctacgtgcca gcagccgcgg taatacgtag gtggcaagcg ttatccggaa ttattgggcg 180
taaagcgcgc gcaggcggtt tcttaagtct gatgtgaaag cccacggctc aaccgtggag 240
ggtcattgga aactggggaa cttgagtgca gaagagaaaa gcggaattcc acgtgtagcg 300
gtgaaatgcg tagagatgtg gaggaacacc agtggcgaag gcggcttttt ggtctgtaac 360
tgacgctgag gcgcgaaagc gtggggagca aacaggatta gataccctgg tagtccacgc 420
cgtaaacgat gagtgctaag tgttagaggg tttccgccct ttagtgctgc agctaacgca 480
ttaagcactc cgcctgggga gtacggtcgc aagactgaaa ctcaaaggaa ttgacggggg 540
cccgcacaag cggtggagca tgtggtttaa ttcgaagcaa cgcgaagaac cttaccaggt 600
cttgacatcc tctgacaact ctagagatag agcgttcccc ttcgggggac agagtgacag 660
gtggtgcatg gttgtcgtca gctcgtgtcg tgagatgttg ggttaagtcc cgcaacg 717

<210> SEQ ID NO 112
<211> LENGTH: 718
<212> TYPE: DNA
<213> ORGANISM: Bacillus aryabhattai
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 112
tctganggnn cacgccgcgt gagtgatgaa ggctttcggg tcgtaaaact ctgttgttag 60
ggaagaacaa gtacgagagt aactgctcgt accttgacgg tacctaacca gaaagccacg 120
gctaactacg tgccagcagc cgcggtaata cgtaggtggc aagcgttatc cggaattatt 180
gggcgtaaag cgcgcgcagg cggtttctta agtctgatgt gaaagcccac ggctcaaccg 240
tggagggtca ttggaaactg gggaacttga gtgcagaaga gaaaagcgga attccacgtg 300
tagcggtgaa atgcgtagag atgtggagga acaccagtgg cgaaggcggc tttttggtct 360
gtaactgacg ctgaggcgcg aaagcgtggg gagcaaacag gattagatac cctggtagtc 420
cacgccgtaa acgatgagtg ctaagtgtta gagggtttcc gccctttagt gctgcagcta 480
acgcattaag cactccgcct ggggagtacg gtcgcaagac tgaaactcaa aggaattgac 540

-continued gggggcccgc acaagcggtg gagcatgtgg tttaattcga agcaacgcga agaaccttac 600
caggtcttga catcctctga caactctaga gatagagcgt tccccttcgg gggacagagt 660
gacaggtggt gcatggttgt cgtcagctcg tgtcgtgaga tgttgggtta agtcccgc 718

<210> SEQ ID NO 113
<211> LENGTH: 716
<212> TYPE: DNA
<213> ORGANISM: Bacillus flexus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 113
ggancaacgc cgcgtgagtg angaaggctt tcgggtcgta aaactctgtt gttagggaag 60
aacaagtaca agagtaactg cttgtacctt gacggtacct aaccagaaag ccacggctaa 120
ctacgtgcca gcagccgcgg taatacgtag gtggcaagcg ttatccggaa ttattgggcg 180
taaagcgcgc gcaggcggtt tcttaagtct gatgtgaaag cccacggctc aaccgtggag 240
ggtcattgga aactggggaa cttgagtgca gaagagaaaa gcggaattcc acgtgtagcg 300
gtgaaatgcg tagagatgtg gaggaacacc agtggcgaag gcggcttttt ggtctgtaac 360
tgacgctgag gcgcgaaagc gtggggagca aacaggatta gataccctgg tagtccacgc 420
cgtaaacgat gagtgctaag tgttagaggg tttccgccct ttagtgctgc agctaacgca 480
ttaagcactc cgcctgggga gtacggtcgc aagactgaaa ctcaaaggaa ttgacggggg 540
cccgcacaag cggtggagca tgtggtttaa ttcgaagcaa cgcgaagaac cttaccaggt 600
cttgacatcc tctgacaact ctagagatag agcgttcccc ttcgggggac agagtgacag 660
gtggtgcatg gttgtcgtca gctcgtgtcg tgagatgttg ggttaagtcc cgcaac 716

<210> SEQ ID NO 114
<211> LENGTH: 676
<212> TYPE: DNA
<213> ORGANISM: Paracoccus kondratievae
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 114
gccgcgtgag tgnnnaagnc cctagggttg taaagctctt tcanctggga agataatgac 60
tgtaccagca gaagaagccc cggctaactc cgtgccagca gccgcggtaa tacggagggg 120
gctagcgttg ttcggaatta ctgggcgtaa agcgcacgta ggcggaccgg aaagttgggg 180
gtgaaatccc ggggctcaac cccggaactg ccttcaaaac tatcggtctg gagttcgaga 240
gaggtgagtg gaattccgag tgtagaggtg aaattcgtag atattcggag gaacaccagt 300
ggcgaaggcg gctcactggc tcgatactga cgctgaggtg cgaaagcgtg gggagcaaac 360
aggattagat accctggtag tccacgccgt aaacgatgaa tgccagtcgt cgggcagcat 420
gctgttcggt gacacaccta acggattaag cattccgcct ggggagtacg gtcgcaagat 480
taaaactcaa aggaattgac gggggcccgc acaagcggtg gagcatgtgg tttaattcga 540
agcaacgcgc agaaccttac caacccttga catcccagga cagcccgaga gatcgggtct 600
ccacttcggt ggcctggaga caggtgctgc atggctgtcg tcagctcgtg tcgtgagatg 660
ttcggttaag tccggc 676

<210> SEQ ID NO 115
<211> LENGTH: 728
<212> TYPE: DNA
<213> ORGANISM: Enterobacter cloacae
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (719)..(719)
<223> OTHER INFORMATION: n is a, c, g, or t
<220> FEATURE:
<221> NAME/KEY: misc_feature
<222> LOCATION: (721)..(722)
<223> OTHER INFORMATION: n is a, c, g, or t

<400> SEQUENCE: 115
ctgnngcagc cntgccgcgt gtatgaagaa ggncttcggg ttgtaaagta ctttcagcgg 60
ggaggaaggt gttgtggtta ataaccacag caattgacgt tacccgcaga agaagcaccg 120
gctaactccg tgccagcagc cgcggtaata cggagggtgc aagcgttaat cggaattact 180
gggcgtaaag cgcacgcagg cggtctgtca agtcggatgt gaaatccccg ggctcaacct 240
gggaactgca ttcgaaactg gcaggctaga gtcttgtaga ggggggtaga attccaggtg 300
tagcggtgaa atgcgtagag atctggagga ataccggtgg cgaaggcggc cccctggaca 360
aagactgacg ctcaggtgcg aaagcgtggg gagcaaacag gattagatac cctggtagtc 420
cacgccgtaa acgatgtcga tttggaggtt gtgcccttga ggcgtggctt ccggagctaa 480
cgcgttaaat cgaccgcctg gggagtacgg ccgcaaggtt aaaactcaaa tgaattgacg 540
ggggcccgca caagcggtgg agcatgtggt ttaattcgat gcaacgcgaa gaaccttacc 600
tggtcttgac atccacagaa ctttccagag atggattggt gccttcggga actgtgagac 660
aggtgctgca tggctgtcgt cagctcgtgt tgtgaaatgt tgggttaagt cccgcaacna 720 nncgcaac 728

<210> SEQ ID NO 116
<211> LENGTH: 717
<212> TYPE: DNA
<213> ORGANISM: Bacillus nealsonii
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 116

```
tgnngganca acgccgcgtg agtgatgaag gttttcggat cgtaaaactc tgttgttagg     60
gaagaacaag tacgagagta actgctcgta ccttgacggt acctaaccag aaagccacgg    120
ctaactacgt gccagcagcc gcggtaatac gtaggtggca agcgttgtcc ggaattattg    180
ggcgtaaagc gcgcgcaggc ggtcctttaa gtctgatgtg aaagcccacg gctcaaccgt    240
ggagggtcat tggaaactgg gggacttgag tgcagaagag aagagtggaa ttccacgtgt    300
agcggtgaaa tgcgtagaga tgtggaggaa caccagtggc gaaggcgact ctttggtctg    360
taactgacgc tgaggcgcga aagcgtgggg agcaaacagg attagatacc ctggtagtcc    420
acgccgtaaa cgatgagtgc taagtgttag agggtttccg ccctttagtg ctgcagcaaa    480
cgcattaagc actccgcctg gggagtacgg ccgcaaggct gaaactcaaa ggaattgacg    540
ggggcccgca caagcggtgg agcatgtggt ttaattcgaa gcaacgcgaa gaaccttacc    600
aggtcttgac atctcctgac aatcctagag ataggacgtt ccccttcggg ggacaggatg    660
acaggtggtg catggttgtc gtcagctcgt gtcgtgagat gttgggttaa gtcccgc       717
```

<210> SEQ ID NO 117
<211> LENGTH: 702
<212> TYPE: DNA
<213> ORGANISM: Bacillus subtilis

<400> SEQUENCE: 117

```
cgccgcgtga gtgatgaagg ttttcggatc gtaaagctct gttgttaggg aagaacaagt     60
gccgttcaaa tagggcggca ccttgacggt acctaaccag aaagccacgg ctaactacgt    120
gccagcagcc gcggtaatac gtaggtggca agcgttgtcc ggaattattg ggcgtaaagg    180
gctcgcaggc ggtttcttaa gtctgatgtg aaagcccccg gctcaaccgg ggagggtcat    240
tggaaactgg ggaacttgag tgcagaagag gagagtggaa ttccacgtgt agcggtgaaa    300
tgcgtagaga tgtggaggaa caccagtggc gaaggcgact ctctggtctg taactgacgc    360
tgaggagcga aagcgtgggg agcgaacagg attagatacc ctggtagtcc acgccgtaaa    420
cgatgagtgc taagtgttag ggggtttccg ccccttagtg ctgcagctaa cgcattaagc    480
actccgcctg gggagtacgg tcgcaagact gaaactcaaa ggaattgacg ggggcccgca    540
caagcggtgg agcatgtggt ttaattcgaa gcaacgcgaa gaaccttacc aggtcttgac    600
atcctctgac aatcctagag ataggacgtc cccttcgggg gcagagtgac aggtggtgca    660
tggttgtcgt cagctcgtgt cgtgagatgt tgggttaagt cc                       702
```

<210> SEQ ID NO 118
<211> LENGTH: 680
<212> TYPE: DNA
<213> ORGANISM: Alcaligenes faecalis
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (262)..(264)
<223> OTHER INFORMATION: n is a, c, g, or t
<220> FEATURE:
<221> NAME/KEY: misc_feature
<222> LOCATION: (272)..(273)
<223> OTHER INFORMATION: n is a, c, g, or t

<400> SEQUENCE: 118

```
cttcgggttg taaagtactt ttggcagaga agaaaaggta tctcctaata cgagatactg     60
```

ctgacggtat ctgcagaata agcaccggct aactacgtgc cancagccgc ggtaatacgt 120
agggtgcaag cgttaatcgg aattactggg cgtaaagcgt gtgtaggcgg ttcggaaaga 180
aagatgtgaa atcccagggc tcaaccttgg aactgcattt ttaactgccg agctagagta 240
tgtcagaggg gggtagaatt cnnntgtagc anngaaatgc gtagatatgt ggaggaatac 300
cgatggcgaa ggcagccccc tgggataata ctgacgctca gacacgaaag cgtggggagc 360
aaacaggatt agataccctg gtagtccacg ccctaaacga tgtcaactag ctgttggggc 420
cgttaggcct tagtagcgca gctaacgcgt gaagttgacc gcctggggag tacggtcgca 480
agattaaaac tcaaaggaat tgacggggac ccgcacaagc ggtggatgat gtggattaat 540
tcgatgcaac gcgaaaaacc ttacctaccc ttgacatgtc tggaaagccg aagagatttg 600
gccgtgctcg caagagaacc ggaacacagg tgctgcatgg ctgtcgtcag ctcgtgtcgt 660
gagatgttgg gttaagtccc 680

<210> SEQ ID NO 119
<211> LENGTH: 640
<212> TYPE: DNA
<213> ORGANISM: Paenibacillus massiliensis
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (13)..(17)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (162)..(162)

<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (189)..(190)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (210)..(211)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (344)..(344)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (364)..(365)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (417)..(418)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (443)..(444)
<223> OTHER INFORMATION: n is a, c, g, or t
<220> FEATURE:

<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (471)..(472)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (490)..(490)
<223> OTHER INFORMATION: n is a, c, g, or t
<220> FEATURE:
<221> NAME/KEY: misc_feature
<222> LOCATION: (492)..(496)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t
<220> FEATURE:
<221> NAME/KEY: misc_feature
<222> LOCATION: (509)..(509)
<223> OTHER INFORMATION: n is a, c, g, or t
<220> FEATURE:
<221> NAME/KEY: misc_feature
<222> LOCATION: (516)..(517)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (562)..(562)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (571)..(572)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(598)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (607)..(608)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (637)..(640)
<223> OTHER INFORMATION: n is a, c, g, or t

<400> SEQUENCE: 119
cttanngnnt gannnnnctt gnnaanaaag ccccggctaa ctacntgcca ncanccgcgg 60
taatacntan ggngcaagcg ttgtccggaa ttattgggcg taaagcgcgc gcaggcggtc 120
ntttaagtct ggtgtttaag cccggggctc aaccccggat cncncgggaa actggatgac 180
ttgantgcnn aanaagagag tggaattccn ngtgtancgg tgaaatgcnt ananatgtgn 240
angaacacca ntggcnaang cnactctctg ggctgtaact gacnctgang cncgaaagcg 300
tggggagcaa acangattan ataccctggt antccacgcc ntanacnatn antgctaggt 360
gttnngggtt tcnataccct tgntgccnaa nttaacacat taancactcc gcctggnnan 420
tacngtcnca anantgaaac tcnnangaan tgacngggac ccgcacaagc nntgnantat 480
gtggtttaan tnnnnncaac ncnaanaanc ttaccnngnc ttgacatctn aatgaccngn 540
gcananatgt ncctttcctt cngnacattc nngacaggtg gtgcatggnt gtcntcnnct 600
cntgtcnngn gatgttgggt taantccccg cancnannnn 640

<210> SEQ ID NO 120

<211> LENGTH: 678
<212> TYPE: DNA
<213> ORGANISM: Bacillus subtilis
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t

<400> SEQUENCE: 120

```
aagctctgtt gttagggaag aacaagtacc gttcgaatag ggcggtacct tgacggtacc     60

taaccagaaa gccacggcta actacgtgcc agcagccgcg gtaatacgta ggtggcaagc    120

gttgtccgga attattgggc gtaaagggct cgcaggcggt ttcttaagtc tgatgtgaaa    180

gcccccggct caaccgggga gggtcattgg aaactgggga acttgagtgc agaagaggag    240

agtggaattc cacgtgtagc ggtgaaatgc gtagagatgt ggaggaacac cagtggcgaa    300

ggcgactctc tggtctgtaa ctgacgctga ggagcgaaag cgtggggagc gaacaggatt    360

agataccctg gtagtccacg ccgtaaacga tgagtgctaa gtgttagggg gtttccgccc    420

cttantgctg cagctaacgc attaagcact ccgcctgggg agtacggtcg caagactgaa    480

actcaaagga attgacgggg gcccgcacaa gcggtggagc atgtggttta attcgaagca    540

acgcgaanaa ccttaccagg tcttgacatc ctctgacaat cctagagata ggacgtcccc    600

ttcgggggca gagtgacagg tggtgcatgg ttgtcgtcan ctcgtgtcgt gagatgttgg    660

nttaagtccc gcaacgag                                                  678
```

<210> SEQ ID NO 121
<211> LENGTH: 743
<212> TYPE: DNA
<213> ORGANISM: Bacillus megaterium
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (689)..(691)
<223> OTHER INFORMATION: n is a, c, g, or t
<220> FEATURE:
<221> NAME/KEY: misc_feature
<222> LOCATION: (693)..(708)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (716)..(717)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (729)..(730)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (740)..(741)
<223> OTHER INFORMATION: n is a, c, g, or t

<400> SEQUENCE: 121

```
aagnctttcg gnncgtaaaa ctctgttgtt agggaagaac aagtacgaga gtaactgctc     60

gtaccttgac ggtacctaac cagaaagcca cggctaacta cgtgccagca gccgcggtaa    120

tacgtaggtg gcaagcgtta tccggaatta ttgggcgtaa agcgcgcgca ggcggtttct    180

taagtctgat gtgaaagccc acggctcaac cgtggagggt cattggaaac tggggaactt    240

gagtgcagaa gagaaaagcg gaattccacg tgtagcggtg aaatgcgtag agatgtggag    300

gaacaccagt ggcgaaggcg gctttttggt ctgtaactga cgctgaggcg cgaaagcgtg    360

gggagcaaac aggattagat accctggtag tccacgccgt aaacgatgag tgctaagtgt    420

tagagggttt ccgcccttta gtgctgcagc taacgcatta agcactccgc ctggggagta    480

cggtcgcaag actgaaactc aaaggaattg acgggggccc gcacaagcgg tggagcatgt    540

ggtttaattc gaagcaacgc gaagaacctt accaggtctt gacatcctct gacaactcta    600

gagatagagc gttccccttc gggggacaga gtgacaggtg gtgcatggtt gtcgtcagct    660

cgtgtcgtga gatgttgggt taagtcccnn ncnnnnnnnn nnnnnnnntc tnaganncgn    720

gctgacnann ccangcaccn ngg                                            743
```

<210> SEQ ID NO 122
<211> LENGTH: 21
<212> TYPE: DNA
<213> ORGANISM: Artificial sequence
<220> FEATURE:
<223> OTHER INFORMATION: Primer

<400> SEQUENCE: 122

```
actcctacgg gaggcagcag t                                               21
```

<210> SEQ ID NO 123
<211> LENGTH: 16
<212> TYPE: DNA
<213> ORGANISM: Artificial sequence
<220> FEATURE:
<223> OTHER INFORMATION: Primer

<400> SEQUENCE: 123

```
gggttgcgct cgttgc                                                     16
```

<210> SEQ ID NO 124
<211> LENGTH: 16
<212> TYPE: DNA
<213> ORGANISM: Artificial sequence -continued

```
<220> FEATURE:
<223> OTHER INFORMATION: Primer

<400> SEQUENCE: 124

gggttgcgct cgttac                                                   16
```

FUSION PROTEINS AND METHODS FOR STIMULATING PLANT GROWTH, PROTECTING PLANTS, AND IMMOBILIZING BACILLUS SPORES ON PLANTS

CROSS-REFERENCE TO RELATED APPLICATIONS

This application is a continuation of U.S. Non-Provisional patent application Ser. No. 14/775,892, filed Sep. 14, 2015, which is a U.S. National Stage Application of PCT Application No. PCT/US2014/030824, filed Mar. 17, 2014, which claims the benefit of U.S. Provisional Patent Application Ser. No. 61/799,262, filed Mar. 15, 2013. Each of the above-cited applications is incorporated herein by reference in its entirety.

FIELD OF THE INVENTION

The present invention generally relates to fusion proteins containing a targeting sequence, an exosporium protein, or an exosporium protein fragment that targets the fusion protein to the exosporium of a *Bacillus cereus* family member. The invention also relates to recombinant *Bacillus cereus* family members expressing such fusion proteins and formulations containing the recombinant *Bacillus cereus* family members expressing the fusion proteins. The invention further relates to methods for stimulating plant growth, for protecting plants from pathogens, and for enhancing stress resistance in plants by applying the recombinant *Bacillus cereus* family members or the formulations to plants or a plant growth medium. The invention also relates to methods for immobilizing spores of a recombinant *Bacillus cereus* family member expressing a fusion protein on plants or on plant matter.

BACKGROUND OF THE INVENTION

Within the zone surrounding a plant's roots is a region called the rhizosphere. In the rhizosphere, bacteria, fungi, and other organisms compete for nutrients and for binding to the root structures of the plant. Both detrimental and beneficial bacteria and fungi can occupy the rhizosphere. The bacteria, fungi, and the root system of the plant can all be influenced by the actions of peptides, enzymes, and other proteins in the rhizosphere. Augmentation of soil or treatment of plants with certain of these peptides, enzymes, or other proteins would have beneficial effects on the overall populations of beneficial soil bacteria and fungi, create a healthier overall soil environment for plant growth, improve plant growth, and provide for the protection of plants against certain bacterial and fungal pathogens. However, previous attempts to introduce peptides, enzymes, and other proteins into soil to induce such beneficial effects on plants have been hampered by the low survival of enzymes, proteins, and peptides in soil. Additionally, the prevalence of proteases naturally present in the soil leads to degradation of the proteins in the soil. The environment around the roots of a plant (the rhizosphere) is a unique mixture of bacteria, fungi, nutrients, and roots that has different qualities than that of native soil. The symbiotic relationship between these organisms is unique, and could be altered for the better with inclusion of exogenous proteins. The high concentration of fungi and bacteria in the rhizosphere causes even greater degradation of proteins due to abnormally high levels of proteases and other elements detrimental to proteins in the soil. In addition, enzymes and other proteins introduced into soil can dissipate away from plant roots quickly.

Thus, there exists a need in the art for a method for effectively delivering peptides, enzymes, and other proteins to plants (e.g., to plant root systems) and for extending the period of time during which such molecules remain active. Furthermore, there exists a need in the art for a method of selectively targeting such peptides, enzymes, and proteins to the rhizosphere and to plant leaves and plant roots in particular.

SUMMARY OF THE INVENTION

The present invention is directed to fusion proteins comprising at least one plant growth stimulating protein or peptide, at least one protein or peptide that enhances stress resistance in a plant, or at least one plant binding protein or peptide. The plant growth stimulating protein or peptide comprises a peptide hormone, a non-hormone peptide, or an enzyme involved in the production or activation of a plant growth stimulating compound. The fusion protein also comprises a targeting sequence, an exosporium protein, or an exosporium protein fragment. The targeting sequence, exosporium protein, or exosporium protein fragment can be: (a) a targeting sequence comprising an amino acid sequence having at least about 43% identity with amino acids 20-35 of SEQ ID NO: 1, wherein the identity with amino acids 25-35 is at least about 54%; (b) a targeting sequence comprising amino acids 1-35 of SEQ ID NO: 1; (c) a targeting sequence comprising amino acids 20-35 of SEQ ID NO: 1; (d) a targeting sequence comprising SEQ ID NO: 1; (e) an exosporium protein comprising an amino acid sequence having at least 85% identity with SEQ ID NO: 2; (f) a targeting sequence comprising amino acids 1-27 of SEQ ID NO: 3; (g) a targeting sequence comprising amino acids 12-27 of SEQ ID NO: 3; (h) a targeting sequence comprising SEQ ID NO: 3; (i) an exosporium protein comprising an amino acid sequence having at least 85% identity with SEQ ID NO: 4; (j) a targeting sequence comprising amino acids 1-38 of SEQ ID NO: 5; (k) a targeting sequence comprising amino acids 23-38 of SEQ ID NO: 5; (1) a targeting sequence comprising SEQ ID NO: 5; (m) an exosporium protein comprising an amino acid sequence having at least 85% identity with SEQ ID NO: 6; (n) a targeting sequence comprising amino acids 1-28 of SEQ ID NO: 7; (o) a targeting sequence comprising amino acids 13-28 of SEQ ID NO: 7; (p) a targeting sequence comprising SEQ ID NO: 7; (q) an exosporium protein comprising an amino acid sequence having at least 85% identity with SEQ ID NO: 8; (r) a targeting sequence comprising amino acids 1-24 of SEQ ID NO: 9; (s) a targeting sequence comprising amino acids 9-24 of SEQ ID NO: 9; (t) a targeting sequence comprising SEQ ID NO: 9; (u) an exosporium protein comprising an amino acid sequence having at least 85% identity with SEQ ID NO: 10; (v) a targeting sequence comprising amino acids 1-33 of SEQ ID NO:11; (w) a targeting sequence comprising amino acids 18-33 of SEQ ID NO: 11; (x) a targeting sequence comprising SEQ ID NO: 11; (y) an exosporium protein comprising an amino acid sequence having at least 85% identity with SEQ ID NO: 12; (z) a targeting sequence comprising amino acids 1-33 of SEQ ID NO: 13; (aa) a targeting sequence comprising amino acids 18-33 of SEQ ID NO: 13; (ab) a targeting sequence comprising SEQ ID NO:13; (ac) an exosporium protein comprising an amino acid sequence having at least 85% identity with SEQ ID NO:14; (ad) a targeting sequence comprising amino acids 1-43 of SEQ ID NO: 15; (ae) a targeting sequence comprising amino acids 28-43 of SEQ ID NO: 15; (af) a targeting sequence comprising SEQ ID NO:15; (ag) an exosporium protein comprising an amino acid sequence having at least 85% identity with SEQ ID NO:16; (ah) a targeting sequence comprising amino acids 1-27 of SEQ ID NO: 17; (ai) a targeting sequence comprising amino acids 12-27 of SEQ ID NO: 17; (aj) a targeting sequence comprising SEQ ID NO:17; (ak) an exosporium protein comprising an amino acid sequence having at least 85% identity with SEQ ID NO:18; (al) a targeting sequence comprising amino acids 1-33 of SEQ ID NO: 19; (am) a targeting sequence comprising amino acids 18-33 of SEQ ID NO: 19; (an) a targeting sequence comprising SEQ ID NO:19; (ao) an exosporium protein comprising an amino acid sequence having at least 85% identity with SEQ ID NO:20; (ap) a targeting sequence comprising amino acids 1-33 of SEQ ID NO: 21; (aq) a targeting sequence comprising amino acids 18-33 of SEQ ID NO: 21; (ar) a targeting sequence comprising SEQ ID NO:21; (as) an exosporium protein comprising an amino acid sequence having at least 85% identity with SEQ ID NO:22; (at) a targeting sequence comprising amino acids 1-24 of SEQ ID NO: 23; (au) a targeting sequence comprising amino acids 9-24 of SEQ ID NO: 23; (av) a targeting sequence comprising SEQ ID NO:23; (aw) an exosporium protein comprising an amino acid sequence having at least 85% identity with SEQ ID NO:24; (ax) a targeting sequence comprising amino acids 1-24 of SEQ ID NO: 25; (ay) a targeting sequence comprising amino acids 9-24 of SEQ ID NO: 25; (az) a targeting sequence comprising SEQ ID NO:25; (ba) an exosporium protein comprising an amino acid sequence having at least 85% identity with SEQ ID NO:26; (bb) a targeting sequence comprising amino acids 1-30 of SEQ ID NO: 27; (bc) a targeting sequence comprising amino acids 15-30 of SEQ ID NO: 27; (bd) a targeting sequence comprising SEQ ID NO:27; (be) an exosporium protein comprising an amino acid sequence having at least 85% identity with SEQ ID NO:28; (bf) a targeting sequence comprising amino acids 1-33 of SEQ ID NO: 29; (bg) a targeting sequence comprising amino acids 18-33 of SEQ ID NO: 29; (bh) a targeting sequence comprising SEQ ID NO:29; (bi) an exosporium protein comprising an amino acid sequence having at least 85% identity with SEQ ID NO:30; (bj) a targeting sequence comprising amino acids 1-24 of SEQ ID NO: 31; (bk) a targeting sequence comprising amino acids 9-24 of SEQ ID NO: 31; (bl) a targeting sequence comprising SEQ ID NO:31; (bm) an exosporium protein comprising an amino acid sequence having at least 85% identity with SEQ ID NO:32; (bn) a targeting sequence comprising amino acids 1-15 of SEQ ID NO: 33; (bo) a targeting sequence comprising SEQ ID NO:33; (bp) an exosporium protein comprising an amino acid sequence having at least 85% identity with SEQ ID NO:34; (bq) a targeting sequence comprising amino acids 1-16 of SEQ ID NO: 35; (br) a targeting sequence comprising SEQ ID NO:35; (bs) an exosporium protein comprising an amino acid sequence having at least 85% identity with SEQ ID NO:36; (bt) a targeting sequence comprising amino acids 1-29 of SEQ ID NO:43; (bu) a targeting sequence comprising amino acids 14-29 of SEQ ID NO: 43; (by) a targeting sequence comprising SEQ ID NO: 43; (bw) an exosporium protein comprising an amino acid sequence having at least 85% identity with SEQ ID NO: 44; (bx) a targeting sequence comprising amino acids 1-35 of SEQ ID NO: 45; (by) a targeting sequence comprising amino acids 20-35 of SEQ ID NO: 45; (bz) a targeting sequence comprising SEQ ID NO: 45; (ca) an exosporium protein comprising an amino acid sequence having at least 85% identity with SEQ ID NO: 46; (cb) a targeting sequence comprising amino acids 1-43 of SEQ ID NO: 47; (cc) a targeting sequence comprising amino acids 28-43 of SEQ ID NO: 47; (cd) a targeting sequence comprising SEQ ID NO: 47; (ce) an exosporium protein comprising an amino acid sequence having at least 85% identity with SEQ ID NO: 48; (cf) a targeting sequence comprising amino acids 1-32 of SEQ ID NO: 49; (cg) a targeting sequence comprising amino acids 17-32 of SEQ ID NO: 49; (ch) a targeting sequence comprising SEQ ID NO: 49; (ci) an exosporium protein comprising an amino acid sequence having at least 85% identity with SEQ ID NO: 50; (cj) a targeting sequence comprising amino acids 1-33 of SEQ ID NO: 51; (ck) a targeting sequence comprising amino acids 18-33 of SEQ ID NO: 51; (cl) a targeting sequence comprising SEQ ID NO: 51; (cm) an exosporium protein comprising an amino acid sequence having at least 85% identity with SEQ ID NO: 52; (cn) a targeting sequence comprising amino acids 1-33 of SEQ ID NO: 53; (co) a targeting sequence comprising amino acids 18-33 of SEQ ID NO: 53; (cp) a targeting sequence comprising SEQ ID NO: 53; (cq) an exosporium protein comprising an amino acid sequence having at least 85% identity with SEQ ID NO: 54; (cr) a targeting sequence comprising amino acids 1-30 of SEQ ID NO: 55; (cs) a targeting sequence comprising amino acids 15-30 of SEQ ID NO: 55; (ct) a targeting sequence comprising SEQ ID NO: 55; (cu) an exosporium protein comprising an amino acid sequence having at least 85% identity with SEQ ID NO: 56; (cv) a targeting sequence comprising amino acids 1-130 of SEQ ID NO: 57; (cw) a targeting sequence comprising amino acids 115-130 of SEQ ID NO: 57; (cx) a targeting sequence comprising SEQ ID NO: 57; (cy) an exosporium protein comprising an amino acid sequence having at least 85% identity with SEQ ID NO: 58; (cz) an exosporium protein fragment comprising an amino acid sequence having at least 85% identity with SEQ ID NO: 59; (da) a targeting sequence comprising SEQ ID NO: 60; (db) a targeting sequence comprising SEQ ID NO: 61; (dc) a targeting sequence comprising SEQ ID NO: 62; (dd) a targeting sequence comprising SEQ ID NO: 63; (de) a targeting sequence comprising SEQ ID NO: 64; (df) a targeting sequence comprising SEQ ID NO: 65; (dg) a targeting sequence comprising SEQ ID NO: 66; (dh) a targeting sequence comprising SEQ ID NO: 67; (di) a targeting sequence comprising SEQ ID NO: 68; (dj) a targeting sequence comprising SEQ ID NO: 69; (dk) a targeting sequence comprising SEQ ID NO: 70; (dl) an exosporium protein comprising an amino acid sequence having at least 85% identity with SEQ ID NO: 71; (dm) an exosporium protein comprising an amino acid sequence having at least 85% identity with SEQ ID NO: 72; (dn) an exosporium protein comprising an amino acid sequence having at least 85% identity with SEQ ID NO: 73; (do) an exosporium protein comprising an amino acid sequence having at least 85% identity with SEQ ID NO: 74; (dp) an exosporium protein comprising an amino acid sequence having at least 85% identity with SEQ ID NO: 75; (dq) an exosporium protein comprising an amino acid sequence having at least 85% identity with SEQ ID NO: 76; (dr) an exosporium protein comprising an amino acid sequence having at least 85% identity with SEQ ID NO: 77; (ds) an exosporium protein comprising an amino acid sequence having at least 85% identity with SEQ ID NO: 78; (dt) an exosporium protein comprising an amino acid sequence having at least 85% identity with SEQ ID NO: 79; (du) an exosporium protein comprising an amino acid sequence having at least 85% identity with SEQ ID NO: 80; (dv) an exosporium protein comprising an amino acid sequence having at least 85% identity with SEQ ID NO: 81; (dw) an exosporium protein comprising an amino acid sequence having at least 85% identity with SEQ ID NO: 82; (dx) an exosporium protein comprising an amino acid sequence having at least 85% identity with SEQ ID NO: 83; (dy) an exosporium protein comprising an amino acid sequence having at least 85% identity with SEQ ID NO: 84; (dz) a targeting sequence comprising amino acids 22-31 of SEQ ID NO: 1; (ea) a targeting sequence comprising amino acids 22-33 of SEQ ID NO: 1; (eb) a targeting sequence comprising amino acids 20-31 of SEQ ID NO: 1; (ec) a targeting sequence comprising amino acids 14-23 of SEQ ID NO: 3; (ed) a targeting sequence comprising amino acids 14-25 of SEQ ID NO: 3; or (ef) a targeting sequence comprising amino acids 12-23 of SEQ ID NO: 3.

The present invention is also directed to fusion proteins comprising a targeting sequence, an exosporium protein, or an exosporium protein fragment and at least one protein or peptide that protects a plant from a pathogen. The targeting sequence, an exosporium protein, or an exosporium protein fragment can be: (a) a targeting sequence consisting of an amino acid sequence consisting of 16 amino acids and having at least about 43% identity with amino acids 20-35 of SEQ ID NO: 1, wherein the identity with amino acids 25-35 is at least about 54%; (b) a targeting sequence consisting of amino acids 1-35 of SEQ ID NO: 1; (c) a targeting sequence consisting of amino acids 20-35 of SEQ ID NO: 1; (d) a targeting sequence consisting of SEQ ID NO: 1; (e) a targeting sequence comprising SEQ ID NO: 60; (f) a targeting sequence comprising amino acids 1-27 of SEQ ID NO: 3; (g) a targeting sequence comprising amino acids 12-27 of SEQ ID NO: 3; (h) a targeting sequence comprising SEQ ID NO: 3; (i) an exosporium protein comprising an amino acid sequence having at least 85% identity with SEQ ID NO: 4; (j) a targeting sequence comprising amino acids 1-38 of SEQ ID NO: 5; (k) a targeting sequence comprising amino acids 23-38 of SEQ ID NO: 5; (1) a targeting sequence comprising SEQ ID NO: 5; (m) an exosporium protein comprising an amino acid sequence having at least 85% identity with SEQ ID NO: 6; (n) a targeting sequence comprising amino acids 1-28 of SEQ ID NO: 7; (o) a targeting sequence comprising amino acids 13-28 of SEQ ID NO: 7; (p) a targeting sequence comprising SEQ ID NO: 7; (q) an exosporium protein comprising an amino acid sequence having at least 85% identity with SEQ ID NO: 8; (r) a targeting sequence comprising amino acids 1-24 of SEQ ID NO: 9; (s) a targeting sequence comprising amino acids 9-24 of SEQ ID NO: 9; (t) a targeting sequence comprising SEQ ID NO: 9; (u) an exosporium protein comprising an amino acid sequence having at least 85% identity with SEQ ID NO: 10; (v) a targeting sequence comprising amino acids 1-33 of SEQ ID NO:11; (w) a targeting sequence comprising amino acids 18-33 of SEQ ID NO: 11; (x) a targeting sequence comprising SEQ ID NO: 11; (y) an exosporium protein comprising an amino acid sequence having at least 85% identity with SEQ ID NO: 12; (z) a targeting sequence comprising amino acids 1-33 of SEQ ID NO: 13; (aa) a targeting sequence comprising amino acids 18-33 of SEQ ID NO: 13; (ab) a targeting sequence comprising SEQ ID NO:13; (ac) an exosporium protein comprising an amino acid sequence having at least 85% identity with SEQ ID NO:14; (ad) a targeting sequence comprising amino acids 1-43 of SEQ ID NO: 15; (ae) a targeting sequence comprising amino acids 28-43 of SEQ ID NO: 15; (af) a targeting sequence comprising SEQ ID NO:15; (ag) an exosporium protein comprising an amino acid sequence having at least 85% identity with SEQ ID NO:16; (ah) a targeting sequence comprising amino acids 1-27 of SEQ ID NO: 17; (ai) a targeting sequence comprising amino acids 12-27 of SEQ ID NO: 17; (aj) a targeting sequence comprising SEQ ID NO:17; (ak) an exosporium protein comprising an amino acid sequence having at least 85% identity with SEQ ID NO:18; (al) a targeting sequence comprising amino acids 1-33 of SEQ ID NO: 19; (am) a targeting sequence comprising amino acids 18-33 of SEQ ID NO: 19; (an) a targeting sequence comprising SEQ ID NO:19; (ao) an exosporium protein comprising an amino acid sequence having at least 85% identity with SEQ ID NO:20; (ap) a targeting sequence comprising amino acids 1-33 of SEQ ID NO: 21; (aq) a targeting sequence comprising amino acids 18-33 of SEQ ID NO: 21; (ar) a targeting sequence comprising SEQ ID NO:21; (as) an exosporium protein comprising an amino acid sequence having at least 85% identity with SEQ ID NO:22; (at) a targeting sequence comprising amino acids 1-24 of SEQ ID NO: 23; (au) a targeting sequence comprising amino acids 9-24 of SEQ ID NO: 23; (av) a targeting sequence comprising SEQ ID NO:23; (aw) an exosporium protein comprising an amino acid sequence having at least 85% identity with SEQ ID NO:24; (ax) a targeting sequence comprising amino acids 1-24 of SEQ ID NO: 25; (ay) a targeting sequence comprising amino acids 9-24 of SEQ ID NO: 25; (az) a targeting sequence comprising SEQ ID NO:25; (ba) an exosporium protein comprising an amino acid sequence having at least 85% identity with SEQ ID NO:26; (bb) a targeting sequence comprising amino acids 1-30 of SEQ ID NO: 27; (bc) a targeting sequence comprising amino acids 15-30 of SEQ ID NO: 27; (bd) a targeting sequence comprising SEQ ID NO:27; (be) an exosporium protein comprising an amino acid sequence having at least 85% identity with SEQ ID NO:28; (bf) a targeting sequence comprising amino acids 1-33 of SEQ ID NO: 29; (bg) a targeting sequence comprising amino acids 18-33 of SEQ ID NO: 29; (bh) a targeting sequence comprising SEQ ID NO:29; (bi) an exosporium protein comprising an amino acid sequence having at least 85% identity with SEQ ID NO:30; (bj) a targeting sequence comprising amino acids 1-24 of SEQ ID NO: 31; (bk) a targeting sequence comprising amino acids 9-24 of SEQ ID NO: 31; (bl) a targeting sequence comprising SEQ ID NO:31; (bm) an exosporium protein comprising an amino acid sequence having at least 85% identity with SEQ ID NO:32; (bn) a targeting sequence comprising amino acids 1-15 of SEQ ID NO: 33; (bo) a targeting sequence comprising SEQ ID NO:33; (bp) an exosporium protein comprising an amino acid sequence having at least 85% identity with SEQ ID NO:34; (bq) a targeting sequence comprising amino acids 1-16 of SEQ ID NO: 35; (br) a targeting sequence comprising SEQ ID NO:35; (bs) an exosporium protein comprising an amino acid sequence having at least 85% identity with SEQ ID NO:36; (bt) a targeting sequence comprising amino acids 1-29 of SEQ ID NO:43; (bu) a targeting sequence comprising amino acids 14-29 of SEQ ID NO: 43; (by) a targeting sequence comprising SEQ ID NO: 43; (bw) an exosporium protein comprising an amino acid sequence having at least 85% identity with SEQ ID NO: 44; (bx) a targeting sequence comprising amino acids 1-35 of SEQ ID NO: 45; (by) a targeting sequence comprising amino acids 20-35 of SEQ ID NO: 45; (bz) a targeting sequence comprising SEQ ID NO: 45; (ca) an exosporium protein comprising an amino acid sequence having at least 85% identity with SEQ ID NO: 46; (cb) a targeting sequence comprising amino acids 1-43 of SEQ ID NO: 47; (cc) a targeting sequence comprising amino acids 28-43 of SEQ ID NO: 47; (cd) a targeting sequence comprising SEQ ID NO: 47; (ce) an exosporium protein comprising an amino acid sequence having at least 85% identity with SEQ ID NO: 48; (cf) a targeting sequence comprising amino acids 1-32 of SEQ ID NO: 49; (cg) a targeting sequence comprising amino acids 17-32 of SEQ ID NO: 49; (ch) a targeting sequence comprising SEQ ID NO: 49; (ci) an exosporium protein comprising an amino acid sequence having at least 85% identity with SEQ ID NO: 50; (cj) a targeting sequence comprising amino acids 1-33 of SEQ ID NO: 51; (ck) a targeting sequence comprising amino acids 18-33 of SEQ ID NO: 51; (cl) a targeting sequence comprising SEQ ID NO: 51; (cm) an exosporium protein comprising an amino acid sequence having at least 85% identity with SEQ ID NO: 52; (cn) a targeting sequence comprising amino acids 1-33 of SEQ ID NO: 53; (co) a targeting sequence comprising amino acids 18-33 of SEQ ID NO: 53; (cp) a targeting sequence comprising SEQ ID NO: 53; (cq) an exosporium protein comprising an amino acid sequence having at least 85% identity with SEQ ID NO: 54; (cr) a targeting sequence comprising amino acids 1-30 of SEQ ID NO: 55; (cs) a targeting sequence comprising amino acids 15-30 of SEQ ID NO: 55; (ct) a targeting sequence comprising SEQ ID NO: 55; (cu) an exosporium protein comprising an amino acid sequence having at least 85% identity with SEQ ID NO: 56; (cv) a targeting sequence comprising amino acids 1-130 of SEQ ID NO: 57; (cw) a targeting sequence comprising amino acids 115-130 of SEQ ID NO: 57; (cx) a targeting sequence comprising SEQ ID NO: 57; (cy) an exosporium protein comprising an amino acid sequence having at least 85% identity with SEQ ID NO: 58; (cz) an exosporium protein fragment consisting of an amino acid sequence having at least 85% identity with SEQ ID NO: 59; (da) a targeting sequence comprising SEQ ID NO: 61; (db) a targeting sequence comprising SEQ ID NO: 62; (dc) a targeting sequence comprising SEQ ID NO: 63; (dd) a targeting sequence comprising SEQ ID NO: 64; (de) a targeting sequence comprising SEQ ID NO: 65; (df) a targeting sequence comprising SEQ ID NO: 66; (dg) a targeting sequence comprising SEQ ID NO: 67; (dh) a targeting sequence comprising SEQ ID NO: 68; (di) a targeting sequence comprising SEQ ID NO: 69; (dj) a targeting sequence comprising SEQ ID NO: 70; (dk) an exosporium protein comprising an amino acid sequence having at least 85% identity with SEQ ID NO: 71; (dl) an exosporium protein comprising an amino acid sequence having at least 85% identity with SEQ ID NO: 72; (dm) an exosporium protein comprising an amino acid sequence having at least 85% identity with SEQ ID NO: 73; (dn) an exosporium protein comprising an amino acid sequence having at least 85% identity with SEQ ID NO: 74; (do) an exosporium protein comprising an amino acid sequence having at least 85% identity with SEQ ID NO: 75; (dp) an exosporium protein comprising an amino acid sequence having at least 85% identity with SEQ ID NO: 76; (dq) an exosporium protein comprising an amino acid sequence having at least 85% identity with SEQ ID NO: 77; (dr) an exosporium protein comprising an amino acid sequence having at least 85% identity with SEQ ID NO: 78; (ds) an exosporium protein comprising an amino acid sequence having at least 85% identity with SEQ ID NO: 79; (dt) an exosporium protein comprising an amino acid sequence having at least 85% identity with SEQ ID NO: 80; (du) an exosporium protein comprising an amino acid sequence having at least 85% identity with SEQ ID NO: 81; (dv) an exosporium protein comprising an amino acid sequence having at least 85% identity with SEQ ID NO: 82; (dw) an exosporium protein comprising an amino acid sequence having at least 85% identity with SEQ ID NO: 83; (dx) an exosporium protein comprising an amino acid sequence having at least 85% identity with SEQ ID NO: 84; (dy) a targeting sequence consisting of amino acids 22-31 of SEQ ID NO: 1; (dz) a targeting sequence consisting of amino acids 22-33 of SEQ ID NO: 1; (ea) a targeting sequence consisting of amino acids 20-31 of SEQ ID NO: 1; (eb) a targeting sequence comprising amino acids 14-23 of SEQ ID NO: 3; (ec) a targeting sequence comprising amino acids 14-25 of SEQ ID NO: 3; or (ed) a targeting sequence comprising amino acids 12-23 of SEQ ID NO: 3.

The present invention is further directed to fusion proteins comprising a targeting sequence, an exosporium protein, or an exosporium protein fragment and at least one protein or peptide that protects a plant from a pathogen. The protein or peptide that protects a plant from a pathogen can comprise a harpin, an α-elastin, a β-elastin, a systemin, a phenylalanine ammonia-lyase, an elicitin, a defensin, a cryptogein, a flagellin protein, a flagellin peptide, a bacteriocin, a lysozyme, a lysozyme peptide, a siderophore, a non-ribosomal active peptide, a conalbumin, an albumin, a lactoferrin, a lactoferrin peptide, or TasA. Alternatively, the protein or peptide that protects a plant from a pathogen has insecticidal activity, helminthicidal activity, suppresses insect or worm predation, or a combination thereof. Alternatively, the protein that protects a plant from a pathogen comprises an enzyme. The targeting sequence, exosporium protein, or exosporium protein fragment can be any of the targeting sequences, exosporium proteins, or exosporium protein fragments listed above in paragraph [0005].

The present invention is also directed to fusion proteins comprising at least one protein or peptide of interest and an exosporium protein. The exosporium protein can be an exosporium protein comprising an amino acid sequence having at least 85% identity with any one of SEQ ID NOs: 71, 75, 80, 81, 82, 83, and 84.

The invention further relates to a recombinant *Bacillus cereus* family member that expresses any of the fusion proteins.

The invention is also directed to formulations comprising any of the recombinant *Bacillus cereus* family members and an agriculturally acceptable carrier.

The present invention also relates to a method for stimulating plant growth. The method comprises introducing into a plant growth medium any of the recombinant *Bacillus cereus* family members expressing a fusion protein comprising at least one plant growth stimulating protein or peptide, or any of the formulations comprising a recombinant *Bacillus cereus* family members expressing a fusion protein comprising at least one plant growth stimulating protein or peptide. Alternatively, the method comprises applying to a plant, a plant seed, or an area surrounding a plant or a plant seed any of the recombinant *Bacillus cereus* family members expressing a fusion protein comprising at least one plant growth stimulating protein or peptide, or any of the formulations comprising a recombinant *Bacillus cereus* family members expressing a fusion protein comprising at least one plant growth stimulating protein or peptide. The plant growth stimulating protein or peptide is physically attached to the exosporium of the recombinant *Bacillus* family member.

The present invention is also directed to a method for stimulating plant growth. The method comprises introducing a recombinant *Bacillus cereus* family member expressing a fusion protein into a plant growth medium or applying a recombinant *Bacillus cereus* family member expressing a fusion protein to a plant, a plant seed, or an area surrounding a plant or a plant seed. The fusion protein comprises at least one plant growth stimulating protein or peptide and a targeting sequence, an exosporium protein, or an exosporium protein fragment. The targeting sequence, an exosporium protein, or an exosporium protein fragment can be any of those listed above in paragraph [0005]. The plant growth stimulating protein or peptide is physically attached to the exosporium of the recombinant *Bacillus* family member.

The invention additionally relates to a method for protecting a plant from a pathogen or enhancing stress resistance in a plant. The method comprises introducing into a plant growth medium any of the recombinant *Bacillus cereus* family member expressing a fusion protein comprising at least one protein or peptide that protects a plant from a pathogen or at least one protein or peptide that enhances stress resistance in a plant, or any of the formulations comprising any of the recombinant *Bacillus cereus* family member expressing a fusion protein comprising at least one protein or peptide that protects a plant from a pathogen or at least one protein or peptide that enhances stress resistance in a plant. Alternatively, the method comprises applying to a plant, a plant seed, or an area surrounding a plant any of the recombinant *Bacillus cereus* family members expressing a fusion protein comprising at least one protein or peptide that protects a plant from a pathogen or at least one protein or peptide that enhances stress resistance in a plant, or any of the formulations comprising any of the recombinant *Bacillus cereus* family members expressing a fusion protein comprising at least one protein or peptide that protects a plant from a pathogen or at least one protein or peptide that enhances stress resistance in a plant. The protein or peptide that protects a plant from a pathogen or the protein or peptide that enhances stress resistance in a plant is physically attached to the exosporium of the recombinant *Bacillus cereus* family member.

The present invention is also directed to a method for immobilizing a recombinant *Bacillus cereus* family member spore on a plant. The method comprises introducing into a plant growth medium any of the recombinant *Bacillus cereus* family members expressing at least one plant binding protein or peptide, or any of the formulations comprising any of the recombinant *Bacillus cereus* family members expressing at least one plant binding protein or peptide. Alternatively, the method comprises applying to a plant, a plant seed, or an area surrounding a plant or a plant seed any of the recombinant *Bacillus cereus* family members expressing at least one plant binding protein or peptide, or any of the formulations comprising any of the recombinant *Bacillus cereus* family members expressing at least one plant binding protein or peptide. The plant binding protein or peptide is physically attached to the exosporium of the recombinant *Bacillus cereus* family member.

Other objects and features will be in part apparent and in part pointed out hereinafter.

BRIEF DESCRIPTION OF THE DRAWINGS

FIG. 1 shows an alignment of the amino acid sequence of the amino-terminal portion of *Bacillus anthracis* Sterne strain BclA and with the corresponding region from various exosporium proteins from *Bacillus cereus* family members.

DEFINITIONS

Figure 2:
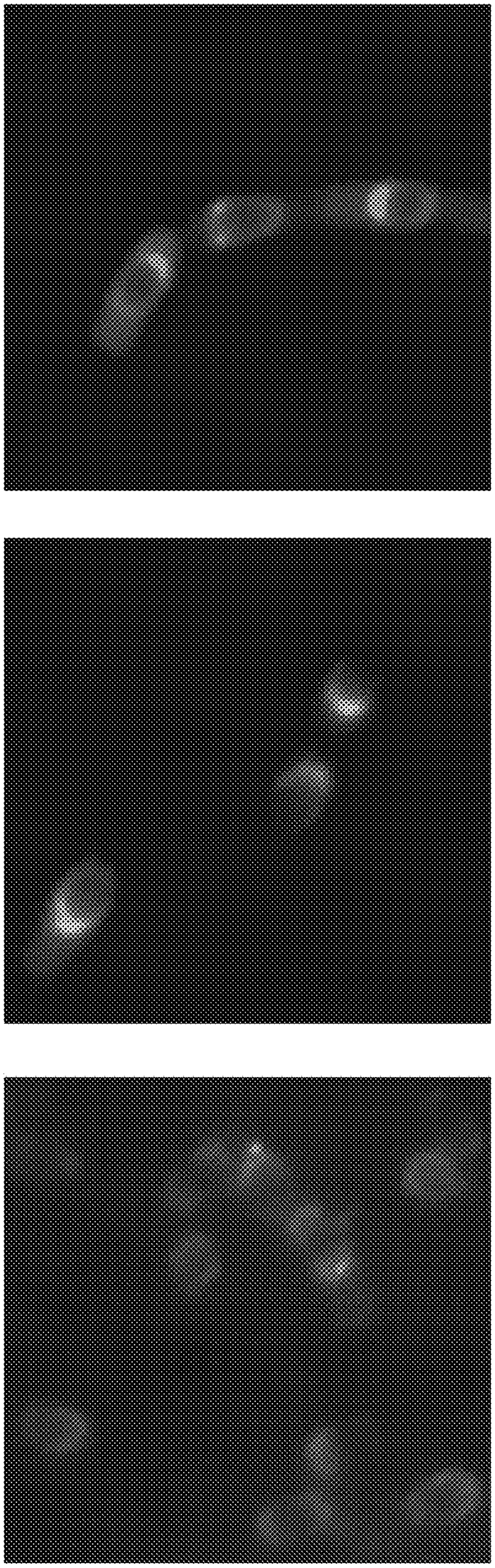
FIG. 2 shows exemplary fluorescent microscopy results for the expression of fusion proteins containing various exosporium proteins linked to an mCherry reporter on the exosporium.

When the articles "a," "an," "one," "the," and "said" are used herein, the mean "at least one" or "one or more" unless otherwise indicated.

The terms "comprising," "including," and "having" are intended to be inclusive and mean that there may be additional elements other than the listed elements.

The term "bioactive peptide" refers to any peptide that exerts a biological activity. "Bioactive peptides" can be generated, for example, via the cleavage of a protein, peptide, proprotein, or preproprotein by a protease or peptidase.

An "enzyme involved in the production or activation of a plant growth stimulating compound" includes any enzyme that catalyzes any step in a biological synthesis pathway for a compound that stimulates plant growth or alters plant structure, or any enzyme that catalyzes the conversion of an inactive or less active derivative of a compound that stimulates plant growth or alters plant structure to an active or more active form of the compound. Such compounds include, for example, but are not limited to, small molecule plant hormones such as auxins and cytokinins, bioactive peptides, and small plant growth stimulating molecules synthesized by bacteria or fungi in the rhizosphere (e.g., 2,3-butanediol).

The term "fusion protein" as used herein refers to a protein having a polypeptide sequence that comprises sequences derived from two or more separate proteins. A fusion protein can be generated by joining together a nucleic acid molecule that encodes all or part of a first polypeptide with a nucleic acid molecule that encodes all or part of a second polypeptide to create a nucleic acid sequence which, when expressed, yields a single polypeptide having functional properties derived from each of the original proteins.

The term "immobilizing a recombinant *Bacillus cereus* family member spore on a plant" refers to the binding of a *Bacillus cereus* family member spore to plant, e.g., to a root of a plant or to an aerial portion of a plant such as a leaf, stem, flower, or fruit, such that the spore is maintained at the plant's root structure or aerial portion instead of dissipating into the plant growth medium or into the environment surrounding the aerial portions of the plant.

A "plant growth medium" includes any material that is capable of supporting the growth of a plant.

A "plant immune system enhancer protein or peptide" as used herein includes any protein or peptide that has a beneficial effect on the immune system of a plant.

The term "plant growth stimulating protein or peptide" as used herein includes any protein or peptide that increases plant growth in a plant exposed to the protein or peptide.

A "protein or peptide that protects a plant from a pathogen" as used herein includes any protein or peptide that makes a plant exposed to the protein or peptide less susceptible to infection with a pathogen.

A "protein or peptide that enhances stress resistance in a plant" as used herein includes any protein or peptide that makes a plant exposed to the protein or peptide more resistant to stress.

The term "plant binding protein or peptide" refers to any peptide or protein capable of specifically or non-specifically binding to any part of a plant (e.g., roots or aerial portions of a plant such as leaves foliage, stems, flowers, or fruits) or to plant matter.

The term "targeting sequence" as used herein refers to a polypeptide sequence that, when present as part of a longer polypeptide or a protein, results in the localization of the longer polypeptide or the protein to a specific subcellular location. The targeting sequences described herein result in localization of proteins to the exosporium of a *Bacillus cereus* family member.

DESCRIPTION OF THE INVENTION

The present invention relates to fusion proteins containing a targeting sequence, an exosporium protein, or an exosporium protein fragment that targets the fusion protein to the exosporium of a *Bacillus cereus* family member and: (a) at least one plant growth stimulating protein or peptide; (b) at least one protein or peptide that protects a plant from a pathogen; (c) at least one protein or peptide that enhances stress resistance of a plant; or (d) at least one plant binding protein or peptide. When expressed in *Bacillus cereus* family member bacteria, these fusion proteins are targeted to the exosporium layer of the spore and are physically oriented such that the protein or peptide is displayed on the outside of the spore.

This *Bacillus* exosporium display (BEMD) system can be used to deliver peptides, enzymes, and other proteins to plants (e.g., to plant foliage, fruits, flowers, stems, or roots) or to a plant growth medium such as soil. Peptides, enzymes, and proteins delivered to the soil or another plant growth medium in this manner persist and exhibit activity in the soil for extended periods of time. Introduction of recombinant *Bacillus cereus* family member bacteria expressing the fusion proteins described herein into soil or the rhizosphere of a plant leads to a beneficial enhancement of plant growth in many different soil conditions. The use of the BEMD to create these enzymes allows them to continue to exert their beneficial results to the plant and the rhizosphere over the first months of a plants life.

Targeting Sequences, Exosporium Proteins, and Exosporium Protein Fragments

For ease of reference, the SEQ ID NOs. for the peptide and protein sequences referred to herein are listed in Table 1 below.

TABLE 1

Peptide and Protein Sequences

| Protein, protein fragment, or targeting sequence (SEQ ID. NO) | Sequence |
| --- | --- |
| AA 1-41 of BclA (*B. anthracis* Sterne) (SEQ ID NO: 1)* | MSNNNYSNGLNPDESLSASAFDPNLVGPTLPPIPPFTLPTG |
| Full length BclA (SEQ ID NO: 2)* | MSNNNYSNGLNPDESLSASAFDPNLVGPTLPPIPPFTLPTGPTGPFTTG PTGPTGPTGPTGPTGPTGPTGPTGPTGDTGTTGPTGPTGPTGPTGPTGPTGP TGPTGPTGFTPTGPTGPTGPTGDTGTTGPTGPTGPTGPTGPTGDTGTTG PTGPTGPTGPTGPTGPTGPTFTGPTGPTGPTGATGLTGPTGPTGPSGLG LPAGLYAFNSGGISLDLGINDPVPFNTVGSQFFTGTAISQLDADTFVISE TGFYKITVIANTATASVLGGLTIQVNGVPVPGTGSSLISLGAPFTIVIQA ITQITTTPSLVEVIVTGLGLSLALGTSASIIIEKVA |
| AA 1-33 of BetA/BAS3290 (*B. anthracis* Sterne) (SEQ ID NO: 3) | MSEKYIILHGTALEPNLIGPTLPPIPPFTFPNG |
| Full length BetA/BAS3290 (SEQ ID NO: 4) | MSEKYIILHGTALEPNLIGPTLPPIPPFTFPNGPTGITGPTGATGFTGIG ITGPTGVTGPTGIGITGPTGATGLGILPVFGTITTDVGIGFSVIVNTNIN FTLPGPVSGTTLNPVDNSIIINTTGVYSVSFSIVFVIQAISSSILNLTIN DSIQFAIESRIGGGPGVRATSARTDLLSLNQGDVLRVRIREATGDIIYSN ASLVVSKVD |
| Met + AA 2-43 of BAS4623 (*B. anthracis* Sterne) (SEQ ID NO: 5) | MVKVVEGNGGKSKIKSPLNSNFKILSDLVGPTFPPVPTGMTGIT |
| Full length BAS4623 (SEQ ID NO: 6) | VVKVVEGNGGKSKIKSPLNSNFKILSDLVGPTFPPVPTGMTGITGSTG ATGNTGPTGETGATGSAGITGSTGPTGNTGGTGSTGPTGNTGATGSTG VTGSTGVTGSTGVTGSTGVTGSTGPTGETGGTGSTGVTGSTGATGST GVTGNTGPTGSTGATGNTGSIGETGGTGSMGPTGETGVTGSTGGTGS TGVTGNTGPTGSTGVTGSTGVTGSTGPTGSTGVTGSTGPTGSTGVTGS TGVTGNMGPTGSTGVTGNTGSTGTTGATGETGPMGSTGATGTTGPT GETGETGETGGTGSTGPTGNTGATGSTGVTGSTGVTGSTGVTGETGP TGSTGATGNTGPTGETGGTGSTGATGSTGVTGNTGPTGSTGVTGNTG ATGETGPTGNTGATGNTGPTGETGVTGSTGPTGETGVTGSTGPTGNT GATGETGATGSTGVTGNTGSTGETGPTGSTGPTGSTGATGVTGNTGP TGSTGATGATGSTGPTGSTGTTGNTGVTGDTGPTGATGVSTTATYAF ANNTSGSVISVLLGGTNIPLPNNQNIGPGITVSGGNTVFTVANAGNYYI AYTINLTAGLLVSSRITVNGSPLAGTINSPTVATGSFSATIIASLPAGAA VSLQLFGVVALATLSTATPGATLTIIRLS |

TABLE 1 -continued

| Peptide and Protein Sequences | |
|---|---|
| Protein, protein fragment, or targeting sequence (SEQ ID. NO) | Sequence |
| AA 1-34 of BclB (*B. anthracis* Sterne) (SEQ ID NO: 7) | MKQNDKLWLDKGIIGPENIGPTFPVLPPIHIPTG |
| Full length BclB (SEQ ID NO: 8) | MKQNDKLWLDKGIIGPENIGPTFPVLPPIHIPTGITGATGATGITGATGP<br>TGTTGATGATGITGVTGATGITGVTGATGITGVTGATGITGVTGPTGIT<br>GATGPTGITGATGPAGITGVTGPTGITGATGPTGTTGVTGPTGDTGLA<br>GATGPTGATGLAGATGPTGDTGATGPTGATGLAGATGPTGATGLTG<br>ATGATGATGGGAIIPFASGTTPALLVNAVLANTGTLLGFGFSQPGIAP<br>GVGGTLTILPGVVGDYAFVAPRDGIITSLAGFFSATAALAPLTPVQIQM<br>QIFIAPAASNTFTPVAPPLLLTPALPAIAIGTTATGIQAYNVPVVAGDKI<br>LVYVSLTGASPIAAVAGFVSAGLNIV |
| AA 1-30 of BAS1882 (*B. anthracis* Sterne) (SEQ ID NO: 9) | MDEFLSSAALNPGSVGPTLPPMQPFQFRTG |
| Full length BAS1882 (SEQ ID NO: 10) | MDEFLSSAALNPGSVGPTLPPMQPFQFRTGPTGSTGAKGAIGNTEPYW<br>HTGPPGIVLLTYDFKSLIISFAFRILPIS |
| AA 1-39 of gene 2280 (*B. weihenstephensis* KBAB4) (SEQ ID NO: 11) | MFDKNEIQKINGILQANALNPNLIGPTLPPIPPFTLPTG |
| Full length KBAB4 gene 2280 (SEQ ID NO: 12) | MFDKNEIQKINGILQANALNPNLIGPTLPPIPPFTLPTGPTGVTGPTGVT<br>GPTGVTGPTGVTGPTGVTGPTGVTGPTGVTGPTGVTGPTGVTGPTGV<br>TGPTGVTGPTGVTGPTGVTGPTGVTGPTGETGPTGGTEGCLCDCCVL<br>PMQSVLQQLIGETVILGTIADTPNTPPLFFLFTITSVNDFLVTVTDGTTT<br>FVVNISDVTGVGFLPPGPPITLLPPTDVGCECECRERPIRQLLDAFIGST<br>VSLLASNGSIAADFSVEQTGLGIVLGTLPINPTTTVRFAISTCKITAVNIT<br>PITM |
| AA 1-39 of gene 3572 (*B. weihenstephensis* KBAB4) (SEQ ID NO: 13) | MFDKNEMKKTNEVLQANALDPNIIGPTLPPIPPFTLPTG |
| Full Length KBAB4 gene 3572 (SEQ ID NO: 14) | MFDKNEMKKTNEVLQANALDPNIIGPTLPPIPPFTLPTGPTGPTGPTGP<br>TGPTGPTGPTGPTGPTGPTGPTGPTGLTGPTGPTGLTGPTGLTGPT<br>GPTGLTGQTGSTGPTGATEGCLCDCCVFPMQEVLRQLVGQTVILATIA<br>DAPNVAPRFFLFNITSVNDFLVTVTDPVSNTTFVVNISDVIGVGFSLTV<br>PPLTLLPPADLGCECDCRERPIRELLDTLIGSTVNLLVSNGSIATGFNVE<br>QTALGIVIGTLPIPINPPPPTLFRFAISTCKITAVDITPTPTAT |
| AA 1-49 of Exosporium Leader Peptide (*B. cereus* VD200) (SEQ ID NO: 15) | MSRKDKFNRSRMSRKDRFNSPKIKSEISISPDLVGPTFPPIPSFTLPTG |
| Full Length Exosporium Leader Peptide (SEQ ID NO: 16) | MSRKDKFNRSRMSRKDRFNSPKIKSEISISPDLVGPTFPPIPSFTLPTGIT<br>GPTFNINFRAEKNVAQSFTPPADIQVSYGNIIFNNGGGYSSVTNTFTAPI<br>NGIYLFSASIGFNPTLGTTSTLRITIRKNLVSVASQTGTITTGGTPQLEIT<br>TIIDLLASQTIDIQFSAAESGTLTVGSSNFFSGALLP |
| AA 1-33 of Exosporium Leader Peptide (*B. cereus* VD166) (SEQ ID NO: 17) | MNEEYSILHGPALEPNLIGPTLPSIPPFTFPTG |
| Full Length Exosporium Leader Peptide (SEQ ID NO: 18) | MNEEYSILHGPALEPNLIGPTLPSIPPFTFPTGPTGITGPTGATGFTGIGI<br>TGPTGVTGPTGIGITGPTGATGPTGIGITGPTG |
| AA 1-39 of hypothetical protein IKG_04663 (*B. cereus* VD200) (SEQ ID NO: 19) | MKNRDNNRKQNSLSSNFRIPPELIGPTFPPVPTGFTGIG |

TABLE 1 -continued

| Protein, protein fragment, or targeting sequence (SEQ ID. NO) | Sequence |
|---|---|
| Peptide and Protein Sequences | |
| Full Length hypothetical protein IKG_04663, partial (SEQ ID NO: 20) | MKNRDNNRKQNSLSSNFRIPPELIGPTFPPVPTGFTGIGITGPTGPQGPT GPQGPRGLQGPMGEMGPTGPQGVQGIQGSVGPIGATGPEGQQGPQGL RGPQGETGATGPGGVQGLQGPIGPTGATGAQGIQGIQGLQGPIGATGP EGSQGIQGVQGLPGATGPQGIQGAQGIQGTPGPSGNTGATGATGATG QGITGPTGITGPTGITGPSGGPPGPTGPTGATGPGGGPSGSTGATGATG NTGATGSTGVTGATGSTGPTGSTGAQGLQGIQGIQGPIGPTGPEGSQGI QGIPGPTGVTGEQGIQGVQGIQGATGATGDQGPQGIQGVIGPQGVTG ATGDQGPQGIQGVPGPSGETGPQGVQGIQGPMGDIGPTGPEGPEGLQ GPQGIQGVPGPVGATGPEGPQGIQGIQGPVGATGPQGPQGIQGIQGVQ GITGATGVQGATGIQGIQGEIGATGPEGPQGVQGAQGAIGPTGPMGPQ GVQGVQGIQGATGAQGVQGPQGIQGIQGPTGATGDMGATGATGEGT TGPTGVTGPTGVTGPSGGPAGPTGPTGPSGPAGVTGPSGGPPGPTGAT GATGVTGDTGATGSTGVTGATGETGATGVTGLQGPQGIQGVQGEIGP TGPQGVQGPQGIQGVTGATGDQGPQGIQGPQGDIGPTGPQGIQGPQGS QGIQGATGGTGAQGPQGIQGPQGDIGLTGSQGPTGIQGIQGEIGPTGPE GPEGLQGPQGIQGIQGPVGATGPEGPQGIQGIQGVQGATGPQGPQGIQ GIQGVQGITGATGAQGATGIQGIQGEIGATGPEGPQGVQGIQGAIGPT GPMGAQGVQGIQGIQGATGAQGVQGPQGIQGVQGPTGATGETGATG ATGEGTTGPTGVTGPTGVTGPSGGPAGPTGPTGPSGPAGVTGPSGGPP GPTGATGATGVTGDTGATGSTGVTGATGATGATGVTGLQGPQGIQG VQGEIGPTGPQGIQGPQGIQGVTGATGAQGPQGIQGPQGDIGPTGSQGI QGPQGPQGIQGATGATGAQGPQGIQGPQGEIGPTGPQGPQGIQGPQGI QGPTG |
| AA 1-39 of YVTN β-propeller protein (*B. weihenstephensis* KBAB4) (SEQ ID NO: 21) | MSDKHQMKKISEVLQAHALDPNLIGPPLPPITPFTFPTG |
| Full length YVTN β-propeller protein KBAB4 (SEQ ID NO: 22) | MSDKHQMKKISEVLQAHALDPNLIGPPLPPITPFTFPTGSTGPTGSTGS TGPTGSTGNTGPTGPTGPPVGTNLDTIYVTNDISNNVSAIDGNTNTVLT TIPVGTNPVGVGVNSSTNLIYVVNNGSDNISVINGSTNTVVATIPVGTQ PFGVGVNPSTNLIYVANRTSNNVSVIKGGTNTVLTTIPVGTNPVGVGV NSSTNLIYVTNEIPNSVSVIKGGTNTVVATIPVGLFPFGVGVNSLTNLIY VVNNSPHNVSVIDGNTNTVLTTISVGTSPVGVGVNLSTNLIYVANEVP NNISVINGNTNTVLTTIPVGTTPFEVGVNSSTNLIYVSNLNSNNVSVIN GSANTVIATVPVGSVPRGIGVKP |
| AA 1-30 of hypothetical protein bcerkbab4_2363 (*B. weihenstephensis* KBAB4) (SEQ ID NO: 23) | MDEFLSFAALNPGSIGPTLPPVPPFQFPTG |
| Full length hypothetical protein bcerkbab4_363 KBAB4 (SEQ ID NO: 24) | MDEFLSFAALNPGSIGPTLPPVPPFQFPTGPTGSTGSTGPTGSTGSTGPT GFNLPAGPASITLTSNETTACVSTQGNNTLFFSGQVLVNGSPTPGVVV SFSFSNPSLAFMVPLAVITNASGNFTAVFLAANGPGTVTVTASLLDSP GTMASVTITIVNCP |
| AA 1-30 of hypothetical protein bcerkbab4_2131 (*B. weihenstephensis* KBAB4) (SEQ ID NO: 25) | MDEFLSSTALNPCSIGPTLPPMQPFQFPTG |
| Full length hypothetical protein bcerkbab4_2131 (SEQ ID NO: 26) | MDEFLSSTALNPCSIGPTLPPMQPFQFPTGPTGSTGTTGPTGSIGPTGNT GLTGNTGPTGITGPTGDTG |
| AA 1-36 of triple helix repeat containing collagen (*B. weihenstephensis* KBAB4) (SEQ ID NO: 27) | MKERDRQNSLNSNFRISPNLIGPTFPPVPTGFTGIG |

TABLE 1 -continued

| Peptide and Protein Sequences | |
|---|---|
| Protein, protein fragment, or targeting sequence (SEQ ID. NO) | Sequence |
| Full length triple helix repeat-containing collagen KBAB4 (SEQ ID NO: 28) | MKERDRQNSLNSNFRISPNLIGPTFPPVPTGFTGIGITGPTGPQGPTGPQ<br>GPRGFQGPMGEMGPTGPQGVQGIQGPAGQMGATGPEGQQGPQGLRG<br>PQGETGATGPQGVQGLQGPIGPTGATGAQGIQGIQGLQGPIGATGPEG<br>PQGIQGVQGVPGATGSQGIQGAQGIQGPQGPSGNTGATGVTGQGISGP<br>TGITGPTGITGPSGGPPGPTGATGATGPGGGPSGSTGATGATGNTGVT<br>GSAGVTGNTGSTGSTGETGAQGLQGIQGVQGPIGPTGPEGPQGIQGIP<br>GPTGVTGEQGIQGVQGIQGITGATGDQGPQGIQGAIGPQGITGATGDQ<br>GPQGIQGVPGPTGDTGSQGVQGIQGPMGDIGPTGPEGPEGLQGPQGIQ<br>GVPGPAGATGPEGPQGIQGIQGPIGVTGPEGPQGIQGIQGIQGITGATG<br>AQGATGVQGVQGNIGATGPEGPQGVQGTQGDIGPTGPMGPQGVQGI<br>QGIQGPTGAQGVQGPQGIQGIQGPTGVTGDTGTTGATGEGTTGATGV<br>TGPSGVTGPSGGPAGPTGPTGPSGPTGLTGPSGGPPGPTGATGVTGGV<br>GDTGATGSTGVTGATGVTGATGATGLQGPQGIQGVQGDIGPTGPQG<br>VQGPQGIQGITGATGDQGPQGIQGPQGIQGPTGPQGIQGGQGPQGIQG<br>ATGATGAQGPQGIQGIQGVQGPTGPQGPTGIQGVQGEIGPTGPQGVQ<br>GLQGPQGPTGDTGPTGPQGPQGIQGPTGATGATGSQGIQGPTGATGA<br>TGSQGIQGPTGATGATGATGATGATGATGATGVTGVSTTATYSFANN<br>TSGSAISVLLGGTNIPLPNNQNIGPGITVSGGNTVFTVTNAGNYYIAYTI<br>NITAALLVSSRITVNGSPLAGTINSPAVATGSFNATIISNLAAGSAISLQ<br>LFGLLAVATLSTTTPGATLTIIRLS |
| AA 1-39 of hypothetical protein bmyco0001_21660 (*B. mycoides* 2048) (SEQ ID NO: 29) | VFDKNEIQKINGILQANALNPNLIGPTLPPIPPFTLPTG |
| Full length hypothetical protein bmyco0001_21660 (SEQ ID NO: 30) | VFDKNEIQKINGILQANALNPNLIGPTLPPIPPFTLPTGPTGGTGPTGVT<br>GPTGVTGPTGVTGPTGVTGPTGVTGPTGVTGPTGVTGPTGVTGPTGV<br>TGPTGVTGPTGVTGPTGVTGPTGGTEGCLCDCCVLPMQSVLQQLIGE<br>TVILGTIADTPNTPPLFFLFTITSVNDFLVTVTDGTTTFVVNISDVTGVG<br>FLPPGPPITLLPPTDVGCECECRERPIRQLLDAFIGSTVSLLASNGSIAAD<br>FSVEQTGLGIVLGTLPINPTTTVRFAISTCKITAVNITPITM |
| AA 1-30 of hypothetical protein bmyco0001_22540 (*B. mycoides* 2048) (SEQ ID NO: 31) | MDEFLYFAALNPGSIGPTLPPVQPFQFPTG |
| Full length hypothetical protein bmyc0001_22540 SEQ ID NO: 32) | MDEFLYFAALNPGSIGPTLPPVQPFQFPTGPTGSTGATGSTGSTGSTGP<br>TGSTGSTGSTGSTGPTGPTGPTGSTGPTGPTGFNLPAGPASITLTSNETT<br>ACVSTQGNNTLFFSGQVLVNGSPTPGVVVSFSFSNPSLAFMVPLAVIT<br>NASGNFTAVFLAANGPGTVTVTASLLDSPGTMASVTITIVNCP |
| AA 1-21 of hypothetical protein bmyc0001_21510 (*B. mycoides* 2048) (SEQ ID NO: 33) | MDSKNIGPTFPPLPSINFPTG |
| Full length hypothetical protein bmyc0001_21510 (SEQ ID NO: 34) | MDSKNIGPTFPPLPSINFPTGVTGETGATGETGATGATGETGATGETG<br>ETGATGATGATGATGETGATGATGATGAAGATGETGATGETGATGE<br>TGATGETGATGVTGETGATGETGAAGETGITGVTGPTGETGATGETG<br>ATGATGITGATGITGVAGATGETGAAGETGPTGATGAIGAIGATGAT<br>GITGVTGATGETGAAGATGITGVTGATGETGAAGATGITGATGITGV<br>AGATGITGPTGIPGTIPTTNLLYFTFSDGEKLIYTNADGIAQYGTTQILS<br>PSEVSYINLFINGILQPQPFYEVTAGQLTLLDDEPPSQGSSIILQFIIIN |
| AA 1-22 of collagen triple helix repeat protein (*B. thuringiensis* 35646) (SEQ ID NO: 35) | MIGPENIGPTFPILPPIYIPTG |
| Full length collagen triple helix repeat protein (SEQ ID NO: 36) | MIGPENIGPTFPILPPIYIPTGETGPTGITGATGETGPTGITGPTGITGA<br>TGETGSTGITGATGETGSTGITGPIGITGATGETGPIGITGATGETGPTG<br>ITGSTGITGLTGVTGLTGETGPIGITGPTGITGPTGVTGATGPTGGIGPI<br>TTTNLLYYTFADGEKLIYTDTDGIPQYGTTNILSPSEVSYINLFVNGILQ<br>PQPLYEVSTGKLTLLDTQPPSQGSSIILQFIIIN |

TABLE 1 -continued

| Peptide and Protein Sequences | |
|---|---|
| Protein, protein fragment, or targeting sequence (SEQ ID. NO) | Sequence |
| AA 1-35 of hypothetical protein WP_69652 (*B. cereus*) (SEQ ID NO: 43) | MSNNNIPSPFFFNNFNPELIGPTFPPIPPLTLPTG |
| Full length hypothetical protein WP_69652 (SEQ ID NO: 44) | MSNNNIPSPFFFNNFNPELIGPTFPPIPPLTLPTGPTGSTGATGATGPTGA TGPTGATGPTGATGATGSTGATGPTGATGTFSSANASIVTPAPQTVNN LAPIQFTAPVLISKNVTFNGIDTFTIQIPGNYFFIGAVMTSNNQAGPVAV GVGFNGIPVPSLDGANYGTPTGQEVVCFGFSGQIPAGTTINLYNISDKT ISIGGATAAGSSIVAARLSFFRIS |
| AA 1-41 of exosporium leader WP016117717 (*B. cereus*) (SEQ ID NO: 45) | MFSEKKRKDLIPDNFLSAPALDPNLIGPTFPPIPSFTLPTG |
| Full length exosporium leader WP016117717 (SEQ ID NO: 46) | MFSEKKRKDLIPDNFLSAPALDPNLIGPTFPPIPSFTLPTGSTGPTGPTG DTGPTGPTATICIRTDPDNGCSVAEGSGTVASGFASHAEACNTQAIGD CSHAEGQFATASGTASHAEGFQTTASGFASHTEGSGTTADANFSHTE GINTIVDVLHPGSHIMGKNGTTRSSFSWHLANGLAVGPSLNSAVIEGV TGNLYLDGVVISPNAADYAEMFETIDGNLIDVGYFVTLYGEKIRKAN ANDDYILGVVSATPAMIADASDLRWHNLFVRDEWGRTQYHEVVVPE KKMAMEE |
| AA 1-49 of exosporium peptide WP002105192 (*B. cereus*) (SEQ ID NO: 47) | MTRKDKFNRSRISRRDRFNSPKIKSEILISPDLVGPTFPPIPSFTLPTG |
| Full length exosporium peptide WP002105192 (SEQ ID NO: 48) | MTRKDKFNRSRISRRDRFNSPKIKSEILISPDLVGPTFPPIPSFTLPTGVT GPTGNTGPTGITGPTGDTGPTGDTGPTGITGP |
| AA 1-38 of hypothetical protein WP87353 (*B. cereus*) (SEQ ID NO: 49) | MSRKDRFNSPKIKSEISISPDLVGPTFPPIPSFTLPTG |
| Full length hypothetical protein WP87353 (SEQ ID NO: 50) | MSRKDRFNSPKIKSEISISPDLVGPTFPPIPSFTLPTGITGPTGNTGPTGD TGPTGPTFNINFRAEKNGAQSFTPPADIQVSYGNIIFNNGGGYSSVTNT FTAPINGIYLFSANIGFNPTLGTTSTLRITIRKNLVSVASQTIDIQFSAAE SGTLTVGSSNFF |
| AA 1-39 of exosporium peptide 02112369 (*B. cereus*) (SEQ ID NO: 51) | MKERDNKGKQHSLNSNFRIPPELIGPTFPPVPTGFTGIG |
| Full length exosporium peptide 02112369 (SEQ ID NO: 52) | MKERDNKGKQHSLNSNFRIPPELIGPTFPPVPTGFTGIGITGPTGPQGPT GPQGPRGFQGPMGEMGPTGPQGVQGIQGPAGQMGATGPEGQQGPEG LRGPVGATGATGLQGVQGIQGPIGSTGATGAQGIQGIQGLQGPIGATG PEGPQGIQGVQGLPGATGPQGVQGVQGVIGPQGPSGSTGGTGATGQG VTGPTGITGSTGVTGPSGGPPGPTGPTGATGPGGGPSGSTGVTGSTGN TGATGSPGVTGATGPTGSTGATGIQGSQGIQGIQGIQGPLGPTGPEGPQ GIQGIPGPTGITGEQGIQGVQGIQGITGATGDQGT |
| AA 1-39 of exosporium protein WP016099770 (*B. cereus*) (SEQ ID NO: 53) | MRERDNKRQQHSLNPNFRISPELIGPTFPPVPTGFTGIG |
| Full length exosporium protein WP016099770 (SEQ ID NO: 54) | MRERDNKRQQHSLNPNFRISPELIGPTFPPVPTGFTGIGITGPTGPQGPT GPQGPRGFQGPMGEMGPTGPQGVQGIQGPVGPIGATGPEGQQGPQGL RGPQGETGATGPGGVQGLQGPIGPTGATGAQGVQGIQGLQGPIGATG PEGPQGIQGVQGLPGATGSQGIQGVQGIQGPQGPSGNTGATGATGQGI TGPTGITGPTGITGPSGGPPGPTGPTGATGPGGGPSGSTGATGATGNTG ATGNTGITGATGSTGPTGSTGAQGLQGIQGIQGPIGPTGPEGPQGIQGIP |

TABLE 1 -continued

| Peptide and Protein Sequences | |
|---|---|
| Protein, protein fragment, or targeting sequence (SEQ ID. NO) | Sequence |
| | GPTGVTGEQGIQGVQGIQGITGATGDQGPQGIQGVIGAQGVTGATGD<br>QGPQGIQGVPGPSGATGPQGVQGIQGPMGDIGPTGPEGPEGLQGPQGI<br>QGVPGPVGATGPEGPQGIQGIQGVQGATGPQGPQGIQGIQGVQGITGA<br>TG |
| AA 1-36 of hypothetical protein YP006612525 (*B. thuringiensis*) (SEQ ID NO: 55) | MKNRDNKGKQQSNFRIPPELIGPTFPPVPTGFTGIG |
| Full length hypothetical protein YP006612525 (SEQ ID NO: 56) | MKNRDNKGKQQSNFRIPPELIGPTFPPVPTGFTGIGITGPTGPQGPTGP<br>QGPRGFQGPMGEMGPTGPQGVQGIQGPVGPIGATGPEGQQGAQGLR<br>GPQGETGATGPQGVQGLQGPIGPTGATGAQGIQGIQGLQGPIGATGPE<br>GPQGIQGVQGLPGATGPQGIQGAQGIQGTQGPSGNTGATGATGQGLT<br>GPTGITGPTGITGPSGGPPGPTGPTGATGPGGGPSGSTGATGATGDTG<br>ATGSTGVTGATGAQGPQGVQGIQGPTGATGATGATGPQGIQGPQGIQ<br>GPTGATGATGSQGPTGNTGPTGSQGIQGPTGPTGAGATGATGATGAT<br>GVSTTATYAFANNTSGSIISVLLGGTNIPLPNNQNIGPGITVSGGNTVFT<br>VANAGNYYIAYTINLTAGLLVSSRITVNGSPLAGTINSPAVAAGSFSAT<br>IIANLPAGAAVSLQLFGVIALATLSTATPGATLTIIRLS |
| AA 1-136 of hypothetical protein TIGR03720 (*B. mycoides*) (SEQ ID NO: 57)** | MKFSKKSTVDSSIVGKRVVSKVNILRFYDARSCQDKDVDGFVDVGEL<br>FTIFRKLNMEGSVQFKAHNSIGKTYYITINEVYVFVTVLLQYSTLIGGS<br>YVFDKNEIQKINGILQANALNPNLIGPTLPPIPPFTLPTG |
| Full length hypothetical protein TIGR03720 (SEQ ID NO: 58)** | MKFSKKSTVDSSIVGKRVVSKVNILRFYDARSCQDKDVDGFVDVGEL<br>FTIFRKLNMEGSVQFKAHNSIGKTYYITINEVYVFVTVLLQYSTLIGGS<br>YVFDKNEIQKINGILQANALNPNLIGPTLPPIPPFTLPTGPTGGTGPTGV<br>TGPTGVTGPTGVTGPTGVTGPTGVTGPTGVTGPTGVTGPTGVTGPTG<br>VTGPTGVTGPTGVTGPTGVTGPTGGTEGCLCDCCVLPMQSVLQQLIG<br>ETVILGTIADTPNTPPLFFLFTITSVNDFLVTVTDGTTTFVVNISDVTGV<br>GFLPPGPPITLLPPTDVGCECECRERPIRQLLDAFIGSTVSLLASNGSIAA<br>DFSVEQTGLGIVLGTLPINPTTTVRFAISTCKITAVNITPITM |
| AA 1-196 of BclA (*B. anthracis* Sterne) (SEQ ID NO: 59)* | MSNNNYSNGLNPDESLSASAFDPNLVGPTLPPIPPFTLPTGPTGPFTTG<br>PTGPTGPTGPTGPTGPTGPTGPTGDTGTTGPTGPTGPTGPTGPTGPTGP<br>TGPTGPTGFTPTGPTGPTGPTGDTGTTGPTGPTGPTGPTGPTGDTGTTG<br>PTGPTGPTGPTGPTGPTFTGPTGPTGPTGATGLTGPTGPTGPSGLG |
| Met + AA 20-35 of BclA (*B. anthracis* Sterne) (SEQ ID NO: 60) | MAFDPNLVGPTLPPIPP |
| Met + AA 12-27 of BetA/BAS3290 (*B. anthracis* Sterne) (SEQ ID NO: 61) | MALEPNLIGPTLPPIPP |
| Met + AA 18-33 of gene 2280 (*B. weihenstephensis* KBAB4) (SEQ ID NO: 62) | MALNPNLIGPTLPPIPP |
| Met + AA 18-33 of gene 3572 (*B. weihenstephensis* KBAB4) (SEQ ID NO: 63) | MALDPNIIGPTLPPIPP |
| Met + AA 12-27 of Exosporium Leader Peptide (*B. cereus* VD166) (SEQ ID NO: 64) | MALEPNLIGPTLPSIPP |

TABLE 1 -continued

Peptide and Protein Sequences

| Protein, protein fragment, or targeting sequence (SEQ ID. NO) | Sequence |
|---|---|
| Met + AA 18-33 of YVTN β-propeller protein (*B. weihenstephensis* KBAB4) (SEQ ID NO: 65) | MALDPNLIGPPLPPITP |
| Met + AA 9-24 of hypothetical protein bcerkbab4_2363 (*B. weihenstephensis* KBAB4) (SEQ ID NO: 66) | MALNPGSIGPTLPPVPP |
| Met + AA 9-24 of hypothetical protein bcerkbab4_2131 (*B. weihenstephensis* KBAB4) (SEQ ID NO: 67) | MALNPCSIGPTLPPMQP |
| Met + AA 9-24 of hypothetical protein bmyc0001_22540 (*B. mycoides* 2048) (SEQ ID NO: 68) | MALNPGSIGPTLPPVQP |
| Met + AA 9-24 of BAS1882 (*B. anthracis* Sterne) (SEQ ID NO: 69) | MALNPGSVGPTLPPMQP |
| Met + AA 20-35 of exosporium leader WP016117717 (*B. cereus*) (SEQ ID NO: 70) | MALDPNLIGPTFPPIPS |
| Full length InhA (*B. mycoides*) (SEQ ID NO: 71) | MKRKTPFKVFSSLAITTMLGCTFALGTSVAYAETTSQSKGSISTTPIDN NLIQEERLAEALKERGTIDQSASKEETQKAVEQYIEKKKGDQPNKEIL PDDPAKEASDFVKKVKEKKMEEKEKVKKSVENASSEQTPSQNKKQL NGKVPTSPAKQAPYNGAVRTDKVLVLLVEFSDYKHNNIEQSPGYMY ANDFSREHYQKMLFGNEPFTLFDGSKVKTFKQYYEEQSGGSYTTDGY VTEWLTVPGKAADYGADGKTGHDNKGPKGARDLVKEALKAAAEKG LDLSQFDQFDRYDTNGDGNQNEPDGVIDHLMVIHAGVGQEAGGGKL GDDAIWSHRSKLAQDPVAIEGTKSKVSYWDGKVAAHDYTIEPEDGA VGVFAHEFGHDLGLPDEYDTNYTGAGSPVEAWSLMSGGSWTGRIAG TEPTSFSPQNKDFLQKNMDGNWAKIVEVDYDKIKRGVGFPTYIDQSV TKSNRPGLVRVNLPEKSVETIKTGFGKHAYYSTRGDDMHTTLETPLF DLTKAANAKFDYKANYELEAECDFIEVHAVTEDGTKTLIDKLGDKVV KGDQDTTEGKWIDKSYDLSQFKGKKVKLQFDYITDPALTYKGFAMD NVNVTVDGKVVFSDDAEGQAKMKLNGFVVSDGTEKKPHYYYLEWR NYAGSDEGLKVGRGPVYNTGLVVWYADDSFKDNWVGRHPGEGFLG VVDSHPEAVVGNLNGKPVYGNTGLQIADAAFSLDQTPAWNVNSFTR GQFNYPGLPGVATFDDSKVYSNTQIPDAGRKVPQLGLKFQVVGQAD DKSAGAIWIRR |
| Full length BAS1141 (ExsY) (*B. anthracis* Sterne) (SEQ ID NO: 72) | MSCNENKHHGSSHCVVDVVKFINELQDCSTTTCGSGCEIPFLGAHNT ASVANTRPFILYTKAGAPFEAFAPSANLTSCRSPIFRVESVDDDSCAVL RVLSVVLGDSSPVPPTDDPICTFLAVPNARLVSTSTCITVDLSCFCAIQC LRDVTI |
| Full length BAS1144 (BxpB/ExsFA) (*B. anthracis* Sterne) (SEQ ID NO: 73) | MFSSDCEFTKIDCEAKPASTLPAFGFAFNASAPQFASLFTPLLLPSVSPN PNITVPVINDTVSVGDGIRILRAGIYQISYTLTISLDNSPVAPEAGRFFLS LGTPANIIPGSGTAVRSNVIGTGEVDVSSGVILINLNPGDLIRIVPVELIG TVDIRAAALTVAQIS |
| Full length BAS1145 (CotY) (*B. anthracis* Sterne) (SEQ ID NO: 74) | MSCNCNEDHHHHDCDFNCVSNVVRFIHELQECATTTCGSGCEVPFLG AHNSASVANTRPFILYTKAGAPFEAFAPSANLTSCRSPIFRVESIDDDD CAVLRVLSVVLGDTSPVPPTDDPICTFLAVPNARLISTNTCLTVDLSCF CAIQCLRDVTI |

TABLE 1 -continued

| Peptide and Protein Sequences | |
|---|---|
| Protein, protein fragment, or targeting sequence (SEQ ID. NO) | Sequence |
| Full length BAS1140 (*B. anthracis* Sterne) (SEQ ID NO: 75) | MEVGGTSVKNKNKSSTVGKPLLYIAQVSLELAAPKTKRIILTNFENED RKEESNRNENVVSSAVEEVIEQEEQQQEQEQEQEEQVEEKTEEEEQV QEQQEPVRTVPYNKSFKDMNNEEKIHFLLNRPHYIPKVRCRIKTATIS YVGSIISYRNGIVAIMPPNSMRDIRLSIEEIKSIDMAGF |
| Full length ExsFB (*B. anthracis* H9401) (SEQ ID NO: 76) | MKERSENMRSSSRKLTNFNCRAQAPSTLPALGFAFNATSPQFATLFTPLL LPSTGPNPNITVPVINDTISTGTGIRIQVAGIYQISYTLTISLDNVPVTP EAARFFLTLNSSTNIIAGSGTAVRSNIIGTGEVDVSSGVILINLNPGDLIQ IVPVEVIGTVDIRSAALTVAQIR |
| Full length InhA1 (*B. thuringiensis* HD74) (SEQ ID NO: 77) | MSKKPFKVLSSIALTAVLGLSFGAGTQSAYAETPVNKTATSPVDDHLI PEERLADALKKRGVIDSKASETETKKAVEKYVENKKGENPGKEAAN GDQLTKDASDFLKKVKDAKADTKEKLNQPATGTPAATGPVKGGLNG KVPTSPAKQKDYNGEVRKDKVLVLLVEYADFKHNNIDKEPGYMYSN DFNKEHYEKMLFGNEPFTLDDGSKIETFKQYYEEQSGGSYTVDGTVT KWLTVPGKAADYGADAPGGGHDNKGPKGPRDLVKDALKAAVDSGI DLSEFDQFDQYDVNGDGNKNQPDGLIDHLMIIHAGVGQEAGGGKLG DDAIWSHRWTVGPKPFPIEGTQAKVPYWGGKMAAFDYTIEPEDGAV GVFAHEYGHDLGLPDEYDTQYSGQGEPIEAWSIMSGGSWAGKIAGTT PTSFSPQNKEFFQKTIGGNWANIVEVDYEKLNKGIGLATYLDQSVTKS ARPGMIRVNLPDKDVKTIEPAFGKQYYYSTKGDDLHTKMETPLFDLT NATSAKFDFKSLYEIEAGYDFLEVHAVTEDGKQTLIERLGEKANSGN ADSTNGKWIDKSYDLSQFKGKKVKLTFDYITDGGLALNGFALDNASL TVDGKVVFSDDAEGTPQLKLDGFVVSNGTEKKKHNYYVEWRNYAG ADNALKFARGPVFNTGMVVWYADSAYTDNWVGVHPGHGFLGVVD SHPEAIVGTLNGKPTVKSSTRFQIADAAFSFDKTPAWKVVSPTRGTFT YDGLAGVPKFDDSKTYINQQIPDAGRILPKLGLKFEVVGQADDNSAG AVRLYR |
| Full length ExsJ (*B. cereus* ATCC 10876) (SEQ ID NO: 78) | MKHNDCFDHNNCNPIVFSADCCKNPQSVPITREQLSQLITLLNSLVSAI SAFFANPSNANRLVLLDLFNQFLIFLNSLLPSPEVNFLKQLTQSIIVLLQ SPAPNLGQLSTLLQQFYSALAQFFFALDLIPISCNSNVDSATLQLLFNL LIQLINATPGATGPTGPTGPTGPTGPAGTGAGPTGATGATGATGPTGA TGPAGTGGATGATGATGVTGATGATGATGPTGPTGATGPTGATGAT GATGPTGATGPTGATGLTGATGAAGGGAIIPFASGTTPSALVNALVA NTGTLLGFGFSQPGVALTGGTSITLALGVGDYAFVAPRAGTITSLAGF FSATAALAPISPVQVQIQILTAPAASNTFTVQGAPLLLTPAFAAIAIGST ASGIIAEAIPVAAGDKILLYVSLTAASPIAAVAGFVSAGINIV |
| Full length ExsH (*B. cereus*) (SEQ ID NO: 79) | MKHNDCFGHNNCNNPIVFTPDCCNNPQTVPITSEQLGRLITLLNSLIAA IAAFFANPSDANRLALLNLFTQLLNLLNELAPSPEGNFLKQLIQSIINLL QSPNPNLGQLLSLLQQFYSALAPFFFSLILDPASLQLLLNLLAQLIGVTP GGGATGPTGPTGPGGGATGPTGPTGPGGGATGPTGATGPTGDTGLAG ATGATGPTGDTGVAGPAGPTGPTGDTGLAGATGPTGPTGDTGLAGA TGPTGATGLAGATGPTGATGLTGATGATGAAGGGAIIPFASGTTPAAL VNALIANTGTLLGFGFSQPGIGLAGGTSITLALGVGDYAFVAPRDGVI TSLAGFFSATAALSPLSPVQVQIQILTAPAASNTFTVQGAPLLLTPAFA AIAIGSTASGIIPEAIPVVAGDKILLYVSLTAASPIAAVAGFVSAGINIV |
| Full length YjcA (*B. anthracis* Ames) (SEQ ID NO: 80) | MLFTSWLLFFIFALAAFRLTRLIVYDKITGFLRRPFIDELEITEPDGSVST FTKVKGKGLRKWIGELLSCYWCTGVWVSAFLLVLYNWIPIVAEPLLA LLAIAGAAAIIETITGYFMGE |
| Full length YjcB (*B. anthracis*) (SEQ ID NO: 81) | MFAVSNNPRQNSYDLQQWYHMQQQHQAQQQAYQEQLQQQGFVKK KGCNCGKKKSTIKHYEE |
| Full length BclC (*B. anthracis* Sterne) (SEQ ID NO: 82) | MSRYDDSQNKFSKPCFPSSAGRIPNTPSIPVTKAQLRTFRAIIIDLTKIIP KLFANPSPQNIEDLIDTLNLLSKFICSLDAASSLKAQGLAIIKNLITILKN PTFVASAVFIELQNLINYLLSITKLFRIDPCTLQELLKLIAALQTALVNS ASFIQGPTGPTGPTGPTGPAGATGATGPQGVQGPAGATGATGPQGVQ GPAGATGATGPQGAQGPAGATGATGPQGAQGPAGATGATGPQGIQG PAGATGATGPQGVQGPTGATGIGVTGPTGPSGGPAGATGPQGPQGNT GATGPQGIQGPAGATGATGPQGAQGPAGATGATGPQGVQGPTGATG IGVTGPTGPSGPSFPVATIVVTNNIQQTVLQFNNFIFNTAINVNNIIFNG TDTVTVINAGIYVISVSISTTAPGCAPLGVGISINGAVATDNFSSNLIGD SLSFTTIETLTAGANISVQSTLNEITIPATGNTNIRLTVFRIA |

TABLE 1 -continued

| Peptide and Protein Sequences | |
|---|---|
| Protein, protein fragment, or targeting sequence (SEQ ID. NO) | Sequence |
| Full length acid phosphatase (*Bacillus thuringiensis* serovar konkukian str. 97-27) (SEQ ID NO: 83) | MKMKRGITTLLSVAVLSTSLVACSGITEKTVAKEEKVKLTDQQLMAD LWYQTAGEMKALYYQGYNIGQLKLDAVLAKGTEKKPAIVLDLDETV LDNSPHQAMSVKTGKGYPYKWDDWINKAEAEALPGAIDFLKYTESK GVDIYYISNRKTNQLDATIKNLERVGAPQATKEHILLQDPKEKGKEKR RELVSQTHDIVLFFGDNLSDFTGFDGKSVKDRNQAVADSKAQFGEKFI IFPNPMYGDWEGALYDYDFKKSDAEKDKIRRDNLKSFDTK |
| Full length InhA2 (*B. thuringiensis* HD74) (SEQ ID NO: 84) | MKKKKKLKPLAVLTTAAVLSSTFAFGGHAAYAETPTSSLPIDEHLIPE ERLAEALKQRGVIDQSASQAETSKAVEKYVEKKKGENPGKEILTGDS LTQEASDFMKKVKDAKMRENEQAQQPEVGPVAGQGAALNPGKLNG KVPTTSAKQEEYNGAVRKDKVLVLLVEFSDFKHNNIDQEPGYMYSK DFNREHYQKMLFGDEPFTLFDGSKINTFKQYYEEQSGGSYTVDGTVT EWLTVPGKASDYGADAGTGHDNKGPLGPKDLVKEALKAAVAKGIN LADFDQYDQYDQNGNGNKNEPDGIIDHLMVVHAGVGQEAGGGKLK DDAIWSHRSKLGSKPYAIDGTKSSVSNWGGKMAAYDYTIEPEDGAV GVFAHEYGHDLGLPDEYDTKYSGQGEPVESWSIMSGGSWAGKIAGT EPTSFSPQNKEFFQKNMKGNWANILEVDYDKLSKGIGVATYVDQSTT KSKRPGIVRVNLPDKDIKNIESAFGKKFYYSTKGNDIHTTLETPVFDLT NAKDAKFDYKAFYELEAKYDFLDVYAIAEDGTKTRIDRMGEKDIKG GADTTDGKWVDKSYDLSQFKGKKVKLQFEYLTDIAVAYKGFALDNA ALTVDGKVVFSDDAEGQPAMTLKGFTVSNGFEQKKHNYYVEWRNY AGSDTALQYARGPVFNTGMVVWYADQSFTDNWVGVHPGEGFLGVV DSHPEAIVGTLNGQPTVKSSTRYQIADAAFSFDQTPAWKVNSPTRGIF DYKGLPGVAKFDDSKQYINSVIPDAGRKLPKLGLKFEVVGQAEDKSA GAVWLHR |

AA = amino acids

**B. anthracis* Sterne strain BclA has 100% sequence identity with *B. thuringiensis* BclA. Thus, SEQ ID NOs: 1,2, and 59 also represent amino acids 1-41 of *B. thuringiensis* BclA, full length *B. thuringiensis* BclA, and amino acids 1-196 of *B. thuringiensis* BclA, respectively. Likewise, SEQ ID NO: 60 also represents a methionine residue plus amino acids 20-35 of *B. thuringiensis* BclA.

***B. mycoides* hypothetical protein TIGR03720 has 100% sequence identity with *B. mycoides* hypothetical protein WP003189234. Thus, SEQ ID NOs: 57 and 58 also represent amino acids 1-136 of *B. mycoides* hypothetical protein WP003189234 and full length *B. mycoides* hypothetical protein WP003189234, respectively.

*Bacillus* is a genus of rod-shaped bacteria. The *Bacillus cereus* family of bacteria includes the species *Bacillus anthracis, Bacillus cereus, Bacillus thuringiensis, Bacillus mycoides, Bacillus pseudomycoides, Bacillus samanii, Bacillus gaemokensis*, and *Bacillus weihenstephensis*. Under stressful environmental conditions, *Bacillus cereus* family bacteria undergo sporulation and form oval endospores that can stay dormant for extended periods of time. The outermost layer of the endospores is known as the exosporium and comprises a basal layer surrounded by an external nap of hair-like projections. Filaments on the hair-like nap are predominantly formed by the collagen-like glycoprotein BclA, while the basal layer is comprised of a number of different proteins. Another collagen-related protein, BclB, is also present in the exosporium and exposed on endospores of *Bacillus cereus* family members. BclA, the major constituent of the surface nap, has been shown to be attached to the exosporium with its amino-terminus (N-terminus) positioned at the basal layer and its carboxy-terminus (C-terminus) extending outward from the spore.

It was previously discovered that certain sequences from the N-terminal regions of BclA and BclB could be used to target a peptide or protein to the exosporium of a *Bacillus cereus* endospore (see U.S. Patent Application Nos. 2010/0233124 and 2011/0281316, and Thompson et al., *Targeting of the BclA and BclB proteins to the Bacillus anthracis spore surface*, Molecular Microbiology 70(2):421-34 (2008), the entirety of each of which is hereby incorporated by reference). It was also found that the BetA/BAS3290 protein of *Bacillus anthracis* localized to the exosporium.

In particular, amino acids 20-35 of BclA from *Bacillus anthracis* Sterne strain have been found to be sufficient for targeting to the exosporium. A sequence alignment of amino acids 1-41 of BclA (SEQ ID NO: 1) with the corresponding N-terminal regions of several other *Bacillus cereus* family exosporium proteins and *Bacillus cereus* family proteins having related sequences is shown in FIG. 1. As can be seen from FIG. 1, there is a region of high-homology among all of the proteins in the region corresponding to amino acids 20-41 of BclA. However, in these sequences, the amino acids corresponding to amino acids 36-41 of BclA contain secondary structure and are not necessary for fusion protein localization to the exosporium. The conserved targeting sequence region of BclA (amino acids 20-35 of SEQ ID NO: 1) is shown in bold in FIG. 1 and corresponds to the minimal targeting sequence needed for localization to the exosporium. A more highly conserved region spanning amino acids 25-35 of BclA within the targeting sequence is underlined in the sequences in FIG. 1, and is the recognition sequence for ExsFA/BxpB/ExsFB and homologs, which direct and assemble the described proteins on the surface of the exosporium The amino acid sequences of SEQ ID NOs. 3, 5, and 7 in FIG. 1 are amino acids 1-33 of *Bacillus anthracis* Sterne strain BetA/BAS3290, a methionine followed by amino acids 2-43 of *Bacillus anthracis* Sterne strain BAS4623, and amino acids 1-34 of *Bacillus anthracis* Sterne strain BclB, respectively. (For BAS4623, it was found that replacing the valine present at position 1 in the native protein with a methionine resulted in better expression.) As can be seen from FIG. 1, each of these sequences contains a conserved region corresponding to amino acids 20-35 of BclA (SEQ ID NO: 1; shown in bold), and a more highly conserved region corresponding to amino acids 20-35 of BclA (underlined).

Additional proteins from *Bacillus cereus* family members also contain the conserved targeting region. In particular, in FIG. 1, SEQ ID NO: 9 is amino acids 1-30 of *Bacillus anthracis* Sterne strain BAS1882, SEQ ID NO: 11 is amino acids 1-39 of the *Bacillus weihenstephensis* KBAB4 2280 gene product, SEQ ID NO: 13 is amino acids 1-39 of the *Bacillus weihenstephensis* KBAB4 3572 gene product, SEQ ID NO: 15 is amino acids 1-49 of *Bacillus cereus* VD200 exosporium leader peptide, SEQ ID NO: 17 is amino acids 1-33 of *Bacillus cereus* VD166 exosporium leader peptide, SEQ ID NO: 19 is amino acids 1-39 of *Bacillus cereus* VD200 hypothetical protein IKG 04663, SEQ ID NO: 21 is amino acids 1-39 of *Bacillus weihenstephensis* KBAB4 YVTN β-propeller protein, SEQ ID NO: 23 is amino acids 1-30 of *Bacillus weihenstephensis* KBAB4 hypothetical protein bcerkbab4_2363, SEQ ID NO: 25 is amino acids 1-30 of *Bacillus weihenstephensis* KBAB4 hypothetical protein bcerkbab4_2131, SEQ ID NO: 27 is amino acids 1-36 of *Bacillus weihenstephensis* KBAB4 triple helix repeat containing collagen, SEQ ID NO: 29 is amino acids 1-39 of *Bacillus mycoides* 2048 hypothetical protein bmyco0001_21660, SEQ ID NO: 31 is amino acids 1-30 of *Bacillus mycoides* 2048 hypothetical protein bmyc0001_22540, SEQ ID NO: 33 is amino acids 1-21 of *Bacillus mycoides* 2048 hypothetical protein bmyc0001_21510, SEQ ID NO: 35 is amino acids 1-22 of *Bacillus thuringiensis* 35646 collagen triple helix repeat protein, SEQ ID NO: 43 is amino acids 1-35 of *Bacillus cereus* hypothetical protein WP_69652, SEQ ID NO: 45 is amino acids 1-41 of *Bacillus cereus* exosporium leader WP016117717, SEQ ID NO: 47 is amino acids 1-49 of *Bacillus cereus* exosporium peptide WP002105192, SEQ ID NO: 49 is amino acids 1-38 of *Bacillus cereus* hypothetical protein WP87353, SEQ ID NO: 51 is amino acids 1-39 of *Bacillus cereus* exosporium peptide 02112369, SEQ ID NO: 53 is amino acids 1-39 of *Bacillus cereus* exosporium protein WP016099770, SEQ ID NO: 55 is amino acids 1-36 of *Bacillus thuringiensis* hypothetical protein YP006612525, and SEQ ID NO: 57 is amino acids 1-136 of *Bacillus mycoides* hypothetical protein TIGR03720. As shown in FIG. 1, each of the N-terminal regions of these proteins contains a region that is conserved with amino acids 20-35 of BclA (SEQ ID NO: 1), and a more highly conserved region corresponding to amino acids 25-35 of BclA.

In the fusion proteins of the present invention, any portion of BclA which includes amino acids 20-35 can be used as the targeting sequence in the present invention. In addition, full-length exosporium proteins or exosporium protein fragments can be used for targeting the fusion proteins to the exosporium. Thus, full-length BclA or a fragment of BclA that includes amino acids 20-35 can be used for targeting to the exosporium. For example, full length BclA (SEQ ID NO: 2) or a midsized fragment of BclA that lacks the carboxy-terminus such as SEQ ID NO: 59 (amino acids 1-196 of BclA) can be used to target the fusion proteins to the exosporium. Midsized fragments such as the fragment of SEQ ID NO: 59 have less secondary structure than full length BclA and has been found to be suitable for use as a targeting sequence. The targeting sequence can also comprise much shorter portions of BclA which include amino acids 20-35, such as SEQ ID NO: 1 (amino acids 1-41 of BclA), amino acids 1-35 of SEQ ID NO: 1, amino acids 20-35 of SEQ ID NO: 1, or SEQ ID NO: 60 (a methionine residue linked to amino acids 20-35 of BclA). Even shorter fragments of BclA which include only some of amino acids 20-35 also exhibit the ability to target fusion proteins to the exosporium. For example, the targeting sequence can comprise amino acids 22-31 of SEQ ID NO: 1, amino acids 22-33 of SEQ ID NO: 1, or amino acids 20-31 of SEQ ID NO: 1.

Alternatively, any portion of BetA/BAS3290, BAS4623, BclB, BAS1882, the KBAB4 2280 gene product, the KBAB4 3572 gene product, *B. cereus* VD200 exosporium leader peptide, *B. cereus* VD166 exosporium leader peptide, *B. cereus* VD200 hypothetical protein IKG_04663*, B. weihenstephensis* KBAB4 YVTN β-propeller protein, *B. weihenstephensis* KBAB4 hypothetical protein bcerkbab4_2363*, B. weihenstephensis* KBAB4 hypothetical protein bcerkbab4_2131*, B. weihenstephensis* KBAB4 triple helix repeat containing collagen, *B. mycoides* 2048 hypothetical protein bmyco0001_21660, *B. mycoides* 2048 hypothetical protein bmyc0001_22540, *B. mycoides* 2048 hypothetical protein bmyc0001_21510, *B. thuringiensis* 35646 collagen triple helix repeat protein, *B. cereus* hypothetical protein WP_69652, *B. cereus* exosporium leader WP016117717, *B. cereus* exosporium peptide WP002105192, *B. cereus* hypothetical protein WP87353, *B. cereus* exosporium peptide 02112369, *B. cereus* exosporium protein WP016099770, *B. thuringiensis* hypothetical protein YP006612525, or *B. mycoides* hypothetical protein TIGR03720 which includes the amino acids corresponding to amino acids 20-35 of BclA can serve as the targeting sequence. As can be seen from FIG. 1, amino acids 12-27 of BetA/BAS3290, amino acids 23-38 of BAS4623, amino acids 13-28 of BclB, amino acids 9-24 of BAS1882, amino acids 18-33 of KBAB4 2280 gene product, amino acids 18-33 of KBAB4 3572 gene product, amino acids 28-43 of *B. cereus* VD200 exosporium leader peptide, amino acids 12-27 of *B. cereus* VD166 exosporium leader peptide, amino acids 18-33 of *B. cereus* VD200 hypothetical protein IKG_04663, amino acids 18-33 *B. weihenstephensis* KBAB4 YVTN β-propeller protein, amino acids 9-24 of *B. weihenstephensis* KBAB4 hypothetical protein bcerkbab4_2363, amino acids 9-24 of *B. weihenstephensis* KBAB4 hypothetical protein bcerkbab4_2131, amino acids 15-30 of *B. weihenstephensis* KBAB4 triple helix repeat containing collagen, amino acids 18-33 of *B. mycoides* 2048 hypothetical protein bmyco0001_21660, amino acids 9-24 of *B. mycoides* 2048 hypothetical protein bmyc0001_22540, amino acids 1-15 of *B. mycoides* 2048 hypothetical protein bmyc0001_21510, amino acids 1-16 of *B. thuringiensis* 35646 collagen triple helix repeat protein, amino acids 14-29 of *B. cereus* hypothetical protein WP_69652, amino acids 20-35 of *B. cereus* exosporium leader WP016117717, amino acids 28-43 of *B. cereus* exosporium peptide WP002105192, amino acids 17-32 of *B. cereus* hypothetical protein WP87353, amino acids 18-33 of *B. cereus* exosporium peptide 02112369, amino acids 18-33 of *B. cereus* exosporium protein WP016099770, amino acids 15-30 of *B. thuringiensis* hypothetical protein YP006612525, and amino acids 115-130 of *B. mycoides* hypothetical protein TIGR03720 correspond to amino acids 20-35 of BclA. Thus, any portion of these proteins that includes the above-listed corresponding amino acids can serve as the targeting sequence.

Furthermore, any amino acid sequence comprising amino acids 20-35 of BclA, or any of the above-listed corresponding amino acids can serve as the targeting sequence.

Thus, the targeting sequence can comprise amino acids 1-35 of SEQ ID NO: 1, amino acids 20-35 of SEQ ID NO: 1, SEQ ID NO: 1, SEQ ID NO: 60, amino acids 22-31 of SEQ ID NO: 1, amino acids 22-33 of SEQ ID NO: 1, or amino acids 20-31 of SEQ ID NO: 1. Alternatively, the targeting sequence consists of amino acids 1-35 of SEQ ID NO: 1, amino acids 20-35 of SEQ ID NO: 1, SEQ ID NO: 1, or SEQ ID NO: 60. Alternatively, the targeting sequence can consist of amino acids 22-31 of SEQ ID NO: 1, amino acids 22-33 of SEQ ID NO: 1, or amino acids 20-31 of SEQ ID NO: 1. Alternatively, the exosporium protein can comprise full length BclA (SEQ ID NO: 2), or the exosporium protein fragment can comprise a midsized fragment of BclA that lacks the carboxy-terminus, such as SEQ ID NO: 59 (amino acids 1-196 of BclA). Alternatively, the exosporium protein fragment can consist of SEQ ID NO: 59.

The targeting sequence can also comprise amino acids 1-27 of SEQ ID NO: 3, amino acids 12-27 of SEQ ID NO: 3, or SEQ ID NO: 3, or the exosporium protein can comprise full length BetA/BAS3290 (SEQ ID NO: 4). It has also been found that a methionine residue linked to amino acids 12-27 of BetA/BAS3290 can be used as a targeting sequence. Thus, the targeting sequence can comprise SEQ ID NO: 61. The targeting sequence can also comprise amino acids 14-23 of SEQ ID NO: 3, amino acids 14-25 of SEQ ID NO: 3, or amino acids 12-23 of SEQ ID NO: 3.

The targeting sequence can also comprise amino acids 1-38 of SEQ ID NO: 5, amino acids 23-38 of SEQ ID NO: 5, or SEQ ID NO: 5, or the exosporium protein can comprise full length BAS4623 (SEQ ID NO: 6).

Alternatively, the targeting sequence can comprise amino acids 1-28 of SEQ ID NO: 7, amino acids 13-28 of SEQ ID NO: 7, or SEQ ID NO: 7, or the exosporium protein can comprise full length BclB (SEQ ID NO:8).

The targeting sequence can also comprise amino acids 1-24 of SEQ ID NO: 9, amino acids 9-24 of SEQ ID NO: 9, or SEQ ID NO: 9, or the exosporium protein can comprise full length BAS1882 (SEQ ID NO: 10). A methionine residue linked to amino acids 9-24 of BAS1882 can also be used as a targeting sequence. Thus, the targeting sequence can comprise SEQ ID NO: 69.

The targeting sequence can also comprise amino acids 1-33 of SEQ ID NO:11, amino acids 18-33 of SEQ ID NO: 11, or SEQ ID NO: 11, or the exosporium protein can comprise the full length *B. weihenstephensis* KBAB4 2280 gene product (SEQ ID NO: 12). A methionine residue linked to amino acids 18-33 of the *B. weihenstephensis* KBAB4 2280 gene product can also be used as a targeting sequence. Thus, the targeting sequence can comprise SEQ ID NO: 62.

The targeting sequence can also comprise amino acids 1-33 of SEQ ID NO: 13, amino acids 18-33 of SEQ ID NO: 13, or SEQ ID NO:13, or the exosporium protein can comprise the full length *B. weihenstephensis* KBAB4 3572 gene product (SEQ ID NO:14). A methionine residue linked to amino acids 18-33 of the *B. weihenstephensis* KBAB4 3572 gene product can also be used as a targeting sequence. Thus, the targeting sequence can comprise SEQ ID NO: 63.

Alternatively, the targeting sequence can comprise amino acids 1-43 of SEQ ID NO: 15, amino acids 28-43 of SEQ ID NO: 15, or SEQ ID NO:15, or the exosporium protein can comprise full length *B. cereus* VD200 exosporium leader peptide (SEQ ID NO:16).

The targeting sequence can also comprise amino acids 1-27 of SEQ ID NO: 17, amino acids 12-27 of SEQ ID NO: 17, or SEQ ID NO:17, or the exosporium protein can comprise full-length *B. cereus* VD166 exosporium leader peptide (SEQ ID NO:18). A methionine residue linked to amino acids 12-27 of the *B. cereus* VD166 exosporium leader peptide can also be used as a targeting sequence. Thus, the targeting sequence can comprise SEQ ID NO: 64.

The targeting sequence can also comprise amino acids 1-33 of SEQ ID NO: 19, amino acids 18-33 of SEQ ID NO: 19, or SEQ ID NO:19, or the exosporium protein can comprise full length *B. cereus* VD200 hypothetical protein IKG_04663 (SEQ ID NO:20).

Alternatively, the targeting sequence comprises amino acids 1-33 of SEQ ID NO: 21, amino acids 18-33 of SEQ ID NO: 21, or SEQ ID NO:21, or the exosporium protein can comprise full length *B. weihenstephensis* KBAB4 YVTN β-propeller protein (SEQ ID NO:22). A methionine residue linked to amino acids 18-33 of the *B. weihenstephensis* KBAB4 YVTN β-propeller protein can also be used as a targeting sequence. Thus, the targeting sequence can comprise SEQ ID NO: 65.

The targeting sequence can also comprise amino acids 1-24 of SEQ ID NO: 23, amino acids 9-24 of SEQ ID NO: 23, or SEQ ID NO:23, or the exosporium protein can comprise full length *B. weihenstephensis* KBAB4 hypothetical protein bcerkbab4_2363 (SEQ ID NO:24). A methionine residue linked to amino acids 9-24 of *B. weihenstephensis* KBAB4 hypothetical protein bcerkbab4_2363 can also be used as a targeting sequence. Thus, the targeting sequence can comprise SEQ ID NO: 66.

The targeting sequence comprise amino acids 1-24 of SEQ ID NO: 25, amino acids 9-24 of SEQ ID NO: 25, or SEQ ID NO:25, or the exosporium protein can comprise full length *B. weihenstephensis* KBAB4 hypothetical protein bcerkbab4_2131 (SEQ ID NO:26). A methionine residue linked to amino acids 9-24 of *B. weihenstephensis* KBAB4 hypothetical protein bcerkbab4_2131 can also be used as a targeting sequence. Thus, the targeting sequence can comprise SEQ ID NO: 67.

Alternatively, the targeting sequence comprises amino acids 1-30 of SEQ ID NO: 27, amino acids 15-30 of SEQ ID NO: 27, or SEQ ID NO:27, or the exosporium protein can comprise full length *B. weihenstephensis* KBAB4 triple helix repeat containing collagen (SEQ ID NO:28).

The targeting sequence can also comprise amino acids 1-33 of SEQ ID NO: 29, amino acids 18-33 of SEQ ID NO: 29, or SEQ ID NO:29, or the exosporium protein can comprise full length *B. mycoides* 2048 hypothetical protein bmyco0001_21660 (SEQ ID NO:30).

The targeting sequence can also comprise amino acids 1-24 of SEQ ID NO: 31, amino acids 9-24 of SEQ ID NO: 31, or SEQ ID NO:31, or the exosporium protein can comprise full length *B. mycoides* 2048 hypothetical protein bmyc0001_22540 (SEQ ID NO:32). A methionine residue linked to amino acids 9-24 of *B. mycoides* 2048 hypothetical protein bmyc0001_22540 can also be used as a targeting sequence. Thus, the targeting sequence can comprise SEQ ID NO: 68.

Alternatively, the targeting sequence comprises amino acids 1-15 of SEQ ID NO: 33, SEQ ID NO:33, or the exosporium protein comprises full length *B. mycoides* 2048 hypothetical protein bmyc0001_21510 (SEQ ID NO:34).

The targeting sequence can also comprise amino acids 1-16 of SEQ ID NO: 35, SEQ ID NO:35, or the exosporium protein can comprise full length *B. thuringiensis* 35646 collagen triple helix repeat protein (SEQ ID NO:36).

The targeting sequence can comprise amino acids 1-29 of SEQ ID NO:43, amino acids 14-29 of SEQ ID NO: 43, or SEQ ID NO: 43, or the exosporium protein can comprise full length *B. cereus* hypothetical protein WP_69652 (SEQ ID NO: 44).

Alternatively, the targeting sequence can comprise amino acids 1-35 of SEQ ID NO: 45, amino acids 20-35 of SEQ ID NO: 45, or SEQ ID NO: 45, or the exosporium protein can comprise full length *B. cereus* exosporium leader WP016117717 (SEQ ID NO: 46). A methionine residue linked to amino acids 20-35 of *B. cereus* exosporium leader WP016117717 can also be used as a targeting sequence. Thus, the targeting sequence can comprise SEQ ID NO: 70.

The targeting sequence can comprise amino acids 1-43 of SEQ ID NO: 47, amino acids 28-43 of SEQ ID NO: 47, or SEQ ID NO: 47, or the exosporium protein can comprise full length *B. cereus* exosporium peptide WP002105192 (SEQ ID NO: 48).

The targeting sequence can comprise amino acids 1-32 of SEQ ID NO: 49, amino acids 17-32 of SEQ ID NO: 49, or SEQ ID NO: 49, or the exosporium protein can comprise full length *B. cereus* hypothetical protein WP87353 (SEQ ID NO: 50).

Alternatively, the targeting sequence can comprise amino acids 1-33 of SEQ ID NO: 51, amino acids 18-33 of SEQ ID NO: 51, or SEQ ID NO: 51, or the exosporium protein can comprise full length *B. cereus* exosporium peptide 02112369 (SEQ ID NO: 52).

The targeting sequence can comprise amino acids 1-33 of SEQ ID NO: 53, amino acids 18-33 of SEQ ID NO: 53, or SEQ ID NO: 53, or the exosporium protein can comprise full length *B. cereus* exosporium protein WP016099770 (SEQ ID NO: 54).

Alternatively, the targeting sequence can comprise acids 1-30 of SEQ ID NO: 55, amino acids 15-30 of SEQ ID NO: 55, or SEQ ID NO: 55, or the exosporium protein can comprise full length *B. thuringiensis* hypothetical protein YP006612525 (SEQ ID NO: 56).

The targeting sequence can also comprise amino acids 1-130 of SEQ ID NO: 57, amino acids 115-130 of SEQ ID NO: 57, or SEQ ID NO: 57, or the exosporium protein can comprise full length *B. mycoides* hypothetical protein TIGR03720 (SEQ ID NO: 58).

In addition, it can readily be seen from the sequence alignment in FIG. 1 that while amino acids 20-35 of BclA are conserved, and amino acids 25-35 are more conserved, some degree of variation can occur in this region without affecting the ability of the targeting sequence to target a protein to the exosporium. FIG. 1 lists the percent identity of each of corresponding amino acids of each sequence to amino acids 20-35 of BclA ("20-35% Identity") and to amino acids 25-35 of BclA ("25-35% Identity"). Thus, for example, as compared to amino acids 20-35 of BclA, the corresponding amino acids of BetA/BAS3290 are about 81.3% identical, the corresponding amino acids of BAS4623 are about 50.0% identical, the corresponding amino acids of BclB are about 43.8% identical, the corresponding amino acids of BAS1882 are about 62.5% identical, the corresponding amino acids of the KBAB4 2280 gene product are about 81.3% identical, and the corresponding amino acids of the KBAB4 3572 gene product are about 81.3% identical. The sequence identities over this region for the remaining sequences are listed in FIG. 1.

With respect to amino acids 25-35 of BclA, the corresponding amino acids of BetA/BAS3290 are about 90.9% identical, the corresponding amino acids of BAS4623 are about 72.7% identical, the corresponding amino acids of BclB are about 54.5% identical, the corresponding amino acids of BAS1882 are about 72.7% identical, the corresponding amino acids of the KBAB4 2280 gene product are about 90.9% identical, and the corresponding amino acids of the KBAB4 3572 gene product are about 81.8% identical. The sequence identities over this region for the remaining sequences are listed in FIG. 1.

Thus, the targeting sequence can comprise an amino acid sequence having at least about 43% identity with amino acids 20-35 of SEQ ID NO: 1, wherein the identity with amino acids 25-35 is at least about 54%. Alternatively, the targeting sequence consists of an amino acid sequence consisting of 16 amino acids and having at least about 43% identity with amino acids 20-35 of SEQ ID NO: 1, wherein the identity with amino acids 25-35 is at least about 54%.

The targeting sequence can also comprise an amino acid sequence having at least about 50% identity with amino acids 20-35 of SEQ ID NO: 1, wherein the identity with amino acids 25-35 is at least about 63%. Alternatively the targeting sequence consists of an amino acid sequence consisting of 16 amino acids and having at least about 50% identity with amino acids 20-35 of SEQ ID NO: 1, wherein the identity with amino acids 25-35 is at least about 63%.

The targeting sequence can also comprise an amino acid sequence having at least about 50% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 50% identity with amino acids 20-35 of SEQ ID NO: 1, wherein the identity with amino acids 25-35 is at least about 72%.

The targeting sequence can also comprise an amino acid sequence having at least about 56% identity with amino acids 20-35 of SEQ ID NO: 1, wherein the identity with amino acids 25-35 is at least about 63%. Alternatively, the targeting sequence consists of an amino acid sequence consisting of 16 amino acids and having at least about 56% identity with amino acids 20-35 of SEQ ID NO: 1, wherein the identity with amino acids 25-35 is at least about 63%.

Alternatively, the targeting sequence can comprise an amino sequence having at least about 62% identity with amino acids 20-35 of SEQ ID NO: 1, wherein the identity with amino acids 25-35 is at least about 72%. The targeting sequence can also consist of an amino acid sequence consisting of 16 amino acids and having at least about 62% identity with amino acids 20-35 of SEQ ID NO: 1, wherein the identity with amino acids 25-35 of SEQ ID NO:1 is at least about 72%.

The targeting sequence can comprise an amino acid sequence having at least 68% identity with amino acids 20-35 of SEQ ID NO: 1, wherein the identity with amino acids 25-35 is at least about 81%. Alternatively, the targeting sequence consists of an amino acid sequence consisting of 16 amino acids and having at least 68% identity with amino acids 20-35 of SEQ ID NO: 1, wherein the identity with amino acids 25-35 is at least about 81%.

The targeting sequence can also comprises an amino sequence having at least about 75% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO:1 is at least about 72%.

The targeting sequence can also comprise an amino sequence having at least about 75% identity with amino acids 20-35 of SEQ ID NO: 1, wherein the identity with amino acids 25-35 is at least about 81%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO:1 is at least about 81%.

The targeting sequence can also comprise an amino acid sequence having at least about 81% identity with amino acids 20-35 of SEQ ID NO:1, wherein the identity with amino acids 25-35 is at least about 81%. Alternatively, the targeting sequence consists of an amino acid sequence consisting of 16 amino acids and having at least about 81% identity with amino acids 20-35 of SEQ ID NO:1, wherein the identity with amino acids 25-35 is at least about 81%.

The targeting sequence can comprise an amino acid sequence having at least about 81% identity with amino acids 20-35 of SEQ ID NO: 1, wherein the identity with amino acids 25-35 is at least about 90%. Alternatively, the targeting sequence consists of an amino acid sequence consisting of 16 amino acids and having at least about 81% identity with amino acids 20-35 of SEQ ID NO: 1, wherein the identity with amino acids 25-35 is at least about 90%.

The skilled person will recognize that variants of the above sequences can also be used as targeting sequences, so long as the targeting sequence comprises amino acids 20-35 of BclA, the corresponding amino acids of BetA/BAS3290, BAS4263, BclB, BAS1882, the KBAB4 2280 gene product, or the KBAB 3572 gene product, or a sequence comprising any of the above noted sequence identities to amino acids 20-35 and 25-35 of BclA is present.

It has further been discovered that certain *Bacillus cereus* family exosporium proteins which lack regions having homology to amino acids 25-35 of BclA can also be used to target a peptide or protein to the exosporium of a *Bacillus cereus* family member. In particular, the fusion proteins can comprise an exosporium protein comprising SEQ ID NO: 71 (*B. mycoides* InhA), an exosporium protein comprising SEQ ID NO: 72 (*B. anthracis* Sterne BAS1141 (ExsY)), an exosporium protein comprising SEQ ID NO: 73 (*B. anthracis* Sterne BAS1144 (BxpB/ExsFA)), an exosporium protein comprising SEQ ID NO: 74 (*B. anthracis* Sterne BAS1145 (CotY)), an exosporium protein comprising SEQ ID NO: 75 (*B. anthracis* Sterne BAS1140), an exosporium protein comprising SEQ ID NO: 76 (*B. anthracis* H9401 ExsFB), an exosporium protein comprising SEQ ID NO: 77 (*B. thuringiensis* HD74 InhA1), an exosporium protein comprising SEQ ID NO: 78 (*B. cereus* ATCC 10876 ExsJ), an exosporium protein comprising SEQ ID NO: 79 (*B. cereus* ExsH), an exosporium protein comprising SEQ ID NO: 80 (*B. anthracis* Ames YjcA), an exosporium protein comprising SEQ ID NO: 81 (*B. anthracis* YjcB), an exosporium protein comprising SEQ ID NO: 82 (*B. anthracis* Sterne BclC), an exosporium protein comprising SEQ ID NO: 83 (*Bacillus thuringiensis* serovar konkukian str. 97-27 acid phosphatase), or an exosporium protein comprising SEQ ID NO: 84 (*B. thuringiensis* HD74 InhA2). Inclusion of an exosporium protein comprising SEQ ID NO: 71, 72, 73, 74, 75, 76, 77, 78, 79, 80, 81, 82, 83, or 84 in the fusion proteins described herein will result in targeting to the exosporium of a *B. cereus* family member.

Moreover, exosporium proteins having a high degree of sequence identity with any of the full-length exosporium proteins or the exosporium protein fragments described above can also be used to target a peptide or protein to the exosporium of a *Bacillus cereus* family member. Thus, the fusion protein can comprise an exosporium protein comprising an amino acid sequence having at least 85% identity with any one of SEQ ID NOs: 2, 4, 6, 8, 10, 12, 14, 16, 18, 20, 22, 24, 26, 28, 30, 32, 34, 36, 44, 46, 48, 50, 52, 54, 56, 58, 59, 71, 72, 73, 74, 75, 76, 77, 78, 79, 80, 81, 82, 83, and 84. Alternatively, the fusion protein can comprise an exosporium protein having at least 90%, at least 95%, at least 98%, at least 99%, or 100% identity with any one of SEQ ID NOs: 2, 4, 6, 8, 10, 12, 14, 16, 18, 20, 22, 24, 26, 28, 30, 32, 34, 36, 44, 46, 48, 50, 52, 54, 56, 58, 59, 71, 72, 73, 74, 75, 76, 77, 78, 79, 80, 81, 82, 83, and 84.

Alternatively, the fusion protein can comprise an exosporium protein fragment consisting of an amino acid sequence having at least 85% identity with SEQ ID NO: 59. Alternatively, the fusion protein can comprise an exosporium protein fragment consisting of an amino acid sequence having at least 90%, at least 95%, at least 98%, at least 99%, or 100% identity with SEQ ID NO: 59.

In any of the targeting sequences, exosporium proteins, or exosporium protein fragments described herein, the targeting sequence, exosporium protein, or exosporium protein fragment can comprise the amino acid sequence GXT at its carboxy terminus, wherein X is any amino acid.

In any of the targeting sequences, exosporium proteins, and exosporium protein fragments described herein, the targeting sequence, exosporium protein, or exosporium protein fragment, can comprise an alanine residue at the position of the targeting sequence that corresponds to amino acid 20 of SEQ ID NO: 1.

Fusion Proteins

The present invention relates to fusion proteins comprising a targeting sequence, an exosporium protein, or an exosporium protein fragment, and at least one plant growth stimulating protein or peptide, wherein the plant growth stimulating protein or peptide comprises a peptide hormone, a non-hormone peptide, or an enzyme involved in the production or activation of a plant growth stimulating compound. The targeting sequence, exosporium protein, or exosporium protein fragment can be any of the targeting sequences, exosporium proteins, or exosporium protein fragments described above in paragraph [0005].

The present invention additionally relates to fusion proteins comprising a targeting sequence, an exosporium protein, or an exosporium protein fragment, and at least one protein or peptide that enhances stress resistance in a plant. The targeting sequence, exosporium protein, or exosporium protein fragment can be any of the targeting sequences, exosporium proteins, or exosporium protein fragments described above in paragraph [0005].

In addition, the present invention relates to fusion proteins comprising a targeting sequence, an exosporium protein, or an exosporium protein fragment, and at least one plant binding protein or peptide. The targeting sequence, exosporium protein, or exosporium protein fragment can be any of the targeting sequences, exosporium proteins, or exosporium protein fragments described above in paragraph [0005].

The present invention also relates to fusion proteins comprising a targeting sequence, an exosporium protein, or an exosporium protein fragment, and at least one protein or peptide that protects a plant from a pathogen. The targeting sequence, exosporium protein, or exosporium protein fragment can be any of the targeting sequences, exosporium proteins, or exosporium protein fragments described above in paragraph [0006].

The present invention further relates to fusion proteins comprising a targeting sequence, an exosporium protein, or an exosporium protein fragment, and at least one protein or peptide that protects a plant from a pathogen. The protein or peptide that protects a plant from a pathogen comprises a harpin, an α-elastin, a β-elastin, a systemin, a phenylalanine ammonia-lyase, an elicitin, a defensin, a cryptogein, a flagellin protein, a flagellin peptide, a bacteriocin, a lysozyme, a lysozyme peptide, a siderophore, a non-ribosomal active peptide, a conalbumin, an albumin, a lactoferrin, a lactoferrin peptide, TasA. Alternatively, the protein or peptide that protects a plant from a pathogen has insecticidal activity, helminthicidal activity, suppresses insect or worm predation, or a combination thereof. Alternatively, the protein that protects a plant from a pathogen comprises an enzyme. The targeting sequence, exosporium protein, or exosporium protein fragment can be any of the targeting sequences, exosporium proteins, or exosporium protein fragments described above in paragraph [0005].

The fusion protein can be made using standard cloning and molecular biology methods known in the art. For example, a gene encoding a protein or peptide (e.g., a gene encoding a plant growth stimulating protein or peptide) can be amplified by polymerase chain reaction (PCR) and ligated to DNA coding for any of the above-described targeting sequences to form a DNA molecule that encodes the fusion protein. The DNA molecule encoding the fusion protein can be cloned into any suitable vector, for example a plasmid vector. The vector suitably comprises a multiple cloning site into which the DNA molecule encoding the fusion protein can be easily inserted. The vector also suitably contains a selectable marker, such as an antibiotic resistance gene, such that bacteria transformed, transfected, or mated with the vector can be readily identified and isolated. Where the vector is a plasmid, the plasmid suitably also comprises an origin of replication. The DNA encoding the fusion protein is suitably under the control of a sporulation promoter which will cause expression of the fusion protein on the exosporium of a *B. cereus* family member endospore (e.g., a native bclA promoter from a *B. cereus* family member). Alternatively, DNA coding for the fusion protein can be integrated into the chromosomal DNA of the *B. cereus* family member host.

The fusion protein can also comprise additional polypeptide sequences that are not part of the targeting sequence, exosporium protein, exosporium protein fragment, or the plant growth stimulating protein or peptide, the protein or peptide that protects a plant from a pathogen, the protein or peptide that enhances stress resistance in a plant, or the plant binding protein or peptide. For example, the fusion protein can include tags or markers to facilitate purification or visualization of the fusion protein (e.g., a polyhistidine tag or a fluorescent protein such as GFP or YFP) or visualization of recombinant *Bacillus cereus* family member spores expressing the fusion protein.

Expression of fusion proteins on the exosporium using the targeting sequences, exosporium proteins, and exosporium protein fragments described herein is enhanced due to a lack of secondary structure in the amino-termini of these sequences, which allows for native folding of the fused proteins and retention of activity. Proper folding can be further enhanced by the inclusion of a short amino acid linker between the targeting sequence, exosporium protein, exosporium protein fragment, and the fusion partner protein.

Thus, any of the fusion proteins described herein can comprise an amino acid linker between the targeting sequence, the exosporium protein, or the exosporium protein fragment and the plant growth stimulating protein or peptide, the protein or peptide that protects a plant from a pathogen, the protein or peptide that enhances stress resistance in a plant, or the plant binding protein or peptide.

The linker can comprise a polyalanine linker or a polyglycine linker. A linker comprising a mixture of both alanine and glycine residues can also be used. For example, where the targeting sequence comprises SEQ ID NO: 1, a fusion protein can have one of the following structures:

No linker: SEQ ID NO: 1—Fusion Partner Protein

Alanine Linker: SEQ ID NO: 1—$A_n$—Fusion Partner Protein

Glycine Linker: SEQ ID NO: 1—$G_n$—Fusion Partner Protein

Mixed Alanine and Glycine Linker: SEQ ID NO: 1—$(A/G)_n$—Fusion Partner Protein where $A_n$, $G_n$, and $(A/G)_n$ are any number of alanines, any number of glycines, or any number of a mixture of alanines and glycines, respectively. For example, n can be 1 to 25, and is preferably 6 to 10. Where the linker comprises a mixture of alanine and glycine residues, any combination of glycine and alanine residues can be used. In the above structures, "Fusion Partner Protein" represents the plant growth stimulating protein or peptide, the protein or peptide that protects a plant from a pathogen, the protein or peptide that enhances stress resistance in a plant, or the plant binding protein or peptide.

Alternatively or in addition, the linker can comprise a protease recognition site. Inclusion of a protease recognition site allows for targeted removal, upon exposure to a protease that recognizes the protease recognition site, of the plant growth stimulating protein or peptide, the protein or peptide that protects a plant from a pathogen, the protein or peptide that enhances stress resistance in a plant, or the plant binding protein or peptide.

Plant Growth Stimulating Proteins and Peptides

As noted above, the present invention relates to fusion proteins comprising a targeting sequence, exosporium protein, or exosporium protein fragment and at least one plant growth stimulating protein or peptide, wherein the plant growth stimulating protein or peptide comprises a peptide hormone, a non-hormone peptide, or an enzyme involved in the production or activation of a plant growth stimulating compound.

For example, where the plant growth stimulating protein or peptide comprises a peptide hormone, the peptide hormone can comprise a phytosulfokine (e.g., phytosulfokine-α), clavata 3 (CLV3), systemin, ZmIGF, or a SCR/SP11.

Where the plant growth stimulating protein or peptide comprises a non-hormone peptide, the non-hormone peptide can comprise a RKN 16D10, Hg-Syv46, an eNOD40 peptide, melittin, mastoparan, Mas7, RHPP, POLARIS, or kunitz trypsin inhibitor (KTI).

The plant growth stimulating protein or peptide can comprise an enzyme involved in the production or activation of a plant growth stimulating compound. The enzyme involved in the production or activation of a plant growth stimulating compound can be any enzyme that catalyzes any step in a biological synthesis pathway for a compound that stimulates plant growth or alters plant structure, or any enzyme that catalyzes the conversion of an inactive or less active derivative of a compound that stimulates plant growth or alters plant structure into an active or more active form of the compound.

The plant growth stimulating compound can comprise a compound produced by bacteria or fungi in the rhizosphere, e.g., 2,3-butanediol.

Alternatively, the plant growth stimulating compound can comprise a plant growth hormone, e.g., a cytokinin or a cytokinin derivative, ethylene, an auxin or an auxin derivative, a gibberellic acid or a gibberellic acid derivative, abscisic acid or an abscisic acid derivative, or a jasmonic acid or a jasmonic acid derivative.

Where the plant growth stimulating compound comprises a cytokinin or a cytokinin derivative, the cytokinin or the cytokinin derivative can comprise kinetin, cis-zeatin, trans-zeatin, 6-benzylaminopurine, dihydroxyzeatin, N6-(D2-isopentenyl) adenine, ribosylzeatin, N6-(D2-isopentenyl) adenosine, 2-methylthio-cis-ribosylzeatin, cis-ribosylzeatin, trans-ribosylzeatin, 2-methylthio-trans-ribosylzeatin, ribosylzeatin-5-monosphosphate, N6-methylaminopurine, N6-dimethylaminopurine, 2'-deoxyzeatin riboside, 4-hydroxy-3-methyl-trans-2-butenylaminopurine, ortho-topolin, meta-topolin, benzyladenine, ortho-methyltopolin, meta-methyltopolin, or a combination thereof.

Where the plant growth stimulating compound comprises an auxin or an auxin derivative, the auxin or the auxin derivative can comprise an active auxin, an inactive auxin, a conjugated auxin, a naturally occurring auxin, or a synthetic auxin, or a combination thereof. For example, the auxin or auxin derivative can comprise indole-3-acetic acid, indole-3-pyruvic acid, indole-3-acetaldoxime, indole-3-acetamide, indole-3-acetonitrile, indole-3-ethanol, indole-3-pyruvate, indole-3-acetaldoxime, indole-3-butyric acid, a phenylacetic acid, 4-chloroindole-3-acetic acid, a glucose-conjugated auxin, or a combination thereof.

The enzyme involved in the production or activation of a plant growth stimulating compound can comprise an acetoin reductase, an indole-3-acetamide hydrolase, a tryptophan monooxygenase, an acetolactate synthetase, an α-acetolactate decarboxylase, a pyruvate decarboxylase, a diacetyl reductase, a butanediol dehydrogenase, an aminotransferase (e.g., tryptophan aminotransferase), a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyltransferase, a phosphatase, an adenosine kinase, an adenine phosphoribosyltransferase, CYP735A, a 5' ribonucleotide phosphohydrolase, an adenosine nucleosidase, a zeatin cis-trans isomerase, a zeatin O-glucosyltransferase, a β-glucosidase, a cis-hydroxylase, a CK cis-hydroxylase, a CK N-glucosyltransferase, a 2,5-ribonucleotide phosphohydrolase, an adenosine nucleosidase, a purine nucleoside phosphorylase, a zeatin reductase, a hydroxylamine reductase, a 2-oxoglutarate dioxygenase, a gibberellic 2B/3B hydrolase, a gibberellin 3-oxidase, a gibberellin 20-oxidase, a chitosinase, a chitinase, a β-1,3-glucanase, a β-1,4-glucanase, a β-1,6-glucanase, an aminocyclopropane-1-carboxylic acid deaminase, or an enzyme involved in producing a nod factor (e.g., nodA, nodB, or nodI).

Where the enzyme comprises a protease or peptidase, the protease or peptidase can be a protease or peptidase that cleaves proteins, peptides, proproteins, or preproproteins to create a bioactive peptide. The bioactive peptide can be any peptide that exerts a biological activity.

Examples of bioactive peptides include RKN 16D10 and RHPP.

The protease or peptidase that cleaves proteins, peptides, proproteins, or preproproteins to create a bioactive peptide can comprise subtilisin, an acid protease, an alkaline protease, a proteinase, an endopeptidase, an exopeptidase, thermolysin, papain, pepsin, trypsin, pronase, a carboxylase, a serine protease, a glutamic protease, an aspartate protease, a cysteine protease, a threonine protease, or a metalloprotease.

The protease or peptidase can cleave proteins in a protein-rich meal (e.g., soybean meal or yeast extract).

Proteins and Peptides that Protects Plants from Pathogens

The present invention relates to fusion proteins comprising a targeting sequence, exosporium protein, or exosporium protein fragment, and at least one protein or peptide that protects a plant from a pathogen.

The protein or peptide that protects a plant from a pathogen can comprise a protein or peptide that stimulates a plant immune response. For example, the protein or peptide that stimulates a plant immune response can comprise a plant immune system enhancer protein or peptide. The plant immune system enhancer protein or peptide can be any protein or peptide that has a beneficial effect on the immune system of a plant. Suitable plant immune system enhancer proteins and peptides include harpins, α-elastins, β-elastins, systemins, phenylalanine ammonia-lyase, elicitins, defensins, cryptogeins, flagellin proteins, and flagellin peptides (e.g., flg22).

Alternatively, the protein or peptide that protects a plant from a pathogen can be a protein or peptide that has antibacterial activity, antifungal activity, or both antibacterial and antifungal activity. Examples of such proteins and peptides include bacteriocins, lysozymes, lysozyme peptides (e.g., LysM), siderophores, non-ribosomal active peptides, conalbumins, albumins, lactoferrins, lactoferrin peptides (e.g., LfcinB), and TasA.

The protein or peptide that protects a plant from a pathogen can also be a protein or peptide that has insecticidal activity, helminthicidal activity, suppresses insect or worm predation, or a combination thereof. For example, the protein or peptide that protects a plant from a pathogen can comprise an insecticidal bacterial toxin (e.g., a VIP insecticidal protein), an endotoxin, a Cry toxin (e.g., a Cry toxin from *Bacillus thuringiensis*), a protease inhibitor protein or peptide (e.g., a trypsin inhibitor or an arrowhead protease inhibitor), a cysteine protease, or a chitinase. Where the Cry toxin is a Cry toxin from *Bacillus thuringiensis*, the Cry toxin can be a Cry5B protein or a Cry21A protein. Cry5B and Cry21A have both insecticidal and nematocidal activity.

The protein that protects a plant from a pathogen can comprise an enzyme. Suitable enzymes include proteases and lactonases. The proteases and lactonases can be specific for a bacterial signaling molecule (e.g., a bacterial lactone homoserine signaling molecule).

Where the enzyme is a lactonase, the lactonase can comprise 1,4-lactonase, 2-pyrone-4,6-dicarboxylate lactonase, 3-oxoadipate enol-lactonase, actinomycin lactonase, deoxylimonate A-ring-lactonase, gluconolactonase L-rhamnono-1,4-lactonase, limonin-D-ring-lactonase, steroid-lactonase, triacetate-lactonase, or xylono-1,4-lactonase.

The enzyme can also be an enzyme that is specific for a cellular component of a bacterium or fungus. For example, the enzyme can comprise a β-1,3-glucanase, a β-1,4-glucanase, a β-1,6-glucanase, a chitosinase, a chitinase, a chitosinase-like enzyme, a lyticase, a peptidase, a proteinase, a protease (e.g., an alkaline protease, an acid protease, or a neutral protease), a mutanolysin, a stapholysin, or a lysozyme.

For any of the above fusion proteins comprising a protein or peptide that protects a plant from a pathogen, the pathogen can be a bacterial pathogen or a fungal pathogen. For example, the pathogen can comprise an α-class Proteobacterium, a β-class Proteobacterium, a γ-class Proteobacterium, or a combination thereof. Particular bacterial pathogens include *Agrobacterium tumefaciens, Pantoea stewartii, Envinia carotovora, Ralstonia solanacearum, Pseudomonas syringae, Pseudomonas aeruginosa, Xanthomonas campestris*, and combinations thereof.

Other bacterial and fungal pathogens include *Acarospora microspora, Aceria guerreronis, Achlya conspicua, Achlya klebsiana, Achlysiella williamsi, Acholeplasmata-*

*ceae, Acidovorax avenae, Acremonium strictum, Acrocalymma medicaginis, Acrodontium simplex, Acrophialophora fusispora, Acrosporium tingitaninum, Aecidium, Aecidium aechmantherae, Aecidium amaryllidis, Aecidium breyniae, Aecidium campanulastri, Aecidium cannabis, Aecidium cantensis, Aecidium caspicum, Aecidium foeniculi, Agrobacterium tumefaciens, Albonectria rigidiuscula, Albugo bliti, Albugo candida, Albugo ipomoeae-panduratae, Albugo laibachii, Albugo occidentalis, Albugo tragopogonis, Alternaria, Alternaria alternata, Alternaria brassicae, Alternaria brassicicola, Alternaria carthami, Alternaria cinerariae, Alternaria citri, Alternaria dauci, Alternaria dianthi, Alternaria dianthicola, Alternaria euphorbiicola, Alternaria helianthi, Alternaria helianthicola, Alternaria japonica, Alternaria leucanthemi, Alternaria limicola, Alternaria linicola, Alternaria mali, Alternaria padwickii, Alternaria panax, Alternaria radicina, Alternaria raphani, Alternaria saponariae, Alternaria senecionis, Alternaria solani, Alternaria tenuissima, Alternaria triticina, Alternaria zinniae, Amazonia, Amphobotrys ricini, Anguillosporella vermiformis, Anguina* (genus), *Anguina agrostis, Anguina amsinckiae, Anguina australis, Anguina balsamophila, Anguina funesta, Anguina graminis, Anguina spermophaga, Anguina tritici, Anisogramma anomala, Anthostomella pullulans, Antrodia albida, Antrodia serialiformis, Antrodia serialis, Aphanomyces cladogamus, Aphanomyces cochlioides, Aphanomyces euteiches, Aphanomyces euteiches* f.sp. *pisi, Aphanomyces raphani, Aphelenchoides, Aphelenchoides arachidis, Aphelenchoides besseyi, Aphelenchoides fragariae, Aphelenchoides parietinus, Aphelenchoides ritzemabosi, Aphelenchus avenae, Apiognomonia errabunda, Apiognomonia veneta, Apiospora montagnei, Appendiculella, Armillaria, Armillaria affinis, Armillaria apalosclera, Armillaria camerunensis, Armillaria duplicate, Armillaria fellea, Armillaria fumosa, Armillaria fuscipes, Armillaria griseomellea, Armillaria heimii, Armillaria mellea, Armillaria melleorubens, Armillaria montagnei, Armillaria omnituens, Armillaria pallidula, Armillaria paulensis, Armillaria pelliculata, Armillaria procera, Armillaria puiggarii, Armillaria singular, Armillaria socialis, Armillaria solidipes, Armillaria tabescens, Armillaria tigrensis, Armillaria umbrinobrunnea, Armillaria viridiflava, Armillaria yungensis, Arthrocladiella, Arthuriomyces peckianus, Ascochyta asparagine, Ascochyta bohemica, Ascochyta caricae, Ascochyta doronici, Ascochyta fabae* f.sp. *lentis, Ascochyta graminea, Ascochyta hordei, Ascochyta humuli, Ascochyta pisi, Ascochyta prasadii, Ascochyta sorghi, Ascochyta spinaciae, Ascochyta tarda, Ascochyta tritici, Ascospora ruborum, Ashbya gossypii, Aspergillus aculeatus, Aspergillus fischerianus, Aspergillus niger, Asperisporium caricae, Asperisporium minutulum, Asteridiella, Asteridiella perseae, Asteroma caryae, Asteroma coryli, Asteroma inconspicuum, Athelia arachnoidea, Athelia rolfsii, Aurantiporus fissilis, Belonolaimus, Belonolaimus gracilis, Belonolaimus longicaudatus, Beniowskia sphaeroidea, Bionectria ochroleuca, Bipolaris, Bipolaris cactivora, Bipolaris cookie, Bipolaris incurvata, Bipolaris sacchari, Biscogniauxia capnodes* var. *capnodes, Biscogniauxia marginata, Biscogniauxia nummularia, Bjerkandera adusta, Blakeslea trispora, Blumeria graminis, Botryodiplodia oncidii, Botryodiplodia ulmicola, Botryosphaeria cocogena, Botryosphaeria corticola, Botryosphaeria disrupta, Botryosphaeria dothidea, Botryosphaeria marconii, Botryosphaeria obtuse, Botryosphaeria quercuum, Botryosphaeria rhodina, Botryosphaeria ribis, Botryosphaeria stevensii, Botryosporium pulchrum, Botryotinia, Botryotinia fuckeliana, Botrytis anthophila, Botrytis cinerea, Botrytis fabae, Bremia lactucae, Brenneria salicis, Briosia ampelophaga, Bulbomicrosphaera, Burkholderia andropogonis, Burkholderia caryophylli, Burkholderia glumae, Cadophora malorum, Caespitotheca, Calonectria indusiata, Calonectria kyotensis, Calonectria quinqueseptata, Calvatia versispora, Camarosporium pistaciae, Camarotella acrocomiae, Camarotella costaricensis, Candidatus Liberibacter, Capitorostrum cocoes, Capnodium footii, Capnodium mangiferum, Capnodium ramosum, Capnodium theae, Caulimoviridae, Cephaleuros virescens, Cephalosporium gramineum, Ceratobasidium cereal, Ceratobasidium cornigerum, Ceratobasidium noxium, Ceratobasidium ramicola, Ceratobasidium setariae, Ceratobasidium stevensii, Ceratocystis adiposa, Ceratocystis coerulescens, Ceratocystis fimbriata, Ceratocystis moniliformis, Ceratocystis paradoxa, Ceratocystis pilifera, Ceratocystis pluriannulata, Ceratorhiza hydrophila, Ceratospermopsis, Cercoseptoria ocellata, Cercospora, Cercospora angreci, Cercospora apii, Cercospora apii* f.sp. *clerodendri, Cercospora apiicola, Cercospora arachidicola, Cercospora asparagi, Cercospora atrofiliformis, Cercospora beticola, Cercospora brachypus, Cercospora brassicicola, Cercospora brunkii, Cercospora cannabis, Cercospora cantuariensis, Cercospora capsici, Cercospora carotae, Cercospora corylina, Cercospora fragariae, Cercospora fuchsiae, Cercospora fusca, Cercospora fusimaculans, Cercospora gerberae, Cercospora halstedii, Cercospora handelii, Cercospora hayi, Cercospora hydrangea, Cercospora kikuchii, Cercospora lentis, Cercospora liquidambaris, Cercospora longipes, Cercospora longissima, Cercospora mamaonis, Cercospora mangiferae, Cercospora medicaginis, Cercospora melongenae, Cercospora minima, Cercospora minuta, Cercospora nicotianae, Cercospora odontoglossi, Cercospora papaya, Cercospora penniseti, Cercospora pisa-sativae, Cercospora platanicola, Cercospora puderii, Cercospora pulcherrima, Cercospora rhapidicola, Cercospora rosicola, Cercospora rubrotincta, Cercospora sojina, Cercospora solani, Cercospora solani-tuberosi, Cercospora sorghi, Cercospora theae, Cercospora tuberculans, Cercospora vexans, Cercospora vicosae, Cercospora zeae-maydis, Cercospora zebrina, Cercospora zonata, Cercosporella rubi, Cereal cyst nematode, Ceriporia spissa, Ceriporia xylostromatoides, Cerrena unicolor, Ceuthospora lauri, Choanephora, Choanephora cucurbitarum, Choanephora infundibulifera, Chondrostereum purpureum, Chrysomyxa ledi* var. *rhododendri, Chrysomyxa ledicola, Chrysomyxa piperiana, Chrysomyxa roanensis, Cladosporium, Cladosporium arthropodii, Cladosporium caryigenum, Cladosporium cladosporioides, Cladosporium cladosporioides* f.sp. *pisicola, Cladosporium cucumerinum, Cladosporium herbarum, Cladosporium musae, Cladosporium oncobae, Clavibacter michiganensis, Claviceps fusiformis, Claviceps purpurea, Claviceps sorghi, Claviceps zizaniae, Climacodon pulcherrimus, Climacodon septentrionalis, Clitocybe parasitica, Clonostachys rosea* f. *rosea, Clypeoporthe iliau, Cochliobolus, Cochliobolus carbonum, Cochliobolus cymbopogonis, Cochliobolus hawaiiensis, Cochliobolus heterostrophus, Cochliobolus lunatus, Cochliobolus miyabeanus, Cochliobolus ravenelii, Cochliobolus sativus, Cochliobolus setariae, Cochliobolus spicifer, Cochliobolus stenospilus, Cochliobolus tuberculatus, Cochliobolus victoriae, Coleosporium helianthi, Coleosporium ipomoeae, Coleosporium madiae, Coleosporium pacificum, Coleosporium tussilaginis, Colletotrichum acutatum, Colletotrichum arachidis, Colletotrichum capsici, Colletotrichum cereale, Colletotrichum crassipes, Colletotrichum dematium, Colletotrichum dematium* f. *spinaciae, Colletotrichum derridis,*

*Colletotrichum destructivum, Colletotrichum fragariae, Colletotrichum gossypii, Colletotrichum higginsianum, Colletotrichum kahawae, Colletotrichum lindemuthianum, Colletotrichum lini, Colletotrichum mangenotii, Colletotrichum musae, Colletotrichum nigrum, Colletotrichum orbiculare, Colletotrichum pisi, Colletotrichum sublineolum, Colletotrichum trichellum, Colletotrichum trifolii, Colletotrichum truncatum, Coniella castaneicola, Coniella diplodiella, Coniella fragariae, Coniothecium chomatosporum, Coniothyrium celtidis-australis, Coniothyrium henriquesii, Coniothyrium rosarum, Coniothyrium wernsdorffiae, Coprinopsis psychromorbida, Cordana johnstonii, Cordana musae, Coriolopsis floccose, Coriolopsis gallica, Corticium invisum, Corticium penicillatum, Corticium theae, Coryneopsis rubi, Corynespora cassiicola, Coryneum rhododendri, Crinipellis sarmentosa, Cronartium ribicola, Cryphonectriaceae, Cryptocline cyclaminis, Cryptomeliola, Cryptoporus volvatus, Cryptosporella umbrina, Cryptosporiopsis tarraconensis, Cryptosporium minimum, Curvularia caricae-papayae, Curvularia penniseti, Curvularia senegalensis, Curvularia trifolii, Cylindrocarpon candidum, Cylindrocarpon ianthothele* var. *ianthothele, Cylindrocarpon magnusianum, Cylindrocarpon musae, Cylindrocladiella camelliae, Cylindrocladiella parva, Cylindrocladium clavatum, Cylindrocladium lanceolatum, Cylindrocladium peruvianum, Cylindrocladium pteridis, Cylindrosporium cannabinum, Cylindrosporium juglandis, Cylindrosporium rubi, Cymadothea trifolii, Cytospora, Cytospora palmarum, Cytospora personata, Cytospora platani, Cytospora sacchari, Cytospora sacculus, Cytospora terebinthi, Cytosporina ludibunda, Dactuliophora elongata, Daedaleopsis confragosa, Dasineura urticae, Datronia scutellata, Davidiella carinthiaca, Davidiella dianthi, Davidiella tassiana, Deightoniella papuana, Deightoniella torulosa, Dendrophoma marconii, Dendrophora erumpens, Denticularia mangiferae, Dermea pseudotsugae, Diaporthaceae, Diaporthe, Diaporthe arctii, Diaporthe citri, Diaporthe dulcamarae, Diaporthe eres, Diaporthe helianthi, Diaporthe lagunensis, Diaporthe lokoyae, Diaporthe melonis, Diaporthe orthoceras, Diaporthe perniciosa, Diaporthe phaseolorum, Diaporthe phaseolorum* var. *caulivora, Diaporthe phaseolorum* var. *phaseolorum, Diaporthe phaseolorum* var. *sojae, Diaporthe rudis, Diaporthe tanakae, Diaporthe toxica, Dibotryon morbosum, Dicarpella dryina, Didymella bryoniae, Didymella fabae, Didymella lycopersici, Didymosphaeria arachidicola, Didymosphaeria taiwanensis, Dilophospora alopecuri, Dimeriella sacchari, Diplocarpon earlianum, Diplocarpon mali, Diplocarpon mespili, Diplocarpon rosae, Diplodia laelio-cattleyae, Diplodia manihoti, Diplodia paraphysaria, Diplodia theae-sinensis, Discosia artocreas, Guignardia fulvida, Discostroma corticola, Distocercospora, Distocercospora livistonae, Ditylenchus, Ditylenchus africanus, Ditylenchus angustus, Ditylenchus destructor, Ditylenchus dipsaci, Dolichodorus heterocephalus, Dothideomycetes, Dothiorella aromatic, Dothiorella dominicana, Dothiorella gregaria, Dothiorella ulmi, Drechslera avenacea, Drechslera campanulata, Drechslera dematioidea, Drechslera gigantea, Drechslera glycines, Drechslera musae-sapientium, Drechslera teres f. maculate, Drechslera wirreganensis, Durandiella pseudotsugae, Eballistra lineata, Eballistra oryzae, Eballistraceae, Echinodontium tinctorium, Ectendomeliola, Elsinoë ampelina, Elsinoë australis, Elsinoë batatas, Elsinoë brasiliensis, Elsinoë fawcettii, Elsinoë leucospila, Elsinoë mangiferae, Elsinoë pini, Elsinoë randii, Elsinoë rosarum, Elsinoë sacchari, Elsinoë theae, Elsinoë veneta, Endomeliola, Endothia radicalis, Endothiella gyrosa, Entoleuca mammata, Entorrhizomycetes, Entyloma ageratinae, Entyloma dahlia, Entyloma ellisii, Epicoccum nigrum, Ergot, Erwinia, Erwinia chrysanthemi, Erwinia psidii, Erysiphaceae, Erysiphales, Erysiphe, Erysiphe alphitoides, Erysiphe betae, Erysiphe brunneopunctata, Erysiphe cichoracearum, Erysiphe cruciferarum, Erysiphe flexuosa, Erysiphe graminis* f.sp. *avenae, Erysiphe graminis* f.sp. *tritici, Erysiphe heraclei, Erysiphe pisi, Eutypella parasitica, Eutypella scoparia, Exobasidium burtii, Exobasidium reticulatum, Exobasidium vaccinii* var. *japonicum, Exobasidium vaccinii-uliginosi, Exobasidium vexans, Exophiala, Flavescence doree, Fomes fasciatus, Fomes lamaensis, Fomes meliae, Fomitopsis cajanderi, Fomitopsis palustris, Fomitopsis rosea, Fomitopsis spraguei, Fomitopsis supina, Forma specialis, Frommeella tormentillae, Fusarium, Fusarium affine, Fusarium arthrosporioides, Fusarium circinatum, Fusarium crookwellense, Fusarium culmorum, Fusarium graminearum, Fusarium incarnatum, Fusarium solani, Fusarium merismoides, Fusarium oxysporum* f.sp. *albedinis, Fusarium oxysporum* f.sp. *asparagi, Fusarium oxysporum* f.sp. *batatas, Fusarium oxysporum* f.sp. *betae, Fusarium oxysporum* f.sp. *cannabis, Fusarium oxysporum* f.sp. *citri, Fusarium oxysporum* f.sp. *coffea, Fusarium oxysporum* f.sp. *cubense, Fusarium oxysporum* f.sp. *cyclaminis, Fusarium oxysporum* f.sp. *dianthi, Fusarium oxysporum* f.sp. *lentis, Fusarium oxysporum* f.sp. *lini, Fusarium oxysporum* f.sp. *lycopersici, Fusarium oxysporum* f.sp. *medicaginis, Fusarium oxysporum* f.sp. *pisi, Fusarium oxysporum* f.sp. *radicis-lycopersici, Fusarium pallidoroseum, Fusarium proliferatum, Fusarium redolens, Fusarium sacchari, Fusarium solani* f.sp. *pisi, Fusarium sporotrichioides, Fusarium subglutinans, Fusarium sulphureum, Fuscoporia torulosa, Fusicladium pisicola, Fusicoccum aesculi, Fusicoccum amygdali, Gaeumannomyces graminis* var *tritici, Gaeumannomyces graminis* var. *avenae, Gaeumannomyces graminis* var. *graminis, Galactomyces candidum, Ganoderma brownii, Ganoderma lobatum, Ganoderma orbiforme, Ganoderma philippii, Ganoderma tornatum, Ganoderma zonatum, Geastrumia polystigmatis, Georgefischeriaceae, Georgefischeriales, Geosmithia morbida, Geotrichum, Geotrichum candidum, Geotrichum candidum* var. *citni-aurantii, Geotrichum klebahnii, Gibberella, Gibberella acuminata, Gibberella avenacea, Gibberella baccata, Gibberella cyanogena, Gibberella fujikuroi, Gibberella fujikuroi* var. *subglutinans, Gibberella intricans, Gibberella pulicaris, Gibberella stilboides, Gibberella xylarioides, Gibberella zeae, Gibellina cerealis, Gilbertella persicaria, Gjaerumiaceae, Gliocladium vermoeseni, Globodera pallida, Globodera rostochiensis, Globodera tabacum, Gloeocercospora sorghi, Gloeocystidiellum porosum, Gloeophyllum mexicanum, Gloeophyllum trabeum, Gloeoporus dichrous, Gloeosporium cattleyae, Gloeosporium theae-sinensis, Glomerella cingulate, Glomerella glycines, Glomerella graminicola, Glomerella tucumanensis, Gnomonia caryae, Gnomonia comari, Gnomonia dispora, Gnomonia iliau, Gnomonia leptostyla, Gnomonia nerviseda, Gnomonia rubi, Golovinomyces cichoracearum* var. *latisporus, Granulobasidium vellereum, Graphiola phoenicis, Graphium rigidum, Graphium rubrum, Graphyllium pentamerum, Grovesinia pyramidalis, Guignardia bidwellii* f. *muscadinii, Guignardia camelliae, Guignardia citricarpa, Guignardia mangiferae, Guignardia musae, Guignardia philoprina, Gummosis, Gymnoconia nitens, Gymnopus dryophilus, Gymnosporangium clavipes, Gymnosporangium sabinae, Gymnosporangium globosum, Gymnosporangium jumperi-virginianae, Gymnosporangium kernianum, Gymnosporangium nelsonii, Gymnosporangium yamadae, Haematonectria haematococca, Hansenula sub-*

*pelliculosa, Hapalosphaeria deformans, Haplobasidion musae, Haustorium, Helicobasidium compactum, Helicobasidium longisporum, Helicobasidium purpureum, Helicoma muelleri, Helicotylenchus, Helicotylenchus dihystera, Helicotylenchus multicinctus, Helminthosporium cookei, Helminthosporium papulosum, Helminthosporium solani, Helotiales, Hemicriconemoides kanayaensis, Hemicriconemoides mangiferae, Hemicycliophora arenaria, Hemlock woolly adelgid, Hendersonia creberrima, Hendersonia theicola, Hericium coralloides, Heterobasidion annosum, Heterodera, Heterodera amygdali, Heterodera arenaria, Heterodera aucklandica, Heterodera avenae, Heterodera bergeniae, Heterodera bifenestra, Heterodera cacti, Heterodera cajani, Heterodera canadensis, Heterodera cardiolata, Heterodera carotae, Heterodera ciceri, Heterodera cruciferae, Heterodera delvii, Heterodera elachista, Heterodera filipjevi, Heterodera gambiensis, Heterodera goettingiana, Heterodera hordecalis, Heterodera humuli, Heterodera latipons, Heterodera medicaginis, Heterodera oryzae, Heterodera oryzicola, Heterodera rosii, Heterodera sacchari, Heterodera schachtii, Heterodera tabacum, Heterodera trifolii, Heteroderidae, Hexagonia hydnoides, Hirschmanniella oryzae, Hoplalaimus galeatus, Hoplolaimidae, Hoplolaimus columbus, Hoplolaimus indicus, Hoplolaimus magnistylus, Hoplolaimus pararobustus, Hoplolaimus seinhorsti, Hoplolaimus uniformis, Huanglongbing, Hyaloperonospora, Hyaloperonospora arabidopsidis, Hyaloperonospora brassicae, Hyaloperonospora parasitica, Hymenula affinis, Hyphodermella corrugata, Hyphodontia aspera, Hyphodontia sambuci, Hypochnus, Hypoxylon tinctor, Idriella lunata, Inonotus arizonicus, Inonotus cuticularis, Inonotus dryophilus, Inonotus hispidus, Inonotus ludovicianus, Inonotus munzii, Inonotus tamaricis, Irenopsis, Irpex destruens, Irpex lacteus, Isariopsis clavispora, Johncouchia mangiferae, Kabatiella caulivora, Kabatiella lini, Karnal bunt, Khuskia oryzae, Kretzschmaria deusta, Kretzschmaria zonata, Kuehneola uredinis, Kutilakesa pironii, Labrella coryli, Laeticorticium roseum, Laetiporus baudonii, Lagenocystis radicicola, Laricifomes officinalis, Lasiodiplodia theobromas, Leandria momordicae, Leifsonia xyli xyli, Lentinus tigrinus, Lenzites betulina, Lenzites elegans, Lepteutypa cupressi, Leptodontidium elatius* var. *elatius, Leptographium microsporum, Leptosphaeria acuta, Leptosphaeria cannabina, Leptosphaeria coniothyrium, Leptosphaeria libanotis, Leptosphaeria lindquistii, Leptosphaeria maculans, Leptosphaeria musarum, Leptosphaeria pratensis, Leptosphaeria sacchari, Leptosphaeria woroninii, Leptosphaerulina crassiasca, Leptosphaerulina trifolii, Leptothyrium nervisedum, Leptotrochila medicaginis, Leucocytospora leucostoma, Leucostoma auerswaldii, Leucostoma kunzei, Leucostoma persoonii, Leveillula compositarum* f. *helianthi, Leveillula leguminosarum* f. *lentis, Leveillula taurica, Lignierа pilorum, Limacinula tenuis, Linochora graminis, Longidorus africanus, Longidorus maximus, Longidorus sylphus, Lopharia crassa, Lophodermium, Lophodermium aucupariae, Lophodermium schweinitzii, Lophodermium seditiosum, Macrophoma mangiferae, Macrophoma theicola, Macrophomina phaseolina, Macrosporium cocos, Magnaporthe, Magnaporthe grisea, Magnaporthe salvinii, Mamianiella coryli, Marasmiellus cocophilus, Marasmiellus inoderma, Marasmiellus scandens, Marasmiellus stenophyllus, Marasmius crinis-equi, Marasmius sacchari, Marasmius semiustus, Marasmius stenophyllus, Marasmius tenuissimus, Massarina walkeri, Mauginiella scaettae, Melampsora, Melampsora lini* var. *lini, Melampsora medusae, Melampsora occidentalis, Melanconis carthusiana, Melanconium juglandinum, Meliola, Meliola mangiferae, Meliolaceae, Meloidogyne acronea, Meloidogyne arenaria, Meloidogyne artiellia, Meloidogyne brevicauda, Meloidogyne chitwoodi, Meloidogyne enterolobii, Meloidogyne fruglia, Meloidogyne gajuscus, Meloidogyne incognita, Meloidogyne javanica, Meloidogyne naasi, Meloidogyne partityla, Meloidogyne thamesi, Meripilus giganteus, Merlinius brevidens, Meruliopsis ambigua, Mesocriconema xenoplax, Microascus brevicaulis, Microbotryum violaceum, Microdochium bolleyi, Microdochium dimerum, Microdochium panattonianum, Microdochium phragmitis, Microsphaera, Microsphaera coryli, Microsphaera diffusa, Microsphaera ellisii, Microsphaera euphorbiae, Microsphaera hommae, Microsphaera penicillata, Microsphaera penicillata* var. *vaccinii, Microsphaera vaccinii, Microsphaera verruculosa, Microstroma juglandis, Moesziomyces bullatus, Monilinia azaleae, Monilinia fructicola, Monilinia fructigena, Monilinia laxa, Monilinia mali, Moniliophthora perniciosa, Moniliophthora roreri, Monilochaetes infuscans, Monochaetia coryli, Monochaetia mali, Monographella albescens, Monographella cucumerina, Monographella nivalis* var. *neglecta, Monographella nivalis* var. *nivalis, Mononegavirales, Monosporascus cannonballus, Monosporascus eutypoides, Monostichella coryli, Mucor circinelloides, Mucor hiemalis, Mucor hiemalis* f. *silvaticus, Mucor mucedo, Mucor paronychius, Mucor piriformis, Mucor racemosus, Mycena citricolor, Mycena maculate, Mycocentrospora acerina, Mycoleptodiscus terrestris, Mycosphaerella angulata, Mycosphaerella arachidis, Mycosphaerella areola, Mycosphaerella berkeleyi, Mycosphaerella bolleana, Mycosphaerella brassicicola, Mycosphaerella caricae, Mycosphaerella caryigena, Mycosphaerella cerasella, Mycosphaerella citri, Mycosphaerella coffeicola, Mycosphaerella confusa, Mycosphaerella cruenta, Mycosphaerella dendroides, Mycosphaerella eumusae, Mycosphaerella fragariae, Mycosphaerella gossypina, Mycosphaerella graminicola, Mycosphaerella henningsii, Mycosphaerella horii, Mycosphaerella juglandis, Mycosphaerella lageniformis, Mycosphaerella linicola, Mycosphaerella louisianae, Mycosphaerella musae, Mycosphaerella musicola, Mycosphaerella palmicola, Mycosphaerella pinodes, Mycosphaerella pistaciarum, Mycosphaerella pistacina, Mycosphaerella platanifolia, Mycosphaerella polymorpha, Mycosphaerella pomi, Mycosphaerella punctiformis, Mycosphaerella pyri, Didymella rabiei, Mycosphaerella recutita, Mycosphaerella rosicola, Mycosphaerella rubi, Mycosphaerella stigmina-platani, Mycosphaerella striatiformans, Mycovellosiella concors, Mycovellosiella fulva, Mycovellosiella koepkei, Mycovellosiella vaginae, Myriogenospora aciculispora, Myrothecium roridum, Myrothecium verrucaria, Nacobbus aberrans, Nacobbus dorsalis, Naevala perexigua, Naohidemyces vaccinii, Nectria, Nectria cinnabarina, Nectria coccinea, Nectria ditissima, ectria foliicola, Nectria mammoidea* var. *rubi, Nectria mauritiicola, Nectria peziza, Nectria pseudotrichia, Nectria radicicola, Nectria ramulariae, Nectriella pironii, Nemania diffusa, Nemania serpens* var. *serpens, Nematospora coryli, Neocosmospora vasinfecta, Neodeightonia phoenicum, Neoerysiphe, Neofabraea malicorticis, Neofabraea perennans, Neofusicoccum mangiferae, Neonectria galligena, Oidiopsis gossypii, Oidium* (genus), *Oidium arachidis, Oidium caricae-papayae, Oidium indicum, Oidium mangiferae, Oidium manihotis, Oidium tingitaninum, Olpidium brassicae, Omphalia tralucida, Oncobasidium theobromae, Onnia tomentosa, Ophiobolus anguillides, Ophiobolus cannabinus, Ophioirenina, Ophiostoma ulmi, Ophiostoma wageneri, Ovulariopsis* papayae, Ovulinia azaleae, Ovulitis azaleae, Oxyporus corticola, Oxyporus latemarginatus, Oxyporus populinus, Oxyporus similis, Ozonium texanum var. parasiticum, Paecilomyces fulvus, Paralongidorus maximus, Paratrichodorus christiei, Paratrichodorus minor, Paratylenchus curvitatus, Paratylenchus elachistus, Paratylenchus hamatus, Paratylenchus macrophallus, Paratylenchus microdorus, Paratylenchus projectus, Paratylenchus tenuicaudatus, Pathovar, Pauahia, Peach latent mosaic viroid, Pectobacterium carotovorum, Peltaster fructicola, Penicillium aurantiogriseum, Penicillium digitatum, Penicillium expansum, Penicillium funiculosum, Penicillium glabrum, Penicillium italicum, Penicillium purpurogenum, Penicillium ulaiense, Peniophora, Peniophora albobadia, Peniophora cinerea, Peniophora quercina, Peniophora sacrata, Perenniporia fraxinea, Perenniporia fraxinophila, Perenniporia medullapanis, Perenniporia subacida, Periconia circinata, Periconiella cocoes, Peridermium californicum, Peronosclerospora miscanthi, Peronosclerospora sacchari, Peronosclerospora sorghi, Peronospora, Peronospora anemones, Peronospora antirrhini, Peronospora arborescens, Peronospora conglomerata, Peronospora destructor, Peronospora dianthi, Peronospora dianthicola, Peronospora farinosa, Peronospora farinosa f.sp. betae, Peronospora hyoscyami f.sp. tabacina, Peronospora manshurica, Peronospora potentillae, Peronospora sparsa, Peronospora trifoliorum, Peronospora valerianellae, Peronospora viciae, Pestalosphaeria concentrica, Pestalotia longiseta, Pestalotia longisetula, Pestalotia rhododendri, Pestalotiopsis, Pestalotiopsis adusta, Pestalotiopsis arachidis, Pestalotiopsis disseminata, Pestalotiopsis guepini, Pestalotiopsis leprogena, Pestalotiopsis longiseta, Pestalotiopsis mangiferae, Pestalotiopsis palmarum, Pestalotiopsis sydowiana, Pestalotiopsis theae, Pestalotiopsis versicolor, Phacidiopycnis padwickii, Phacidium infestans, Phaeochoropsis mucosa, Phaeocytostroma iliau, Phaeocytostroma sacchari, Phaeoisariopsis bataticola, Phaeolus schweinitzii, Phaeoramularia angolensis, Phaeoramularia dissiliens, Phaeoramularia heterospora, Phaeoramularia manihotis, Phaeoseptoria musae, Phaeosphaerella mangiferae, Phaeosphaerella theae, Phaeosphaeria avenaria f.sp. avenaria, Phaeosphaeria avenaria f.sp. triticae, Phaeosphaeria herpotrichoides, Phaeosphaeria microscopica, Phaeosphaeria nodorum, Phaeosphaeriopsis obtusispora, Phaeotrichoconis crotalariae, Phakopsora gossypii, Phakopsora pachyrhizi, Phanerochaete allantospora, Phanerochaete arizonica, Phanerochaete avellanea, Phanerochaete burtii, Phanerochaete carnosa, Phanerochaete chrysorhizon, Phanerochaete radicata, Phanerochaete salmonicolor, Phanerochaete tuberculata, Phanerochaete velutina, Phellinus ferreus, Phellinus gilvus, Phellinus igniarius, Phellinus pini, Phellinus pomaceus, Phellinus weirii, Phialophora asteris, Phialophora cinerescens, Phialophora gregata, Phialophora tracheiphila, Phloeospora multimaculans, Pholiota variicystis, Phoma, Phoma caricae-papayae, Phoma clematidina, Phoma costaricensis, Phoma cucurbitacearum, Phoma destructiva, Phoma draconis, Phoma eupyrena, Phoma exigua, Phoma exigua var. exigua, Phoma exigua var. foveata, Phoma exigua var. linicola, Phoma glomerata, Phoma glycinicola, Phoma herbarum, Phoma insidiosa, Phoma medicaginis, Phoma microspora, Phoma nebulosa, Phoma oncidii-sphacelati, Phoma pinodella, Phoma scabra, Phoma sclerotioides, Phoma strasseri, Phoma tracheiphila, Phomopsis arnoldiae, Phomopsis asparagi, Phomopsis asparagicola, Phomopsis azadirachtae, Phomopsis cannabina, Phomopsis caricae-papayae, Phomopsis coffeae, Phomopsis elaeagni, Phomopsis ganjae, Phomopsis javanica, Phomopsis lokoyae, Phomopsis mangiferae, Phomopsis obscurans, Phomopsis perseae, Phomopsis prunorum, Phomopsis scabra, Phomopsis sclerotioides, Phomopsis tanakae, Phomopsis theae, Photoassimilate, Phragmidium, Phragmidium mucronatum, Phragmidium rosae-pimpinellifoliae, Phragmidium rubi-idaei, Phragmidium violaceum, Phyllachora cannabis, Phyllachora graminis var. graminis, Phyllachora gratissima, Phyllachora musicola, Phyllachora pomigena, Phyllachora sacchari, Phyllactinia, Phyllactinia angulata, Phyllactinia guttata, Phyllody, Phyllosticta, Phyllosticta alliariaefoliae, Phyllosticta anacardiacearum, Phyllosticta arachidis-hypogaeae, Phyllosticta batatas, Phyllosticta capitalensis, Phyllosticta caricae-papayae, Phyllosticta carpogena, Phyllosticta circumscissa, Phyllosticta coffeicola, Phyllosticta concentrica, Phyllosticta coryli, Phyllosticta cucurbitacearum, Phyllosticta cyclaminella, Phyllosticta erratica, Phyllosticta hawaiiensis, Phyllosticta lentisci, Phyllosticta manihotis, Phyllosticta micropuncta, Phyllosticta mortonii, Phyllosticta nicotianae, Phyllosticta palmetto, Phyllosticta penicillariae, Phyllosticta perseae, Phyllosticta platani, Phyllosticta pseudocapsici, Phyllosticta sojaecola, Phyllosticta solitaria, Phyllosticta theae, Phyllosticta theicola, Phymatotrichopsis omnivora, Physalospora abdita, Physalospora disrupta, Physalospora perseae, Physarum cinereum, Physoderma alfalfae, Physoderma leproides, Physoderma trifolii, Physopella ampelopsidis, Phytophthora, Phytophthora alni, Phytophthora boehmeriae, Phytophthora cactorum, Phytophthora cajani, Phytophthora cambivora, Phytophthora capsici, Phytophthora cinnamomi, Phytophthora citricola, Phytophthora citrophthora, Phytophthora cryptogea, Phytophthora drechsleri, Phytophthora erythroseptica, Phytophthora fragariae, Phytophthora fragariae var. rubi, Phytophthora gallica, Phytophthora hibernalis, Phytophthora infestans, Phytophthora inflata, Phytophthora iranica, Phytophthora katsurae, Phytophthora kernoviae, Phytophthora lateralis, Phytophthora medicaginis, Phytophthora megakarya, Phytophthora megasperma, Phytophthora nicotianae, Phytophthora palmivora, Phytophthora phaseoli, Phytophthora plurivora, Phytophthora ramorum, Phytophthora sojae, Phytophthora syringae, Phytophthora tentaculata, Phytoplasma, Pichia membranifaciens, Pichia subpelliculosa, Pileolaria terebinthi, Pilidiella quercicola, Plasmodiophora brassicae, Plasmopara, Plasmopara halstedii, Plasmopara helianthi f. helianthi, Plasmopara lactucae-radicis, Plasmopara nivea, Plasmopara obducens, Plasmopara penniseti, Plasmopara pygmaea, Plasmopara viticola, Platychora ulmi, Plenodomus destruens, Plenodomus meliloti, Pleochaeta, Pleosphaerulina sojicola, Pleospora alfalfae, Pleospora betae, Pleospora herbarum, Pleospora lycopersici, Pleospora tarda, Pleospora theae, Pleurotus dryinus, Podosphaera, Podosphaera clandestina var. clandestine, Podosphaera fusca, Podosphaera leucotricha, Podosphaera macularis, Podosphaera pannosa, Podosphaera tridactyla, Podosphaera tridactyla var. tridactyla, Podosphaera xanthii, Polymyxa graminis, Polyscytalum pustulans, Polystigma fulvum, Poria hypobrunnea, Postia tephroleuca, Potato cyst nematode, Pratylenchus alleni, Pratylenchus brachyurus, Pratylenchus coffeae, Pratylenchus crenatus, Pratylenchus dulscus, Pratylenchus fallax, Pratylenchus flakkensis, Pratylenchus goodeyi, Pratylenchus hexincisus, Pratylenchus loosi, Pratylenchus minutus, Pratylenchus mulchandi, Pratylenchus musicola, Pratylenchus neglectus, Pratylenchus penetrans, Pratylenchus pratensis, Pratylenchus reniformia, Pratylenchus scribneri, Pratylenchus thornei, Pratylenchus vulnus, Pratylenchus zeae, Pseudocercospora, Pseudocercospora arecacearum,

*Pseudocercospora cannabina, Pseudocercospora fuligena, Pseudocercospora gunnerae, Pseudocercospora kaki, Pseudocercospora mali, Pseudocercospora pandoreae, Pseudocercospora puderi, Pseudocercospora purpurea, Pseudocercospora rhapisicola, Pseudocercospora subsessilis, Pseudocercospora theae, Pseudocercospora vitis, Pseudocercosporella capsellae, Pseudocochliobolus eragrostidis, Pseudoepicoccum cocos, Pseudomonas amygdali, Pseudomonas asplenii, Pseudomonas avellanae, Pseudomonas caricapapayae, Pseudomonas cichorii, Pseudomonas coronafaciens, Pseudomonas corrugate, Pseudomonas ficuserectae, Pseudomonas flavescens, Pseudomonas fuscovaginae, Pseudomonas helianthi, Pseudomonas marginalis, Pseudomonas meliae, Pseudomonas oryzihabitans, Pseudomonas palleroniana, Pseudomonas papaveris, Pseudomonas salomonii, Pseudomonas savastanoi, Pseudomonas syringae, Pseudomonas tomato, Pseudomonas tremae, Pseudomonas turbinellae, Pseudomonas viridiflava, Pseudoperonospora cannabina, Pseudoperonospora cubensis, Pseudoperonospora humuli, Pseudopezicula tetraspora, Pseudopezicula tracheiphila, Pseudopeziza jonesii, Pseudopeziza medicaginis, Pseudopeziza trifolii, Pseudoseptoria donacis, Puccinia, Puccinia angustata, Puccinia arachidis, Puccinia aristidae, Puccinia asparagi, Puccinia cacabata, Puccinia campanulae, Puccinia carthami, Puccinia coronate, Puccinia coronata* var. *hordei, Puccinia dioicae, Puccinia erianthi, Puccinia extensicola* var. *hieraciata, Puccinia helianthi, Puccinia hordei, Puccinia jaceae* var. *solstitialis, Puccinia kuehnii, Puccinia mariae-wilsoniae, Puccinia melanocephala, Puccinia menthae, Puccinia pelargonii-zonalis, Puccinia pittieriana, Puccinia poarum, Puccinia psidii, Puccinia purpurea, Puccinia recondita, Puccinia schedonnardii, Puccinia sessilis, Puccinia striiformis f.* sp. *hordei, Puccinia striiformis* var. *striiformis, Puccinia subnitens, Puccinia substriata* var. *indica, Puccinia verruca, Puccinia xanthii, Pucciniaceae, Pucciniastrum, Pucciniastrum americanum, Pucciniastrum arcticum, Pucciniastrum coryli, Pucciniastrum epilobii, Pucciniastrum hydrangeas, Punctodera chalcoensis, Pycnoporus cinnabarinus, Pycnoporus sanguineus, Pycnostysanus azaleae, Pyrenochaeta lycopersici, Pyrenochaeta terrestris, Pyrenopeziza brassicae, Pyrenophora, Pyrenophora avenae, Pyrenophora chaetomioides, Pyrenophora graminea, Pyrenophora seminiperda, Pyrenophora teres, Pyrenophora teres* f. *maculata, Pyrenophora teres* f. *teres, Pyrenophora tritici-repentis, Pythiaceae, Pythiales, Pythium, Pythium acanthicum, Pythium aphanidermatum, Pythium aristosporum, Pythium arrhenomanes, Pythium buismaniae, Pythium debaryanum, Pythium deliense, Pythium dissotocum, Pythium graminicola, Pythium heterothallicum, Pythium hypogynum, Pythium irregulare, Pythium iwayamae, Pythium mastophorum, Pythium middletonii, Pythium myriotylum, Pythium okanoganense, Pythium paddicum, Pythium paroecandrum, Pythium perniciosum, Pythium rostratum, Pythium scleroteichum, Pythium spinosum, Pythium splendens, Pythium sulcatum, Pythium sylvaticum, Pythium tardicrescens, Pythium tracheiphilum, Pythium ultimum, Pythium ultimum* var. *ultimum, Pythium vexans, Pythium violae, Pythium volutum, Quinisulcius acutus, Quinisulcius capitatus, Radopholous similis, Radopholus similis, Ralstonia solanacearum, Ramichloridium musae, Ramularia, Ramularia beticola, Ramularia brunnea, Ramularia coryli, Ramularia cyclaminicola, Ramularia macrospora, Ramularia menthicola, Ramularia necator, Ramularia primulae, Ramularia spinaciae, Ramularia subtilis, Ramularia tenella, Ramulispora sorghi, Ramulispora sorghicola, Resinicium bicolor, Rhabdocline pseudotsugae, Rhabdocline weirii Rhabdoviridae, Rhinocladium corticola, Rhizoctonia, Rhizoctonia leguminicola, Rhizoctonia rubi, Rhizoctonia solani, Rhizomorpha subcorticalis, Rhizophydium graminis, Rhizopus arrhizus, Rhizopus circinans, Rhizopus microsporus* var. *macrospores, Rhizopus oryzae, Rhodococcus fascians, Rhynchosporium, Rhynchosporium secalis, Rhytidhysteron rufulum, Rhytisma acerinum, Rhytisma vitas, Rigidoporus lineatus, Rigidoporus microporus, Rigidoporus ulmarius, Rigidoporus vinctus, Rosellinia arcuata, Rosellinia bunodes, Rosellinia necatrix, Rosellinia pepo, Rosellinia subiculata, Rotylenchulus, Rotylenchulus parvus, Rotylenchulus reniformis, Rotylenchus brachyurus, Rotylenchus robustus, Saccharicola taiwanensis, Saccharomyces florentinus, Saccharomyces kluyveri, Sarocladium oryzae, Saw adaea, Saw adaea tulasnei, Schiffnerula cannabis, Schizoparme straminea, Schizophyllum commune, Schizopora flavipora, Schizothyrium pomi, Scleroderris canker, Sclerophthora macrospora, Sclerophthora rayssiae, Sclerospora graminicola, Sclerospora mischanthi, Sclerotinia borealis, Sclerotinia minor, Sclerotinia ricini, Sclerotinia sclerotiorum, Sclerotinia spermophila, Sclerotinia trifoliorum, Sclerotium, Sclerotium cinnamomi, Sclerotium delphinii, Scutellonema brachyurum, Scutellonema cavenessi, Scytinostroma galactinum, Seimatosporium mariae, Seimatosporium rhododendri, Selenophoma linicola, Septobasidium, Septobasidium bogoriense, Septobasidium pilosum, Septobasidium pseudopedicellatum, Septobasidium theae, Septocyta ruborum, Septogloeum potentillae, Septoria, Septoria aciculosa, Septoria ampelina, Septoria azalea, Septoria bataticola, Septoria campanulae, Septoria cannabis, Septoria caryae, Septoria citri, Septoria cucurbitacearum, Septoria darrowii, Septoria dianthi, Septoria eumusae, Septoria fragariae, Septoria fragariaecola, Septoria glycines, Septoria helianthi, Septoria humuli, Septoria hydrangeas, Septoria lactucae, Septoria liquidambaris, Septoria lycopersici, Septoria lycopersici* var. *malagutii, Septoria menthae, Septoria ostryae, Septoria passerinii, Septoria pisi, Septoria pistaciae, Septoria platanifolia, Septoria rhododendri, Septoria secalis, Septoria selenophomoides, Setosphaeria rostrata, Setosphaeria turcica, Sirosporium diffusum, Sparassis, Sphaceloma, Sphaceloma arachidis, Sphaceloma coryli, Sphaceloma menthae, Sphaceloma perseae, Sphaceloma poinsettiae, Sphaceloma pyrinum, Sphaceloma randii, Sphaceloma sacchari, Sphaceloma theae, Sphacelotheca reiliana, Sphaerella platanifolia, Sphaeropsis tumefaciens, Sphaerotheca, Sphaerotheca castagnei, Sphaerotheca fitliginea, Sphaerulina oryzina, Sphaerulina rehmiana, Sphaerulina rubi, Sphenospora kevorkianii, Spiniger meineckellus, Spiroplasma, Spongipellis unicolor, Sporisorium cruentum, Sporisorium ehrenbergi, Sporisorium scitamineum, Sporisorium sorghi, Sporonema phacidioides, Stagonospora avenae* f.sp. *triticae, Stagonospora meliloti, Stagonospora recedens, Stagonospora sacchari, Stagonospora tainanensis, Steccherinum ochraceum, Stegocintractia junci, Stegophora ulmea, Stemphylium alfalfa, Stemphylium bolickii, Stemphylium cannabinum, Stemphylium globuliferum, Stemphylium lycopersici, Stemphylium sarciniforme, Stemphylium solani, Stemphylium vesicarium, Stenella anthuriicola, Stereum, Stereum hirsutum, Stereum rameale, Stereum sanguinolentum, Stigmatomycosis, Stigmella platani-racemosae, Stigmina carpophila, Stigmina liquidambaris, Stigmina palmivora, Stigmina platani, Stigmina platani-racemosae, Subanguina radicicola, Subanguina wevelli, Sydowia polyspora, Sydowiella depressula, Sydowiellaceae, Synchytrium endobioticum, Synchytrium fragariae, Synchytrium liquidambaris, Taiwanofungus camphoratus, Tapesia acuformis, Tapesia yallundae, Taph-*

*rina aurea, Taphrina bullata, Taphrina caerulescens, Taphrina coryli, Taphrina deformans, Taphrina entomospora, Taphrina johansonii, Taphrina potentillae, Taphrina ulmi, Taphrina wiesneri, Thanatephorus cucumeris, Thielaviopsis, Thielaviopsis basicola, Thyrostroma compactum, Tilletia barclayana, Tilletia caries, Tilletia controversa, Tilletia laevis, Tilletia tritici, Tilletia walkeri, Tilletiariaceae, Tobacco necrosis virus, Togniniaceae, Trachysphaera fructigena, Trametes gibbosa, Trametes hirsute, Trametes nivosa, Trametes pubescens, Tranzschelia discolor* f.sp. *persica, Tranzschelia pruni-spinosae* var. *discolor, Trichaptum biforme, Trichoderma harzianum, Trichoderma koningii, Trichoderma viride, Trichothecium roseum, Tripospermum acerinum, Truncatella, Truncatella laurocerasi, Tubercularia lateritia, Tubercularia ulmea, Tubeufia pezizula, Tunstallia aculeata, Tylenchorhynchus, Tylenchorhynchus brevilineatus, Tylenchorhynchus claytoni, Tylenchorhynchus dubius, Tylenchorhynchus maximus, Tylenchorhynchus nudus, Tylenchorhynchus phaseoli, Tylenchorhynchus vulgaris, Tylenchorhynchus zeae, Tylenchulus semipenetrans, Typhula idahoensis, Typhula incarnate, Typhula ishikariensis, Typhula ishikariensis* var. *canadensis, Typhula variabilis, Typhulochaeta, Tyromyces calkinsii, Tyromyces chioneus, Tyromyces galactinus, Ulocladium atrum, Ulocladium consortiale, Uncinula, Uncinula macrospora, Uncinula necator, Uredo behnickiana, Uredo kriegeriana, Uredo musae, Uredo nigropuncta, Uredo rangelii, Urocystis, Urocystis agropyri, Urocystis brassicae, Urocystis occulta, Uromyces, Uromyces apiosporus, Uromyces beticola, Uromyces ciceris-arietini, Uromyces dianthi, Uromyces euphorbiae, Uromyces graminis, Uromyces inconspicuus, Uromyces lineolatus* subsp. *nearcticus, Uromyces medicaginis, Uromyces musae, Uromyces oblongus, Uromyces pisi-sativi, Uromyces proeminens* var. *poinsettiae, Uromyces trifolii-repentis* var. *fallens, Uromyces viciae-fabae* var. *viciae-fabae, Urophlyctis leproides, Urophlyctis trifolii, Urophora cardui, Ustilaginales, Ustilaginoidea vixens, Ustilaginomycetes, Ustilago, Ustilago avenae, Ustilago hordei, Ustilago maydis, Ustilago nigra, Ustilago nuda, Ustilago scitaminea, Ustilago tritici, Valsa abietis, Valsa ambiens, Valsa auerswaldii, Valsa ceratosperma, Valsa kunzei, Valsa nivea, Valsa sordida, Valsaria insitiva, Venturia carpophila, Venturia inaequalis, Venturia pirina, Venturia pyrina, Veronaea musae, Verticillium, Verticillium albo-atrum, Verticillium albo-atrum* var. *menthae, Verticillium dahliae, Verticillium longisporum, Verticillium theobromas, Villosiclava vixens, Virescence, Waitea circinata, Wuestneiopsis Georgiana, Xanthomonas ampelina, Xanthomonas axonopodis, Xanthomonas campestris, Xanthomonas campestris* pv. *campestris, Xanthomonas oryzae, Xeromphalina fraxinophila, Xiphinema americanum, Xiphinema bakeri, Xiphinema brevicolle, Xiphinema diversicaudatum, Xiphinema insigne, Xiphinema rivesi, Xiphinema vuittenezi, Xylaria mali, Xylaria polymorpha, Xylella fastidiosa, Xylophilus, Xylophilus ampelinus, Zopfia rhizophila, Zygosaccharomyces bailii*, and *Zygosaccharomyces florentinus.*

Insect and worm pathogens include *Acalymma, Acyrthosiphon pisum*, African armyworm, Africanized bee, *Agromyzidae, Agrotis munda, Agrotis porphyricollis, Aleurocanthus woglumi, Aleyrodes proletella, Alphitobius diaperinus, Altica chalybea, Anasa tristis, Anguina tritici, Anisoplia austriaca, Anthonomus pomorum, Anthonomus signatus, Aonidiella aurantii, Apamea apamiformis, Apamea niveivenosa, Aphelenchoides* spp., aphid, *Aphis gossypii*, apple maggot, Argentine ant, army cutworm, *Arotrophora arcuatalis, Asterolecanium coffeae, Athous haemorrhoidalis, Aulacophora*, Australian plague locust, *Bactericera cockerelli, Bactrocera, Bactrocera correcta, Bagrada hilaris*, banded hickory borer, beet armyworm, *Belonolaimus* spp., black bean aphid, *Blepharidopterus chlorionis*, Bogong moth, boll weevil, *Bradysia similigibbosa, Brassica* pod midge, *Brevicoryne brassicae*, brown locust, brown marmorated stink bug, brown planthopper, *Bursephelenchus* spp., cabbage Moth, cabbage worm, *Callosobruchus maculatus*, cane beetle, carrot fly, cereal cyst nematodes, *Cecidomyiidae, Ceratitis capitata, Ceratitis rosa*, cereal leaf beetle, *Chlorops pumilionis*, citrus long-horned beetle, *Coccus viridis*, codling moth, coffee borer beetle, colorado potato beetle, confused flour beetle, *crambus*, cucumber beetle, *Curculio nucum, Curculio occidentis*, cutworm, *Cyclocephala borealis*, dark sword-grass, date stone beetle, *Delia* spp., *Delia antiqua, Delia floralis, Delia radicum, Desert locust, Diabrotica, Diabrotica balteata, Diabrotica speciosa*, diamondback moth, *Diaphania indica, Diaphania nitidalis, Diaphorina citri, Diaprepes abbreviatus, Diatraea saccharalis*, differential grasshopper, *Ditylenchus* spp., *Dociostaurus maroccanus, Drosophila suzukii, Dryocosmus kuriphilus, Earias perhuegeli, Epicauta vittata, Epilachna varivestis, Erionota thrax, Eriosomatinae, Euleia heraclei, Eumetopina flavipes, Eupoecilia ambiguella*, European corn borer, *Eurydema oleracea, Eurygaster integriceps*, forest bug, *Frankliniella tritici, Galleria mellonella*, garden dart, glassy-winged sharpshooter, greenhouse whitefly, *Gryllotalpa orientalis, Gryllus pennsylvanicus*, gypsy moths, *Helicoverpa armigera, Helicoverpa gelotopoeon, Helicoverpa punctigera, Helicoverpa zea, Heliothis virescens, Henosepilachna vigintioctopunctata, Hessian fly, Heterodera* spp., *Jacobiasca formosana*, Japanese beetle, Khapra beetle, *Lampides boeticus*, leaf miner, *Lepidiota consobrina, Lepidosaphes beckii, Lepidosaphes ulmi, Leptoglossus zonatus, Leptopterna dolabrata*, lesser wax moth, *Leucoptera* (moth), *Leucoptera caffeina*, light brown apple moth, *Lissorhoptrus oryzophilus*, long-tailed Skipper, *Lygus, Lygus hesperus, Maconellicoccus hirsutus, Macrodactylus subspinosus, Macrosiphum euphorbiae*, maize weevil, *Manduca sexta, Mayetiola hordei, Mealybug, Meloidogyne* spp., *Megacopta cribraria, Metcalfa pruinosa*, moths, leek moth, *Myzus persicae, Naccobus* spp., *Nezara viridula*, oak processionary, olive fruit fly, *Ophiomyia simplex, Opisina arenosella, Opomyza, Opomyza florum, Opomyzidae, Oscinella frit, Ostrinia furnacalis, Oxycarenus hyalinipennis, papaya* mealy bug, *Papilio demodocus, Paratachardina pseudolobata, Pentatomoidea, Phthorimaea operculella, Phyllophaga, Phylloxera, Phylloxeridae, Phylloxeroidea, Pieris brassicae*, pink bollworm, *Planococcus citri, Platynota idaeusalis, Plum curculio, Pratylenchus* spp., *Prionus californicus, Pseudococcus viburni, Pyralis farinalis*, red imported fire ant, red locust, root lesion nematodes, root knot nematodes, *Radopholus* spp., *Rotylenchulus* spp., *Rhagoletis cerasi, Rhagoletis indifferens, Rhagoletis mendax, Rhopalosiphum maidis, Rhyacionia frustrana, Rhynchophorus ferrugineus, Rhynchophorus palmarum, Rhyzopertha*, rice moth, rice stink bug, Russian wheat aphid, San Jose scale, scale insect, *Schistocerca americana, Sciaridae, Scirtothrips dorsalis, Scutelleridae, Scutiphora pedicellata*, seed gall nematodes, serpentine leaf miner, silverleaf whitefly, *Sipha flava*, small hive beetle, Southwestern corn borer, soybean aphid, *Spodoptera cilium, Spodoptera litura*, spotted cucumber beetle, squash vine borer, stem Nematodes, *Stenotus binotatus, Strauzia longipennis*, striped flea beetle, sunn pest, sweetpotato bug, tarnished plant bug, *thrips, Thrips angusticeps, Thrips palmi, Toxoptera citricida, Trichodorus* spp., *Trioza erytreae*, turnip moth, *Tuta absoluta, Tylenchulus* spp., varied carpet beetle, *Virachola iso-*

*crates*, waxworm, Western corn rootworm, Western flower *thrips*, wheat fly, wheat weevil, whitefly, winter moth, and *Xiphenema* spp.

For example, the insect or worm pathogen can be army worm, black cutworm, European corn borer, fall armyworm, cutworm, Japanese beetle, lesser cornstalk borer, maize billbug, seed corn maggot, webworm, southern cornstalk borer, southern corn rootworm, southern potato wireworm, stalk borer, sugarcane beetle, white grubs, cabbage looper, boll weevil, yellow striped armyworm, cereal leaf beetle, chinch bug, aphids, beet armyworm, Mexican bean beetle, soybean looper, soybean stem borer, or a combination thereof.

Proteins and Peptides that Enhance Stress Resistance in Plants

The invention also relates to fusion proteins comprising a targeting sequence, exosporium protein, or exosporium protein fragment and at least one protein or peptide that enhances stress resistance in a plant.

For example, the protein or peptide that enhances stress resistance in a plant comprises an enzyme that degrades a stress-related compound. Stress-related compounds include, but are not limited to, aminocyclopropane-1-carboxylic acid (ACC), reactive oxygen species, nitric oxide, oxylipins, and phenolics. Specific reactive oxygen species include hydroxyl, hydrogen peroxide, oxygen, and superoxide. The enzyme that degrades a stress-related compound can comprise a superoxide dismutase, an oxidase, a catalase, an aminocyclopropane-1-carboxylic acid deaminase, a peroxidase, an antioxidant enzyme, or an antioxidant peptide.

The protein or peptide that enhances stress resistance in a plant can also comprise a protein or peptide that protects a plant from an environmental stress. The environmental stress can comprise, for example, drought, flood, heat, freezing, salt, heavy metals, low pH, high pH, or a combination thereof. For instance, the protein or peptide that protects a plant from an environmental stress can comprises an ice nucleation protein, a prolinase, a phenylalanine ammonia lyase, an isochorismate synthase, an isochorismate pyruvate lyase, or a choline dehydrogenase.

Plant Binding Proteins and Peptides

The invention also relates to fusion proteins comprising a targeting sequence, exosporium protein, or exosporium protein fragment and at least plant binding protein or peptide. The plant binding protein or peptide can be any protein or peptide that is capable of specifically or non-specifically binding to any part of a plant (e.g., a plant root or an aerial portion of a plant such as a leaf, stem, flower, or fruit) or to plant matter. Thus, for example, the plant binding protein or peptide can be a root binding protein or peptide, or a leaf binding protein or peptide.

Suitable plant binding proteins and peptides include adhesins (e.g., rhicadhesin), flagellins, omptins, lectins, expansins, biofilm structural proteins (e.g., TasA or YuaB) pilus proteins, curlus proteins, intimins, invasins, agglutinins, and afimbrial proteins.

Other Fusion Proteins

The present invention further relates to fusion proteins comprising at least one protein or peptide of interest and an exosporium protein comprising an exosporium protein comprising an amino acid sequence having at least 85% identity with any one of SEQ ID NOs: 71, 75, 80, 81, 82, 83, and 84. Alternatively, the exosporium protein can comprise an amino acid sequence having at least 90%, at least 95%, at least 98%, at least 99%, or at least 100% identity with any one of SEQ ID NOs: 71, 75, 80, 81, 82, 83, and 84.

The protein or peptide of interest can comprise any protein or peptide. For example, the protein or peptide of interest can comprise any of the proteins or peptides described herein. For example, the protein or peptide of interest can comprise any of the plant growth stimulating proteins or peptides described herein, any of the proteins or peptides that protect a plant from a pathogen described herein, any of the proteins or peptides that enhances stress resistance in a plant described herein, or any of the a plant binding proteins or peptides described herein.

Thus, where the protein or peptide of interest comprises a plant growth stimulating protein or peptide, the plant growth stimulating protein or peptide can comprise a peptide hormone, a non-hormone peptide, or an enzyme involved in the production or activation of a plant growth stimulating compound. Alternatively, the plant growth stimulating protein or peptide can comprise any of the enzymes that degrade or modify a bacterial, fungal, or plant nutrient source described hereinbelow.

Recombinant *Bacillus cereus* Family Members that Express the Fusion Proteins

The present invention also relates to a recombinant *Bacillus cereus* family member that expresses a fusion protein. The fusion protein can be any of the fusion proteins discussed above.

The recombinant *Bacillus cereus* family member can coexpress two or more of any of the fusion proteins discussed above. For example, the recombinant *Bacillus cereus* family member can coexpress at least one fusion protein that comprises a plant binding protein or peptide, together with at least one fusion protein comprising a plant growth stimulating protein or peptide, at least one fusion protein comprising a protein or peptide that protects a plant from a pathogen, or at least one protein or peptide that enhances stress resistance in a plant.

The recombinant *Bacillus cereus* family member can comprise *Bacillus anthracis, Bacillus cereus, Bacillus thuringiensis, Bacillus mycoides, Bacillus pseudomycoides, Bacillus samanii, Bacillus gaemokensis, Bacillus weihenstephensis*, or a combination thereof. For example, the recombinant *Bacillus cereus* family member can comprise *Bacillus cereus, Bacillus thuringiensis, Bacillus pseudomycoides*, or *Bacillus mycoides*. In particular, the recombinant *Bacillus cereus* family member can comprise *Bacillus thuringiensis* or *Bacillus mycoides*.

To generate a recombinant *Bacillus cereus* family member expressing a fusion protein, any *Bacillus cereus* family member can be conjugated, transduced, or transformed with a vector encoding the fusion protein using standard methods known in the art (e.g., by electroporation). The bacteria can then be screened to identify transformants by any method known in the art. For example, where the vector includes an antibiotic resistance gene, the bacteria can be screened for antibiotic resistance. Alternatively, DNA encoding the fusion protein can be integrated into the chromosomal DNA of a *B. cereus* family member host. The recombinant *Bacillus cereus* family member can then exposed to conditions which will induce sporulation. Suitable conditions for inducing sporulation are known in the art. For example, the recombinant *Bacillus cereus* family member can be plated onto agar plates, and incubated at a temperature of about 30° C. for several days (e.g., 3 days).

Inactivated strains, non-toxic strains, or genetically manipulated strains of any of the above species can also suitably be used. For example, a *Bacillus thuringiensis* that lacks the Cry toxin can be used. Alternatively or in addition, once the recombinant *B. cereus* family spores expressing the fusion protein have been generated, they can be inactivated to prevent further germination once in use. Any method for inactivating bacterial spores that is known in the art can be used. Suitable methods include, without limitation, heat treatment, gamma irradiation, x-ray irradiation, UV-A irradiation, UV-B irradiation, chemical treatment (e.g., treatment with gluteraldehyde, formaldehyde, hydrogen peroxide, acetic acid, bleach, or any combination thereof), or a combination thereof. Alternatively, spores derived from nontoxigenic strains, or genetically or physically inactivated strains, can be used.

Recombinant *Bacillus cereus* Family Members Having Plant-Growth Promoting Effects and/or Other Beneficial Attributes Many *Bacillus cereus* family member strains have inherent beneficial attributes. For example, some strains have plant-growth promoting effects. Any of the fusion proteins described herein can be expressed in such strains.

For example, the recombinant *Bacillus cereus* family member can comprise a plant-growth promoting strain of bacteria.

The plant-growth promoting strain of bacteria can comprise a strain of bacteria that produces an insecticidal toxin (e.g., a Cry toxin), produces a fungicidal compound (e.g., a β-1,3-glucanase, a chitosinase, a lyticase, or a combination thereof), produces a nematocidal compound (e.g., a Cry toxin), produces a bacteriocidal compound, is resistant to one or more antibiotics, comprises one or more freely replicating plasmids, binds to plant roots, colonizes plant roots, forms biofilms, solubilizes nutrients, secretes organic acids, or any combination thereof.

For example, where the recombinant *Bacillus cereus* family member comprises a plant-growth promoting strain of bacteria, the plant growth-promoting strain of bacteria can comprise *Bacillus mycoides* BT155 (NRRL No. B-50921), *Bacillus mycoides* EE118 (NRRL No. B-50918), *Bacillus mycoides* EE141 (NRRL No. B-50916), *Bacillus mycoides* BT46-3 (NRRL No. B-50922), *Bacillus cereus* family member EE128 (NRRL No. B-50917), *Bacillus thuringiensis* BT013A (NRRL No. B-50924), or *Bacillus cereus* family member EE349 (NRRL No. B-50928). Each of these strains was deposited with the United States Department of Agriculture (USDA) Agricultural Research Service (ARS), having the address 1815 North University Street, Peoria, Ill. 61604 U.S.A., on Mar. 10, 2014, and is identified by the NRRL deposit number provided in parentheses.

These plant-growth promoting strains were isolated from the rhizospheres of various vigorous plants and were identified by their 16S rRNA sequences (provided herein as SEQ ID NOs. 104-110), and through biochemical assays. The strains were identified at least to their genus designation by means of conventional biochemistry and morphological indicators. Biochemical assays for confirmed Gram-positive strains such as *Bacillus* included growth on PEA medium and nutrient agar, microscopic examination, growth on 5% and 7.5% NaCl medium, growth at pH 5 and pH 9, growth at 42° C. and 50° C., the ability to produce acid upon fermentation with cellobiose, lactose, glycerol, glucose, sucrose, d-mannitol, and starch; fluorescent pigment production; gelatin hydrolysis; nitrate reduction; catalase production, starch hydrolysis; oxidase reaction, urease production and motility. Identification of these strains and demonstration of their plant-growth promoting effects are described further in the Examples hereinbelow.

For example, the recombinant *Bacillus cereus* family member comprising a plant-growth promoting strain of bacteria can comprise *Bacillus mycoides* BT155, *Bacillus mycoides* EE141, or *Bacillus thuringiensis* BT013A. The recombinant *Bacillus cereus* family member can express any of the fusion proteins described herein, e.g., a fusion protein comprising the targeting sequence of SEQ ID NO: 60 and a non-hormone peptide (e.g., kunitz trypsin inhibitor (KTI)), an enzyme involved in the production or activation of a plant growth stimulating compound (e.g., a chitosinase), a plant binding protein or peptide (e.g., TasA); a protein or peptide that protects a plant from a pathogen (e.g., TasA), or an enzyme that degrades or modifies a bacterial, fungal, or plant nutrient source (e.g., a phosphatase such as PhoA or phytase, or an endoglucanase).

Promoters

In any of the recombinant *Bacillus cereus* family members described herein, the fusion protein can be expressed under the control of a promoter that is native to the targeting sequence, the exosporium protein, or the exosporium protein fragment of the fusion protein. For example, where the fusion protein comprises a targeting sequence derived from *B. anthracis* Sterne BclA (e.g., amino acids 20-35 of SEQ ID NO: 1, amino acids 1-35 of SEQ ID NO: 1, SEQ ID NO: 1, or SEQ ID NO: 60) or where the fusion protein comprises full length BclA (SEQ ID NO: 2) or a fragment of full length BclA (e.g., SEQ ID NO: 59), the fusion protein can be expressed under the control of a promoter that is normally associated with the BclA gene in the genome of *B. anthracis* Sterne (e.g., the promoter of SEQ ID NO: 85).

Alternatively, the fusion protein can be expressed under the control of a high-expression sporulation promoter. In some cases, the promoter that is native to the targeting sequence, exosporium protein, or exosporium protein fragment will be a high-expression sporulation promoter. In other cases, the promoter that is native to the targeting sequence, exosporium protein, or exosporium protein fragment will not be a high-expression sporulation promoter. In the latter cases, it may be advantageous to replace the native promoter with a high-expression sporulation promoter. Expression of the fusion protein under the control of a high-expression sporulation promoter provides for increased expression of the fusion protein on the exosporium of the *Bacillus cereus* family member.

The high-expression sporulation promoter can comprise one or more sigma-K sporulation-specific polymerase promoter sequences.

Suitable high-expression sporulation promoters for use in expressing the fusion proteins in a *Bacillus cereus* family member include those listed in Table 2 below:

TABLE 2

| Promoter Sequences | |
|---|---|
| Promoter<br>(SEQ ID NO.) | Sequence |
| BclA promoter<br>(*B. anthracis* Sterne)<br>(SEQ ID NO: 85) | TAATCACCCTCTTCCAAATCAAT**CATATGTTA**TA**CATATACTA**AACTT<br>TCCATTTTTTTAAATTGTTCAAGTAGTTTAAGATTTCTTTTCAATAAT<br>TCAAATGTCCGTGTCATTTTCTTTCGGTTTTG**CATCTACTA**TATAATG<br>AACGCTTTATGGAGGTGAATTTATG |
| BetA promoter<br>(*B. anthracis* Sterne)<br>(SEQ ID NO: 86) | ATTTATTTCATTCAATTTTTCCTATTTAGTACCTACCGCACTCACAAAA<br>AGCACCTCTCATTAATTTATATTATAGTCATTGAAATCTAATTTAATGA<br>AATCAT**CATACTATA**TGTTTTATAAGAAGTAAAGGTAC**CATACTTAA**<br>TTAATACATATCTATACACTTCAATATCACAGCATGCAGTTGAATTAT<br>ATCCAACTTTCATTTCAAATTAAATAAGTGCCTCCGCTATTGTGAATG<br>TCATTTACTCTCCCTACTA**CATTTAATA**ATTATGACAAGCAATCATAG<br>GAGGTTACTACATG |
| BAS1882 promoter<br>(*B. anthracis* Sterne)<br>(SEQ ID NO: 87) | AATTACATAACAAGAACTACATTAGGGAGCAAGCAGTCTAGCGAAAG<br>CTAACTGCTTTTTTATTAAATAACTATTTTATTAAATTTCATATATACA<br>ATCGCTTGTCCATTTCATTTGGCTCTACCCACG**CATTTACTA**TTAGTA<br>ATATGAATTTTTCAGAGGTGGATTTTATT |
| Gene 3572 promoter<br>(*B. weihenstephensis*<br>KBAB 4)<br>(SEQ ID NO: 88) | CTATGATTTAAGATACACAATAGCAAAAGAGAAA**CATATTATA**TAAC<br>GATAAATGAAACTTATGTATATGTATGGTAACTGTATATATTACTACA<br>ATACAGTATACTCATAGGAGGTAGGTATG |
| YVTN β-propeller<br>protein promoter<br>(*B. weihenstephensis*<br>KBAB 4)<br>(SEQ ID NO: 89) | GGTAGGTAGATTTGAAATATGATGAAGAAAAGGAATAACTAAAAGGA<br>GTCGATATCCGACTCCTTTTAGTTATAAATAATGTGGAATTAGAGTAT<br>AATTTTATATAGGTATATTGTATTAGATGAACGCTTTATCCTTTAATTG<br>TGATTAATGATGGATTGTAAGAGAAGGGGCTTACAGTCCTTTTTTTAT<br>GGTGTTCTATAAGCCTTTTTAAAAGGGGTACCACCCCACACCCAAAAA<br>CAGGGGGGGTTATAACTACATATTGGATGTTTTGTAACGTACAAGAAT<br>CGGTATTAATTACCCTGTAAATAAGTTATGTGTATATAAGGTAACTT**T**<br>**ATATATTC**TCCTACAATAAAATAAAGGAGGTAATAAAGTG |
| CrylA promoter<br>(*B. thuringiensis*<br>HD-73)<br>(SEQ ID NO: 90) | AACCCTTAATGCATTGGTTAAACATTGTAAAGTCTAAAGCATGGATAA<br>TGGGCGAGAAGTAAGTAGATTGTTAACACCCTGGGTCAAAAATTGAT<br>ATTTAGTAAAATTAGTTGCACTTTGTGCATTTTTT**CATAAGATG**AGT**C**<br>**ATATGTTT**TAAATTGTAGTAATGAAAAACAGTAT**TATATCATAATGA**<br>**A**TTGGTATCTTAATAAAAGAGATGGAGGTAACTTA |
| ExsY promoter<br>(*B. thuringiensis*<br>serovar konkukian<br>str. 97-27)<br>(SEQ ID NO: 91) | TAATTCCACCTTCCCTTATCCTCTTTCGCCTATTTAAAAAAAGGTCTTG<br>AGATTGTGACCAAATCTCCTCAACTCC**AATATCTTA**TTAATGTAAATA<br>CAAACAAGAAGATAAGGAGTGACATTAA |
| CotY promoter<br>(*B. thuringiensis* Al<br>Hakam)<br>(SEQ ID NO: 92) | AGGATGTCTTTTTTTATATTGTATTATGTACATCCCTACTATATAAATT<br>CCCTGCTTTTATCGTAAGAATTAACGTAATATCAACCATATCCCGTT**C**<br>**ATATTGTA**GTAGTGTATGTCAGAACTCACGAGAAGGAGTGAACATAA |
| YjcA promoter<br>(*B. thuringiensis*<br>serovar kurstaki str.<br>HD73)<br>(SEO ID NO: 93) | TTAATGTCACTCCTTATCTTCTTGTTTGTATTTACATT**AATAAGATA**TT<br>GGAGTTGAGGAGATTTGGTCACAATCTCAAGACCTTTTTTTTAAATAG<br>GCGAAAGAGGATAAGGGAAGGTGGAATTA |
| YjcB promoter<br>(*B. thuringiensis*<br>serovar kurstaki str.<br>HD73)<br>(SEO ID NO: 94) | ATATATTTTCATAATACGAGAAAAAGCGGAGTTTAAAAGAATGAGGG<br>AACGGAAATAAAGAGTTGTT**CATATAGTA**AATAGACAGAATTGACAG<br>TAGAGGAGA |
| BxpB promoter<br>(*B. thuringiensis* Al<br>Hakam)<br>SEQ ID NO: 95) | AAACTAAATAATGAGCTAAGCATGGATTGGGTGGCAGAATTATCTGC<br>CACCCAATC**CATGCTTAA**CGAGTATTATTATGTAAATTTCTTAAAATT<br>GGGAACTTGTCTAGAACATAGAACCTGTCCTTTT**CATTAACTG**AAAG<br>TAGAAACAGATAAAGGAGTGAAAAACA |
| Rhamnose promoter<br>(*B. thuringiensis* Al<br>Hakam)<br>(SEQ ID NO: 96) | ATTCACTACAACGGGGATGAGTTTGATGCGGATA**CATATGAGA**AGTA<br>CCGGAAAGTGTTTGTAGAA**CATTACAA**AGATATATTATCTCCATCATA<br>AAGGAGAGATGCAAAG |
| CotY/CotZ promoter<br>(*B. anthracis* Sterne)<br>(SEQ ID NO: 97) | CGCGCACCACTTCGTCGTACAACAACGCAAGAAGAAGTTGGGGATAC<br>AGCAGTATTCTTATTCAGTGATTTAGCACGCGGCGTAACAGGAGAAA<br>ACATTCACGTTGATTCAGGGTAT**CATATCTTA**GGATAAATATAATATT<br>AATTTTAAAGGACAATCTCTACATGTTGAGATTGTCCTTTTTATTTGTT |

TABLE 2 -continued

Promoter Sequences

| Promoter (SEQ ID NO.) | Sequence |
|---|---|
| | CTTAGAAAGAACGATTTTTAACGAAAGTTCTTACCACGTTATGAATAT<br>AAGTATAATAGTACACGATTTATTCAGCTACGTA |
| BclC promoter<br>(B. anthracis Sterne)<br>(SEQ ID NO: 98) | TGAAGTATCTAGAGCTAATTTACGCAAAGGAATCTCAGGACAACACT<br>TTCGCAACACCTATATTTTAAATTTAATAAAAAAAGAGACTCCGGAGT<br>CAGAAATTATAAAGCTAGCTGGGTTCAAATCAAAAATTTCACTAAAA<br>CGATATTATCAATACGCAGAAAATGGAAAAAACGCCTTATCATAAGG<br>CGTTTTTTCCATTTTTTCTTCAAACAAACGATTTTACTATGACCATTTA<br>ACTAATTTTTG**CATCTACTA**TGATGAGTTTCATTCACATTCTCATTAG<br>AAAGGAGAGATTTAATG |
| Sigma K promoter<br>(B. anthracis Sterne)<br>(SEQ ID NO: 99) | TATATCATATGTAAAATTAGTTCTTATTCCCA**CATATCATA**TAGAATC<br>GC**CATATTATA**CATGCAGAAAACTAAGTATGGTATTATTCTTAAATTG<br>TTTAGCACCTTCTAATATTACAGATAGAATCCGTCATTTTCAACAGTG<br>AACATGGATTTCTTCTGAACACAACTCTTTTTCTTTCCTTATTTCCAAA<br>AAGAAAAGCAGCCCATTTTAAAATACGGCTGCTTGTAATGTACATTA |
| InhA promoter<br>(B. thuringiensis Al Hakam)<br>(SEQ ID NO: 100) | TATCACATAACTCTTTATTTTTAATATTTCGA**CATAAAGTG**AAACTTT<br>AATCAGTGGGGGCTTTGTTCATCCCCCCACTGATTATTAATTGAACCA<br>AGGGATAAAAAGATAGAGGGTCTGACCAGAAAACTGGAGGGCATGA<br>GGAGGGTAGTAAACAGAGATTTGGACAAAAATGCACCGATTTATCTG<br>AATTTTAAGTTTTATAAAGGGGAGAAATG |
| BclA cluster glycosyl transferase operon 1<br>(B. thuringiensis serovar konkukian str. 97-27)<br>(SEQ ID NO: 101) | ATTTTTTACTTAGCAGTAAAACTGATATCAGTTTTACTGCTTTTTCATT<br>TTTAAATTCAATCATTAAATCTTCCTTTTCTACATAGT**CATAATGTT**GT<br>ATGACATTCCGTAGGAGGCACTTATA |
| BclA cluster glycosyl transferase operon 2<br>(B. thuringiensis serovar kurstaki str. HD73)<br>(SEQ ID NO: 102) | ACATAAATTCACCTCCATAAAGCGTTCATTATATAGTAGATGCAAAAC<br>CGAAAGAAAATGACACGGACATTTGAATTATTGAAAAGAAATCTTAA<br>ACTACTTGAACAATTTAAAAAAATGGAAAGTTTAGTATATGTATAA**C<br>ATATGATT**GATTTGGAAGAGGGTGATTA |
| Glycosyl transferase promoter<br>(B. thuringiensis Al Hakam)<br>(SEQ ID NO: 103) | TTCTATTTTCCAA**CATAACATG**CTACGATTAAATGGTTTTTTGCAAAT<br>GCCTTCTTGGGAAGAAGGATTAGAGCGTTTTTTTATAGAAACCAAAAG<br>TCATTAACAATTTTAAGTTAATGACTTTTTTGTTTGCCTTTAAGAGGTT<br>TTATGTTACTATAATTATAGTATCAGGTACTAATAACAAGTATAAGTA<br>TTTCTGGGAGGATATATCA |

In the promoter sequences listed in Table 2 above, the locations of the sigma-K sporulation-specific polymerase promoter sequences are indicated by bold and underlined text. The Cry1A promoter (*B. thuringiensis* HD-73; SEQ ID NO: 90) has a total of four sigma-K sequences, two of which overlap with one another, as indicated by the double underlining in Table 2.

Preferred high-expression sporulation promoters for use in expressing the fusion proteins in a *Bacillus cereus* family member include the BetA promoter (*B. anthracis* Sterne; SEQ ID NO: 86), the BclA promoter (*B. anthracis* Sterne; SEQ ID NO: 85), the BclA cluster glycosyl transferase operons 1 and 2 promoters (*B. anthracis* Sterne; SEQ ID NOs: 101 and 102), and the YVTN β-propeller protein promoter (*B. weihenstephensis* KBAB 4; SEQ ID NO: 89).

In any of the recombinant *Bacillus cereus* family members described herein, the fusion protein can be expressed under the control of a sporulation promoter comprising a nucleic acid sequence having at least 80%, at least 90%, at least 95%, at least 98%, at least 99%, or 100% identity with a nucleic acid sequence of any one of SEQ ID NOs: 85-103.

When the sporulation promoter comprising a nucleic acid sequence having at least 80%, at least 90%, at least 95%, at least 98%, or at least 99% identity with a nucleic acid sequence of any one of SEQ ID NOs: 85-103, the sigma-K sporulation-specific polymerase promoter sequence or sequences preferably have 100% identity with the corresponding nucleotides of SEQ ID NO: 85, 86, 87, 88, 89, 90, 91, 92, 93, 94, 95, 96, 97, 98, 99, 100, 101, 102, or 103. For example, as illustrated in Table 2 above, the BclA promoter of *B. anthracis* Sterne (SEQ ID NO: 85) has sigma-K sporulation-specific polymerase promoter sequences at nucleotides 24-32, 35-43, and 129-137. Thus, if the sporulation promoter comprises a sequence having at least 90% identity with the nucleic acid sequence of SEQ ID NO: 85, it is preferred that the nucleotides of the sporulation promoter corresponding to nucleotides 24-32, 35-43, and 129-137 of SEQ ID NO: 85 have 100% identity with nucleotides 24-32, 35-43, and 129-137 of SEQ ID NO: 85.

Formulations

The present invention also relates to formulations comprising any of the recombinant *Bacillus cereus* family members discussed in the preceding section and an agriculturally acceptable carrier.

The agriculturally acceptable carrier can be any carrier suitable for agricultural use. For example, suitable agriculturally acceptable carriers include, but are not limited to dispersants, surfactants, additives, water, thickeners, anti-caking agents, residue breakdown, composting formulations, granular applications, diatomaceous earth, oils, coloring agents, stabilizers, preservatives, polymers, coatings, and combinations thereof.

The additive can comprise an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutane dioate, a benzene acetonitrile derivative, a proteinaceous material (e.g., a milk product, wheat flour, soybean meal, blood, albumin, gelatin, or a combination thereof), or a combination thereof.

The thickener can comprise a long chain alkylsulfonate of polyethylene glycol, a polyoxyethylene oleate, or a combination thereof.

The surfactant can comprise a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination thereof.

The anti-caking agent comprises a sodium salt, a calcium carbonate, diatomaceous earth, or a combination thereof. For example, the sodium salt can comprise a sodium salt of monomethyl naphthalene sulfonate, a sodium salt of dimethyl naphthalene sulfonate, a sodium sulfite, a sodium sulfate, or a combination thereof.

Suitable agriculturally acceptable carriers include vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination thereof.

The formulation can comprise a seed coating formulation, a liquid formulation for application to plants or to a plant growth medium, or a solid formulation for application to plants or to a plant growth medium.

For example, the seed coating formulation can comprise an aqueous or oil-based solution for application to seeds. Alternatively, the seed coating formulation can comprise a powder or granular formulation for application to seeds.

The liquid formulation for application to plants or to a plant growth medium can comprise a concentrated formulation or a ready-to-use formulation.

The solid formulation for application to plants or to a plant growth medium can comprises a granular formulation or a powder agent.

Any of the above formulations can also comprise an agrochemical, for example, a fertilizer, a micronutrient fertilizer material, an insecticide, a herbicide, a plant growth amendment, a fungicide, an insecticide, a molluscicide, an algicide, a bacterial inoculant, a fungal inoculant, or a combination thereof.

The fertilizer can comprise a liquid fertilizer.

The fertilizer can comprise ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, sulfur-coated urea, polymer-coated urea, isobutylidene diurea, $K_2SO_4$-$2MgSO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, humic acid, or a combination thereof.

The micronutrient fertilizer material can comprise boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination thereof.

The insecticide can comprise an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof.

The herbicide can comprise a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carbamate, a carbanilate, chloropyridinyl, a cyclohexenone derivative, a dinitroaminobenzene derivative, a fluorodinitrotoluidine compound, isoxazolidinone, nicotinic acid, isopropylamine, an isopropylamine derivatives, oxadiazolinone, a phosphate, a phthalate, a picolinic acid compound, a triazine, a triazole, a uracil, a urea derivative, endothall, sodium chlorate, or a combination thereof.

The fungicide can comprise a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof.

The fungal inoculant can comprise a fungal inoculant of the family Glomeraceae, a fungal inoculant of the family Claroidoglomeraceae, a fungal inoculant of the family Gigasporaceae, a fungal inoculant of the family Acaulosporaceae, a fungal inoculant of the family Sacculosporaceae, a fungal inoculant of the family Entrophosporaceae, a fungal inoculant of the family Pacidsporaceae, a fungal inoculant of the family Diversisporaceae, a fungal inoculant of the family Paraglomeraceae, a fungal inoculant of the family Archaeosporaceae, a fungal inoculant of the family Geosiphonaceae, a fungal inoculant of the family Ambisporaceae, a fungal inoculant of the family Scutellosporaceae, a fungal inoculant of the family Dentiscultataceae, a fungal inoculant of the family Racocetraceae, a fungal inoculant of the phylum Basidiomycota, a fungal inoculant of the phylum Ascomycota, a fungal inoculant of the phylum Zygomycota, or a combination thereof.

The bacterial inoculant can comprise a bacterial inoculant of the genus *Rhizobium*, a bacterial inoculant of the genus *Bradyrhizobium*, a bacterial inoculant of the genus *Mesorhizobium*, a bacterial inoculant of the genus *Azorhizobium*, a bacterial inoculant of the genus *Allorhizobium*, a bacterial inoculant of the genus *Sinorhizobium*, a bacterial inoculant of the genus *Kluyvera*, a bacterial inoculant of the genus *Azotobacter*, a bacterial inoculant of the genus *Pseudomonas*, a bacterial inoculant of the genus *Azospirillum*, a bacterial inoculant of the genus *Bacillus*, a bacterial inoculant of the genus *Streptomyces*, a bacterial inoculant of the genus *Paenibacillus*, a bacterial inoculant of the genus *Paracoccus*, a bacterial inoculant of the genus *Enterobacter*, a bacterial inoculant of the genus *Alcaligenes*, a bacterial inoculant of the genus *Mycobacterium*, a bacterial inoculant of the genus *Trichoderma*, a bacterial inoculant of the genus *Gliocladium*, a bacterial inoculant of the genus *Glomus*, a bacterial inoculant of the genus *Klebsiella*, or a combination thereof.

The bacterial inoculant can comprise a plant-growth promoting strain of bacteria. The plant-growth promoting strain of bacteria can comprise a strain of bacteria that produces an insecticidal toxin (e.g., a Cry toxin), produces a fungicidal compound (e.g., a β-1,3-glucanase, a chitosinase, a lyticase, or a combination thereof), produces a nematocidal compound (e.g., a Cry toxin), produces a bacteriocidal compound, is resistant to one or more antibiotics, comprises one or more freely replicating plasmids, binds to plant roots, colonizes plant roots, forms biofilms, solubilizes nutrients, secretes organic acids, or any combination thereof.

For example, the bacterial inoculant can comprise *Bacillus aryabhattai* CAP53 (NRRL No. B-50819), *Bacillus aryabhattai* CAP56 (NRRL No. B-50817), *Bacillus flexus* BT054 (NRRL No. B-50816), *Paracoccus kondratievae* NC35 (NRRL No. B-50820), *Bacillus mycoides* BT155 (NRRL No. B-50921), *Enterobacter cloacae* CAP12 (NRRL No. B-50822), *Bacillus nealsonii* BOBA57 (NRRL No. NRRL B-50821), *Bacillus mycoides* EE118 (NRRL No. B-50918), *Bacillus subtilis* EE148 (NRRL No. B-50927), *Alcaligenes faecalis* EE107 (NRRL No. B-50920), *Bacillus mycoides* EE141 (NRRL NO. B-50916), *Bacillus mycoides* BT46-3 (NRRL No. B-50922), *Bacillus cereus* family member EE128 (NRRL No. B-50917), *Bacillus thuringiensis* BT013A (NRRL No. B-50924), *Paenibacillus massiliensis* BT23 (NRRL No. B-50923), *Bacillus cereus* family member EE349 (NRRL No. B-50928), *Bacillus subtilis* EE218 (NRRL No. B-50926), *Bacillus megaterium* EE281 (NRRL No. B-50925), or a combination thereof. Each of these strains was deposited with the United States Department of Agriculture (USDA) Agricultural Research Service (ARS), having the address 1815 North University Street, Peoria, Ill. 61604 U.S.A., on Mar. 7, 2013 (*Bacillus aryabhattai* CAP53, *Bacillus aryabhattai* CAP56, *Bacillus flexus* BT054, *Paracoccus kondratievae* NC35, *Enterobacter cloacae* CAP12, and *Bacillus nealsonii* BOBA57) or on Mar. 10, 2014 (*Bacillus mycoides* BT155, *Bacillus mycoides* EE118, *Bacillus subtilis* EE148, *Alcaligenes faecalis* EE107, *Bacillus mycoides* EE141, *Bacillus mycoides* BT46-3, *Bacillus cereus* family member EE128, *Bacillus thuringiensis* BT013A, *Paenibacillus massiliensis* BT23, *Bacillus cereus* family member EE349, *Bacillus subtilis* EE218, and *Bacillus megaterium* EE281), and is identified by the NRRL numbers provided in parentheses.

These plant-growth promoting strains were isolated from the rhizospheres of various vigorous plants and were identified by their 16S rRNA sequences (provided herein as SEQ ID NOs. 104-121), and through biochemical assays. The strains were identified at least to their genus designation by means of conventional biochemistry and morphological indicators. Biochemical assays for confirmed Gram-negative strains such as *Paracoccus kondratievae, Alcaligenes faecalis*, and *Enterobacter cloacae* included growth on MacConkey medium and nutrient agar, microscopic examination, growth on 5% and 7.5% NaCl medium, growth at pH 5 and pH 9, growth at 42° C. and 50° C., the ability to produce acid upon fermentation with cellobiose, lactose, glycerol, glucose, sucrose, d-mannitol, and starch; fluorescent pigment production; gelatin hydrolysis; nitrate reduction; starch hydrolysis; oxidase reaction, catalase production, urease production and motility. Similarly, the biochemical assays for confirmed Gram-positive strains such as *Bacillus* and *Paenibacillus* included growth on PEA medium and nutrient agar, microscopic examination, growth on 5% and 7.5% NaCl medium, growth at pH 5 and pH 9, growth at 42° C. and 50° C., the ability to produce acid upon fermentation with cellobiose, lactose, glycerol, glucose, sucrose, d-mannitol, and starch; fluorescent pigment production; gelatin hydrolysis; nitrate reduction; catalase production, starch hydrolysis; oxidase reaction, urease production and motility. Identification of these strains and demonstration of their plant-growth promoting effects are described further in the Examples hereinbelow.

For example, the formulation can comprise a plant-growth promoting strain of bacteria comprising *Paracoccus kondratievae* NC35, *Bacillus aryabhattai* CAP53, or *Bacillus megaterium* EE281, wherein the formulation further comprises any of the recombinant *Bacillus cereus* family members described herein, including any of the recombinant plant-growth promoting *Bacillus cereus* family member strains herein (e.g., recombinant *Bacillus mycoides* BT155, *Bacillus mycoides* EE141, or *Bacillus thuringiensis* BT013A). The recombinant plant-growth promoting *Bacillus cereus* family member strain can express any of the fusion proteins described herein, e.g., a fusion protein comprising the targeting sequence of SEQ ID NO: 60 and a non-hormone peptide (e.g., kunitz trypsin inhibitor (KTI)), an enzyme involved in the production or activation of a plant growth stimulating compound (e.g., a chitosinase), a plant binding protein or peptide (e.g., TasA); a protein or peptide that protects a plant from a pathogen (e.g., TasA), or an enzyme that degrades or modifies a bacterial, fungal, or plant nutrient source (e.g., a phosphatase such as PhoA or phytase, or an endoglucanase).

Methods for Promoting Plant Growth

The present invention also relates to methods for stimulating plant growth. The method for stimulating plant growth comprises introducing into a plant growth medium any of the recombinant *Bacillus cereus* family members discussed above or any of the formulations discussed above. Alternatively, any of the recombinant *Bacillus cereus* family members discussed above or any of the formulations discussed above can be applied to a plant, to a plant seed, or to an area surrounding a plant or a plant seed. In such methods, the plant growth stimulating protein or peptide is physically attached to the exosporium of the recombinant *Bacillus* family member.

Alternatively, the method for stimulating plant growth comprises introducing a recombinant *Bacillus cereus* family member expressing a fusion protein into a plant growth medium or applying a recombinant *Bacillus cereus* family member expressing a fusion protein to plant, a plant seed, or an area surrounding a plant or a plant seed. The fusion protein comprises at least one plant growth stimulating protein or peptide and a targeting sequence, exosporium protein, or exosporium protein fragment. The plant growth stimulating protein or peptide is physically attached to the exosporium of the recombinant *Bacillus* family member. The targeting sequence, exosporium protein, or exosporium protein fragment can be any of the targeting sequences, exosporium proteins, or exosporium protein fragments listed above in paragraph [0005].

Furthermore, the targeting sequence can consist of 16 amino acids and have at least about 43% identity with amino acids 20-35 of SEQ ID NO: 1, wherein the identity with amino acids 25-35 is at least about 54%. Alternatively, the targeting sequence can consist of amino acids 1-35 of SEQ ID NO: 1, amino acids 20-35 of SEQ ID NO: 1; SEQ ID NO: 1, or SEQ ID NO: 60.

The targeting sequence can comprise an amino acid sequence having at least about 50% identity with amino acids 20-35 of SEQ ID NO: 1, wherein the identity with amino acids 25-35 is at least about 63%. Alternatively, the targeting sequence consists of an amino acid sequence consisting of 16 amino acids and having at least about 50% identity with amino acids 20-35 of SEQ ID NO: 1, wherein the identity with amino acids 25-35 is at least about 63%.

The targeting sequence can comprise an amino acid sequence having at least about 50% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 50% identity with amino acids 20-35 of SEQ ID NO: 1, wherein the identity with amino acids 25-35 is at least about 72%.

The targeting sequence can comprises an amino acid sequence having at least about 56% identity with amino acids 20-35 of SEQ ID NO: 1, wherein the identity with amino acids 25-35 is at least about 63%. Alternatively, the targeting sequence consists of an amino acid sequence consisting of 16 amino acids and having at least about 56% identity with amino acids 20-35 of SEQ ID NO: 1, wherein the identity with amino acids 25-35 is at least about 63%.

The targeting sequence can comprise an amino sequence having at least about 62% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 62% identity with amino acids 20-35 of SEQ ID NO: 1, wherein the identity with amino acids 25-35 of SEQ ID NO:1 is at least about 72%.

The targeting sequence can comprise an amino acid sequence having at least about 68% identity with amino acids 20-35 of SEQ ID NO: 1, wherein the identity with amino acids 25-35 is at least about 81%. Alternatively, the targeting sequence consists of an amino acid sequence consisting of 16 amino acids and having at least about 68% identity with amino acids 20-35 of SEQ ID NO: 1, wherein the identity with amino acids 25-35 is at least about 81%.

The targeting sequence can comprise an amino sequence having at least about 75% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO:1 is at least about 72%.

The targeting sequence can comprise an amino sequence having at least about 75% identity with amino acids 20-35 of SEQ ID NO: 1, wherein the identity with amino acids 25-35 is at least about 81%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO:1 is at least about 81%.

The targeting sequence can comprise an amino acid sequence having at least about 81% identity with amino acids 20-35 of SEQ ID NO:1, wherein the identity with amino acids 25-35 is at least about 81%. Alternatively, the targeting sequence consists of an amino acid sequence consisting of 16 amino acids and having at least about 81% identity with amino acids 20-35 of SEQ ID NO:1, wherein the identity with amino acids 25-35 is at least about 81%.

The targeting sequence can comprise an amino acid sequence having at least about 81% identity with amino acids 20-35 of SEQ ID NO: 1, wherein the identity with amino acids 25-35 is at least about 90%. Alternatively, the targeting sequence consists of an amino acid sequence consisting of 16 amino acids and having at least about 81% identity with amino acids 20-35 of SEQ ID NO: 1, wherein the identity with amino acids 25-35 is at least about 90%.

Alternatively, the exosporium protein or exosporium protein fragment can comprise an amino acid sequence having at least 90%, at least 95%, at least 98%, at least 99%, or 100% identity with any one of SEQ ID NOs: 2, 4, 6, 8, 10, 12, 14, 16, 18, 20, 22, 24, 26, 28, 30, 32, 34, 36, 44, 46, 48, 50, 52, 54, 56, 58, 59, 71, 72, 73, 74, 75, 76, 77, 78, 79, 80, 81, 82, 83, and 84.

The plant growth stimulating protein can comprise an enzyme. For example, the enzyme can comprise an enzyme that degrades or modifies a bacterial, fungal, or plant nutrient source. Such enzymes include cellulases, lipases, lignin oxidases, proteases, glycoside hydrolases, phosphatases, nitrogenases, nucleases, amidases, nitrate reductases, nitrite reductases, amylases, ammonia oxidases, ligninases, glucosidases, phospholipases, phytases, pectinases, glucanases, sulfatases, ureases, xylanases, and siderophores. When introduced into a plant growth medium or applied to a plant, seed, or an area surrounding a plant or a plant seed, fusion proteins comprising enzymes that degrade or modify a bacterial, fungal, or plant nutrient source can aid in the processing of nutrients in the vicinity of the plant and result in enhanced uptake of nutrients by the plant or by beneficial bacteria or fungi in the vicinity of the plant.

Suitable cellulases include endocellulases (e.g., an endogluconase such as a *Bacillus subtilis* endoglucanase, a *Bacillus thuringiensis* endoglucanase, a *Bacillus cereus* endoglucanase, or a *Bacillus clausii* endoglucanase), exocellulases (e.g., a *Trichoderma reesei* exocellulase), and β-glucosidases (e.g., a *Bacillus subtilis* β-glucosidase, a *Bacillus thuringiensis* β-glucosidase, a *Bacillus cereus* β-glucosidase, or a *Bacillus clausii* B-glucosidase).

The lipase can comprise a *Bacillus subtilis* lipase, a *Bacillus thuringiensis* lipase, a *Bacillus cereus* lipase, or a *Bacillus clausii* lipase.

Suitable lignin oxidases comprise lignin peroxidases, laccases, glyoxal oxidases, ligninases, and manganese peroxidases.

The protease can comprise a subtilisin, an acid protease, an alkaline protease, a proteinase, a peptidase, an endopeptidase, an exopeptidase, a thermolysin, a papain, a pepsin, a trypsin, a pronase, a carboxylase, a serine protease, a glutamic protease, an aspartate protease, a cysteine protease, a threonine protease, or a metalloprotease.

The phosphatase can comprise a phosphoric monoester hydrolase, a phosphomonoesterase (e.g., PhoA4), a phosphoric diester hydrolase, a phosphodiesterase, a triphosphoric monoester hydrolase, a phosphoryl anhydride hydrolase, a pyrophosphatase, a phytase (e.g., *Bacillus subtilis* EE148 phytase or *Bacillus thuringiensis* BT013A phytase), a trimetaphosphatase, or a triphosphatase.

The nitrogenase can comprise a Nif family nitrogenase (e.g., *Paenibacillus massiliensis* NifBDEHKNXV).

In any of the above methods for stimulating plant growth, plants grown in the plant growth medium comprising the recombinant *Bacillus cereus* family member exhibit increased growth as compared to the growth of plants in the identical plant growth medium that does not contain the recombinant *Bacillus cereus* family member.

In any of the above methods for stimulating plant growth, the recombinant *Bacillus cereus* family member can comprise any of the recombinant plant-growth promoting strains of bacteria described above.

In any of the above methods for stimulating plant growth, the fusion protein can be expressed under the control of any of the promoters described above.

Methods for Protecting a Plant from a Pathogen

The present invention further relates to methods for protecting a plant from a pathogen. Such methods comprise introducing any of the recombinant *Bacillus cereus* family members discussed above or any of the formulations discussed above into a plant growth medium. Alternatively, such methods comprise applying any of the recombinant *Bacillus cereus* family members discussed above or any of the formulations discussed above to a plant, to a plant seed, or to an area surrounding a plant or a plant seed. In these methods, the protein or peptide that protects a plant from a pathogen is physically attached to the exosporium of the recombinant *Bacillus cereus* family member.

Plants grown in the plant growth medium comprising the recombinant *Bacillus cereus* family member are less susceptible to infection with the pathogen as compared to plants grown in the identical plant growth medium that does not contain the recombinant *Bacillus cereus* family member. The reduced susceptibility the pathogen can be a result of stimulation of the plant's immune system by the protein or peptide that protects a plant from a pathogen, or can result from a direct or indirect effect of the protein or peptide that protects a plant from a pathogen on the pathogen.

Methods for Enhancing Stress Resistance in a Plant

The present invention further relates to methods for enhancing stress resistance in a plant. Such methods comprise introducing any of the recombinant *Bacillus cereus* family members discussed above or any of the formulations discussed above into a plant growth medium. Alternatively, such methods comprise applying any of the recombinant *Bacillus cereus* family members discussed above or any of the formulations discussed above to a plant, to a plant seed, or to an area surrounding a plant or a plant seed. In these methods, the protein or peptide that enhances stress resistance in a plant is physically attached to the exosporium of the recombinant *Bacillus cereus* family member.

Plants grown in the plant growth medium comprising the recombinant *Bacillus cereus* family member are less susceptible to stress as compared to plants grown in the identical plant growth medium that does not contain the recombinant *Bacillus cereus* family member.

Methods for Immobilizing *Bacillus cereus* Family Member Spores on a Plant

The present invention is also directed to methods for immobilizing a recombinant *Bacillus cereus* family member spore on a plant. These methods comprise introducing any of the recombinant *Bacillus cereus* family members discussed above or any of the formulations discussed above into a plant growth medium. Alternatively, such methods comprise applying any of the recombinant *Bacillus cereus* family members discussed above or any of the formulations discussed above to a plant, to a plant seed, or to an area surrounding a plant or a plant seed. The plant binding protein or peptide is physically attached to the exosporium of the recombinant *Bacillus* family member.

These methods allow the *Bacillus cereus* family member spore to bind to a plant, such that the spore is maintained on the plant. For example, these methods allow the *Bacillus cereus* family member spore to bind to a root of a plant or to an aerial portion of a plant (e.g., foliage, stems, fruits, or flowers), such that the spore is maintained at the plant's root structure or on the aerial portion of a plant instead of dissipating into the plant growth medium or into the environment surrounding the aerial portion of the plant.

In any of the methods for immobilizing a recombinant *Bacillus cereus* family member spore on a plant, the plant binding protein or peptide can selectively target and maintain the *Bacillus cereus* family member on the plant or on at plant structure or substructure (e.g., at plant roots and substructures of plant roots or at an aerial portion of a plant or a substructure of an aerial portion of a plant).

Plant Growth Medium

In any of the above methods, the plant growth medium is material that is capable of supporting the growth of a plant. The plant growth medium can comprise soil, water, an aqueous solution, sand, gravel, a polysaccharide, mulch, compost, peat moss, straw, logs, clay, soybean meal, yeast extract, or a combination thereof. For example, the plant growth medium comprises soil, compost, peat moss, or a combination thereof.

The plant growth medium can optionally be supplemented with a substrate for an enzyme. For example, the substrate can comprise tryptophan, an adenosine monophosphate, an adenosine diphosphate, an adenosine triphosphate (e.g., adenosine-3-triphosphate), indole, a trimetaphosphate, ferrodoxin, acetoin, diacetyl, pyruvate, acetolactate, pectin, cellulose, methylcellulose, starch, chitin, pectin, a protein meal, a cellulose derivative, a phosphate, acetoin, chitosan, an inactive derivative of indole-3-acetic acid, an inactive derivative of gibberellic acid, a xylan, choline, a choline derivative, proline, a polyproline, a proline rich meal, a proline-rich protein, phenylalanine, chorismate, an arabinoxylan, a fat, a wax, an oil, a phytic acid, a lignin, a humic acid, choline, a choline derivative, or a combination thereof.

Application Methods

In any of the above methods, the recombinant *Bacillus cereus* family member or formulation can be introduced into the plant growth medium or applied to a plant, to a plant seed, or to an area surrounding a plant or a plant seed.

For example, the method can comprise coating seeds with the recombinant *Bacillus cereus* family member or a formulation containing the recombinant *Bacillus cereus* family member prior to planting.

Alternatively, the method can comprise applying the recombinant *Bacillus cereus* family member or formulation to an aerial portion of a plant, e.g., to foliage, stems, fruits, or flowers. For example, the recombinant *Bacillus cereus* family member or formulation can be sprayed, brushed, dipped, or otherwise applied to the leaves or other aerial portions of a plant.

The method can comprise introducing the recombinant *Bacillus cereus* family member into the plant growth medium by applying a liquid or solid formulation containing the recombinant *Bacillus cereus* family member to the medium (e.g., soil, compost, peat moss, or a combination thereof).

The formulation can be applied to the plant growth medium prior to, concurrently with, or after planting of seeds, seedlings, cuttings, bulbs, or plants in the plant growth medium.

Co-Application of Agrochemicals

Any of the above methods can further comprise introducing at least one agrochemical into the plant growth medium or applying at least one agrochemical to plants or seeds. The agrochemical can be any of those listed above for inclusion in the formulations, or any combination thereof.

Plants

The above methods can be practiced with a variety of plants. For example, the plant can be a dicotyledon, a monocotyledon, or a gymnosperm.

For example, where the plant is a dicotyledon, the dicotyledon can be selected from the group consisting of bean, pea, tomato, pepper, squash, alfalfa, almond, aniseseed, apple, apricot, arracha, artichoke, avocado, bambara groundnut, beet, bergamot, black pepper, black wattle, blackberry, blueberry, bitter orange, bok-choi, Brazil nut, breadfruit, broccoli, broad bean, Brussels sprouts, buckwheat, cabbage, camelina, Chinese cabbage, cacao, cantaloupe, caraway seeds, cardoon, carob, carrot, cashew nuts, cassava, castor bean, cauliflower, celeriac, celery, cherry, chestnut, chickpea, chicory, chili pepper, *chrysanthemum*, cinnamon, citron, clementine, clove, clover, coffee, cola nut, colza, corn, cotton, cottonseed, cowpea, *crambe*, cranberry, cress, cucumber, currant, custard apple, drumstick tree, earth pea, eggplant, endive, fennel, fenugreek, fig, filbert, flax, geranium, gooseberry, gourd, grape, grapefruit, guava, hemp, hempseed, henna, hop, horse bean, horseradish, indigo, jasmine, Jerusalem artichoke, jute, kale, kapok, kenaf, kohlrabi, kumquat, lavender, lemon, lentil, *lespedeza*, lettuce, lime, liquorice, litchi, loquat, lupine, macadamia nut, mace, mandarin, mangel, mango, medlar, melon, mint, mulberry, mustard, nectarine, *niger* seed, nutmeg, okra, olive, opium, orange, *papaya*, parsnip, pea, peach, peanut, pear, pecan nut, persimmon, pigeon pea, pistachio nut, plantain, plum, pomegranate, pomelo, poppy seed, potato, sweet potato, prune, pumpkin, quebracho, quince, trees of the genus Cinchona, *quinoa*, radish, ramie, rapeseed, raspberry, rhea, rhubarb, rose, rubber, rutabaga, safflower, sainfoin, salsify, sapodilla, Satsuma, scorzonera, sesame, shea tree, soybean, spinach, squash, strawberry, sugar beet, sugarcane, sunflower, swede, sweet pepper, tangerine, tea, teff, tobacco, tomato, trefoil, tung tree, turnip, urena, vetch, walnut, watermelon, yerba mate, wintercress, shepherd's purse, garden cress, peppercress, watercress, pennycress, star anise, laurel, bay laurel, *cassia*, jamun, dill, tamarind, peppermint, oregano, rosemary, sage, soursop, pennywort, calophyllum, balsam pear, kukui nut, Tahitian chestnut, basil, huckleberry, hibiscus, passionfruit, star apple, *sassafras*, cactus, St. John's wort, loosestrife, hawthorn, cilantro, curry plant, kiwi, thyme, zucchini, ulluco, jicama, waterleaf, spiny monkey orange, yellow mombin, starfruit, amaranth, wasabi, Japanese pepper, yellow plum, mashua, Chinese toon, New Zealand spinach, bower spinach, ugu, tansy, chickweed, jocote, Malay apple, paracress, sowthistle, Chinese potato, horse parsley, hedge mustard, campion, agate, cassod tree, thistle, burnet, star gooseberry, saltwort, glasswort, sorrel, silver lace fern, collard greens, primrose, cowslip, purslane, knotgrass, terebinth, tree lettuce, wild *betel*, West African pepper, yerba santa, tarragon, parsley, chervil, land cress, burnet saxifrage, honeyherb, butterbur, shiso, water pepper, *perilla*, bitter bean, oca, kampong, Chinese celery, lemon basil, Thai basil, water *mimosa*, cicely, cabbage-tree, moringa, mauka, ostrich fern, rice paddy herb, yellow sawah lettuce, lovage, pepper grass, maca, bottle gourd, hyacinth bean, water spinach, catsear, fishwort, Okinawan spinach, lotus sweetjuice, gallant soldier, culantro, arugula, cardoon, caigua, mitsuba, chipilin, samphire, mampat, ebolo, ivy gourd, cabbage thistle, sea kale, chaya, huauzontle, Ethiopian mustard, magenta spreen, good king henry, epazole, lamb's quarters, centella plumed cockscomb, caper, rapini, napa cabbage, mizuna, Chinese savoy, kai-lan, mustard greens, Malabar spinach, chard, marshmallow, climbing wattle, China jute, paprika, annatto seed, spearmint, savory, marjoram, cumin, chamomile, lemon balm, allspice, bilberry, cherimoya, cloudberry, damson, pitaya, durian, elderberry, feijoa, jackfruit, jambul, jujube, physalis, purple mangosteen, rambutan, redcurrant, blackcurrant, salal berry, satsuma, ugli fruit, azuki bean, black bean, black-eyed pea, borlotti bean, common bean, green bean, kidney bean, lima bean, mung bean, navy bean, pinto bean, runner bean, mangetout, snap pea, broccoflower, calabrese, nettle, bell pepper, raddichio, daikon, white radish, skirret, tat soi, broccolini, black radish, burdock root, fava bean, broccoli raab, lablab, lupin, sterculia, velvet beans, winged beans, yam beans, mulga, ironweed, umbrella bush, tjuntjula, wakalpulka, witchetty bush, wiry wattle, chia, beech nut, candlenut, colocynth, mamoncillo, Maya nut, mongongo, ogbono nut, paradise nut, and cempedak.

Alternatively, the dicotyledon can be from a family selected from the group consisting of Acanthaceae (acanthus), Aceraceae (maple), Achariaceae, Achatocarpaceae (achatocarpus), Actinidiaceae (Chinese gooseberry), Adoxaceae (moschatel), Aextoxicaceae, Aizoaceae (fig marigold), Akaniaceae, Alangiaceae, Alseuosmiaceae, Alzateaceae, Amaranthaceae (amaranth), Amborellaceae, Anacardiaceae (sumac), Ancistrocladaceae, Anisophylleaceae, Annonaceae (custard apple), Apiaceae (carrot), Apocynaceae (dogbane), Aquifoliaceae (holly), Araliaceae (*ginseng*), Aristolochiaceae (birthwort), Asclepiadaceae (milkweed), Asteraceae (aster), Austrobaileyaceae, Balanopaceae, Balanophoraceae (balanophora), Balsaminaceae (touch-me-not), Barbeyaceae, Barclayaceae, Basellaceae (basella), Bataceae (saltwort), Begoniaceae (*begonia*), Berberidaceae (barberry), Betulaceae (birch), Bignoniaceae (trumpet creeper), Bixaceae (lipstick tree), Bombacaceae (kapok tree), Boraginaceae (borage), Brassicaceae (mustard, also Cruciferae), Bretschneideraceae, Brunelliaceae (brunellia), Bruniaceae, Brunoniaceae, Buddlejaceae (butterfly bush), Burseraceae (frankincense), Buxaceae (boxwood), Byblidaceae, Cabombaceae (water shield), Cactaceae (cactus), Caesalpiniaceae, Callitrichaceae (water starwort), Calycanthaceae (strawberry shrub), Calyceraceae (calycera), Campanulaceae (bellflower), Canellaceae (canella), Cannabaceae (hemp), Capparaceae (caper), Caprifoliaceae (honeysuckle), Cardiopteridaceae, Caricaceae (*papaya*), Caryocaraceae (souari), Caryophyllaceae (pink), Casuarinaceae (she-oak), Cecropiaceae (cecropia), Celastraceae (bittersweet), Cephalotaceae, Ceratophyllaceae (hornwort), Cercidiphyllaceae (katsura tree), Chenopodiaceae (goosefoot), Chloranthaceae (chloranthus), Chrysobalanaceae (cocoa plum), Circaeasteraceae, Cistaceae (rockrose), Clethraceae (clethra), Clusiaceae (mangosteen, also Guttiferae), Cneoraceae, Columelliaceae, Combretaceae (Indian almond), Compositae (aster), Connaraceae (cannarus), Convolvulaceae (morning glory), Coriariaceae, Cornaceae (dogwood), Corynocarpaceae (karaka), Crassulaceae (stonecrop), Crossosomataceae (crossosoma), Crypteroniaceae, Cucurbitaceae (cucumber), Cunoniaceae (cunonia), Cuscutaceae (dodder), Cyrillaceae (cyrilla), Daphniphyllaceae, Datiscaceae (datisca), Davidsoniaceae, Degeneriaceae, Dialypetalanthaceae, Diapensiaceae (diapensia), Dichapetalaceae, Didiereaceae, Didymelaceae, Dilleniaceae (dillenia), Dioncophyllaceae, Dipentodontaceae, Dipsacaceae (teasel), Dipterocarpaceae (meranti), Donatiaceae, Droseraceae (sundew), Duckeodendraceae, Ebenaceae (ebony), Elaeagnaceae (*oleaster*), Elaeocarpaceae (elaeocarpus), Elatinaceae (waterwort), Empetraceae (crowberry), Epacridaceae (epacris), Eremolepidaceae (catkin-mistletoe), Ericaceae (heath), Erythroxylaceae (coca), Eucommiaceae, Eucryphiaceae, Euphorbiaceae (spurge), Eupomatiaceae, Eupteleaceae, Fabaceae (pea or legume), Fagaceae (beech), Flacourtiaceae (flacourtia), Fouquieriaceae (ocotillo), Frankeniaceae (frankenia), Fumariaceae (fumitory), Garryaceae (silk tassel), Geissolomataceae, Gentianaceae (gentian), Geraniaceae (geranium), Gesneriaceae (gesneriad), Globulariaceae, Gomortegaceae, Goodeniaceae (goodenia), Greyiaceae, Grossulariaceae (currant), Grubbiaceae, Gunneraceae (gunnera), Gyrostemonaceae, Haloragaceae (water milfoil), Hamamelidaceae (witch hazel), Hernandiaceae (hernandia), Himantandraceae, Hippocastanaceae (horse chestnut), Hippocrateaceae (hippocratea), Hippuridaceae (mare's tail), Hoplestigmataceae, Huaceae, Hugoniaceae, Humiriaceae, Hydnoraceae, Hydrangeaceae (*hydrangea*), Hydrophyllaceae (waterleaf), Hydrostachyaceae, Icacinaceae (icacina), Idiospermaceae, Illiciaceae (star anise), Ixonanthaceae, Juglandaceae (walnut), Julianiaceae, Krameriaceae (krameria), Lacistemataceae, Lamiaceae (mint, also Labiatae), Lardizabalaceae (lardizabala), Lauraceae (laurel), Lecythidaceae (brazil nut), Leeaceae, Leitneriaceae (corkwood), Lennoaceae (lennoa), Lentibulariaceae (bladderwort), Limnanthaceae (meadow foam), Linaceae (flax), Lissocarpaceae, Loasaceae (loasa), Loganiaceae (logania), Loranthaceae (showy mistletoe), Lythraceae (loosestrife), Magnoliaceae (*magnolia*), Malesherbiaceae, Malpighiaceae (barbados cherry), Malvaceae (mallow), Marcgraviaceae (shingle plant), Medusagynaceae, Medusandraceae, Melastomataceae (melastome), Meliaceae (mahogany), Melianthaceae, Mendonciaceae, Menispermaceae (moonseed), Menyanthaceae (buckbean), Mimosaceae, Misodendraceae, Mitrastemonaceae, Molluginaceae (carpetweed), Monimiaceae (monimia), Monotropaceae (Indian pipe), Moraceae (mulberry), Moringaceae (horseradish tree), Myoporaceae (*myoporum*), Myricaceae (bayberry), Myristicaceae (nutmeg), Myrothamnaceae, Myrsinaceae (myrsine), Myrtaceae (myrtle), Nelumbonaceae (lotus lily), Nepenthaceae (East Indian pitcherplant), Neuradaceae, Nolanaceae, Nothofagaceae, Nyctaginaceae (four-o'clock), Nymphaeaceae (water lily), Nyssaceae (sour gum), Ochnaceae (ochna), Olacaceae (olax), Oleaceae (olive), Oliniaceae, Onagraceae (evening primrose), Oncothecaceae, Opiliaceae, Orobanchaceae (broom rape), Oxalidaceae (wood sorrel), Paeoniaceae (peony), Pandaceae, Papaveraceae (poppy), Papilionaceae, Paracryphiaceae, Passifloraceae (passionflower), Pedaliaceae (sesame), Pellicieraceae, Penaeaceae, Pentaphragmataceae, Pentaphylacaceae, Peridiscaceae, Physenaceae, Phytolaccaceae (pokeweed), Piperaceae (pepper), Pittosporaceae (*pittosporum*), Plantaginaceae (plantain), Platanaceae (plane tree), Plumbaginaceae (leadwort), Podostemaceae (river weed), Polemoniaceae (*phlox*), Polygalaceae (milkwort), Polygonaceae (buckwheat), Portulacaceae (purslane), Primulaceae (primrose), Proteaceae (protea), Punicaceae (pomegranate), Pyrolaceae (shinleaf), Quiinaceae, Rafflesiaceae (rafflesia), Ranunculaceae (buttercup orranunculus), Resedaceae (mignonette), Retziaceae, Rhabdodendraceae, Rhamnaceae (buckthorn), Rhizophoraceae (red mangrove), Rhoipteleaceae, Rhynchocalycaceae, Rosaceae (rose), Rubiaceae (madder), Rutaceae (rue), Sabiaceae (sabia), Saccifoliaceae, Salicaceae (willow), Salvadoraceae, Santalaceae (sandalwood), Sapindaceae (soapberry), Sapotaceae (sapodilla), Sarcolaenaceae, Sargentodoxaceae, Sarraceniaceae (pitcher plant), Saururaceae (lizard's tail), Saxifragaceae (saxifrage), Schisandraceae (schisandra), Scrophulariaceae (figwort), Scyphostegiaceae, Scytopetalaceae, Simaroubaceae (quassia), Simmondsiaceae (jojoba), Solanaceae (potato), Sonneratiaceae (sonneratia), Sphaerosepalaceae, Sphenocleaceae (spenoclea), Stackhousiaceae (stackhousia), Stachyuraceae, Staphyleaceae (bladdernut), Sterculiaceae (cacao), Stylidiaceae, Styracaceae (storax), Surianaceae (suriana), Symplocaceae (sweetleaf), Tamaricaceae (*tamarix*), Tepuianthaceae, Tetracentraceae, Tetrameristaceae, Theaceae (tea), Theligonaceae, Theophrastaceae (theophrasta), Thymelaeaceae (mezereum), Ticodendraceae, Tiliaceae (linden), Tovariaceae, Trapaceae (water chestnut), Tremandraceae, Trigoniaceae, Trimeniaceae, Trochodendraceae, Tropaeolaceae (nasturtium), Turneraceae (turnera), Ulmaceae (elm), Urticaceae (nettle), Valerianaceae (valerian), Verbenaceae (*verbena*), Violaceae (violet), Viscaceae (Christmas mistletoe), Vitaceae (grape), Vochysiaceae, Winteraceae (wintera), Xanthophyllaceae, and Zygophyllaceae (creosote bush).

Where the plant is a monocotyledon, the monocotyledon can be selected from the group consisting of corn, wheat, oat, rice, barley, millet, banana, onion, garlic, asparagus, ryegrass, millet, fonio, raishan, nipa grass, turmeric, saffron, galangal, chive, cardamom, date palm, pineapple, shallot, leek, scallion, water chestnut, ramp, Job's tears, bamboo, ragi, spotless watermeal, arrowleaf elephant ear, Tahitian spinach, abaca, *areca*, bajra, *betel* nut, broom millet, broom sorghum, citronella, coconut, cocoyam, maize, dasheen, durra, durum wheat, edo, Pique, formio, ginger, orchard grass, esparto grass, Sudan grass, guinea corn, Manila hemp, henequen, hybrid maize, jowar, lemon grass, maguey, bulrush millet, finger millet, foxtail millet, Japanese millet, proso millet, New Zealand flax, oats, oil palm, palm palmyra, sago palm, redtop, sisal, sorghum, spelt wheat, sweet corn, sweet sorghum, taro, teff, timothy grass, triticale, vanilla, wheat, and yam.

Alternatively, the monocotyledon can be from a family selected from the group consisting of Acoraceae (calamus), Agavaceae (century plant), Alismataceae (water plantain), Aloeaceae (aloe), Aponogetonaceae (cape pondweed), Araceae (*arum*), Arecaceae (palm), Bromeliaceae (bromeliad), Burmanniaceae (burmannia), Butomaceae (flowering rush), Cannaceae (*canna*), Centrolepidaceae, Commelinaceae (spiderwort), Corsiaceae, Costaceae (costus), Cyanastraceae, Cyclanthaceae (Panama hat), Cymodoceaceae (manatee grass), Cyperaceae (sedge), Dioscoreaceae (yam), Eriocaulaceae (pipewort), Flagellariaceae, Geosiridaceae, Haemodoraceae (bloodwort), Hanguanaceae (hanguana), Heliconiaceae (*heliconia*), Hydatellaceae, Hydrocharitaceae (tape grass), Iridaceae (iris), Joinvilleaceae (joinvillea), Juncaceae (rush), Juncaginaceae (arrow grass), Lemnaceae (duckweed), Liliaceae (lily), Limnocharitaceae (water poppy), Lowiaceae, Marantaceae (prayer plant), Mayacaceae (mayaca), Musaceae (banana), Najadaceae (water nymph), Orchidaceae (orchid), Pandanaceae (screw pine), Petrosaviaceae, Philydraceae (philydraceae), Poaceae (grass), Pontederiaceae (water hyacinth), Posidoniaceae (posidonia), Potamogetonaceae (pondweed), Rapateaceae, Restionaceae, Ruppiaceae (ditch grass), Scheuchzeriaceae (scheuchzeria), Smilacaceae (catbrier), Sparganiaceae (bur reed), Stemonaceae (stemona), Strelitziaceae, Taccaceae (tacca), Thurniaceae, Triuridaceae, Typhaceae (cattail), Velloziaceae, Xanthorrhoeaceae, Xyridaceae (yellow-eyed grass), Zannichelliaceae (horned pondweed), Zingiberaceae (ginger), and Zosteraceae (eelgrass).

Where the plant is a gymnosperm, the gymnosperm can be from a family selected from the group consisting of Araucariaceae, Boweniaceae, Cephalotaxaceae, Cupressaceae, Cycadaceae, Ephedraceae, Ginkgoaceae, Gnetaceae, Pinaceae, Podocarpaceae, Taxaceae, Taxodiaceae, Welwitschiaceae, and Zamiaceae.

EXAMPLES

The following non-limiting examples are provided to further illustrate the present invention.

Example 1. Use of a Recombinant *Bacillus cereus* Family Member Displaying a Lipase or an Endoglucanase to Stimulate Plant Growth in Soybeans The *Bacillus subtilis* lipase and endoglucanase genes were amplified via polymerase chain reaction (PCR) using the following primers shown below in Table 3:

TABLE 3

| | lipase | endoglucanase |
|---|---|---|
| forward | ggatccatggctgaa cacaatcc (SEQ ID NO: 37) | ggatccatgaaacg gtcaatc SEQ ID NO: 39) |
| reverse | ggatccttaattcgt attctggcc (SEQ ID NO: 38) | ggatccttactaatt tggttctgt (SEQ ID NO: 40) |

To create fusion constructs, genes were fused to the native bclA promoter of *Bacillus thuringiensis* DNA encoding the first 35 amino acids of BclA (amino acids 1-35 of SEQ ID NO:1) using the splicing by overlapping extension (SOE) technique. Correct amplicons were cloned into the *E. coli/Bacillus* shuttle vector pHP13, and correct clones screened by DNA sequencing. Correct clones were electroporated into *Bacillus thuringiensis* (Cry-, plasmid-) and screened for chloramphenicol resistance. Correct transformants were grown in brain heart infusion broth overnight at 30° C., plated onto nutrient agar plates, and incubated at 30° C. for 3 days. Spores expressing the fusion construct (BEMD spores) were collected off of the plates by washing in phosphate buffered saline (PBS) and purified by centrifugation and additional washes in PBS. Non-transformed control *Bacillus thuringiensis* (B.t.) spores were created identically.

Soybeans (strain Jake 011-28-04) were planted 2.54 cm deep in 10 cm deep pots filled with standard loam topsoil. Spores were diluted to a concentration of $1\times10^4$/ml in 50 ml of water and applied to each seed at planting. Plants were grown under ideal light using T5 lamps, 54 watts, and exposed to 11 hours of light a day under controlled temperature conditions between 15.5-25.5° C. Plants were watered to saturation every three days over a two week trial. At the end of two weeks, the height of each plant was measured and measurements were normalized to control *Bacillus thuringiensis* spores. Two independent trials were performed.

Results are shown in Table 4, together with the standard error of the mean. In both trials, soybeans grown in the presence of BEMD spores displaying either lipase or endoglucanase grew significantly taller than control B.t. spore treated soybeans (statistical analysis assayed via a t-test).

TABLE 4

| | | Soybeans | | |
|---|---|---|---|---|
| | Treatment | Avg. Height, cm | Comparison to Control | SEM |
| Trial #1 | Control Bt | 14.034 | 100.0% | .521 |
| | Lipase, BEMD | 17.93 | 127.8% | .395 |
| | Endocellulase, BEMD | 16.31 | 116.2% | .411 |
| Trial #2 | Control Bt | 15.39 | 100.0% | .749 |
| | Lipase, BEMD | 19.15 | 124.4% | .428 |
| | Endocellulase, BEMD | 17.65 | 114.7% | .313 |

Example 2. Use of a Recombinant *Bacillus cereus* Family Member Displaying an Endoglucanase to Stimulate Plant Growth in Corn BEMD spores expressing endoglucanase were created in an identical fashion as described above in Example 1. Field corn was planted 3.8 cm deep in 10 cm deep pots filled with standard loam topsoil. Spores, control and BEMD expressing endoglucanase, were diluted to a concentration of $1\times10^4$/ml in 50 ml of water and applied to each plant at planting. A water-only control was also included. Plants were grown under ideal light using T5 lamps, 54 watts, and exposed to 11 hours of light a day under controlled temperature conditions between 15.5-25.5° C. Plants were watered to saturation every three days over the one week trial. At the end of one week, the height of each plant was measured, and measurements were normalized to control *Bacillus thuringiensis* spores.

Results are shown in Table 5, together with the standard error of the mean. Corn grown in the presence of BEMD spores displaying endoglucanase grew significantly taller than both control B.t. spore treated soybeans and water-only control plants (statistical analysis assayed via a t-test).

TABLE 5

| | Height, cm | Comparison | SEM |
|---|---|---|---|
| $H_2O$ | 15.44 | 100% | 0.318 |
| Bt | 18.92 | 122.50% | 0.645 |
| BEMD Endo | 22.71 | 143.40% | 0.616 |

Example 3. Use of a Recombinant *Bacillus cereus* Family Member Displaying an Endoglucanase or a Protease to Stimulate Plant Growth in Wheat BEMD spores expressing endoglucanase were created in an identical fashion as described above in Example 1. BEMD spores expressing *E. coli* protease PtrB were created using similar methods to those described above in Example 1 and the following primers: ggatccatgctaccaaaagcc (forward, SEQ ID NO: 41) and ggatccttagtccgcaggcgtagc (reverse, SEQ ID NO: 42).

Winter hard wheat was planted 2.54 cm deep in 10 cm deep pots filled with standard loam topsoil. Spores, control and BEMD expressing endoglucanase or protease, were diluted to a concentration of $1\times10^4$/ml in 50 ml of water and applied to each plant at planting. A water-only control was also included. Plants were grown under ideal light using T5 lamps, 54 watts, and exposed to 11 hours of light a day under controlled temperature conditions between 15.5-25.5° C. Plants were watered to saturation every three days over the one week trial. At the end of one week, the height of each plant was measured, and measurements were normalized to control water only plants.

Results are shown in Table 6, together with the standard error of the mean. Wheat grown in the presence of BEMD spores displaying endoglucanase or protease grew significantly taller than control B.t. spore treated or water control soybeans (statistical analysis assayed via a t-test).

TABLE 6

| | Height, cm | Comparison | SEM |
|---|---|---|---|
| $H_2O$ | 18.11 | 100% | 0.721 |
| Bt Control | 19.96 | 110.33% | 0.752 |
| BEMD Endo | 24.76 | 136.80% | 0.21 |
| BEMD Protease | 22.35 | 123.40% | 0.354 |

Example 4. Use of Recombinant *Bacillus cereus* Family Members Displaying an Endoglucanase to Stimulate Plant Growth in Ryegrass BEMD spores expressing endoglucanase were created in an identical fashion as described above in Example 1. Perennial ryegrass was planted 6.4 mm deep in 10 cm deep pots filled with standard loam topsoil. Spores, both control and BEMD expressing endoglucanase, were diluted to a concentration of $1\times10^4$/ml in 50 ml of water and applied to each plant at planting. A water-only control was also included. Plants were grown under ideal light using T5 lamps, 54 watts, and exposed to 11 hours of light a day under controlled temperature conditions between 15.5-25.5° C. Plants were watered to saturation every three days over the two week trial. At the end of two weeks, the height of each plant was measured, and measurements were normalized to control water only plants.

Results are shown in Table 7, together with the standard error of the mean. Ryegrass grown in the presence of BEMD spores displaying endocellulase grew significantly taller than control B.t. spore treated or water control ryegrass (statistical analysis assayed via a t-test).

TABLE 7

| | Height, cm | Comparison | SEM |
|---|---|---|---|
| $H_2O$ | 11.43 | 100.0% | 0.137 |
| Bt Control | 12.29 | 107.7% | 0.128 |
| BEMD Endo | 12.78 | 111.9% | 0.137 |

Example 5. Use of Recombinant *Bacillus cereus* Family Members Displaying Enzymes Involved in the Synthesis or Activation of Plant Hormones to Stimulate Plant Growth The BEMD system can also be used to display enzymes involved in the synthesis of plant hormones. For example, the plant hormone indole-3-acetic acid is a potent growth stimulator in plants. Indole-3-acetic acid is synthesized in vivo from tryptophan by the enzymes tryptophan monooxygenase and indole-3-acetamide hydrolase. Indole-3-acetic acid and other auxin hormones can also be synthesized in vivo from tryptophan and/or indole by the enzymes nitrilase, tryptophan aminotransferase, indole-3-acetaldehyde dehydrogenase, indole-3-pyruvate decarboxylase, amine oxidase, tryptophan decarboxylase, and tryptophan side chain oxidases.

The BEMD system can also be used to display enzymes involved in the modification of plant growth hormones into bioactive or inactive forms. For example, nitrilase can be expressed on the BEMD system to catalyze the conversion of indole-3-acetonitrile into the bioactive indole-3-acetic acid. Additionally, inactive forms of plant hormones, such as indole-3-acetonitrile can be added into the plant growth media with the BEMD-expressed nitrilase to provide a gradual release of active hormone into the plant growth media. Many other inactive or less active forms of plant hormones can be modified using their corresponding enzymes.

Related plant growth hormones (auxins) include indole-3-pyruvic acid, indole-3-acetaldoxime, indole-3-acetamide, indole-3-acetonitrile, indole-3-ethanol, indole-3-pyruvate, indole-3-butyric acid, phenylacetic acids, 4-chloroindole-3-acetic acid, and indole-3-acetaldoxime. These hormones are synthesized from tryptophan and/or indole in vivo via the enzymes tryptophan monooxygenase, indole-3-acetamide hydrolase, nitrilase, nitrile hydrolase, acetolactate synthetase, alpha acetolactate decarboxylase, tryptophan aminotransferase, indole-3-acetaldehyde dehydrogenase, indole-3-pyruvate decarboxylase, amine oxidase, tryptophan decarboxylase, and tryptophan side chain oxidases.

Growth hormones of the cytokinin family can also be synthesized by enzymes expressed in the BEMD system. Examples of cytokinins include kinetin, zeatin (cis and trans), 6-benzylaminopurine, dihydroxyzeatin, N6-(D2-isopentenyl) adenine, ribosylzeatin, N6-(D2-isopentenyl) adenosine, 2 methylthio-cis-ribosylzeatin, cis ribosylzeatin, ribosylzeatin-5-monosphosphate, N6-methylaminopurine, N6-dimethylaminopurine, 2'-deoxyzeatin riboside, 4-hydroxy-3-methyl-trans-2-butenylaminopurine, ortho-topolin, meta-topolin, benzyladenine, ortho-methyltopolin, and meta-methyltopolin. These plant growth stimulating compounds are synthesized in vivo from mevalonate or adenosine mono/di/triphosphate by enzymes including adenosine phosphate isopentenyltransferases, phosphatases, adenosine kinases, adenine phosphoribosyltransferase, CYP735A, 5' ribonucleotide phosphohydrolase, adenosine nucleosidases, zeatin cis-trans isomerase, zeatin 0-glucosyltransferases, β-glucosidases, cis-hydroxylases, CK cis-hydroxylases, CK N-glucosyltransferases, 2,5-ribonucleotide phosphohydrolases, adenosine nucleosidases, purine nucleoside phosphorylases, and zeatin reductases.

Using methods similar to those described above in Example 1, any of these enzymes can be incorporated into the BEMD system for display on BEMD spores by creating a fusion construct comprising the enzyme and a targeting sequence that targets the expressed enzyme to the exosporium when the fusion construct is expressed in a *Bacillus cereus* family member. A recombinant *Bacillus cereus* family member expressing such a construct can then be added to the soil or other plant growth medium or applied directly to plant foliage using methods similar to those described above in Example 1 for stimulation of plant growth.

The plant growth medium can be supplemented with precursors or substrates for the enzymes. For example, the plant growth medium can be supplemented with tryptophan, adenosine monophosphates, adenosine diphosphates, adenosine triphosphates, or indole. Suitable concentrations of these substrates are between 100 nM and 100 μM.

Example 6. Use of Recombinant *Bacillus cereus* Family Members Displaying Proteases or Peptidases that Cleave Proteins, Peptides, Proproteins, or Preproproteins into Bioactive Peptides for Stimulation of Plant Growth Proteases and peptidases can be expressed in the BEMD system that can enzymatically cleave available proteins in the plant growth media to bioactive peptides that can act on the plant directly or indirectly. Examples include the enzymatic cleavage of soybean meal, yeast extract, or other protein rich meals added to the plant growth medium into active peptides that can directly stimulate plant growth. Bioactive peptides generated by enzymatic cleavage of protein meals include RHPP and RKN 16D10, potent stimulators of plant root development. Additionally, proproteins or preproproteins can be cleaved into active forms by BEMD-expressed proteases and peptidases to their bioactive forms. Inactive proproteins or preproproteins can be added in the plant growth medium to facilitate their gradual cleavage by BEMD proteases and slow release of bioactive proteins.

Using methods similar to those described above in Example 1, any of these proteases and peptidases can be incorporated into the BEMD system for display on BEMD spores by creating a fusion construct comprising the protease or peptidase and a targeting sequence that targets the expressed enzyme to the exosporium when the fusion construct is expressed in a *Bacillus cereus* family member. A recombinant *Bacillus cereus* family member expressing such a construct can then be added to soil or other plant growth medium supplemented with soybean meal, yeast extract, or another-protein-rich meal for stimulation of plant growth. The soybean meal, yeast extract, or other protein-rich meal is suitably added to the plant growth medium in the form of a liquid composition comprising about 10 μg/L to about 100 mg/L of the protein meal, yeast extract, or other protein-rich meal.

Example 7. Use of BEMD Spores Expressing the Protease PtrB for Stimulation of Plant Growth BEMD spores expressing *E. coli* protease PtrB were created as described above in Example 3. Soybean seeds were planted 2.54 cm deep in 10 cm deep pots filled with standard loam topsoil. Spores, both control and BEMD expressing protease, were diluted to a concentration of $1\times10^4$/ml in 50 ml of water and applied to each plant at planting. A water-only control was also included. Soybean meal at 25 mg/pot was added in water at planting. Plants were grown under ideal light using T5 lamps, 54 watts, and exposed to 13 hours of light a day under controlled temperature conditions between 15.5-25.5° C. Plants were watered to saturation every three days over the one week trial. At the end of two weeks, the height of each plant was measured, and measurements were normalized to control water only plants.

Results are shown in Table 8, together with the standard error of the mean as a percentage of water control. Soy grown in the presence of BEMD spores displaying protease grew significantly taller than control B.t. spore treated or water control soybeans (statistical analysis assayed via a t-test). The addition of soybean meal to water control or *B. thuringiensis* control plants had little effect. By contrast, in the presence of the soybean meal and the BEMD protease system, the soybean plants responded significantly over all other treatments.

TABLE 8

| Treatment | Soybean Meal | Height (cm) | Normalized to water | SEM, as percentage of water |
|---|---|---|---|---|
| Water only | No | 12.10 | 100% | 3.1% |
| Water only | 25 mg/pot | 12.43 | 102.7% | 7.4% |
| *B. thuringiensis* | No | 12.52 | 103.5% | 5.2% |
| *B. thuringiensis* | 25 mg/pot | 11.99 | 99.1% | 5.0% |
| BEMD Protease | No | 12.97 | 107.2% | 6.1% |
| BEMD Protease | 25 mg/pot | 14.44 | 119.3% | 4.8% |

Example 8. Use of Recombinant *Bacillus cereus* Family Members Displaying Proteins or Peptides Involved in the Stimulation of Plant Growth The BEMD system can also be used to display proteins or peptides that are directly involved in the promotion of plant growth. For example, plant peptide hormones or non-hormone peptides that stimulate plant growth can be expressed in the BEMD system. For example, non-hormone peptides that directly bind to and active plant receptors can be expressed in the BEMD system to directly act on receptors in the plant and roots of target plants. Such peptide hormones and non-hormone peptides include phytosulfokine, calcalva 3 (CLV3), systemin, RKN 16D10, Hg-Syv46, eNOD40, NOD family proteins, ZmIGF, SCR/SP11 family proteins and peptides, RHPP, POLARIS, and KTI. These peptides and related peptides can be expressed in the BEMD system and delivered to plant growth medium or directly applied to foliage to stimulate plant growth.

Using methods similar to those described above in Example 1, any of these proteins or peptides can be incorporated into the BEMD system for display on BEMD spores by creating a fusion construct comprising the enzyme and a targeting sequence that targets the expressed enzyme to the exosporium when the fusion construct is expressed in a *Bacillus cereus* family member. A recombinant *Bacillus cereus* family member expressing such a construct can then be added to the soil or other plant growth medium or applied directly to plant foliage using methods similar to those described above in Example 1 for stimulation of plant growth.

Example 9. Use of BEMD Spores Expressing POLARIS or KTI for Stimulation of Plant Growth BEMD spores expressing the plant peptide POLARIS and soy peptide KTI were created by synthesizing genes coding for the POLARIS or KIT peptides linked to the targeting sequence of SEQ ID NO: 60. The genes were then introduced genes into *Bacillus thuringiensis* and spores were made as described in Example 1. Soybean seeds were planted 2.54 cm deep in 10 cm deep pots filled with standard loam topsoil. BEMD spores expressing POLARIS or KTI were diluted to a concentration of $1\times10^4$/ml in 50 ml of water and applied to each plant at planting. A water-only control was also included. Pure POLARIS and KTI peptides were also tested for their effects on soybeans at 0.05 mg/pot. Plants were grown under ideal light using T5 lamps, 54 watts, and exposed to 13 hours of light a day under controlled temperature conditions between 15.5-25.5° C. Plants were watered to saturation every three days over the two week trial. At the end of two weeks, the height of each plant was measured, the roots measured, and measurements were normalized to control water only plants.

Results are shown in Table 9, together with the standard error of the mean as a percentage of water control. Soy grown in the presence of BEMD spores displaying POLARIS grew taller and had a slight increase in root development than water control soybeans. The presence of free KTI peptide led to a significant stunting of the plants, losing between 6-8% of their heights, but adding 15% to the length of the roots. Expression of KTI on the BEMD system led to the root growth benefit, but without the stunting effect on the plant height. Importantly, the presence of the *Bacillus thuringiensis* control spores with the free KTI peptide did not prevent the stunting effect of KTI, while the BEMD with KTI displayed no such stunting.

TABLE 9

| Treatment | Peptide | Roots Normalized to Water | SEM | Height, Normalized to Water | SEM |
|---|---|---|---|---|---|
| Water | No | 100% | 6.8% | 100% | 4.3% |
| Water | KTI, 0.05 mg/Pot | 115% | 8.4% | 91.8% | 3.1% |
| BEMD POLARIS | No | 106.3% | 7.9% | 107.3% | 1.7% |
| BEMD KTI | No | 113.3% | 5.8% | 99.4% | 3.4% |
| *B. thuringiensis* | KTI, 0.05 mg/pot | 115% | 7.7% | 93.4% | 4.2% |

Example 10. Use of Recombinant *Bacillus cereus* Family Members Displaying Enzymes that Degrade or Modify a Bacterial, Fungal, or Plant Nutrient Source to Stimulate Plant Growth and/or Process Nutrients The BEMD system can also be used to display enzymes that degrade or modify beneficially a bacterial, fungal, or plant nutrient source present in soil or another plant growth medium. Such enzymes degrade products present in the soil or other plant growth medium into forms that can easily be taken up by plants and/or the beneficial bacteria and/or fungi of the rhizosphere. Such enzymes include, for example, glucoside hydrolases to degrade complex carbohydrates, cellulases to degrade cellulose; lipases to degrade lipids, including oil, fats, and waxes; lignin oxidases to degrade lignin and humic acids; proteases to degrade polypeptides; phospholipases to degrade membranes; amidases and nitrogenases to recover nitrogen; amylases to process starches; nucleases to recover nucleotides, pectinases to break down pectin, sulfatases to recover sulfur, and xylanases to break down xylans and arabinoxylans. The resultant products, including simple sugars, amino acids, fatty acids, and other nutrients will be readily available for direct uptake by plants and/or for stimulating beneficial bacteria and/or fungi to grow and thrive in the rhizospheres of the plants.

In addition, enzymes and other biological molecules can be utilized to release or sequester phosphate, nitrogen, and other key elemental nutrients for plant uptake from their various organic and inorganic forms in soil. For example, phosphatases can be used to degrade phosphates in the environment into usable inorganic phosphates for plant use. The phosphates can be naturally occurring phosphates present in a plant growth medium. Alternatively or in addition, the plant growth medium can be supplemented with phosphates such as trimetaphosphate, a common agricultural amendment. Examples of useful phosphatases include phosphoric monoester hydrolases, phosphomonoesterases, phosphoric diester hydrolases, phosphodiesterases, triphosphoric monoester hydrolases, phosphoryl anhydride hydrolases, pyrophosphatases, phytase, trimetaphosphatases, and triphosphatases. For example, the enzymes trimetaphosphatase, triphosphatase, and pyrophosphatase sequentially break down trimetaphosphate into usable inorganic phosphate.

The nitrogenase family of enzymes converts atmospheric nitrogen ($N_2$) into ammonia, thereby converting nitrogen that would otherwise be inaccessible to plants into a usable form. Suitable enzymes belong to the Nif family of nitrogenases.

Chemical energy can also be directly added into the plant growth medium as adenosine-3-triphosphate, ferrodoxin, or additional enzymes that create such energy into the BEMD system. These are cofactors for the nitrogenases and are limited in soil. Thus, such cofactors can be added to soil to enhance the reactions described above.

Other supplements that can be added to the plant growth medium include starches, cellulose and cellulose derivatives, pectins, xylans and arabinoxylans, fats, waxes, oils, phytic acids, lignins, humic acids, and other nutrient sources that the above enzyme classes exert activity upon.

Using methods similar to those described above in Example 1, any of these enzymes can be incorporated into the BEMD system for display on BEMD spores by creating a fusion construct comprising the enzyme and a targeting sequence for targeting the fusion construct to the exosporium of a *Bacillus cereus* family member. The fusion construct can then be expressed in a *Bacillus cereus* family member, and this recombinant *Bacillus cereus* family member can be added to soil or another plant growth medium using methods similar to those described above in Example 1 for stimulation of plant growth.

Example 11. Use of BEMD Spores Expressing a Phosphatase for Stimulation of Plant Growth BEMD spores expressing *Bacillus subtilis* Phosphatase A4 (PhoA4) were created by synthesizing a gene coding for PhoA4 linked to the targeting sequence of SEQ ID NO: 60. This gene was then introduced into *Bacillus thuringiensis* and spores were made as in Example 1. Corn was planted 2.54 cm deep in 10 cm deep pots filled with standard loam topsoil. BEMD spores expressing PhoA4, were diluted to a concentration of $1\times10^4$/ml in 50 ml of water and applied to each plant at planting. A water-only control was also included. Polyphosphate was added to pots in liquid at a rate of 0.5 mg/pot. Plants were grown under ideal light using T5 lamps, 54 watts, and exposed to 13 hours of light a day under controlled temperature conditions between 15.5-25.5° C. Plants were watered to saturation every three days over the two week trial. At the end of two weeks, the height of each plant was measured, and measurements were normalized to control water only plants.

Results are shown in Table 10. Corn grown in the presence of BEMD spores displaying PhoA4 exhibit enhanced growth, especially in the presence of added polyphosphate. This effect was greater than the effect of the polyphosphate alone.

TABLE 10

| Treatment | Additive | Growth, Comparison to Water |
|---|---|---|
| Water | None | 100% |
| Water | Polyphosphate | 110.8% |
| BEMD PhoA4 | None | 108.3% |
| BEMD PhoA4 | Polyphosphate | 114.8% |

Example 12. Use of Recombinant *Bacillus cereus* Family Members Displaying Enzymes Involved in the Synthesis of 2,3-Butanediol or the Synthesis or Activation of Gibberellic Acid for Stimulation of Plant Growth The BEMD system can also be used display enzymes involved in the synthesis of the plant-growth promoting compound 2,3-butanediol. In vivo, 2,3-butanediol is synthesized by beneficial bacteria and fungi in the rhizosphere from acetoin, diacetyl, acetolactate, or pyruvate by the enzymes acetolactate synthetase, α-acetolactate decarboxylase, pyruvate decarboxylase, diacetyl reductase, butanediol dehydrogenases, and acetoin reductase.

The BEMD system can also be used to display enzymes involved in the synthesis or activation of the plant-growth promoting compound gibberellic acid. Gibberellic acid can be produced from inactive or less active forms via the action of enzymes, including but not limited to hydroxylamine reductases, 2-oxogluturate dioxygenases, gibberellin 2B/3B hydrolases, gibberellin 3-oxidases, and gibberellin 20-oxidases.

Any of these enzymes can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or another plant growth medium for stimulation of plant growth.

To increase the effect of the enzymes displayed on BEMD, the soil can be supplemented with substrates for the enzymes. For example, the soil or other plant growth medium can be supplemented with acetoin, which is a substrate for acetoin reductase; pyruvate, which is a substrate for pyruvate decarboxylase; diacetyl, which is a substrate for diacetyl reductase; and/or acetolactate, which is a substrate for acetolactate decarboxylase. Alternatively or in addition, the soil or other plant growth medium can be supplemented with less potent or inactive forms of gibberellic acid, which will converted into more active forms by the enzymes described above in the soil or other plant growth medium.

Example 13. Use of Recombinant *Bacillus cereus* Family Members Displaying Proteases for Protecting Plants from Pathogens The BEMD system can also be used display proteases that protect plants from one or more pathogens. For example, certain bacterial pathogens can communicate between individual members via secretion of bacterial lactone homoserines or related signaling molecules. Thus, proteases specific for bacterial lactone homoserine signaling molecules can protect plants from such bacterial pathogens by disrupting communication between bacteria, a step essential for the bacteria to secrete toxins and upregulate virulence factors. Suitable proteases specific for bacterial lactone homoserine signaling molecules include endopeptidases and exopeptidases.

Proteases specific for bacterial lactone homoserine signaling molecules can be incorporated into the BEMD system using methods similar to those described above in Example 1. A fusion construct can be prepared that comprises the protease and a targeting sequence that targets the protease to the exosporium when the fusion construct is expressed in a *Bacillus cereus* family member. The fusion construct is then expressed in a *Bacillus cereus* family member, and the *Bacillus cereus* family member is added to soil or another plant growth medium. The protease can then degrade the bacterial lactone homoserine signaling molecules, blocking a key step in the virulence of these organisms and thereby helping to protect the plant from these pathogens. Other proteases and peptidases work effectively in this capacity on the BEMD system as demonstrated above in Example 6 and 7.

Example 14. Use of Recombinant *Bacillus cereus* Family Members Displaying Antimicrobial Proteins and Peptides for Protecting Plants from Pathogens The BEMD system can also be used display enzymes that exhibit antibacterial and/or antifungal activities that can help protect plants from one or more pathogens. For example, antimicrobial proteins and peptides such as bacteriocins, lysozymes (e.g., LysM), siderophores, conalbumin, albumin, lactoferrins (e.g., LfcinB), or TasA can all be expressed in the BEMD system to exert their effect on bacterial and fungal pathogens of plants. Bacteriocins, albumin, conalbumin, lysozymes, and lactoferrin exert direct antimicrobial action on their targets, whereas siderophores bind essential nutrients that pathogens require for virulence. For example, the peptide LfcinB of lactoferrin, when expressed on the surface of the BEMD system would lyse bacteria cells that are susceptible to the lactoferrin peptides in the plant growth medium. These proteins and peptides have specific action on select microbes, and can selectively target a group of pathogens without obstructing all microbes in the plant growth medium.

Any of these proteins or peptides can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or another plant growth medium for protection of plants from one or more pathogens.

Example 15. Use of BEMD Spores Expressing Antimicrobial Peptides for Protecting Plants from Bacteria Genes were synthesized that coded for either of two antimicrobial peptides, LfcinB (derived from bovine lactoferrin) and LysM (derived from chicken lysozyme), linked to a BclA targeting sequence (SEQ ID NO: 60), under the control of the BclA promoter (SEQ ID NO: 85). The genes were introduced into *Bacillus thuringiensis* BT013A and spores were made by growing an overnight culture of the transformed *Bacillus* in brain heart infusion broth, plating onto nutrient agar plates at 30° C. and allowing to grow for 3 days. Spores were washed off the plates and rinsed 3× in PBS. *Staphylococcus epidermidis* cultures were grown overnight in TSB broth at 37° C. The overnight culture was then pelleted, washed in PBS, and resuspended in PBS at an Abs595=0.2. $1\times10^4$BEMD expressing the LysM or LfcinB peptides was incubated in the PBS with the *S. epidermidis* for 3 hours at 37° C., with shaking. A control sample of *S. epidermidis* was left untreated (no BEMD spores). After the 3 hour incubation, dilution plates of the *S. epidermidis* were made and incubated at 37° C. overnight. *S. epidermidis* cultures were counted the next day, and percent killing quantified. In Table 11 below, a record of the killing activity was recorded. The BEMD expressed peptides killed a significant number of *S. epidermidis* cells. This would directly translate into killing of bacteria on the rhizosphere, seed, or other plant material. The selection of peptides specific to certain classes of bacteria can also skew the population of the microorganisms near the plant in a beneficial way, or can selectively target key pathogens.

TABLE 11

| Treatment | Survival | % Killed |
|---|---|---|
| None | 100% | 0% |
| BEMD LysM | 71% | 29% |
| BEMD LfcinB | 23% | 77% |

Example 16. Use of Recombinant *Bacillus cereus* Family Members Displaying Enzymes for Protecting Plants from Pathogens The BEMD system can also be used display enzymes that protect plants from one or more pathogens. For example, yeast and mold cell walls are degraded by enzymes such as β-1,3-glucanases, β-1,4-glucanases, β-1,6-glucanases, chitosinases, chitinases, chitosinase-like proteins, and lyticases. Bacteria cell walls are degraded by enzymes selected from proteinases, proteases, mutanolysin, stapholysin, and lysozymes. Each of these cell wall degrading enzymes can be expressed on the BEMD system and added to plant growth medium for selective inhibition of pathogenic microbes in the rhizosphere.

The BEMD system can also be used to display enzymes or proteins that protect plants from insect or worm pathogens, for example by suppressing insect and/or worm predation of desired plants. Examples of such proteins and enzymes of interest include endotoxins, Cry toxins, other insecticidal protein toxins, protease inhibitors, cysteine proteases, the Cry5B protein, the Cry 21A protein, chitinase, protease inhibitor proteins, protease inhibitor peptides, trypsin inhibitors, and arrowhead protease inhibitors.

Any of these proteins or peptides can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or another plant growth medium for protection of plants from pathogens.

Example 17. Use of BEMD Spores Expressing an Antifungal Enzyme for Protecting Plants, and Demonstration of Efficacy Against *Saccharomyces*

A gene was synthesized that encoded an antifungal enzyme, β-1,3-glucanase from *Bacillus subtilis*, linked to a BclA targeting sequence (SEQ ID NO: 60) under the control of the BclA promoter (SEQ ID NO: 85). The gene was and introduced into *Bacillus thuringiensis* BT013A and pores were made by growing an overnight culture of the transformed *Bacillus* in brain heart infusion broth, plating onto nutrient agar plates at 30° C., and allowing to grow for 3 days. Spores were washed off the plates and rinsed 3× in PBS. *Saccharomyces cerevisiae* cultures were grown overnight in YZ broth at 37° C. The overnight culture was then pelleted, washed in PBS, and resuspended in PBS at an Abs595=0.2. $1\times10^4$ BEMD expressing β-1,3-glucanase was incubated in the PBS with the *Saccharomyces* for 1 hour at 37° C., with shaking. A control sample of *Saccharomyces* was left untreated (no BEMD spores). After the 3 hour incubation, dilution plates of the *Saccharomyces* were made and incubated at 37° C. overnight. *Saccharomyces* cultures were counted the next day, and percent killing quantified. In Table 12 below shows the killing activity of the BEMD spores expressing β-1,3-glucanase. The BEMD-expressed enzyme killed a significant number of *Saccharomyces* cells. This would directly translate into killing of fungal microorganisms on the rhizosphere, seed, or other plant material. The selection of proteins specific to certain classes of fungi can also skew the population of the microorganisms near the plant in a beneficial way, or can selectively target key fungal pathogens.

TABLE 12

| Treatment | Survival | % Killed |
|---|---|---|
| None | 100% | 0% |
| BEMD β-1,3-glucanase | 83% | 17% |

Example 18. Use of Recombinant *Bacillus cereus* Family Members Displaying Plant Immune System Stimulatory Peptides or Proteins for Protecting Plants from Pathogens The BEMD system can also be used display plant immune system enhancer peptides and proteins. These proteins can be expressed on the outside of the BEMD spore and delivered into the plant growth medium to stimulate the plant immune system to allow the plant to protect itself from plant pathogens. Example proteins and peptides include harpin, α-elastins, β-elastins, systemins, phenylalanine ammonia-lyase, elicitins, defensins, cryptogein, and flagellin proteins and peptides. Exposure of plants to these proteins and peptides will stimulate resistance to many plant pathogens in plants.

Any of these proteins or peptides can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the

*Bacillus cereus* family member is added to soil or another plant growth medium for protection of plants from pathogens.

Example 19. Use of Recombinant *Bacillus cereus* Family Members Displaying a Root or Leaf Binding Protein or Peptide to Immobilize the Recombinant *Bacillus cereus* Family Member on a Root System of a Plant or on Plant Leaves Root and leaf binding proteins and peptides can also be incorporated into the BEMD system to allow the BEMD spores to be immobilized on a root system or on leaves of a plant. Display of such root or leaf binding ligands on the BEMD spores allows for targeting of the spores to the root system of a plant or to substructures of the root system or to the leaves or to substructures of leaves to maintain the BEMD spores at an optimal location for other displayed biological molecules and enzymes to be effective.

For example, rhicadhesin is a root binding ligand that binds to root hairs. Thus, display of rhicadhesin on the BEMD spores thus targets the spores to root hairs. Additional proteins that could be utilized for selective binding to plant roots or leaves include adhesins, flagellin, omptins, lectins, pili proteins, curlus proteins, intimins, invasins, agglutinin, afimbrial proteins, TasA, or YuaB.

Such root or leaf binding proteins and peptides can be incorporated into the BEMD system using methods similar to those described above in Example 1. A fusion construct can be prepared that comprises the root or leaf binding protein or peptide and a targeting sequence that targets the protein or peptide to the exosporium when the construct is expressed in a *Bacillus cereus* family member. The fusion construct containing the root or leaf binding ligand is then expressed in a *Bacillus cereus* family member. Such fusion constructs can be coexpressed with one or more additional fusion constructs comprising any of the beneficial enzymes discussed herein (e.g., an enzyme involved in the synthesis of a plant hormone, an enzyme that degrades a nutrient source, or a proteases that protects a plant from a pathogen). The recombinant *Bacillus cereus* family member is added to soil or another plant growth medium, or applied to the leaves of a plant. The root or leaf binding ligand targets the *Bacillus cereus* family member to the root system of the plant or to the leaves of the plant and immobilizes it there, thus allowing the coexpressed fusion construct to exert its effects in close proximity to the root or leaf system.

Example 20. Use of Recombinant *Bacillus cereus* Family Members Displaying Proteins or Enzymes to Enhance Stress Resistance of Plants Proteins, peptides, and enzymes that enhance stress resistance in a plant can be incorporated into the BEMD system and delivered to target plants via addition to roots, leaves, or the plant growth medium. During periods of stress, plants release stress-related compounds, including aminocyclopropane-1-carboxlic acid (ACC), reactive oxygen species, and others, resulting in a negative impact on plant growth. The BEMD system can be used to display enzymes that degrade such stress-related compounds, such as aminocyclopropane-1-carboxylic acid deaminase, superoxide dismutases, oxidases, catalases, and other enzymes that act on reactive oxygen species. Such enzymes reduce the amount of these stress-related compounds and allow plants to continue to grow and even thrive under stressed conditions.

Any of these proteins or peptides can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or to another plant growth medium or applied to the leaves of a plant for enhancing the stress resistance of a target plant.

Example 21. Preparation of BEMD Spores Expressing the Protective Enzyme Catalase A gene was synthesized that encoded the protective enzyme catalase from *Bacillus cereus* linked to a BetA targeting sequence (SEQ ID NO: 61) under the control of the BetA promoter (SEQ ID NO: 86). This gene was and introduced into *Bacillus thuringiensis* BT013A. Spores were made by growing an overnight culture of the transformed *Bacillus* and wildtype strain in brain heart infusion broth, plating onto nutrient agar plates at 30° C., and allowing to grow for 3 days. Spores were washed off the plates and rinsed 3× in PBS. 3 drops of hydrogen peroxide was added to each spore pellet. The enzyme catalase converts the hydrogen peroxide into water and $O_2$ gas. The control spores did not bubble, while the BEMD-catalase spores readily did, demonstrating enzyme activity on the surface of the spores. Other protective enzymes can be displayed in a similar fashion and delivered to the plant to act upon free radicals produced during stress by the plants.

Example 22. Use of Recombinant *Bacillus cereus* Family Members Displaying Proteins or Enzymes that Protect Seeds or Plants from an Environmental Stress Proteins, peptides, and enzymes that protect a plant from an environmental stress can be incorporated into the BEMD system and delivered to target plants via addition to roots, leaves, fruit, or the plant growth medium. During periods of freezing, plants can be damaged by the effect of ice. The BEMD system can be used to display peptides, proteins, or enzymes that protect plants from such effects. For example, the BEMD system can be used to display choline dehydrogenases, which act by producing protective products that protect the plant or seed from frost. Substrates for these enzymes (e.g., choline and/or choline derivatives) can also be added to the plant growth medium. Addition of such substrates can enhance the amount of protectant (betaine and related chemistries) produced in the plant environment by the BEMD expressed enzymes. Betaine derivatives are known to protect seeds from cold stress.

Any of these proteins or peptides can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or to another plant growth medium or applied to the leaves of a plant for protecting the plant from environmental stresses and factors.

Example 23. Enhanced Expression of Fusion Constructs on the BEMD System by Use of Enhanced or Alternative Promoter Elements The BEMD system can display a wide range of proteins, peptides, and enzymes using one or more of the targeting sequences described herein. Some of these targeting sequences have a high affinity for the exosporium which would be beneficial for fusion protein expression, but their low fusion protein expression level limits their use on the BEMD system. For such fusion proteins and sequences, alternative high-expression sporulation promoters can be used instead of the native promoters.

For example, SEQ ID NO: 13 (amino acids 1-39 of *B. weihenstephensis* KBAB4 gene 3572) provides a very effective N-terminal sequence for the delivery of proteins to the exosporium of *Bacillus cereus* family members, as shown in Table 13 below. All genes were synthesized in their complete form (including promoter regions and regions coding for fusion proteins) as described herein. When the native promoter elements for *B. weihenstephensis* KBAB4 gene 3572 (SEQ ID NO: 88) were used to express a fusion protein comprising the targeting sequence of SEQ ID NO: 13 fused to a β-galactosidase enzyme (from *E. coli*), a low level of fusion protein was expressed, leading to a reduction in enzyme activity on the surface of the spore. Enzyme activity was measure by the conversion of 0.5M o-nitrophenylgalactoside in solution over 10 minutes. Enzyme conversion was measured with a spectrophotometer at $ABS_{540}$. Replacement of the native promoter elements of the *B. weihenstephensis* KBAB4 gene 3572 with the high-expression promoters of SEQ ID NO: 86 (*B. anthracis* BetA/BAS3290) or SEQ ID NO: 89 (*B. weihenstephensis* KBAB4 YVTN β-propeller protein) led to a dramatic increase in the enzymatic activity of the spores. On the other hand, replacement of the native promoter elements for *B. weihenstephensis* KBAB4 gene 3572 with the promoter native to *B. anthracis* Sterne BAS1882 (SEQ ID NO: 87) led to a decrease in the enzymatic activity of the spores. The expression level of the targeting sequence of SEQ ID NO: 13 fused to β-galactosidase was much lower (0.38×) when driven by the promoter of BAS1882 (SEQ ID NO: 87), and was greatly improved when driven from the BetA promoter (SEQ ID NO: 86) or YVTN protein promoter (SEQ ID NO: 89).

TABLE 13

| Promoter | Fusion Protein | β-galactosidase activity on BEMD system, normalized | Fold Change |
|---|---|---|---|
| SEQ ID NO: 88 | SEQ ID NO: 13-β-galactosidase | 100% | |
| SEQ ID NO: 86 | SEQ ID NO: 13-β-galactosidase | 213.4% | 2.13X |
| SEQ ID NO: 89 | SEQ ID NO: 13-β-galactosidase | 220.7% | 2.21X |
| SEQ ID NO: 87 | SEQ ID NO: 13-β-galactosidase | 38.1% | 0.38X |

Example 24. Isolation and Identification of Plant-Growth Promoting Bacterial Strains Soil samples from rhizospheres of the healthiest and most resistant potato (*Solanum tuberosum*), yellow summer squash (*Cucurbita pepo*), tomato (*Solanum lycopersicum*), and pole bean (*Phaseolus coccineus*) plants were collected, diluted in sterile water, and spread onto nutrient agar plates. Bacterial isolates that demonstrated high growth rates and were able to be passaged and propagated were selected for further study. The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten lettuce seeds per treatment were planted at a depth of 1 cm in loam top soil (Columbia, Mo.) that was sieved to remove large debris. Seeds were inoculated at planting in 4 cm pots with 0.5 μl of resuspended bacteria in water mixed into 10 ml of $H_2O$. Ten ml of $H_2O$ was sufficient to deliver the bacteria into the 3 $in^3$ (7.62 $cm^3$) of soil as well as saturate the soil for proper germination of seeds. Plants were grown at temperatures between 65-75° F. (18-24° C.) with 11 hours of light/day, and 5 ml of watering every 3 days. After one week, plant heights and leaf diameters, as well as overall health of the plants were collected. Initial screening of rhizosphere isolates resulted in obtaining greater than 200 distinct species of bacteria and fungi from the rhizosphere of the four plants. Some of the bacterial species are described in Table 14. Identified strains are indicated by their proper bacterial identifications. Other strains are indicated by their unknown identification number. Inoculants giving results near control (+/−2%) were not included in the table.

TABLE 14

| | Butterhead Lettuce | | |
|---|---|---|---|
| Bacterial Inoculant | Avg. Height (cm) | Comparison | SEM |
| Uninoculated | 1.8 | Control | .07 |
| *Paracoccus kondratiavae* NC35 | 2 | 111.1% | .05 |
| *B. aryabhattai* CAP53 | 3.65 | 202.8% | .45 |
| *B. flexus* BT054 | 2.45 | 136.1% | .11 |
| *Bacillus mycoides* strain BT155 | 2.17 | 120.4% | .21 |
| *B. aryabhattai* CAP56 | 2.1 | 116.7% | .20 |
| *B. nealsonii* BOBA57 | 2.8 | 155.6% | .03 |
| *E. cloacae* CAP12 | 2.4 | 133.3% | .41 |
| Unknown 8 | 1.77 | 77.8% | .65 |
| Unknown 122 | 1.9 | 105.6% | .11 |
| Unknown 15 | 1.4 | 77.8% | .41 |
| Unknown 39 | 1.8 | 100.0% | .20 |
| Unknown 401 | 2 | 111.1% | .21 |
| Unknown 402 | 1.53 | 85.2% | .27 |
| Unknown 41 | 1.45 | 80.6% | .31 |
| Unknown 42 | 1.4 | 77.8% | .15 |
| Unknown 44 | 2.2 | 133.3% | .08 |
| Unknown 51 | 1.83 | 102.9% | .21 |

Bacterial strains that produced the greatest effect on the overall plant health and plant height in the initial lettuce trial were subjected to further identification. Bacterial strains were grown overnight in Luria Bertani broth at 37° C., and overnight cultures were spun down in a centrifuge. Media was decanted and the remaining bacterial pellet was subjected to chromosomal DNA isolation using the Qiagen Bacterial Chromosomal DNA Isolation kit. Chromosomal DNA was subjected to PCR amplification of the 16S rRNA coding regions using the primers E338F 5'-ACT CCT ACG GGA GGC AGC AGT-3' (SEQ ID NO: 122), E1099R A 5'-GGG TTG CGC TCG TTG C-3' (SEQ ID NO: 123), and E1099R B 5'-GGG TTG CGC TCG TTA C-3' (SEQ ID NO: 124). PCR amplicons were purified using a Promega PCR purification kit, and the resultant amplicons were diluted and sent to the University of Missouri DNA Core for DNA sequencing. DNA sequences were compared to the NCBI BLAST database of bacterial isolates, and genus and species were identified by direct comparison to known strains. Top identified species are indicated in Table 14. In many cases, 16S rRNA DNA sequences were only able to delineate the genus of the selected bacterial strain. In cases where a direct identification was not forthcoming, additional biochemistry analyses, using methods standard in the field, were performed to differentiate strains at the species and strain levels, and are listed in Table 15.

TABLE 15

| Test | *E. cloacae* CAP12 | *P. kondratiavae* NC35 | *B. aryabhattai* CAP53 | *B. flexus* BT054 | *B. mycoides* BT155 | *B. aryabhattai* CAP56 | *B. nealsoni* BOBA57 |
|---|---|---|---|---|---|---|---|
| Urease | − | − | − | − | − | − | + |
| Catalase | + | + | + | + | + | + | + |
| Oxidase | − | + | + | + | − | − | − |
| Nitrate | + | + | − | + | + | − | + |
| Growth, 5% NaCl | + | − | + | + | − | + | + |
| Growth, 7.5% NaCl | − | − | + | + | − | + | − |
| Growth, 42° C. | + | + | + | + | + | + | + |
| Growth, 50° C. | − | − | + | + | − | + | − |
| Growth, pH 5 | + | − | + | + | − | + | − |
| Growth, pH 9 | + | + | + | + | + | + | + |
| Acid, Cellobiose | + | − | + | + | + | + | − |
| Acid, Lactose | + | − | + | + | + | − | + |
| Acid, Starch | − | − | − | + | − | + | − |

Example 25. Isolation and Identification of Additional Plant-Growth Promoting Bacterial Strains Soil samples from agricultural fields near Gas, Kansas were collected, diluted in sterile water, and spread onto nutrient agar plates. Bacterial isolates that demonstrated high growth rates and were able to be passaged and propagated were selected for further study. The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Corn seeds were coated with commercial seed polymer mixed with water alone (1.6 μl per seed total) or commercial seed polymer containing selected bacterial strains (1.6 μl per seed total). Coated seeds were planted in (3 inch) 7.62 cm diameter pots at a depth of 1 inch (2.54 cm) in loam top soil (Columbia, Mo.) that was sieved to remove large debris. Plants were grown at temperatures between 18-24° C. (65-75° F.) with 11 hours of light/day, and 50 ml of watering at planting and every 3 days. After two weeks, plant heights and leaf diameters, as well as overall health of the plants were collected. For germination assays and determining 3 day root length, seeds were coated as indicated above and evenly dispersed at 10 seeds per paper towel. The paper towels were wetted with 10 mls of water, rolled up, placed in a small plastic bag and incubated at 30° C. or placed on a germination heat mat at 27-30° C. (80-85° F.). Root measurements were recorded after 3 days. Initial screening of rhizosphere isolates resulted in obtaining greater than 100 distinct species of bacteria and fungi from the rhizosphere. Some of the bacterial species are described in Table 16. Identified strains are indicated by their proper bacterial identifications.

TABLE 16

| Bacterial Inoculant | Corn Seed Treatments: Avg. Height (2 weeks) normalized to polymer control (%) | Corn Seed Treatments: Avg. Root Length (3 days) normalized to polymer control (%) |
|---|---|---|
| Polymer control | 100 | 100 |
| *B. mycoides* EE118 | 111.1 | 189.1 |
| *B. subtilis* EE148 | 99.4 | 172.8 |
| *Alcaligenes faecalis* EE107 | 111.5 | 129.2 |
| *B. mycoides* EE141 | 109.2 | 143.5 |
| *B. mycoides* BT46-3 | 105.6 | 141.3 |
| *B. cereus* family member EE128 | 105.6 | — |
| *B. thuringiensis* BT013A | 101.8 | 103.8 |
| *Paenibacillus massiliensis* BT23 | 104.2 | 139.4 |
| *B. cereus* family member EE349 | 105.2 | — |
| *B. subtilis* EE218 | 106.6 | — |
| *B. megaterium* EE281 | 107.8 | — |

Bacterial strains that produced the greatest effect on plant health are described in Table 16. Bacterial strains were grown overnight in Luria Bertani broth at 37° C., and overnight cultures were spun down in a centrifuge. Media was decanted and the remaining bacterial pellet was subjected to chromosomal DNA isolation using the Qiagen Bacterial Chromosomal DNA Isolation kit. Chromosomal DNA was subjected to PCR amplification of the 16S rRNA coding regions using the primers E338F 5'-ACT CCT ACG GGA GGC AGC AGT-3' (SEQ ID NO: 122), E1099R A 5'-GGG TTG CGC TCG TTG C-3' (SEQ ID NO: 123), and E1099R B 5'-GGG TTG CGC TCG TTA C-3' (SEQ ID NO: 124). PCR amplicons were purified using a Promega PCR purification kit, and the resultant amplicons were diluted and sent to the University of Missouri DNA Core for DNA sequencing. DNA sequences were compared to the NCBI BLAST database of bacterial isolates, and genus and species were identified by direct comparison to known strains. Top identified species are indicated in Table 16. In many cases, 16S rRNA DNA sequences were only able to delineate the genus of the selected bacterial strain. In cases where a direct identification was not forthcoming, additional biochemistry analyses, using methods standard in the field, were performed to differentiate strains at the species and strain levels, and the differentiated strains are listed in Table 17.

TABLE 17

| Test | *B. thuringiensis* BT013A | *B. cereus* family member EE349 | *B. subtilis* EE148 | *B. subtilis* EE218 | *B. megaterium* EE281 | *Paenibacillus massiliensis* BT23 |
|---|---|---|---|---|---|---|
| Motility | + | + | + | + | + | + |
| Rhizoid Colony | − | − | − | − | − | + |
| Catalase | + | + | + | + | + | + |
| Oxidase | + | − | − | − | − | − |
| Nitrate | + | + | wk | − | − | − |
| Growth, 5% NaCl | + | wk | − | + | + | − |
| Growth, 7.5% NaCl | wk | − | − | + | + | − |
| Growth, 42° C. | − | + | + | + | + | + |
| Growth, 50° C. | − | − | − | − | − | − |
| Growth, pH 5 | wk | − | + | + | + | − |
| Growth, pH 9 | + | + | − | + | + | − |
| Acid, Cellobiose | − | − | wk | + | − | + |
| Acid, Lactose | − | + | + | + | + | − |
| Acid, Starch | − | + | − | + | + | − |

| Test | *B. mycoides* BT46-3 | *Alcaligenes faecalis* EE107 | *B. mycoides* EE118 | *B. cereus* family member EE128 | *B. mycoides* EE141 |
|---|---|---|---|---|---|
| Motility | − | + | − | − | − |
| Rhizoid Colony | + | − | + | − | + |
| Catalase | + | + | + | + | + |
| Oxidase | − | + | − | − | − |
| Nitrate | + | + | + | + | + |
| Growth, 5% NaCl | + | + | − | + | − |
| Growth, 7.5% NaCl | − | − | − | − | − |
| Growth, 42° C. | + | + | − | + | − |
| Growth, 50° C. | − | − | − | − | − |
| Growth, pH 5 | wk | + | − | + | − |
| Growth, pH 9 | wk | + | + | + | − |
| Acid, Cellobiose | + | wk | + | − | wk |
| Acid, Lactose | + | + | − | + | wk |
| Acid, Starch | + | wk | + | + | − |

wk = weak growth or low growth

Example 26. Testing of Plant-Growth Promoting Bacterial Strains on Alfalfa

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and bacteria resuspended in an equal amount of distilled water. Ten Zeba-coated alfalfa seeds were planted for each treatment at a depth of 0.6 cm in loam top soil (Columbia, Mo.) that was sieved to remove large debris. Seeds were inoculated at planting with 0.5 μl of resuspended bacteria in water mixed into 10 ml of $H_2O$. Ten ml of $H_2O$ was sufficient to deliver the bacteria into the 3 $in^3$ (7.62 $cm^3$) of soil as well as saturate the soil for proper germination of seeds. Plants were grown at temperatures between 65-75° F. (18-24° C.) with 11 hours of light/day, and 5 ml of watering every 3 days. Alfalfa was allowed to grow for 1 week to analyze emergence and initial outgrowth of plants under described conditions. Identified strains indicated by their proper bacterial identifications and final height data are listed in Table 18.

TABLE 18

| | Alfalfa | | |
|---|---|---|---|
| Bacterial Inoculant | Avg. Height (cm) | Comparison | SEM |
| Uninoculated | 4.82 | — | .008 |
| *B. aryabhattai* CAP56 | 4.85 | 101.20% | .016 |
| *B. nealsonii* BOBA57 | 4.86 | 101.70% | .021 |
| *E. cloacae* CAP12 | 5.6 | 116.23% | .020 |

Example 27. Testing of Plant-Growth Promoting Bacterial Strains on Cucumbers

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in equal amount of distilled water. Ten cucumber seeds were planted for each treatment at a depth of 1 cm in loam top soil (Columbia, Mo.) that was sieved to remove large debris. Seeds were inoculated at planting with 0.5 μl of resuspended bacteria in water mixed into 10 ml of $H_2O$. Ten ml of $H_2O$ was sufficient to deliver the bacteria into the 3 $in^3$ (7.62 $cm^3$) of soil as well as saturate the soil for proper germination of seeds. Plants were grown at temperatures between 65-75° F. (18-24° C.) with 11 hours of light/day, and 5 ml of watering every 3 days. Cucumbers were allowed to grow for 2 weeks to analyze emergence and initial outgrowth of plants under described conditions. Identified strains indicated by their proper bacterial identifications and final height data are listed in Table 19.

TABLE 19

| | Cucumbers | | |
|---|---|---|---|
| Bacterial Inoculant | Avg. Height (cm) | Comparison | SEM |
| Uninoculated | 11.23 | — | .067 |
| *B. aryabhattai* CAP53 | 11.5 | 102.00% | .023 |
| *B. aryabhattai* CAP56 | 11.35 | 101.20% | .035 |
| *B. nealsonii* BOBA57 | 11.33 | 101.10% | .014 |

Example 28. Testing of Plant-Growth Promoting Bacterial Strains on Yellow Squash The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten yellow squash seeds were planted for each treatment at a depth of 1 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 $in^3$ (7.62 $cm^3$) of soil as well as saturate the soil for proper germination of seeds. Plants were grown at temperatures between 65-75° F. (18-24° C.) with 11 hours of light/day, and 5 ml of watering every 3 days. Squash was allowed to grow for 2 weeks to analyze emergence and initial outgrowth of plants under described conditions. Identified strains indicated by their proper bacterial identifications, final height data, and final leaf diameter (by span of the two leaves) data are listed in Table 20.

TABLE 20

| | Yellow Squash | | | | |
|---|---|---|---|---|---|
| Bacterial Inoculant | Avg. Height (cm) | Comparison | SEM | Leaf Diameter (cm) | Comparison |
| Uninoculated | 10.16 | — | .028 | 5.08 | — |
| *B. aryabhattai* CAP53 | 11.75 | 115.60% | .055 | 7.25 | 142.60% |
| *B. flexus* BT054 | 11.88 | 116.90% | .017 | 6.36 | 125.20% |
| *Bacillus mycoides* BT155 | 11.92 | 117.20% | .051 | 6.33 | 124.60% |
| *B. aryabhattai* CAP56 | 11.95 | 117.60% | .027 | 6.33 | 124.60% |
| *B. nealsonii* BOBA57 | 11.89 | 117.00% | .118 | 6.42 | 126.40% |
| *E. cloacae* CAP12 | 11.42 | 112.30% | .039 | 6.83 | 134.40% |

Example 29. Testing of Plant-Growth Promoting Bacterial Strains on Ryegrass

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Thirty ryegrass seeds were planted for each treatment at a depth of 0.3 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 $in^3$ (7.62 $cm^3$) of soil as well as saturate the soil for proper germination of seeds. Plants were grown at temperatures between 65-75° F. (18-24° C.) with 11 hours of light/day, and 5 ml of watering every 3 days. Ryegrass was allowed to grow for 1.5 weeks to analyze emergence and initial outgrowth of plants under described conditions. Identified strains indicated by their proper bacterial identifications and height data are listed in Table 21.

TABLE 21

| | Ryegrass | | |
|---|---|---|---|
| Bacterial Inoculant | Avg. Height (cm) | Comparison | SEM |
| Uninoculated | 1.61 | — | .023 |
| *B. aryabhattai* CAP53 | 2.01 | 124.70% | .012 |
| *B. flexus* BT054 | 2.21 | 137.30% | .034 |
| *Bacillus mycoides* BT155 | 2.29 | 142.20% | .049 |
| *B. aryabhattai* CAP56 | 2.19 | 136.00% | .009 |
| *B. nealsonii* BOBA57 | 2.29 | 142.40% | .045 |
| *E. cloacae* CAP12 | 1.98 | 122.50% | .015 |

Example 30. Testing of Plant-Growth Promoting Bacterial Strains on Corn

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten corn seeds were planted for each treatment at a depth of 2.5 cm in loam top soil (Columbia, Mo.) that was sieved to remove large debris. Seeds were inoculated at planting with 0.5 nl of resuspended bacteria in water mixed into 10 ml of $H_2O$. Ten ml of $H_2O$ was sufficient to deliver the bacteria into the 3 $in^3$ (7.62 $cm^3$) of soil as well as saturate the soil for proper germination of seeds. Plants were grown at temperatures between 65-75° F. (18-24° C.) with 11 hours of light/day, and 5 ml of watering every 3 days. Corn was allowed to grow for 2 weeks to analyze emergence and initial outgrowth of plants under described conditions. Identified strains indicated by their proper bacterial identifications and final height data are listed in Table 22.

TABLE 22

| | Corn | | |
|---|---|---|---|
| Bacterial Inoculant | Avg. Height (cm) | Comparison | SEM |
| Uninoculated | 8.9 | — | .039 |
| *B. aryabhattai* CAP53 | 11.01 | 123.60% | .081 |
| *B. flexus* BT054 | 9.96 | 112.00% | .095 |
| *Bacillus mycoides* strain BT155 | 9.6 | 107.90% | .041 |
| *B. aryabhattai* CAP56 | 9.54 | 107.10% | .088 |
| *B. nealsonii* BOBA57 | 9.23 | 103.70% | .077 |

Example 31. Testing of Plant-Growth Promoting Bacterial Strains on Soybeans

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight, or for *Bradyrhizobium* or *Rhizobium* on yeast mannitol media). Overnight cultures (30° C.) of selected strains were spun down, media decanted off, and resuspended in equal amount of distilled water. Ten soybean seeds were planted for each treatment at a depth of 2.5 cm in loam top soil (Columbia, Mo.) that was sieved to remove large debris. Seeds were inoculated at planting with 0.5 µl of resuspended bacteria in water mixed into 10 ml of $H_2O$. When testing two bacterial strains, 0.5 µl of each resuspended bacteria was mixed into 10 ml of $H_2O$. Ten ml of $H_2O$ was sufficient to deliver the bacteria into the 3 $in^3$ (7.62 $cm^3$) of soil as well as saturate the soil for proper germination of seeds. Plants were grown at temperatures between 65-75° F. (18-24° C.) with 11 hours of light/day, and 5 ml of watering every 3 days. Soybeans were allowed to grow for 2 weeks to analyze emergence and initial outgrowth of plants under described conditions. Identified strains indicated by their proper bacterial identifications and final height data are listed in Table 23. Co-inoculation of bacteria strains in the present invention with members of the *Bradyrhizobium* sp. or *Rhizobium* sp. lead to an increase in plant growth compared to either inoculant alone.

TABLE 23

| | Soybeans | | |
|---|---|---|---|
| Bacterial Inoculant | Avg. Height (cm) | Comparison | SEM |
| Uninoculated | 13.94 | — | .089 |
| *B. aryabhattai* CAP53 | 16.32 | 117.1% | .146 |
| *B. flexus* BT054 | 17.85 | 128.0% | .177 |
| *Bacillus mycoides* strain BT155 | 18.93 | 135.8% | .117 |
| *B. aryabhattai* CAP56 | 17.23 | 123.6% | .133 |
| *B. aryabhattai* CAP53 | 16.32 | 117.1% | .077 |
| *B. aryabhattai* CAP53 and *Bradyrhizobium* sp. | 16.72 | 119.9% | .182 |
| *B. aryabhattai* CAP53 and *Rhizobium* sp. | 17.32 | 124.2% | .086 |
| *Bradyrhizobium* sp. | 14.25 | 102.2% | |
| *Rhizobium* sp. | 14.75 | 105.8% | |

Example 32. *Bacillus cereus* Family Members with Plant Growth Promoting Attributes

*Bacillus mycoides* strain BT155, *Bacillus mycoides* strain EE118, *Bacillus mycoides* strain EE141, *Bacillus mycoides* strain BT46-3, *Bacillus cereus* family member strain EE349, *Bacillus thuringiensis* strain BT013A, and *Bacillus megaterium* strain EE281 were grown in Luria Bertani broth at 37° C. and overnight cultures were spun down, media decanted off, and resuspended in equal amount of distilled water. 20 corn seeds were planted for each treatment at a depth of 2.5 cm in loam top soil (Columbia, Mo.) that was sieved to remove large debris. Seeds were inoculated at planting with 0.5 µl of resuspended bacteria in water mixed into 50 ml of $H_2O$. Fifty ml of $H_2O$ was sufficient to deliver the bacteria into the 29 $in^3$ (442.5 $cm^3$) of soil as well as saturate the soil for proper germination of seeds. Plants were grown at temperatures between 65-72° F. with 13 hours of light/day, and 5 ml of watering every 3 days. Seedlings were allowed to grow for 2 weeks to analyze emergence and initial outgrowth of plants under described conditions. Identified strains indicated by their proper bacterial identifications and final height data are listed in Table 24.

TABLE 24

| Bacterial Inoculant | Avg. Height, cm, Corn | Percentage | SEM, |
|---|---|---|---|
| H2O Control | 11.41 | 100% | .123 |
| *B. mycoides* EE118 | 12.43 | 108.9% | .207 |
| *B. mycoides* EE141 | 12.84 | 112.5% | .231 |
| *B. mycoides* BT46-3 | 11.81 | 103.5% | .089 |
| *Bacillus thuringiensis* BT013A | 12.05 | 105.6% | .148 |
| *Bacillus cereus* family member EE128 | 13.12 | 114.9% | .159 |
| *Bacillus mycoides* BT155 | 12.85 | 112.6% | .163 |
| *Bacillus megaterium* EE281 | 11.99 | 105.1% | .098 |

All plant growth promoting bacteria tested had a beneficial effect on corn height at two weeks under the described conditions. The *Bacillus cereus* family member EE128 strain had the greatest effect in this trial, giving a greater than at 14% boost in corn height.

Example 33. Enhanced Selection of *Bacillus cereus* Family Members to Screen for Plant Growth-Promoting and Other Beneficial Activities as BEMD Expression Host The BEMD system can be used to display a wide range of proteins, peptides, and enzymes using any of the targeting sequences described herein to provide beneficial agricultural effects. Additional beneficial effects can be obtained by selecting an expression host (a *Bacillus cereus* family member) having inherent beneficial attributes. Many strains of members of the *Bacillus cereus* family have plant-growth promoting benefits. Additionally, many *Bacillus cereus* family member strains provide have protective effects, through direct fungicidal, insecticidal, nematocidal, or other protective activities. By using such strains these as the expression host for the BEMD system, the end spore product would have a combination of positive benefits in agriculture.

Table 25 provides results for an experiments wherein a fusion protein was expressed in various *Bacillus cereus* family member strains. All strains are expressed a fusion protein comprising amino acids 1-35 of SEQ ID NO: 1 and the phosphatase PhoA4 from *Bacillus subtilis*, a beneficial enzyme for enhanced phosphate uptake in corn. The gene was synthesized, cloned into the pMK4 vector, and introduced into each of the *Bacillus* spp. indicated in Table 25 below. Strains were taken into sporulation by incubation at 30° C. on nutrient agar plates containing chloramphenicol 10 µg/ml for three days. Spores were collected, washed, and applied to corn at planting at a rate of $1\times10^5$ CFU/ml in 50 ml of water per 7.62 cm diameter pot with 5 mg polyphosphate per pot. Corn was grown in silt loam soil for two weeks. Plants were grown under ideal light using T5 lamps, 54 watts, and exposed to 13 hours of light a day under controlled temperature conditions between 15.5-25.5° C. Plants were watered to saturation every three days over a two week trial. At the end of two weeks, the height of each plant was measured and measurements were normalized to control *Bacillus thuringiensis* spores. Expression of the SEQ ID NO: 1—Phosphatase fusion protein led to an increase in corn height at 2 weeks regardless of the expression host strain selected. As shown in Table 25, use of a plant-growth promoting *Bacillus cereus* family member further increased corn height

TABLE 25

| *Bacillus* Species | Strain | Fusion Protein | Height at 2 weeks, Normalized |
|---|---|---|---|
| *B. thuringiensis* | Strain BT013A | None | 100% |
| *B. thuringiensis* | Strain BT013A | SEQ ID NO: 1-Phosphatase | 117.4% |
| *B. mycoides* | Strain EE141 | None | 107.3% |
| *B. mycoides* | Strain EE141 | SEQ ID NO: 1-Phosphatase | 123.3% |
| *B. cereus* family member | Strain EE128 | None | 124.1% |
| *B. cereus* family member | Strain EE128 | SEQ ID NO: 1-Phosphatase | 131.7% |
| *B. mycoides* | Strain BT155 | None | 104.8% |
| *B. mycoides* | Strain BT155 | SEQ ID NO: 1-Phosphatase | 121.9% |

Example 34. Use of Various Targeting Sequences to Express β-Galactosidase on the Surface of *Bacillus thuringiensis*

A wide variety of targeting sequences that that have a high degree homology with amino acids 20-35 of BclA (amino acids 20-35 of SEQ ID NO: 1) can be used to display enzymes, proteins, and peptides on the surface of *Bacillus cereus* family members. Several targeting sequences were compared by making fusion proteins containing the targeting sequences linked to *Bacillus subtilis* lipase. Fusion constructs were synthesized using the promoters native to the targeting sequence, cloned into the replicating plasmid pMK4, and introduced into *Bacillus thuringiensis* BT013A. Strains were taken into sporulation by incubation at 30° C. on nutrient agar plates containing chloramphenicol 10 μg/ml for 3 days. Spores were collected, washed, and resuspended in PBS at a rate of $1\times10^8$/ml. $1\times10^5$ spores for each fusion construct spores were suspended in 400 μl $dH_2O$. The reactions were warmed with the reaction components to the desired reaction temperature (40° C.). 200 μl working buffer was added (9:1 Solution A: Solution B). Solution A was 50 mM Tris pH 10 and 13.6 mM deoxycholic acid and Solution B was 3 mg/ml p-nitrophenyl palmitate in isopropanol. The reaction was incubated at 40° C. for 10 minutes and placed on ice, centrifuged to remove spores, and absorbance at 420 nm was recorded. The results are shown in Table 26 below. Activity was normalized to a control fusion protein comprising amino acids 1-35 of SEQ ID NO: 1 fused to *Bacillus subtilis* lipase.

TABLE 26

| Strain | Targeting sequence | Enzyme | Relative activity |
|---|---|---|---|
| *B. thuringiensis* BT013A | Amino acids 1-35 of SEQ ID NO: 1 | Lipase | 100% |
| *B. thuringiensis* BT013A | Amino acids 1-27 of SEQ ID NO: 3 | Lipase | 92.5% |
| *B. thuringiensis* BT013A | Amino acids 1-28 of SEQ ID NO: 7 | Lipase | 13.5% |
| *B. thuringiensis* BT013A | Amino acid 1-24 of SEQ ID NO: 9 | Lipase | 24.8% |
| *B. thuringiensis* BT013A | Amino acid 1-33 of SEQ ID NO: 13 | Lipase | 98.5% |
| *B. thuringiensis* BT013A | Amino acid 1-33 of SEQ ID NO: 21 | Lipase | 107.8% |

TABLE 26-continued

| Strain | Targeting sequence | Enzyme | Relative activity |
|---|---|---|---|
| *B. thuringiensis* BT013A | SEQ ID NO: 60 | Lipase | 137.1% |
| *B. thuringiensis* BT013A | SEQ ID NO: 62 | Lipase | 146.3% |
| *B. thuringiensis* BT013A | SEQ ID NO: 64 | Lipase | 115.7% |
| *B. thuringiensis* BT013A | SEQ ID NO: 68 | Lipase | 81.5% |

Several targeting sequences linked to lipase result in higher expression levels and activity of enzyme on the surface of spores. In particular, SEQ ID NOs. 60, 62, and 64, each containing a shorter targeting sequence, resulted in enhanced fusion expression on the surface of the BEMD spores. All the fusion proteins containing targeting sequences tested resulted in surface display of lipase.

Example 35. Use of Various Exosporium Sequences to Express Lipase on the Surface of *Bacillus thuringiensis* and Demonstration of Fusion Protein Localization to the Exosporium Surface A wide variety of exosporium proteins can be used to display enzymes, proteins, and peptides on the surface of *Bacillus cereus* family members. Several different exosporium proteins were compared by making fusion proteins containing the exosporium proteins linked to *Bacillus subtilis* lipase as described in Example 34. Fusion constructs were synthesized using the promoter native to the exosporium protein indicated in Table 27 below, cloned into the replicating plasmid pMK4, and introduced into *Bacillus thuringiensis* BT013A. Spores displaying the various exosporium protein-*Bacillus subtilis* 168 lipase fusions were made by growing the transformed bacteria in brain heart infusion broth with selective pressure from 10 μg/ml chloramphenicol, plating onto nutrient agar plates, and incubating at 30° C. for 3 days. After 3 days, the spores were washed off the plates, purified by centrifugation, and resuspended in PBS at $1\times10^8$ CFU/ml.

$1\times10^5$ spores for each fusion construct were resuspended in 400 μl $dH_2O$. The reactions were warmed with the reaction components to the desired reaction temperature (40° C.). 200 μl of working buffer was added (9:1 Solution A: Solution B). Solution A was 50 mM Tris pH 10 and 13.6 mM deoxycholic acid and Solution B was 3 mg/ml p-nitrophenyl palmitate in isopropanol. The reaction was incubated at 40° C. for 10 minutes and placed on ice, centrifuged to remove spores and absorbance at 420 nm was recorded. Results are shown in Table 27 below. Activity was normalized to SEQ ID NO: 72 linked to lipase.

TABLE 27

| Strain | Exosporium protein | Enzyme | Relative activity |
|---|---|---|---|
| *B. thuringiensis* BT013A | SEQ ID NO: 72 | Lipase | 100% |
| *B. thuringiensis* BT013A | SEQ ID NO: 73 | Lipase | 134.5% |
| *B. thuringiensis* BT013A | SEQ ID NO: 76 | Lipase | 17.8% |
| *B. thuringiensis* BT013A | SEQ ID NO: 80 | Lipase | 19.8% |
| *B. thuringiensis* BT013A | SEQ ID NO: 81 | Lipase | 8.2% |

Use of the exosporium proteins of SEQ ID NOs. 72 and 73 resulted in the highest enzyme activity on the spore. All the fusion proteins containing exosporium proteins resulted in surface display of active *Bacillus subtilis* 168 lipase, albeit at different levels.

Additional exosporium proteins were demonstrated to result in targeting of fusion proteins to the exosporium using the fluorescent reporter mCherry. Fusion constructs were created that contained the exosporium proteins of SEQ ID NOs. 74, 83, and 73 linked to the mCherry reporter. Spores were grown for 1.5 days, collected, and resuspended as described above. 7 μl of fluorescent spores were put under a Nikon E1000 microscope and imaged during late sporulation. Circular localization in a ring is indicative of outer spore layer localization, and the appearance matches that of an exosporium protein. Fluorescent microscopy results are shown in FIG. 2. FIGS. 2A, 2B, and 2C are fluorescent microscopy images of spores expressing fusion proteins comprising the exosporium proteins of SEQ ID NOs. 74, 83, and 73, respectively, and the mCherry reporter. All three fusions demonstrated high levels of fluorescence and exosporium localization, demonstrating their potential utility for the expression of foreign proteins on the surface of the exosporium.

Example 36. Use of Various Targeting Sequences and Exosporium Proteins to Express Phosphatase in *Bacillus subtilis* Spores and Effects of the Phosphatase-Expressing Spores in Soybeans BEMD spores expressing *Bacillus subtilis* EE148 Phosphatase A4 (PhoA4) were created by gene synthesis of the genes coding for various targeting sequences and exosporium proteins under the control of their native promoters linked to PhoA4. The synthesized genes were cloned into pMK4 and introduced into *Bacillus thuringiensis* BT013A. Spores displaying the various exosporium protein-*Bacillus subtilis* EE148 PhoA4 fusions were made by growing the transformed bacteria in brain heart infusion broth with selective pressure from 10 μg/ml chloramphenicol, plating onto nutrient agar plates, and incubating at 30° C. for three days. After three days, the spores were washed off the plates, purified by centrifugation, and resuspended in PBS at 1×10$^8$ CFU/ml.

Soybeans were planted 2.54 cm deep in 10 cm deep pots filled with standard loam topsoil. BEMD spores expressing PhoA4 were diluted to a concentration of 1×10$^4$/ml in 50 ml of water and applied to each plant at planting. A water-only control was also included. Polyphosphate was added to pots in liquid at a rate of 0.5 mg/pot. Plants were grown under ideal light using T5 lamps, 54 watts, and exposed to 13 hours of light a day under controlled temperature conditions between 15.5-25.5° C. Plants were watered to saturation every three days over the two week trial. At the end of two weeks, the height of each plant was measured, and measurements were normalized to control water-only plants.

Results are shown in Table 28. Soy grown in the presence of BEMD spores expressing fusion proteins containing PhoA4 linked to various targeting sequences and exosporium proteins with different fusion partners with PhoA4 all exhibited enhanced growth, but the extent of the effect varied depending on the targeting sequence or exosporium protein used.

TABLE 28

| *Bacillus* species | Targeting sequence or exosporium protein linked to PhoA4 | Height at 2 weeks, Normalized |
|---|---|---|
| H2O (No bacteria) | N/A | 100% |
| *Bacillus thuringiensis* Strain BT013A | Amino acids 1-35 of SEQ ID NO: 1 | 100% |
| *Bacillus thuringiensis* Strain BT013A | Amino acids 1-28 of SEQ ID NO: 3 | 117.4% |
| *Bacillus thuringiensis* Strain BT013A | Amino acids 1-33 of SEQ ID NO: 21 | 107.3% |
| *Bacillus thuringiensis* Strain BT013A | SEQ ID NO: 60 | 123.3% |
| *Bacillus thuringiensis* Strain BT013A | SEQ ID NO: 62 | 124.1% |
| *Bacillus thuringiensis* Strain BT013A | SEQ ID NO: 72 | 131.7% |
| *Bacillus thuringiensis* Strain BT013A | SEQ ID NO: 73 | 104.8% |

Example 37. Co-Application of BEMD Spores and Seed Treatments, Liquid Fertilizers, and Other Additives BEMD spores expressing fusion proteins were tested for compatibility with various seed treatments. The BEMD spores expressed fusion proteins comprising the targeting sequence of amino acids 1-35 SEQ ID NO: 1 linked to a phosphatase (PhoA4) from *Bacillus subtilis* EE148 or the POLARIS peptide. The synthesized genes were cloned into pMK4 and introduced into *Bacillus thuringiensis* BT013A. Spores displaying the various exosporium protein-*Bacillus subtilis* EE148 PhoA4 or POLARIS fusions were made by growing the transformed bacteria in brain heart infusion broth with selective pressure from 10 μg/ml chloramphenicol, plating onto nutrient agar plates, and incubating at 30° C. for three days. After three days, the spores were washed off the plates, purified by centrifugation, and resuspended in PBS at 1×10$^8$ CFU/ml.

Plants were grown under ideal light using T5 lamps, 54 watts, and exposed to 13 hours of light a day under controlled temperature conditions between 15.5-25.5° C. Plants were watered to saturation every three days over the two week trial. At the end of two weeks, the height of each plant was measured, and measurements were normalized to control water only plants. Results are shown in Table 29 below. Drench=applied to soil at 50 ml per pot. Polymer=ACCELERON seed coating polymer only. BEMD spores were added at 1×10$^4$ cells/50 ml for drench applications. BEMD spores were added at 1.3×10$^4$/cells/seed for seed coating applications. 10-34-0 and 6-24-6 are standard commercial starter fertilizer compositions. 10-34-0 is liquid ammonium phosphate. 6-24-6 is low salt liquid phosphate fertiliser with an ortho/poly formulation. Colorant=Becker Underwood red seed coating coloring agent. MACHO, APRON, and CRUISER are commercial fungicides used on seeds. MACHO contains the active ingredient imidacloprid, APRON contains the active ingredient mefenoxam, and CRUISER contains a mixture of the active ingredients thiamethoxam, mefenoxam, and fludioxonil. The spores were found to be compatible with many seed applications and retained their ability to stimulate plant growth in corn.

TABLE 29

| BEMD treatment | Chemical | Corn height at 2 weeks, normalized |
|---|---|---|
| None | None (Water Drench) | 100% |
| None | Polymer Only | 101.3% |
| BEMD PhoA4 | N/A (Drench) | 111.3% |
| BEMD POLARIS | N/A (Drench) | 106.7% |
| BEMD PhoA4 | Polymer | 109.3% |
| BEMD POLARIS | Polymer | 107.3% |
| BEMD PhoA4 | Polymer + Colorant | 102.3% |
| BEMD PhoA4 | Polymer + MACHO | 107.9% |
| BEMD PhoA4 | Polymer + APRON | 112.3% |
| BEMD PhoA4 | Polymer + CRUISER | 116.8% |
| BEMD PhoA4 | Polymer + Colorant + MACHO + APRON + CRUISER | 113.7% |
| None | 10-34-0 Starter (Drench) | 108.5% |
| BEMD PhoA4 | 10-34-0 Starter Fertilizer (Drench) | 114.7% |
| None | 6-24-6 Starter Fertilizer (Drench) | 102.6% |
| BEMD PhoA4 | 6-24-6 Starter Fertilizer (Drench) | 112.9% |

BEMD spores were found to be compatible with all seed coating amendments tested. There was a slight decrease in activity when BEMD PhA4 spores were combined with colorant and polymer alone, but the spores regained full activity with colorant in combination with other fungicides. BEMD spores also worked well with liquid fertilizers. Starter fertilizers contributed to plant growth most likely through direct nutrient supplementation. BEMD spores worked with both starter fertilizers, suggesting that phosphatase activity can still lead to increased plant growth in the presence of excess nutrients. Combinations of BEMD spores with fungicides exhibited greater increases in plant growth than BEMD spores alone, likely due to protection given to young corn plants during early growth.

Example 38. The Use of the BEMD Spores as a Foliar Addition for Reducing Stress Inhibition of Growth on Corn The BEMD spore display system can be used to deliver enzymes that can alleviate some stress from growing plants in the field or greenhouse. To accomplish this, enzymes were selected that selectively act upon reactive oxygen species in soil. Reactive oxygen species are a key marker of stress in plants.

BEMD spores expressing fusion proteins comprising the targeting sequence of amino acids 1-35 of SEQ ID NO: 1 linked to chitosinase, superoxide dismutase, catalase, or β1,3 glucanase from *Bacillus thuringiensis* BT013A were generated. The synthesized genes were cloned into pMK4 and introduced into *Bacillus thuringiensis* BT013A. Spores displaying the various protein fusions were made by growing the transformed bacteria in brain heart infusion broth with selective pressure from 10 μg/ml chloramphenicol, plating onto nutrient agar plates, and incubating at 30° C. for three days. After three days, the spores were washed off the plates, purified by centrifugation, and resuspended in PBS at $1\times10^8$ CFU/ml.

Three week old corn plants at the V5 stage were grown under ideal light using T5 lamps, 54 watts, and exposed to 13 hours of light a day under controlled temperature conditions between 15.5-25.5° C. Plants were watered to saturation every three days over the course of the trial. As the plants reach V5, BEMD spores or positive control chemicals were sprayed on the leaves at either $1\times10^5$ BEMD spores/ml or at the recommended rates for the chemicals. A total of 1 ml of spray was applied to each plant individually. Plant heights were taken just prior to the application of the foliar sprays. The corn plants were then stressed by warming to 32.2° C. and decreasing watering to once per week. Plants were kept under stressed conditions for two weeks. At the end of the two weeks, plant heights were again measured, and visual appearance recorded. Under these stressed conditions, plant growth was minimal in control treatments. The ability to continue to grow under stressed conditions was measured by an increase in plant height over the two week span as compared to the water-only control. Results are shown in Table 30 below.

TABLE 30

| Treatment | Rate | Change in plant Height over 2 week stress |
|---|---|---|
| None | None | 0% |
| *Bacillus thuringiensis* BT013A spores | 1 ml/plant | −1.6% |
| BEMD Chitosinase | 1 ml/plant | 0.3% |
| BEMD Chitosinase and Chitosan | 1 ml/plant and 5 mM | 4.7% |
| BEMD Superoxide Dismutase | 1 ml/plant | 8.3% |
| BEMD B1,3 Glucanase | 1 ml/plant | 4.9% |
| Salicylic Acid | 1 ml/plant | 5.8% |
| Benzothiadiazole (BTH) | 1 ml/plant | 7.3% |
| BEMD Catalase | 1 ml/plant | −0.5% |

Several destressing enzymes were applied to corn using the BEMD system, as shown in in Table 30 above. Control spores had no significant effect (decrease in plant height of −1.6%. The BEMD chitosinase enzyme had a positive effect when combined with its substrate, chitosan. The two best performing enzymes were BEMD β-1,3-glucanase and BEMD superoxide dismutase. BEMD β-1,3-glucanase has a primarily antifungal activity, but can also have direct effects on plants. Salicylic acid and BTH were positive controls for the foliar assay, and positive responses were seen for both. This foliar delivery method can be used for delivering destressing enzymes to the plants at various times of the season.

Example 39. Expression Levels of Fusion Proteins Using Various Sigma-K Containing Promoters As shown in Example 23 above, replacing native promoter of a targeting sequence, exosporium protein, or exosporium protein fragment can greatly affect the level of fusion protein expressed on the exosporium of a *Bacillus cereus* family spore. For example, replacing the native BclA promoter with the BclB promoter greatly reduces the level of fusion protein on the surface of *Bacillus cereus* family member spores. Alternatively, replacement of native BclB promoter with the BclA promoter increases fusion protein levels on the exosporium dramatically.

Relative promoter expression levels for various exosporium proteins under the control of their native sporulation promoters were obtained from microarray data from Bergman et al., 2008. The relative expression levels were determined during late sporulation timing (300 minutes after the start of the experiment), when sigma K promoters are most active. Sigma K promoters are key promoters for expression of exosporium localized genes and associated proteins. Relative expression is the increase in a gene's expression level when compared to the average of all other genes of the chromosome at all given times. Table 31 below shows the relative expression levels of a variety of sigma K driven genes in *Bacillus cereus* family members.

TABLE 31

| Protein (Promoter SEQ ID NO.) | Relative Expression (Fold increase in mRNA) |
|---|---|
| CotY (SEQ ID NO: 97) | 79.21 |
| Rhamnose Promoters (SEQ ID NO: 96) | 75.69 |
| BclC (SEQ ID NO: 98) | 14.44 |
| Sigma K (SEQ ID NO: 99) | 64 |
| BclA adjacent US Glycosyl transferase promoter 1 (SEQ ID NO: 101) | 72.25 |
| BclA adjacent DS Glycosyl transferase promoter 2 (SEQ ID NO: 102) | 73.96 |
| BclA (SEQ ID NO: 85) | 77.44 |

TABLE 31-continued

| Protein (Promoter SEQ ID NO.) | Relative Expression (Fold increase in mRNA) |
|---|---|
| ExsY (SEQ ID NO: 91) | 32.49 |
| YjcA (SEQ ID NO: 93) | 64 |
| YjcB (SEQ ID NO: 94) | 70.56 |
| BxpB/ExsFA (SEQ ID NO: 95) | 30.25 |
| InhA (SEQ ID NO: 100) | 34.25 |

In view of the above, it will be seen that the several objects of the invention are achieved and other advantageous results attained.

As various changes could be made in the above fusion proteins, *Bacillus cereus* family members, formulations, and methods without departing from the scope of the invention, it is intended that all matter contained in the above description and shown in the accompanying drawing shall be interpreted as illustrative and not in a limiting sense.

What is claimed is:

1. A recombinant *Bacillus cereus* family member that expresses a fusion protein, wherein the fusion protein comprises:

a targeting sequence, exosporium protein, or exosporium protein fragment selected from the group consisting of:

(a) an amino acid sequence having at least about 43% identity with amino acids 20-35 of SEQ ID NO: 1, wherein the identity with amino acids 25-35 is at least 54%;

(b) a targeting sequence comprising amino acids 1-35 of SEQ ID NO: 1;

(c) a targeting sequence comprising amino acids 20-35 of SEQ ID NO: 1;

(d) a targeting sequence comprising SEQ ID NO: 1;

(e) a targeting sequence comprising SEQ ID NO: 60;

(f) a targeting sequence comprising amino acids 22-31 of SEQ ID NO: 1;

(g) a targeting sequence comprising amino acids 22-33 of SEQ ID NO: 1; and (h) a targeting sequence comprising amino acids 20-31 of SEQ ID NO: 1; and a phospholipase.

2. The recombinant *Bacillus cereus* family member of claim 1, wherein the targeting sequence comprises an amino acid sequence having at least 50% identity with amino acids 20-35 of SEQ ID NO: 1, wherein the identity with amino acids 25-35 is at least 63%.

3. The recombinant *Bacillus cereus* family member of claim 1, wherein the targeting sequence comprises an amino sequence having at least 62% identity with amino acids 20-35 of SEQ ID NO: 1, wherein the identity with amino acids 25-35 is at least 72%.

4. The recombinant *Bacillus cereus* family member of claim 1, wherein the targeting sequence comprises an amino acid sequence having at least 81% identity with amino acids 20-35 of SEQ ID NO: 1, wherein the identity with amino acids 25-35 is at least 90%.

5. The recombinant *Bacillus cereus* family member of claim 1, wherein the targeting sequence consists of:

(a) an amino acid sequence consisting of 16 amino acids and having at least 43% identity with amino acids 20-35 of SEQ ID NO: 1, wherein the identity with amino acids 25-35 is at least 54%;

(b) amino acids 1-35 of SEQ ID NO: 1;

(c) amino acids 20-35 of SEQ ID NO: 1;

(d) SEQ ID NO: 1; or (e) SEQ ID NO: 60.

6. The recombinant *Bacillus cereus* family member of claim 1, wherein the targeting sequence comprises SEQ ID NO: 60.

7. The recombinant *Bacillus cereus* family member of claim 1, wherein the targeting sequence, exosporium protein, or exosporium protein fragment further comprises a methionine residue at the amino acid position immediately preceding the first amino acid of the targeting sequence, exosporium protein, or exosporium protein fragment.

8. The recombinant *Bacillus cereus* family member of claim 1, wherein targeting sequence, the exosporium protein, or the exosporium protein fragment comprises the amino acid sequence GXT at its carboxy terminus, wherein X is any amino acid.

9. The recombinant *Bacillus cereus* family member of claim 1, wherein the fusion protein further comprises an amino acid linker between the targeting sequence, the exosporium protein, or the exosporium protein fragment and the phospholipase.

10. The recombinant *Bacillus cereus* family member of claim 1, wherein the linker comprises a polyalanine linker, a polyglycine linker, or a linker comprising a mixture of both alanine and glycine residues.

11. The recombinant *Bacillus cereus* family member of claim 1, wherein the recombinant *Bacillus cereus* family member comprises *Bacillus anthracis, Bacillus cereus, Bacillus thuringiensis, Bacillus mycoides, Bacillus pseudomycoides, Bacillus samanii, Bacillus gaemokensis, Bacillus weihenstephensis*, or a combination thereof.

12. The recombinant *Bacillus cereus* family member of claim 1, wherein the recombinant *Bacillus cereus* family member comprises a plant-growth promoting strain of bacteria.

13. The recombinant *Bacillus cereus* family member of claim 1, wherein the recombinant *Bacillus cereus* family member is inactivated.

14. A formulation comprising a recombinant *Bacillus cereus* family member of claim 1 and an agriculturally acceptable carrier.

15. The formulation of claim 14, wherein the formulation further comprises at least one agrochemical.

16. The formulation of claim 15, wherein the agrochemical comprises a fertilizer, a micronutrient fertilizer material, an insecticide, a herbicide, a fungicide, a molluscicide, an algicide, a plant growth amendment, a bacterial inoculant, a fungal inoculant, or a combination thereof.

17. The formulation of claim 16, wherein the agrochemical comprises the fertilizer.

18. The formulation of claim 17, wherein the fertilizer comprises ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrate, magnesian limestone, magnesia, urea, urea-formaldehyde, urea ammonium nitrate, sulfur-coated urea, polymer-coated urea, isobutylidene diurea, $K_2SO_4$-$2MgSO_4$, kainite, sylvinite, kieserite, Epsom salts, elemental sulfur, marl, ground oyster shells, fish meal, oil cakes, fish manure, blood meal, rock phosphate, superphosphate, slag, bone meal, wood ash, manure, bat guano, peat moss, compost, green sand, cottonseed meal, feather meal, crab meal, fish emulsion, humic acid, or a combination thereof.

19. A plant seed treated with a recombinant *Bacillus cereus* family member of claim 1.

20. The plant seed of claim 19, wherein the plant seed is coated with the recombinant *Bacillus cereus* family member of claim 1.

21. A plant seed treated with a formulation of claim 14.

22. The plant seed of claim 21, wherein the plant seed is coated with the formulation.

* * * * *